US 7,141,570 B2

(12) United States Patent
Hester, Jr. et al.

(10) Patent No.: US 7,141,570 B2
(45) Date of Patent: Nov. 28, 2006

(54) N-ARYL-2-OXAZOLIDINONE-5-CARBOXAMIDES AND THEIR DERIVATIVES

(75) Inventors: Jackson Boling Hester, Jr., Galesburg, MI (US); Christina R. Harris, Troy, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 429 days.

(21) Appl. No.: 10/717,237

(22) Filed: Nov. 19, 2003

(65) Prior Publication Data

US 2004/0142939 A1 Jul. 22, 2004

Related U.S. Application Data

(60) Provisional application No. 60/445,530, filed on Feb. 6, 2003, provisional application No. 60/428,025, filed on Nov. 21, 2002.

(51) Int. Cl.
*A61K 31/535* (2006.01)
*A61K 31/497* (2006.01)
*C07D 413/10* (2006.01)
*C07D 401/10* (2006.01)
*C07D 205/04* (2006.01)

(52) U.S. Cl. ............... 514/235.8; 514/254.04; 544/121; 544/367; 544/374; 548/953

(58) Field of Classification Search ............ 514/235.8, 514/254.04; 544/121, 367, 374; 548/953
See application file for complete search history.

(56) References Cited

U.S. PATENT DOCUMENTS

| 4,705,799 | A | 11/1987 | Gregory | 514/376 |
|---|---|---|---|---|
| 5,043,443 | A | 8/1991 | Carlson et al. | 544/112 |
| 5,164,510 | A | 11/1992 | Brickner | 548/231 |
| 5,182,403 | A | 1/1993 | Brickner | 548/231 |
| 5,225,565 | A | 7/1993 | Brickner | 548/229 |
| 5,231,188 | A | 7/1993 | Brickner | 548/221 |
| 5,247,090 | A | 9/1993 | Brickner | 546/89 |
| 5,523,403 | A | 6/1996 | Barbachyn | 544/137 |
| 5,529,998 | A | 6/1996 | Habich et al. | 514/233.8 |
| 5,547,950 | A | 8/1996 | Hutchinson et al. | 514/252 |
| 5,565,571 | A | 10/1996 | Barbachyn et al. | 546/144 |
| 5,627,181 | A | 5/1997 | Riedl et al. | 514/236.8 |
| 5,652,238 | A | 7/1997 | Brickner et al. | 514/235.8 |
| 5,684,023 | A | 11/1997 | Riedl et al. | 514/337 |
| 5,688,792 | A | 11/1997 | Barbachyn et al. | 514/235.5 |
| 5,698,574 | A | 12/1997 | Riedl et al. | 514/376 |
| 5,792,765 | A | 8/1998 | Riedl et al. | 514/236.8 |
| 5,827,857 | A | 10/1998 | Riedl et al. | 514/301 |
| 5,843,967 | A | 12/1998 | Riedl et al. | 514/340 |
| 5,861,413 | A | 1/1999 | Habich et al. | 514/312 |
| 5,869,659 | A | 2/1999 | Stolle et al. | 544/114 |
| 5,952,324 | A | 9/1999 | Barbachyn et al. | 514/211 |
| 5,968,962 | A | 10/1999 | Thomas et al. | 514/376 |
| 5,981,528 | A | 11/1999 | Gravestock | 514/252 |
| 6,043,266 | A | 3/2000 | Ennis et al. | 514/376 |
| 6,051,716 | A | 4/2000 | Hutchinson et al. | 548/229 |
| 6,069,145 | A | 5/2000 | Betts | 514/252 |
| 6,069,160 | A | 5/2000 | Stolle et al. | 514/367 |
| 6,110,936 | A | 8/2000 | Gravestock | 514/315 |
| 6,166,056 | A | 12/2000 | Thomas et al. | 514/376 |
| 6,194,441 | B1 | 2/2001 | Roberts et al. | 514/340 |
| 6,239,152 | B1 | 5/2001 | Gordeev et al. | 514/340 |
| 6,271,383 | B1 | 8/2001 | Gravestock | 546/209 |
| 6,313,307 | B1 | 11/2001 | Ennis et al. | 548/229 |
| 6,362,189 | B1* | 3/2002 | Hester et al. | 514/254.01 |
| 6,642,238 | B1* | 11/2003 | Hester, Jr. | 514/254.02 |
| 2002/0086900 | A1 | 7/2002 | Perrault et al. | 514/478 |

FOREIGN PATENT DOCUMENTS

| EP | 1130016 A1 | 11/1999 |
|---|---|---|
| WO | WO 94/01110 | 1/1994 |
| WO | WO 95/07271 | 3/1995 |
| WO | WO 95/14684 | 6/1995 |
| WO | WO 95/25106 | 9/1995 |
| WO | WO 96/13502 | 5/1996 |
| WO | WO 96/15130 | 5/1996 |
| WO | WO 96/23788 | 8/1996 |
| WO | WO 96/35691 | 11/1996 |
| WO | WO 97/09328 | 3/1997 |
| WO | WO 97/10223 A1 | 3/1997 |
| WO | WO 97/10235 A1 | 3/1997 |
| WO | WO 97/19089 A1 | 5/1997 |
| WO | WO 97/21708 A1 | 6/1997 |
| WO | WO 97/30981 A1 | 8/1997 |
| WO | WO 97/30995 | 8/1997 |
| WO | WO 98/54161 | 12/1998 |
| WO | WO 99/03846 | 1/1999 |
| WO | WO 99/29688 | 6/1999 |
| WO | WO 99/37641 | 7/1999 |
| WO | WO 99/37652 | 7/1999 |
| WO | WO 99/40094 | 8/1999 |
| WO | WO 00/21960 | 4/2000 |
| WO | WO 01/40222 A1 | 6/2001 |
| WO | WO 01/40236 A2 | 6/2001 |

(Continued)

OTHER PUBLICATIONS

M. Bianchi, et al., Eur. J. Med. Chem. (1988), 23, 45-52.

(Continued)

*Primary Examiner*—Golam M. M. Shameem
*Assistant Examiner*—Ebenezer Sackey
(74) *Attorney, Agent, or Firm*—Robert N. Young; Eric J. Baude; Charles W. Ashbrook

(57) ABSTRACT

The present invention provides antibacterial agents having the formula I described herein.

40 Claims, No Drawings

FOREIGN PATENT DOCUMENTS

| | | |
|---|---|---|
| WO | WO 01/44212 A1 | 6/2001 |
| WO | WO 01/58885 | 8/2001 |
| WO | WO 01/81350 | 11/2001 |
| WO | WO 03/007870 | 1/2003 |

OTHER PUBLICATIONS

J. Org. Chem. 67(1), 24A (2002).

R. E. Notari, "Theory and Practice of Prodrug Kinetics," Methods in Enzymology, 112:309-323 (1985).

N. Bodor, "Novel Approaches in Prodrug Design," Drugs of the Future, 6(3):165-182, (1981).

H. Bundgaard, "Design of Prodrugs: Bioreversible-Derivatives for Various Functional Groups and Chemical Entities," in Design of Prodrugs (H. Bundgaard, ed.), Elsevier, N.Y. (1985).

* cited by examiner

N-ARYL-2-OXAZOLIDINONE-5-CARBOXAMIDES AND THEIR DERIVATIVES

CROSS REFERENCE TO RELATED APPLICATIONS

This application claims the benefit of U.S. Provisional Application Ser. No., 60/428,025, filed, Nov. 21, 2002, and U.S. Provisional Application Ser. No., 60/445,530, filed, Feb. 6, 2003, both of which are incorporated herein by reference in their entireties.

FIELD OF INVENTION

The present invention relates to novel N-Aryl-2-oxazolidinone-5-carboxamides, derivatives thereof, and their preparations. These compounds have potent antibacterial activity.

BACKGROUND OF THE INVENTION

The oxazolidinone antibacterial agents are a novel synthetic class of antimicrobials with potent activity against a number of human and veterinary pathogens, including Gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*.

SUMMARY OF THE INVENTION

In one aspect, the invention features compounds of Formula I.

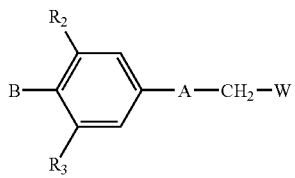

I or pharmaceutically acceptable salts thereof wherein:
A is a structure i, ii, iii, or iv;

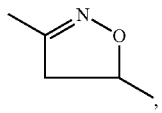

i

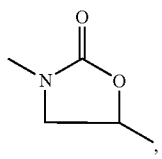

ii

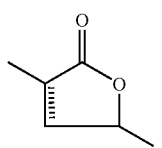

iii

B is

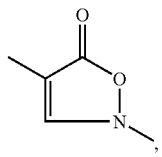

iv

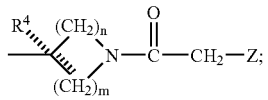

(a)

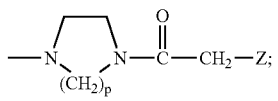

(b)

W is —N(H)C(X)—$R_1$, Het, or —Y-HET, in which the Het or —Y-HET is optionally substituted with =S or =O, provided that when A is structure iv, W is not —Y-HET or Het;

X is O or S;
Y is NH, O, or S;

Z is

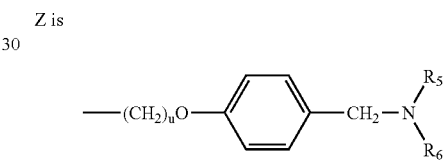

(a)

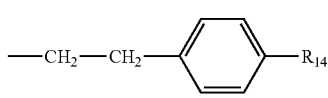

(b)

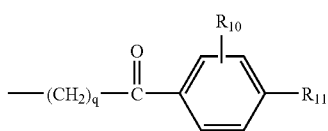

(c)

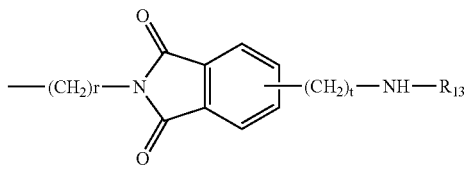

(d)

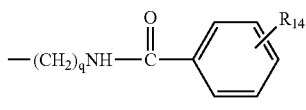

(e)

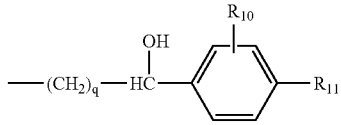

(f)

$R_1$ is a) H,
b) $NH_2$,
c) $NHC_{1-4}$alkyl,
d) $C_{1-4}$ alkyl,
e) $C_{2-4}$ alkenyl, f) O—C$_{1-4}$ alkyl,
g) S—C$_{1-4}$alkyl, or
h) (CH$_2$)$_s$ C$_{3-6}$ cycloalkyl, in which each occurrence of alkyl or cycloalkyl in R$_1$ is optionally substituted by one, two or three halogens (F or Cl);

Each R$_2$ and R$_3$ is independently hydrogen, halogen (F or Cl), methyl or ethyl;

R$_4$ is H, CH$_3$ or F;
R$_5$ is H or C$_{1-4}$ alkyl;
R$_6$ is H, C$_{1-4}$ alkyl, or

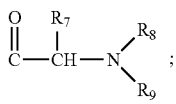

or R$_5$ and R$_6$ together form an optionally substituted saturated heterocycle;

R$_7$ is H, or C$_{1-4}$ alkyl which can be optionally substituted by —OH, —NH$_2$, —NH—C(=NH)—NH$_2$, —SH, —SCH$_3$, —COOH, —C(O)NH$_2$, phenyl which can be optionally substituted with —OH;

R$_8$ is H or CH$_3$;
R$_9$ is H, CH$_3$, —C(O)—CH(R$_7$)—NR$_8$R$_8$,

R$_{10}$ or R$_{11}$ is halo, C$_{1-4}$alkyl, CF$_3$, —CN, —NO$_2$, —OH, —O—C$_{1-4}$alkyl, —NH—S(O)$_w$C$_{1-4}$alkyl;

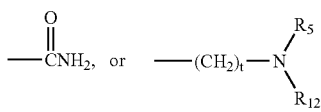

R$_{12}$ is H, C$_{1-4}$alkyl, —S(O)$_2$—C$_{1-4}$alkyl,

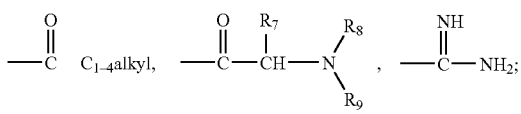

or R$_5$ and R$_{12}$ together form a saturated heterocycle;
R$_{13}$ is H, or

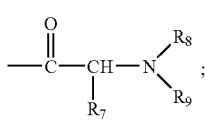

R$_{14}$ is —(CH$_2$)$_r$NHR$_{13}$, —OH, —OC$_{1-4}$alkyl;
m is 0, 1, 2, 3, 4;
n is 0, 1, 2, 3, 4 with the proviso that m plus n is 2, 3, 4, or 5;
p is 2, 3;

q is 1, 2;
r, s and t are independently 0, 1;
u and w are independently 0, 1, 2; and
provided that W is not Het or —Y-HET when Z is a, b, or d, and further provided that Z is not b when A is formula iii.

Embodiments of the invention may have one or more of the following. R$_{10}$ is CF$_3$. R$_{11}$ is CF$_3$. Heterocycle is piperidino, pyrrolidino, morpholino, thiomorpholino, or 4-methyl-1-piperazinyl. Het is a triazole or a tetrazole. B is

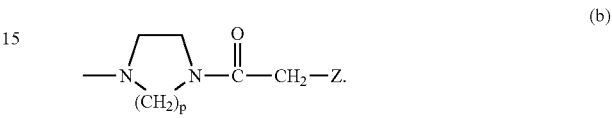

p is 2. B is

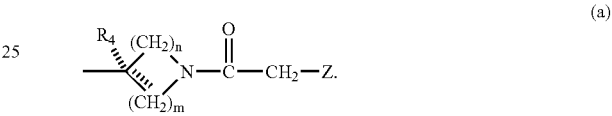

n and m are both 2. n and m are both 1. R$_4$ is —CH$_3$. Z is (a). R$_5$ and R$_6$ are C$_{1-4}$ alkyl. R$_5$ and R$_6$ together form an optionally substituted saturated heterocycle. R$_5$ and R$_6$ form an optionally substituted morpholinyl and piperazinyl. R$_5$ and R$_6$ form a morpholinyl and piperazinyl each of which are substituted with C$_{1-4}$ alkyl. u=0. Z is (c). R$_{10}$ is H. R$_{11}$ is —C(O)—NH$_2$, —NHS(O)$_u$C$_{1-4}$alkyl, or —(CH$_2$)$_t$—NR$_5$R$_{12}$. R$_{11}$ is —CH$_2$N(C$_{1-4}$alkyl)$_2$, —CH$_2$-saturated heterocycle, —CH$_2$—NH—C$_{1-4}$alkyl, —CH$_2$—N(C1-4alkyl)-C(O)—CHR$_7$—NR$_8$R$_9$, —CH$_2$—NH—C(O)—C$_{1-4}$alkyl, —CH$_2$—NH—SO$_2$—(C1-4alkyl), —CH$_2$—NH$_2$, or —NH—C(O)—CHR$_7$—NR$_8$R$_9$. R$_{10}$ is ortho to R$_{11}$. q is 1. Z is (b). R$_{14}$ is —OC$_{1-4}$ alkyl, —OH, or —NH—C(O)—CH(R$_7$)—NR$_8$R$_9$.

In another aspect, the invention features a method for the treatment of microbial infections in mammals by administering an effective amount of compound of formula I to a mammal. The compound may be administered to the mammal orally, parenterally, transdermally, or topically. The compound may be part of a pharmaceutical composition. The compound may be administered in an amount of from about 0.1 to about 100 mg/kg of body weight/day, e.g., from about 1 to about 50 mg/kg of body weight/day.

In another aspect, the invention features a pharmaceutical composition including a compound of claim 1 and a pharmaceutically acceptable carrier.

Specific compounds of the invention include:
N-[((5S)-3-{4-[4-({4-[(Diethylamino)methyl] phenoxy}acetyl)piperazin-1-yl]-3-fluorophenyl}-2-oxo-1,3-oxazolidin-5-yl)methyl]propanethioamide.
N-[((5S)-3-{4-[4-({4-[(Diethylamino)methyl] phenoxy}acetyl)piperazin-1-yl]-3-fluorophenyl}-2-oxo-1,3-oxazolidin-5-yl)methyl]cyclopropanecarbothioamide.
N-[((5S)-3-{4-[4-({4-[(Diethylamino)methyl] phenoxy}acetyl)piperazin-1-yl]-3fluorophenyl}-2-oxo-1, 3-oxazolidin-5-yl)methyl]acetamide.

N-[((5S)-3{4-[4-({4-[(Dimethylamino)methyl]
phenoxy}acetyl)piperazin-1-yl]-3-fluorophenyl}-2-oxo-
1,3-oxazolidin-5-yl)methyl]propanethioamide.

N-[((5S)-3-{4-[4-({4-[(Dimethylamino)methyl]
phenoxy}acetyl)piperazin-1-yl]-3-fluorophenyl}-2-oxo-
1,3-oxazolidin-5-yl)methyl]cyclopropanecarbothioam-
ide.

N-[((5S)-3-{4-[4-({4-[(Dimethylamino)methyl]
phenoxy}acetyl)piperazin-1-yl]-3-fluorophenyl}-2-oxo-
1,3-oxazolidin-5-yl)methyl]acetamide.

N-({(5S)-3-[3-Fluoro-4-(4-{[4-(morpholin-4-ylmethyl)phe-
noxy]acetyl}piperazin-1-yl)phenyl]-2-oxo-1,3-oxazoli-
din-5-yl}methyl)propanethioamide.

N-({(5S)-3-[3-Fluoro-4-(4-{[4-(morpholin-4-ylmethyl)phe-
noxy]acetyl}piperazin-1-yl)phenyl]-2-oxo-1,3-oxazoli-
din-5-yl}methyl)cyclopropanecarbothioamide.

N-({(5S)-3-[3-Fluoro-4-(4-{[4-(morpholin-4-ylmethyl)phe-
noxy]acetyl}piperazin-1-yl)phenyl]-2-oxo-1,3-oxazoli-
din-5-yl}methyl)acetamide.

N-[((5S)-3-{3-Fluoro-4-[4-({4-[(4-methylpiperazin-1-yl)
methyl]phenoxy}acetyl)piperazin-1-yl]phenyl}-2-oxo-1,
3-oxazolidin-5-yl)methyl]propanethioamide.

N-[((5S)-3-{3-Fluoro-4-[4-({4-[(4-methylpiperazin-1-yl)
methyl]phenoxy}acetyl)piperazin-1-yl]phenyl}-2-oxo-1,
3-oxazolidin-5-yl)methyl]cyclopropanecarbothioamide
(38)

N-[((5S)-3-{3-Fluoro-4-[4-({4-[(4-methylpiperazin-1-yl)
methyl]phenoxy}acetyl)piperazin-1-yl]phenyl}-2-oxo-1,
3-oxazolidin-5-yl)methyl]acetamide.

N-[((5S)-3-{4-[4-(4-{4-[(Dimethylamino)methyl]phenyl}-
4-oxobutanoyl)-1-piperazinyl]-3-fluorophenyl}-2-oxo-1,
3-oxazolidin-5-yl)methyl]propanethioamide.

N-[((5S)-3-{4-[4-(4-{4-[(Dimethylamino)methyl]phenyl}-
4-oxobutanoyl)-1-piperazinyl]-3-fluorophenyl}-2-oxo-1,
3-oxazolidin-5-yl)methyl]cyclopropanecarbothioamide.

N-[((5S)-3-{4-[4-(4-{4-[(Dimethylamino)methyl]phenyl}-
4-oxobutanoyl)-1-piperazinyl]-3-fluorophenyl}-2-oxo-1,
3-oxazolidin-5-yl)methyl]acetamide.

N-({(5S)-3-[3-Fluoro-4-(4-{4-[4-(4-morpholinylmethyl)
phenyl]-4-oxobutanoyl}-1-piperazinyl)phenyl]-2-oxo-1,
3-oxazolidin-5-yl}methyl)propanethioamide.

N-({(5S)-3-[3-Fluoro-4-(4-{4-[4-(4-morpholinylmethyl)
phenyl]-4-oxobutanoyl}-1-piperazinyl)phenyl]-2-oxo-1,
3-oxazolidin-5-yl}methyl)acetamide.

N-({(5S)-3-[3-Fluoro-4-(4-{4-[4-(4-morpholinylmethyl)
phenyl]-4-oxobutanoyl}-1-piperazinyl)phenyl]-2-oxo-1,
3-oxazolidin-5-yl}methyl)cyclopropanecarbothioamide.

N-[((5S)-3-{3-Fluoro-4-[4-(4-{4-[(methylamino)methyl]
phenyl}-4-oxobutanoyl)piperazin-1-yl]phenyl}-2-oxo-1,
3-oxazolidin-5-yl)methyl]acetamide.

$N^1$-(4-{4-[4-(4-{(5S)-5-[(Acetylamino)methyl]-2-oxo-1,3-
oxazolidin-3-yl}-2-fluorophenyl)-piperazin-1-yl]-4-
oxobutanoyl}benzyl-$N^1$-methylglycinamide.

$N^1$-(4-{4-[4-(4-{(5S)-5-[(Acetylamino)methyl]-2-oxo-1,3-
oxazolidin-3-yl}-2-fluorophenyl)piperazin-1-yl]-4-
oxobutanoyl}benzyl)-$N^1,N^2,N^2$-trimethylglycinamide.

$N^1$-(4-{4-[4-(4-{(5S)-5-[(Acetylamino)methyl]-2-oxo-1,3-
oxazolidin-3-yl}-2-fluorophenyl)piperazin-1-yl]-4-
oxobutanoyl}benzyl)-$N^2,N^2$-dimethylglycinamide.

$N^1$-(4-{4-[4-[2-Fluoro-4-{(5S)-2-oxo-5-[(propanethioly-
lamino)methyl]-1,3-oxazolidin-3-yl}phenyl]piperazin-1-
yl]-4-oxobutanoyl}benzyl)-$N^2,N^2$-dimethylglycinamide.

(S)-$N^1$-(4-{4-[4-(2-Fluoro-4-{(5S)-2-oxo-5-[(propanethioy-
lamino)methyl]-1,3-oxazolidin-3-yl}phenyl)piperazin-1-
yl]-4-oxobutanoyl}benzyl)alaninamide.

(S)-$N^1$-(4-{4-[4-(4-{(5S)-5-[(Acetylamino)methyl]-2-oxo-
1,3-oxazolidin-3yl}-2-fluorophenyl)piperazin-1-yl]-2-
oxobutanoyl}benzyl)alaninamide.

$N^1$-(4-{4-[4-(2-Fluoro-4-{(5S)-2-oxo-5-[(propanethioy-
lamino)methyl]-1,3-oxazolidin-3-yl}phenyl)piperazin-1-
yl]-4-oxobutanoyl}benzyl)glycinamide.

(S)-Alanyl-(S)-$N^1$-(4-{4-[4-(2-fluoro-4-{(5S)-2-oxo-5-
[(propanethioylamino)methyl]-1,3-oxazolidin-3-
yl}phenyl)piperazin-1-yl]-4-oxobutanoyl}benzyl)alani-
namide.

(S)-Alanyl-(S)-$N^1$-(4-{4-[4-(4-{(5S)-5-[(acetylamino)me-
thyl]-2-oxo-1,3-oxazolidin-3-yl }-2-fluorophenyl)piper-
azin-1-yl]-4-oxobutanoyl}benzyl)alaninamide.

N-(4-{4-[4-(4-{(5S)-5-[(Acetylamino)methyl]-2-oxo-1,3-
oxazolidin-3-yl}-2-fluorophenyl)-1-piperazinyl]-4-
oxobutanoyl}benzyl)acetamide.

N-(4-{4-[4-(2-Fluoro-4-{(5S)-2-oxo-5-[(propanethioy-
lamino)methyl]-1,3-oxazolidin-3-yl}phenyl)-1-piperazi-
nyl]-4-oxobutanoyl}benzyl)acetamide.

N-{[(5S)-3-(3-Fluoro-4-{4-[4-(4-{[(methylsulfonyl)amino]
methyl}phenyl)-4-oxobutanoyl]-1-piperazinyl}phenyl)-
2-oxo-1,3-oxazolidin-5-yl]methyl}acetamide.

N-{[(5S)-3-(3-Fluoro-4-{4-[4-(4-{[(methylsulfonyl)amino]
methyl}phenyl)-4-oxobutanoyl]-1-piperazinyl}phenyl)-
2-oxo-1,3-oxazolidin-5-yl]methyl}propanethioamide.

N-({(5S)-3-[4-(4-{4-[4-(Aminomethyl)phenyl]-4-oxobu-
tanoyl}-1-piperazinyl)-3-fluorophenyl]-2-oxo-1,3-oxazo-
lidin-5-yl}methyl)propanethioamide.

N-({(5S)-3-[4-(4-{4-[4-(Aminomethyl)phenyl]-4-oxobu-
tanoyl}-1-piperazinyl)-3-fluorophenyl]-2-oxo-1,3-oxazo-
lidin-5-yl}methyl)acetamide.

$N^1$-(4-{4-[4-(4-{(5S)-5-[(Acetylamino)methyl]-2-oxo-1,3-
oxazolidin-3-yl}-2-fluorophenyl)piperazin-1-yl]-4-
oxobutanoyl}benzyl)glycinamide.

2-[3-methyl-3-(4-{(5S)-2-oxo-5-[(propionylamino)methyl]-
1,3-oxazolidin-3-yl}phenyl)azetidin-1-yl]-2-oxoethyl
4-(aminomethyl)benzamide.

N-{[(5S)-3-(4-{1-[4-(4-aminophenyl)-4-oxobutanoyl]-3-
methylazetidin-3-yl}phenyl)-2-oxo-1,3-oxazolidin-5-yl]
methyl}propanamide.

N-({(5S)-3-[4-(1-{4-[4-(glycylamino)phenyl]-4-oxobu-
tanoyl}-3-methylazetidin-3-yl)phenyl]-2-oxo-1,3-oxazo-
lidin-5-yl}methyl)propanamide.

N-{[(5S)-3-(4-{1-[4-(4-aminophenyl)-4-oxobutanoyl]-3-
methylazetidin-3-yl}-3-fluorophenyl)-2-oxo-1,3-oxazoli-
din-5-yl]methyl}acetamide.

$N{\sim}1{\sim}$-(4-{4-[3-(4-{(5S)-5-[(acetylamino)methyl]-2-oxo-1,
3-oxazolidin-3-yl}-2-fluorophenyl)-3-methylazetidin-1-
yl]-4-oxobutanoyl}phenyl)glycinamide.

2-[3-(4-{(5S)-5-[(acetylamino)methyl]-2-oxo-1,3-oxazoli-
din-3-yl}-2-fluorophenyl)-3-methylazetidin-1-yl]-2-oxo-
ethyl-4-(aminomethyl)benzamide.

N-{[(5S)-3-(3-Fluoro-4-{4-[4-(4-methoxyphenyl)butanoyl]
piperazine-1-yl}phenyl)2-oxo-1,3-oxazolidin-5-yl]
methyl}acetamide.

N-{[(5S)-3-(3-Fluoro-4-{4-[4-(4-hydroxyphenyl)butanoyl]
piperazin-1-yl}phenyl)-2-oxo-1,3-oxazolidin-5-yl]
methyl}acetamide.

2,2-Difluoro-N-{[(5S)-3-(3-fluoro-4-{4-[4-(4-methoxyphe-
nyl)butanoyl]piperazin-1-yl}phenyl)-2-oxo-1,3-oxazoli-
din-5-yl]methyl}ethanethioamide.

N-{[(5S)-3-(4-{4-[4-(4-Bromophenyl)-4-oxobutanoyl]-1-
piperazinyl}-3-fluorophenyl)-2-oxo-1,3-oxazolidin-5-yl]
methyl}acetamide.

N-{[(5S)-3-(4-{4-[4-(4-Bromophenyl)-4-oxobutanoyl]-1-
piperazinyl}-3-fluorophenyl)-2-oxo-1,3-oxazolidin-5-yl]
methyl}ethanethioamide.

N-{[(5S)-3-(4-{4-[4-(4-Cyanophenyl)-4-oxobutanoyl]-1-piperazinyl}-3-fluorophenyl-2-oxo-1,3-oxazolidin-5-yl]methyl}acetamide.

4-{4-[4-(4-{(5S)-5-[(Acetylamino)methyl]-2-oxo-1,3-oxazolidin-3-yl}-2-fluorophenyl)-1-piperazinyl]-4-oxobutanoyl}benzamide.

4-{4-[4-(4-{(5S)-5-[(Ethanethiolylamino)methyl]-2-oxo-1,3-oxazolidin-3-yl}-2-fluorophenyl)-1-piperazinyl]-4-oxobutanoyl}benzamide.

N-{[(5S)-3-(4-{4-[4-(4-Chlorophenyl)-4-oxobutanoyl]-1-piperazinyl}-3-fluorophenyl)-2-oxo-1,3-oxazolidin-5-yl]methyl}acetamide.

N-{[(5S)-3-(4-{4-[4-(4-chlorophenyl)-4-oxobutanoyl]-1-piperazinyl}-3-fluorophenyl)-2-oxo-1,3-oxazolidin-5-yl]methyl}ethanethioamide.

N-[((5S)-3-{3-Fluoro-4-[4-(4-{4-[(methylsulfonyl)amino]phenyl}-4-oxobutanoyl)-1-piperazinyl]phenyl}-2-oxo-1,3-oxazolidin-5-yl)methyl]propanethioamide.

N-[((5S)-3-{3-Fluoro-4-[4-(4-{4-[(methylsulfonyl)amino]phenyl}-4-oxobutanoyl-1-piperazinyl]phenyl}-2-oxo-1,3-oxazolidin-5-yl)methyl]acetamide. N-(4-{4-[4-(2-Fluoro-4-{(5S)-2-oxo-5-[(propanethiolylamino)methyl]-1,3-oxazolidin-3-yl}phenyl)-1-piperazinyl]-4-oxobutanoyl}phenyl)acetamide.

2-Amino-N-(4-{4-[4-(2-fluoro-4-{(5S)-2-oxo-5-[(propanethiolylamino)methyl]1,3-oxazolidin-3-yl}phenyl)-1-piperazinyl]-4-oxobutanoyl}phenyl)acetamide.

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}phenyl)-2-aminoacetamide.

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}phenyl)-(2S)-2-aminopropanamide.

N-1-(4-{4-[4-(4-{(5S)-5-[(Ethanethiolylamino)methyl]-2-oxo-1,3-oxazolidin-3-yl}-2-fluorophenyl)piperazin-1-yl]-4-oxobutanoyl}phenyl)-(S)-alaninamide.

$N^1$-[4-(5-{4-[4-((5S)-5-{[(2,2-Difluoroethanethioyl)amino]methyl}-2-oxo-1,3-oxazolidin-3-yl)-2-fluorophenyl]piperazin-1-yl}-5-oxopentanoyl)phenyl]glycinamide.

$N^1$-(4-{5-[4-(4-{(5S)-5-[(Acetylamino)methyl]-2-oxo-1,3-oxazolidin-3-yl}-2-fluorophenyl)piperazin-1-yl]-5-oxopentanoyl}phenyl)glycinamide.

N-(4-{4-[4-(4-{(5S)-5-[(Acetylamino)methyl]-2-oxo-1,3-oxazolidin-3-yl}-2-fluorophenyl)-1-piperazinyl]-4-oxobutyl}phenyl)-2-aminoacetamide.

2-Amino-N-(4-{4-[4-(2-fluoro-4-{(5S)-2-oxo-5-[(propanethiolylamino)methyl]-1,3-oxazolidin-3-yl}phenyl)-1-piperazinyl]-4-oxobutyl}phenyl)acetamide.

(S)-2-Amino-N-(4-{4-[4-(2-fluoro-4-{(5S)-2-oxo-5-[(propanethiolylamino)methyl]-1,3-oxazolidin-3-yl}phenyl)-1-piperazinyl]-4-oxobutyl}phenyl)propanamide.

N-(4-{4-[4-(4-{(5S)-5-[(Acetylamino)methyl]-2-oxo-1,3-oxazolidin-3-yl}-2-fluorophenyl)piperazin-1-yl]-4-oxobutyl}phenyl)-2-(dimethylamino)acetamide.

N-(4-{4-[4-(4-{(5S)-5-[(Ethanethiolylamino)methyl]-2-oxo-1,3-oxazolidin-3-yl}-2-fluorophenyl)piperazin-1-yl]-4-oxobutyl}phenyl)-2-(dimethylamino)acetamide $N^1$-(3-{4-[4-(4-{(5S)-5-[(Acetylamino)methyl]-2-oxo-1,3-oxazolidin-3-yl}-2-fluorophenyl)piperazin-1-yl]-1-hydroxy-4-oxobutyl}phenyl)glycinamide.

$N^1$-[3-(4-{4-[4-((5S)-5-{[(2,2-Difluoroethanethiolyl)amino]methyl}-2-oxo-1,3-oxazolidin-3-yl)-2-fluorophenyl]piperazin-1-yl}-4-oxobutanoyl)phenyl]glycinamide.

N-{[(5S)-3-(3-Fluoro-4-{4-[4-(3-nitrophenyl)-4-oxobutanoyl]piperazin-1yl}phenyl)-2-oxo-1,3-oxazolidin-5-yl]methyl}actamide.

$N^1$-(3-{4-[4-(4-{(5S)-5-[(Acetylamino)methyl]-2-oxo-1,3-oxazolidin-3-yl}-2-fluorophenyl)piperazin-1-yl]-4-oxobutanoyl}phenyl)glycinamide.

N-{[(5S)-3-(4-{4-[4-(2-Aminophenyl)-4-oxobutanoyl]piperazin-1-yl}-3-fluorophenyl)-2-oxo-1,3-oxazolidin-5-yl]methyl}acetamide.

N-{[(5S)-3-(4-{4-[(5-Amino-1,3-dioxo-1,3-dihydro-2H-isoindol-2-yl)acetyl]piperazin-1-yl}-3-fluorophenyl)-2-oxo-1,3-oxazolidin-5-yl]methyl}acetamide.

$N^1$-(2-{2-[4-(4-{(5S)-5-[(Acetylamino)methyl]-2-oxo-1,3-oxazolidin-3-yl{-2-fluorophenyl)piperazin-1-yl]-2-oxoethyl}-1,3-dioxo-2,3-dihydro-1H-isoindol-5-yl)glycinamide.

$N^1$-[2-(3-{4-[4-((5S)-5-{[(2,2-Difluoroethanethiolyl)amino]methyl}-2-oxo-1,3-oxazolidin-3-yl)-2-fluorophenyl]piperazin-1-yl}-3-oxopropyl)-1,3-dioxo-2,3-dihydro-1H-isoindol-5-yl)glycinamide.

Compounds of Formula I have antibacterial activity against a number of human and veterinary pathogens including Gram-positive aerobic bacteria such as multiply-resistant-staphylococci, streptococci and enterococci, Gram-negative organisms such as *H. influenzae* and *M. catarrhalis,* anaerobic organisms such as Bacteroides spp. and *clostridia* spp., *Mycobacterium tuberculosis, M. avium* and *M.* spp. and in organisms such as *Mycoplasma* spp. For use as antibacterial agents the compounds of this invention can be administered orally or parenterally in a dosage range of about 0.1–100 mg/kg or preferably of about 1.0–50 mg/kg of body weight per day. Advantageously, the compound of the invention exhibit antibacterial activity against *S. aureus* resistant organisms.

DETAILED DESCRIPTION OF THE INVENTION

The following definitions are used, unless otherwise described.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "halo" refers to a halogen atom selected from Cl, Br, I, and F.

The term "alkyl" refers to both straight- and branched-chain moieties. Unless otherwise specifically stated alkyl moieties include between 1 and 6 carbon atoms.

The term "alkenyl" refers to both straight- and branched-chain moieties containing at least one —C=C—. Unless otherwise specifically stated alkenyl moieties include between 1 and 6 carbon atoms.

The term "alkoxy" refers to —O-alkyl groups.

The term "cycloalkyl" refers to a cyclic alkyl moiety. Unless otherwise specifically stated cycloalkyl moieties will include between 3 and 7 carbon atoms.

The term "amino" refers to —$NH_2$.

The term "aryl" refers to phenyl and naphthyl.

The term "het" refers to mono- or bicyclic ring systems containing at least one heteroatom selected from O, S, and N. Each monocyclic ring may be aromatic, saturated, or partially unsaturated. A bicyclic ring system may include a monocyclic ring containing at least one heteroatom fused with a cycloalkyl or aryl group. A bicyclic ring system may also include a monocyclic ring containing at least one heteroatom fused with another het, monocyclic ring system.

Examples of "het" include, but are not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo[2.2.1]heptyl.

The term "heterocycle" refers to a fully saturated het, examples of which include, but are not limited to, morpholinyl, thiomorpholinyl, and tertrahydropyranyl.

Specific $R_3$ and $R_4$ substituents include H, F, Cl, Br, CN, $NH_2$, $NO_2$, $CH_3$.

Specific structures of A include

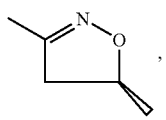
i

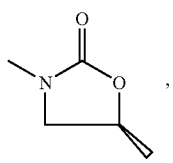
ii

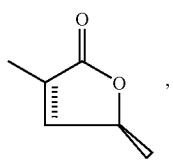
iii

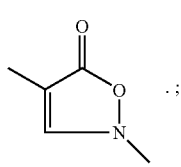
iv

Mammal refers to human or animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature) as described in J.Org.Chem., 67–1, 24A, 2002.

Other abbreviations and definitions used are defined as follows:
Hunig's base means diisopropylethyl amine;
HATU means O-(7-Azabenzotriazol-1-yl)-N,N,N',N'-tetramethyluronium hexaflourophosphate;
in vacuo means at reduced pressure;
EDCI or EDC means 1-ethyl-3-(3-dimethylaminopropyl) carbodimide;
HOBT means hydroxybenztriazole;
Fmoc means 9-fluorenylmethoxycarbonyl;
trisamine resin means tris(2-aminoethyl)amine, polymer-bound.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

The compounds of Formula I of this invention contain a chiral center, such as at C-5 of the isoxazoline ring, and as such there exist two enantiomers or a racemic mixture of both. This invention relates to both the enantiomers, as well as mixtures containing both the isomers. In addition, depending on substituents, additional chiral centers and other isomeric forms may be present in any of A, B, Z or $R_1$ group, and this invention embraces all possible stereoisomers and geometric forms in these groups.

The compounds of this invention are useful for treatment of microbial infections in humans and other warm blooded animals, under both parenteral and oral administration.

The pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 1.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 four times per day.

The compounds according to this invention may be administered parenterally, i.e., by injection, for example, by intravenous injection or by other parenteral routes of administration. Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds according to this invention are advantageously administered orally in solid and liquid dosage forms.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA.

Compounds in this invention can be prepared as shown in Schemes I to IV. In Scheme I an amine (1) is condensed with a suitably substituted carboxylic acid (HOOC—CH₂Z') to give an amide (2) where Z' represents Z of formula I or a group that can be transformed to Z by subsequent chemistry and where W' represents W of formula I plus NP where P is a suitable nitrogen protecting group that can be removed at an appropriate time in a manner that is compatible with other substituents on the molecule to give the primary amine (W'=NH₂) which can then be used to prepare compounds where W is NHC(X)R₁ (see the preparation of 7 in Scheme II). A variety of reagents and reaction condensations can be used for the condensations of 1 with the carboxylic acids (HOO—CH₂Z'). These include but are not limited to the carbodiimides such as dicyclohexylcarbodiimide (DCC) and 1-(3-dimethylaminopropyl)-3-ethylcarbodiimide hydrochloride (EDC) which can be used with promoters such as 4-(dimethylamino)pyridine (DMAP) or 1-hydroxybenzotriazole (HOBT) in solvents such as DMF or pyridine at 0° C. to 50° C.; and the chloroformates such as isobutyl chloroformate with a tertiary amine such as triethylamine or diisopropylethylamine in solvents such as THF at 0° C. to 25° C.

Scheme II illustrates the preparation of compounds of formula I where Z is (a).

In this scheme, 3 (compound 2 of Scheme I where B" is (b), Z' is

and W' is NHBoc) is allowed to react with triphenylphosphine and carbon tetrabromide in a solvent such as CH₂Cl₂ at 20° C. to 40° C. to give the bromide (4). Alkylation of primary and secondary amines with 4 can be conveniently carried out in solvents such as MeOH, EtOH and/or acetone at 0° C. to 30° C. Sodium iodide can be used as a catalyst for this reaction. Removal of the tert-butyoxycarbonyl (Boc) protecting group of 5 (R' and R"=alkyl) to give 6 can be accomplished with an acid catalyst, conveniently 4N HCl in dioxane at 0° C. to 30° C. Acylation of 6 with an activated carboxylic acid derivative such as acetic anhydride in pyridine or propionyl chloride and triethylamine in CH₂Cl₂ will give the corresponding amides (7, X=O). Thioacylation of 6 to give 7 (X=S) can be accomplished by the reactions of 6 with dithioesters and triethylamine in methanol; difluorothioacetamides are conveniently prepared by the reactions of 6 with an ester of difluorothioacetic acid, such as O-(3, 3-diphenylpropyl)difluoroethanethioate, in a solvent such as CH₂Cl₂ and/or MeOH. A tertiary amine can be used to neutralize a salt of 6 in this reaction. Compounds of formula 7 where R' or R" is hydrogen can best be obtained by protecting the secondary amine (5) in this sequence with an acid stable protecting group. The 9-fluorenylmethyl carbamate (Fmoc) is suitable for this purpose. It can be removed from compound 7 by the reaction with a mild base such as piperidine. Compounds of formula 7 where both R' and R" are hydrogen can be obtained by allowing compound 4 to react with sodium azide in DMF. The resulting azide can then be reduced to the amine (5 where R' and R" are hydrogen) by hydrogenation with a platinum or palladium catalyst. Fmoc protection of this amine, conversion to the Fmoc protected analogs of 6 and 7 and subsequent deprotection will give the desired compounds of formula 7 (R'=R"=H). Acylation of 5 (where R' and/or R" is hydrogen) with Fmoc protected amino acids or dipeptides using for example, conditions described for the preparation of 2 in Scheme I, conversion to the Fmoc protected analogs of 6 and 7 and deprotection will give 7 where R' or R" is C(O)CH(R$_7$)NR$_8$R$_9$.

Scheme III and IV illustrate the preparation of compounds of formula I where Z is (b), (c) or (d). For this type of compound it is often convenient to begin with a preformed side chain. Thus, for example, bromination of 8 with N-bromosuccinimide and light in chloroform gives 9 which is allowed to react with primary or secondary amines (HNR'R") in acetone to give 10. At this stage secondary amines (R' or R"=H) can be acylated with activated carboxylic acid or sulfonic acid derivatives or protected with, for example, Boc, Fmoc or benzyloxycarbonyl (Cbz) groups. The ester is then hydrolyzed with an alkali metal hydroxide. It is convenient to use lithium hydroxide in mixtures of MeOH and water at ambient temperature for this reaction and the resulting salt (11) or the corresponding acid can be condensed with 1 as described in Scheme I to obtain 12. Primary amines (12, R'=R"=H) are obtained by allowing 9 to react with sodium azide in DMF. Hydrolysis of the resulting azido ester to the corresponding acid and condensation with 1 gives 13. Reduction of the azide (13) by hydrogenation with a palladium catalyst or other method known in the art will then give 12 (R'=R"=H) which can be converted to other desired compounds of formula I.

By using the chemistry described in Scheme III and employing other side chains known in the literature or described in the examples other compounds of formula I where Z is (b), (c), or (d) can be prepared. This is further illustrated in Scheme IV where the nitro substituted phthalimide (14), prepared as described in Scheme I, can be reduced by transfer hydrogenation with cyclohexene and a palladium catalyst in refluxing ethanol to give 15. Condensation of 15 with a protected amino acid will then give 16 which can be converted to compounds of formula I as described in Schemes II and III.

Scheme I

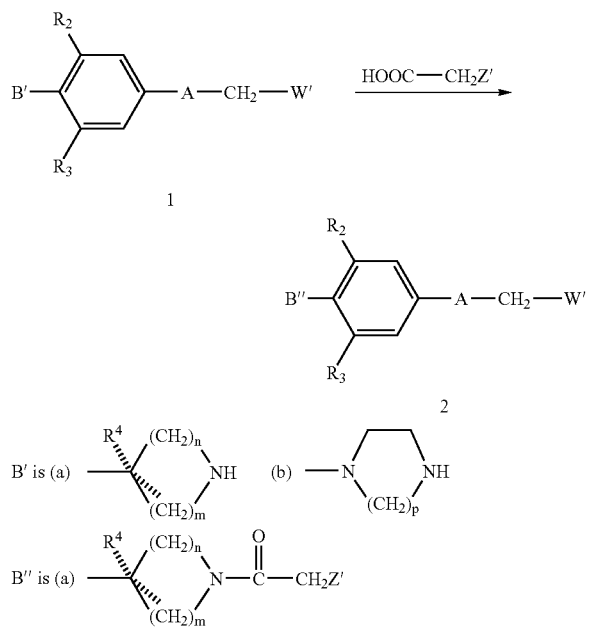

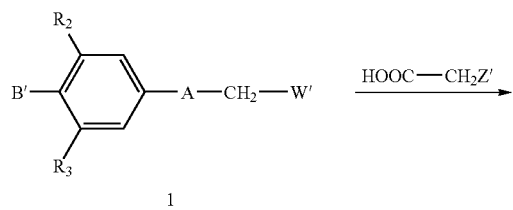

-continued

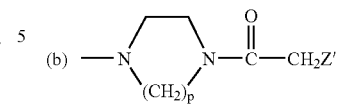

Scheme II

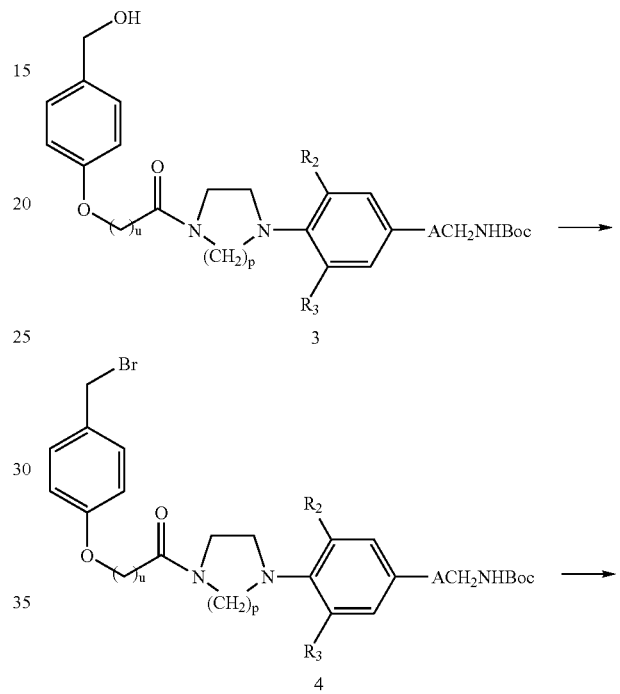

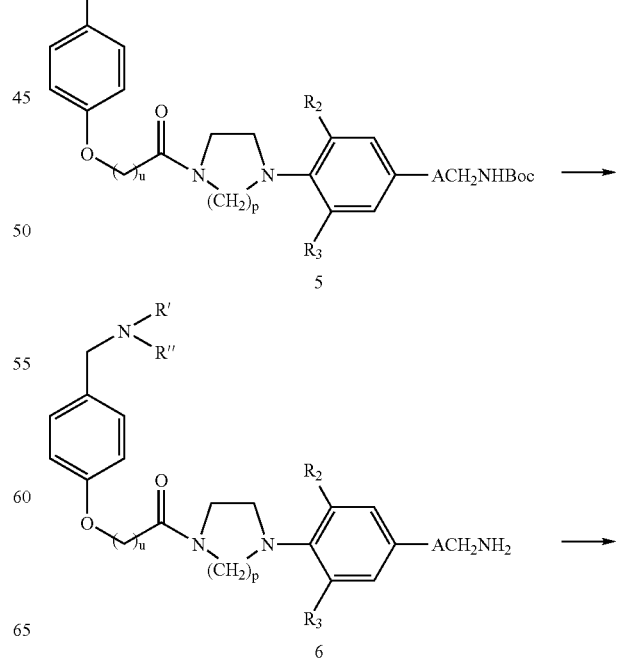

-continued
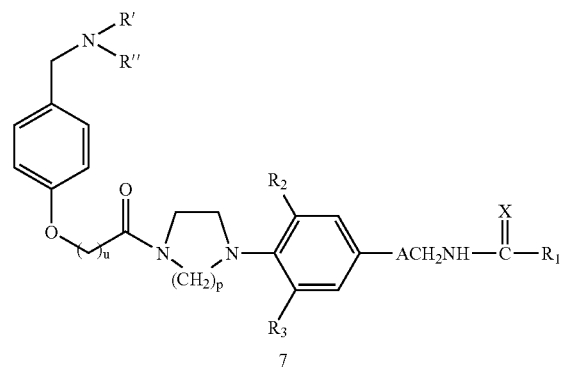
7
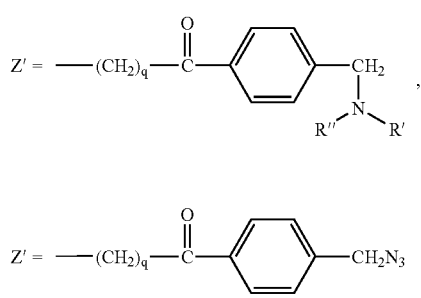
12
13
Scheme III
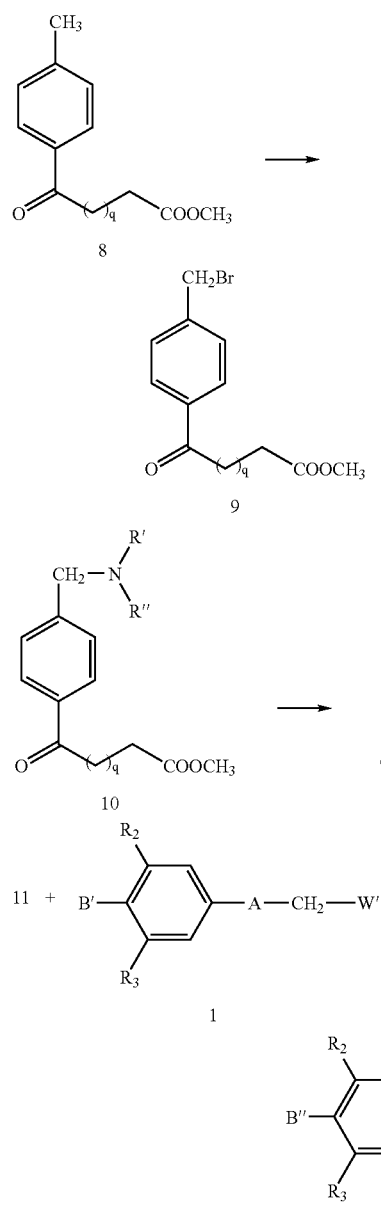
Scheme IV
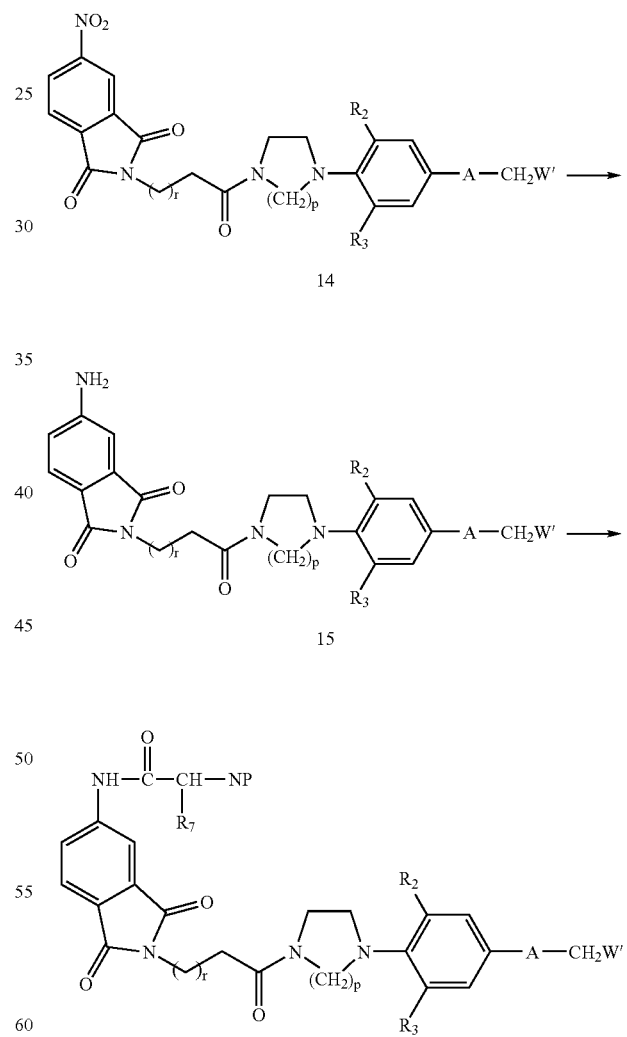
Suitable intermediates useful in preparating compounds of formula I and additional synthetic methods to assist in producing compounds of formula I may be found, for example, in the following publications each of which is hereby incorporated by reference.

U.S. Pat. Nos. 5,225,565; 5,182,403; 5,164,510; 5,247,090; 5,231,188; 5,565,571; 5,547,950; 5,529,998; 5,627,181; 5,843,967; 5,861,413; 5,827,857; 5,869,659; 5,952,324; 5,968,962; 5,688,792; 6,069,160; 6,239,152; 5,792,765; 4,705,799; 5,043,443; 5,652,238; 5,827,857; 5,529,998; 5,684,023; 5,627,181; 5,698,574; 6,166,056; 6,194,441; 6,110,936; 6,069,145; 6,271,383; 5,981,528; 6,051,716; 6,043,266; 6,313,307; and 5,523,403.

U.S. patent application Publication 2002/0086900.

PCT Application and publications PCT/US93/04850, WO94/01110; PCT/US94/08904, WO95/07271; PCT/US95/02972, WO95/25106; PCT/US95/10992, WO96/13502; PCT/US96/05202, WO96/35691; PCT/US96/12766; PCT/US96/13726; PCT/US96/14135; PCT/US96/17120; PCT/US96/19149; PCT/US97/01970; PCT/US95/12751, WO96/15130, PCT/US96/00718, WO96/23788, WO98/54161, WO99/29688, WO99/03846, WO99/37641, WO99/37652, WO99/40094, WO97/30995, WO97/09328, WO01/81350, WO01/40236, WO00/21960 WO01/4022, and WO95/07271.

In some embodiments, the antibacterial compounds are prodrugs of the compounds of formula I. The expression "prodrug" denotes a derivative of a known direct acting drug, which is transformed into the active drug by an enzymatic or chemical process. Prodrugs of the compounds of formula I are prepared by modifying functional groups present on the compound in such a way that the modifications are cleaved, either in routine manipulation or in vivo, to the parent compound. Prodrugs include, but are not limited to, compounds of structure (I) wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

N-[((5S)-3-{4-[4-({4-[(Diethylamino)methyl]phenoxy}acetyl) piperazin-1-yl]-3-fluorophenyl}-2-oxo-1,3-oxazolidin-5-yl)methyl]propanethioamide (22)

Step 1:

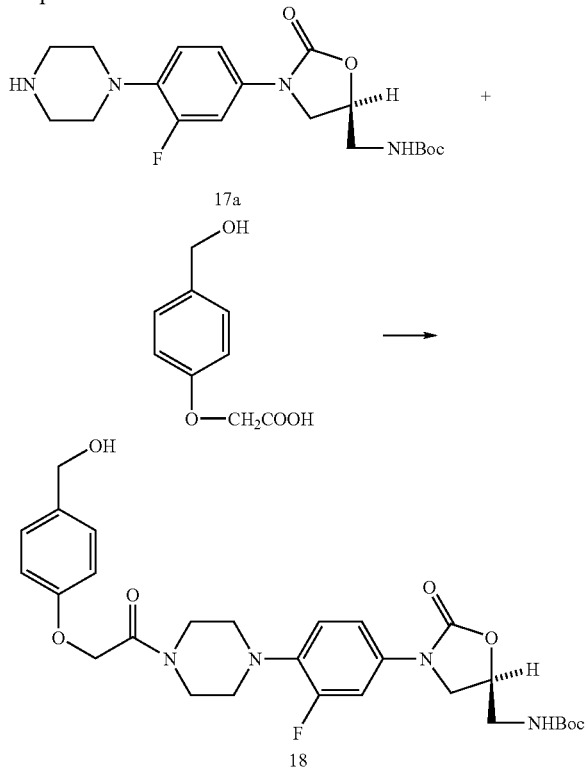

An ice cold, stirred mixture of 17a (15.1 g, 38.3 mmol), 4-(hydroxymethyl)phenoxyacetic acid (6.98 g, 38.3 mmol), 1-hydroxybenzotriazole hydrate (HOBT, 5.69 g, 42.1 mmol) and DMF (195 ml) was treated with 1-(3-dimethylaminopropyl)-3-ethylcarbodiimide hydrochloride (EDC, 14.7 g, 76.6 mmol), allowed to warm slowly to ambient temperature and stand for 18 h. It was then mixed with water (500 ml) and $Et_2O$ (500 ml); the precipitate was collected by filtration, washed carefully with water and then 1:1 heptane: $Et_2O$ and dried to give 19.8 g of 18, an off-white solid. A sample of this material that had been purified by silica gel chromatography with 2.5% MeOH—$CH_2Cl_2$ and trituration with EtOAc-heptane had: mp 148–154° C.; $^1H$ NMR [300 MHz, $(CD_3)_2SO$] δ 1.34 (s, 9H), 2.92, 2.98 (s, s, 4H), 3.25 (m, 2H), 3.60 (s, 4H), 3.73 (dd, 1H), 4.06 (t, 1H), 4.39 (d, 2H), 4.67 (m, 1H), 4.82 (s, 2H), 5.04 (t, 1H), 6.87 (d, 2H), 7.06 (t, 1H), 7.18 (m, 4H), 7.49 (dd, 1H);

Step, 2:

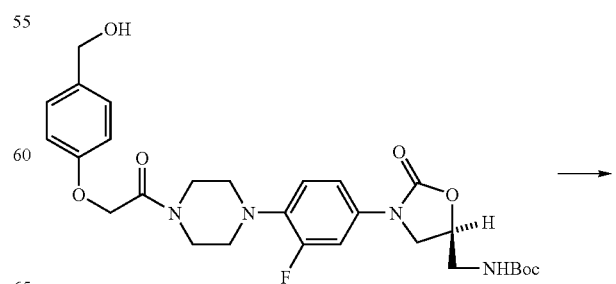

-continued

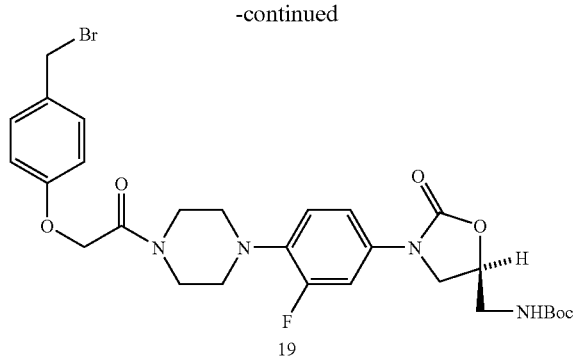

19

A stirred mixture of 18 (3.00 g, 5.37 mmol) and triphenylphosphine (2.16 g, 8.22 mmol) in $CH_2Cl_2$ (90 ml) was treated with carbon tetrabromide (2.69 g, 8.6 mmol) and kept at ambient temperature for 1 h. Additional triphenylphosphine (216 mg) and carbon tetrabromide (269 mg) were added and the mixture was stirred for 20 min and then concentrated in vacuo. The residue was stirred for 2 h with a mixture of $Et_2O$ (80 ml), heptane (80 ml), and water (60 ml) and then filtered. The solid was washed with water, 1:1 $Et_2O$: heptane and heptane and dried to give 3.76 g of 19 which was used without further purification: $^1H$ NMR [300 MHz, $(CD_3)_2SO$] δ 1.34 (s, 9H), 2.93, 2.99 (s, s, 4H), 3.25 (m, 2H), 3.60 (s, 4H), 3.74 (dd, 1H), 4.06 (t, 1H), 4.67 (m, 1H), 4.68 (s, 2H), 4.87 (s, 2H), 6.89 (d, 2H), 7.06 (t, 1H), 7.18 (m, 2H), 7.35 (d, 2H), 7.48 (dd, 1H)

Step 3:

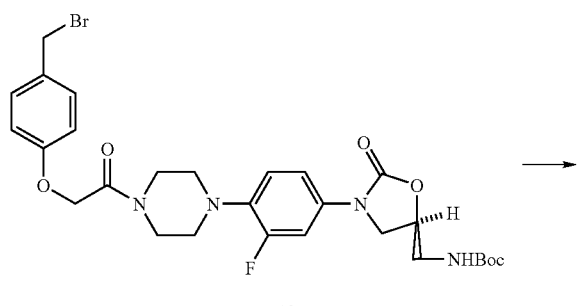

19

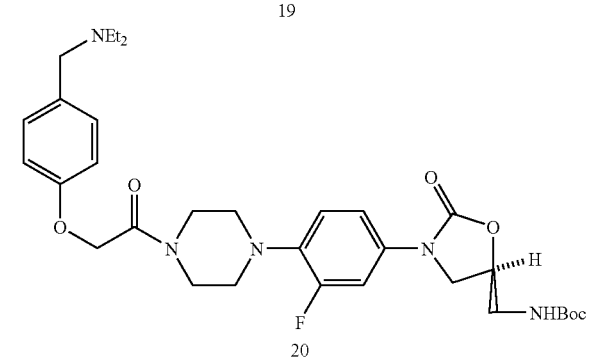

20

A stirred mixture of 19 (2.50 g), diethylamine (1.98 ml, 19.1 mmol), sodium iodide (15 mg) and acetone (98 ml) was kept at ambient temperature for 18 h and mixed with water (50 ml). It was extracted with $CH_2Cl_2$. The extract was dried ($MgSO_4$) and concentrated to give 2.44 g of 20, a light brown foam: MS (EI) m/z 613.0 (M⁺), 541.0, 485.5, 441.1, 277.1, 221.5; IR (drift) 3411, 3331, 1746, 1708, 1675 cm⁻¹.

Step 4:

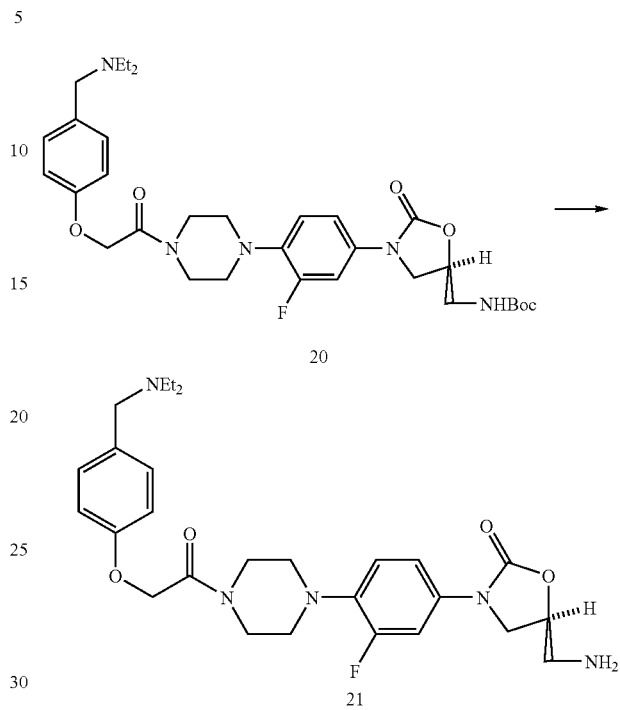

20

21

Compound 20 (2.44 g) was cooled in an ice bath and treated with 4N HCl in dioxane (30 ml). The mixture was stirred in the ice bath for 1 h and at ambient temperature for 1 h and then concentrated in vacuo. The residue was triturated three times with $CH_2Cl_2$ (70 ml) with concentration after each addition. A mixture of the resulting material and saturated $NaHCO_3$ (60 ml) was extracted with $CH_2Cl_2$. The extract was dried ($MgSO_4$) and concentrated. Chromatography of the residue on silica gel with 10% MeOH-1% $NH_4OH$—$CH_2Cl_2$ and crystallization of the product from EtOAc-MeOH-heptane gave 1.01 g of 21: mp 98° C. with softening and foaming from 92° C.; $^1H$ NMR [300 MHz, $(CD_3)_2SO$] δ 0.93 (t, 6H), 2.02 (broad s), 2.39 (q, 4H), 2.79 (m, 2H), 2.92, 2.98 (s, s, 4H), 3.42 (s, 2H), 3.60 (s, 4H), 3.80 (dd, 1H), 4.01 (t, 1H), 4.58 (m, 1H), 4.81 (s, 2H); 6.85 (d, 2H), 7.05 (t, 1H), 7.18 (m, 3H), 7.50 (dd, 1H),; MS (EI) m/z 513.0 (M⁺), 498.2, 484.1, 441.2, 412.1, 350.0, 335.3, 293.6.

Step 5:

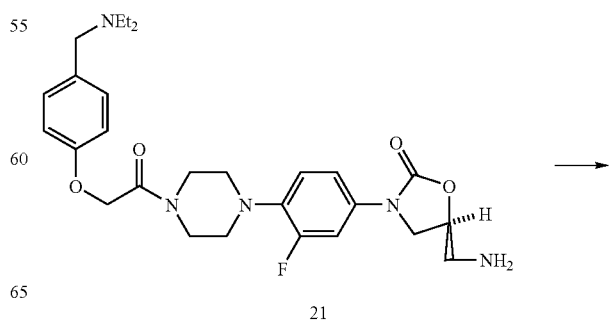

21

-continued

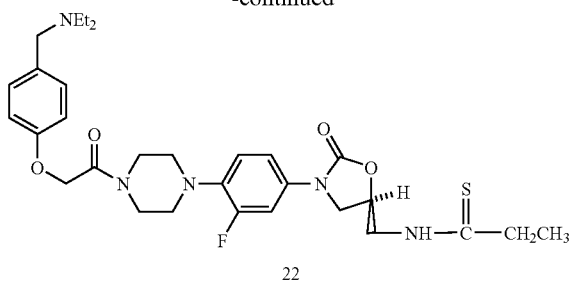

22

A stirred mixture of 21 (300 mg, 0.584 mmol), triethylamine (204 μL, 1.46 mmol) and MeOH (6.5 ml) was treated with ethyl dithiopropionate (94 mg, 0.701 mmol) and kept at ambient temperature for 18 h. It was then diluted with CH$_2$Cl$_2$, mixed with silica gel (2.5 g) and concentrated in vacuo. Chromatography of the residue on silica gel with 5% MeOH-0.5% NH$_4$OH—CH$_2$Cl$_2$ and crystallization of the product from EtOAc-heptane-Et$_2$O gave 155 mg of 22, an off white solid: $^1$H NMR [300 MHz, (CD$_3$)$_2$SO] δ 0.94 (t, 6H), 1.22 (t, 3H), 2.39 (m, 4H), 2.56 (q, 2H), 2.92, 2.99 (s, s, 4H), 3.42 (s, 2H), 3.60 (s, 4H), 3.78 (dd, 1H), 3.90 (t, 2H), 4.11 (t, 1H), 4.82 (s, 2H), 4.93 (m, 1H), 6.85 (d, 2H), 7.06 (t, 1H), 7.16 (m, 3H), 7.49 (dd, 1H), 10.32 (s, 1H).

Example 2

N-[((5S)-3-{4-[4-({4-[(Diethylamnino)methyl]phenoxy}acetyl) piperazin-1-yl]-3-fluorophenyl}-2-oxo-1,3-oxazolidin-5-yl)methyl]cyclopropanecarbothioamide (23)

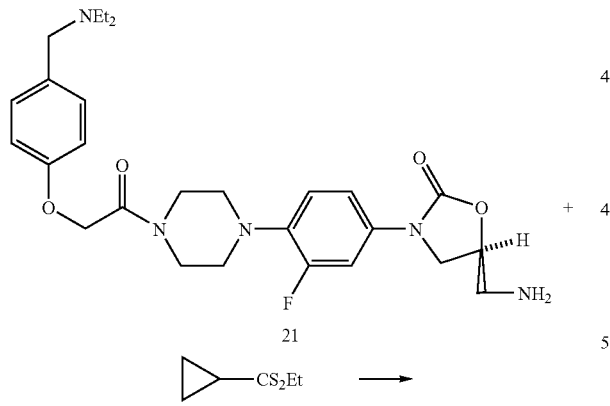

As described for the preparation of 22, the reaction of 7 (300 mg, 0.584 mmol) with ethyl cyclopropanecarbodithio- ate gave 146 mg of 23; $^1$HNMR [300 MHz, (CD$_3$)$_2$SO] δ 0.94 (m, 10H), 2.14 (m, 1H), 2.39 (m, 4H), 2.93, 2.99 (s, s, 4H), 3.42 (s, 2H), 3.61 (s, 4H), 3.79 (dd, 1H), 3.94 (m, 2H), 4.12 (t, 1H), 4.82 (s, 2H), 4.93 (m, 1H), 6.85 (d, 2H), 7.06 (t, 1H), 7.18 (m, 3H), 7.50 (dd, 1H), 10.52 (t, 1H); MS (EI) m/z 597.2 (M$^+$), 553.4, 524.4, 247.7.

Example 3

N-[((5S)-3-{4-[4-({4-[(Diethylamnino)methyl]phenoxy}acetyl)piperazin-1-yl]-3-fluorophenyl}-2-oxo-1,3-oxazolidin-5-yl)methyl]acetamide (24)

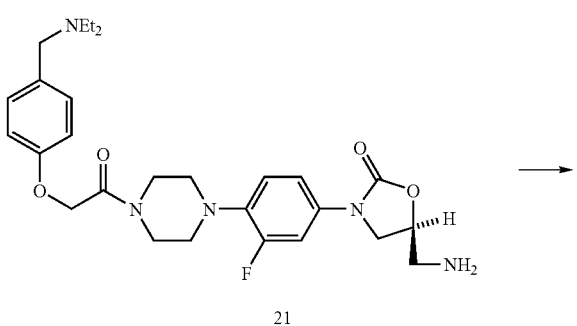

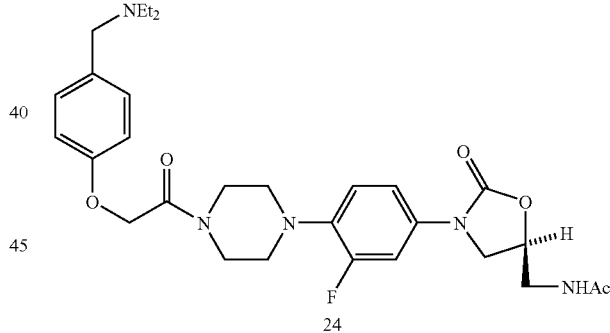

A stirred mixture of 21 (300 mg, 0.584 mmol), triethylamine (0.65 ml, 4.7 mmol), THF (5.8 ml) and CH$_2$Cl$_2$ (5.8 ml) was treated with acetyl chloride (76 μL, 0.88 mmol) and kept at ambient temperature for 18 h. It was then diluted with CH$_2$Cl$_2$, mixed with silica gel (2.5 g) and concentrated. Chromatography of the residue on silica gel with 5% MeOH-0.5% NH$_4$OH—CH$_2$Cl$_2$ and crystallization of the product from EtOAc-heptane-Et$_2$O gave 122 mg of 24, a white solid: $^1$H NMR [300 MHz, (CD$_3$)$_2$SO] δ 1.17 (m, 6H), 1.81 (s, 3H), 3.02 (m, 8H), 3.38 (t, 2H), 3.60 (s, 4H), 3.70 (dd, 1H), 4.07 (t, 1H), 4.19 (d, 2H), 4.79 (m, 1H), 4.91 (s, 2H), 6.98 (d, 2H), 7.06 (t, 1H), 7.16 (dd, 1H), 7.48 (m, 3H), 8.26 (t, 1H).

Example 4

N-[((5S)-3{4-[4-({4-[(Dimethylamino)methyl]phenoxy}acetyl)piperazin-1-yl]-3-fluorophenyl}-2-oxo-1,3-oxazolidin-5-yl)methyl]propanethioamide (27)

Step 1:

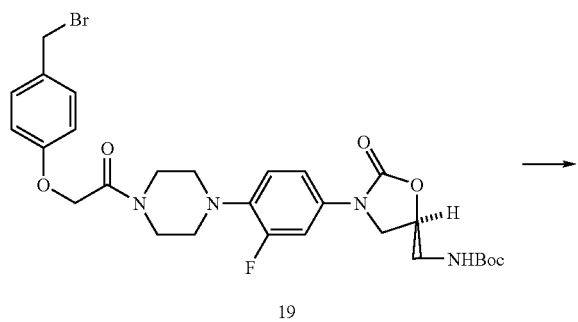

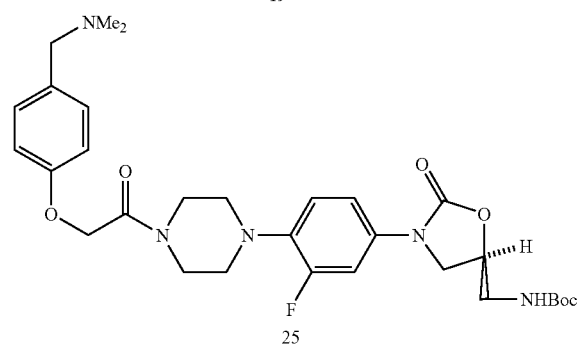

A stirred mixture of 19 (1.88 g), 2M dimethylamine in MeOH (5.1 ml, 10.2 mmol), sodium iodide (36 mg) and acetone (66 ml) was kept at ambient temperature for 20 min and concentrated in vacuo. A mixture of the residue and 1N HCl was washed with Et$_2$O and EtOAc, cooled in an ice bath and made alkaline with solid NaHCO$_3$. This was extracted with CH$_2$Cl$_2$ and the extract was concentrated. Chromatography of the residue on silica gel with 5% MeOH-0.5% NH$_4$OH—CH$_2$Cl$_2$ gave 979 mg of 25 that was used without further purification in subsequent reactions: $^1$H NMR [300 MHz, (CD$_3$)$_2$SO] δ 1.33 (s, 9H), 2.14 (s, 6H), 2.92, 2.98 (s, s, 4H), 3.24 (t, 2H), 3.36 (s, 2H), 3.60 (s, 4H), 3.74 (dd, 1H), 4.06 (t, 1H), 4.66 (m, 1H), 4.83 (s, 2H), 6.87 (d, 2H), 7.05 (t, 1H), 7.16 (m, 4H), 7.48 (dd, 1H); MS (EZ) m/z 585.1 (M+), 541.3, 528.2, 512.2, 485.2, 470.2, 277.2, 262.5.

Step 2:

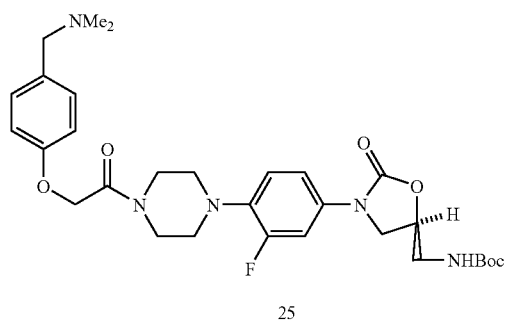

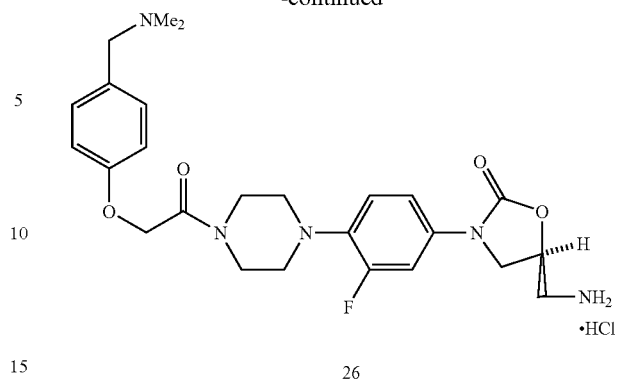

Solid 25 (357 mg) was cooled in an ice bath and treated with 4N HCl in dioxane (10 ml). The stirred mixture was kept in the ice bath for 1 h and at ambient temperature for 1 h and then concentrated in vacuo. The residue was triturated three times with 50 ml portions of CH$_2$Cl$_2$, concentrating the mixture after each addition, to give 26, a white solid: MS (EI) m/z 485.2 (M$^+$), 470.3, 442.4, 335.7, 293.6, 261.6; IR(drift) 3330, 1757, 1662, 1627 cm$^{-1}$.

Step 3:

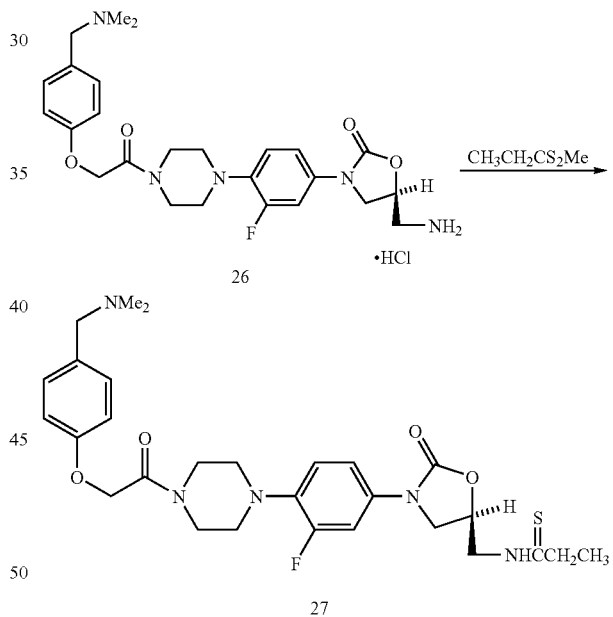

A stirred mixture of 26 (prepared from 357 mg of 25), triethylamine (0.68 ml, 4.88 mmol) and MeOH (8.5 ml) was treated with methyl dithiopropionate[4] (293 mg, 2.44 mmol), and kept at ambient temperature for 3 h. It was then concentrated in vacuo. Chromatography of the residue on silica gel with 5% MeOH-0.5% NH$_4$OH—CH$_2$Cl$_2$ and crystallization of the product from EtOAc gave 204 mg of 13 a white solid: mp 163–164° C.; $^1$HNMR [300 MHz, (CD$_3$)$_2$SO] δ 1.12 (t, 3H), 2.09 (s, 6H), 2.56 (q, 2H), 2.92, 2.99 (s, s, 4H), 3.28 (s, 2H), 3.60 (s, 4H), 3.78 (dd, 1H), 3.90 (t, 2H), 4.11 (t, 1H), 4.82 (s, 2H), 4.93 (m, 1H), 6.86 (d, 2H), 7.06 (t, 1H), 7.15 (m, 3H), 7.49 (dd, 1H), 10.30 (t, 1H); MS (EI) m/z 557.1 (M$^+$), 513.1, 354.1, 165.4; MS (CD) m/z 558.1 (M+H$^+$); IR (drift) 3235, 1750, 1653 cm$^{-1}$. Anal. calcd for $C_{28}H_{36}FN_5O_4S$: C, 60.30; H, 6.51; N, 12.56. Found: C, 60.08; H, 6.47; N, 12.44 cm$^{-1}$.

Example 5

N-[((5S)-3-{4-[4-({4-[(Dimethylamino)methyl] phenoxy}acetyl)piperazin-1-yl]-3-fluorophenyl}-2-oxo-1,3-oxazolidin-5-yl)methyl]cyclopropanecarbothioamide (28)

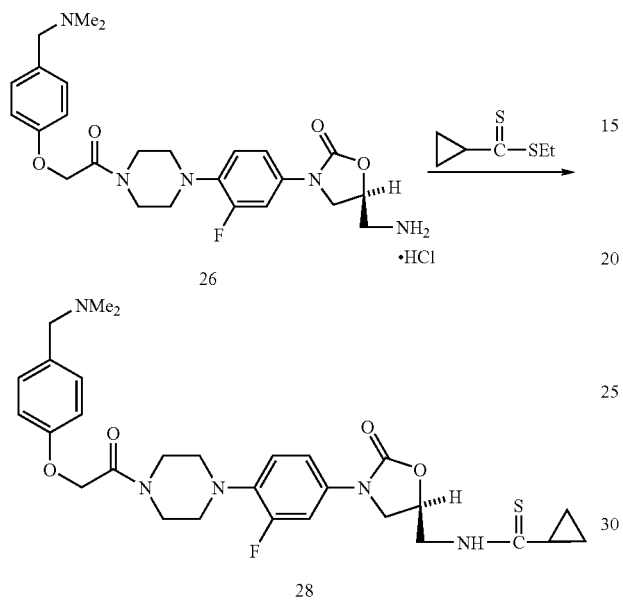

As described for the preparation of 27, the reaction of 26 (prepared from 357 mg of 25) with ethyl cyclopropanecarbodithioate and triethylamine gave the thioamide which was mixed with saturated NaHCO$_3$ and extracted with CH$_2$Cl$_2$. The extract was dried (MgSO$_4$) and concentrated. Chromatography of the residue on silica gel with 5% MeOH-0.5% NH$_4$OH—CH$_2$Cl$_2$ and crystallization of the product from Et$_2$O—CH$_2$Cl$_2$-heptane gave 74 mg of 28: mp 169–170° C.; $^1$H NMR [300 MHz, (CD$_3$)$_2$SO] δ 0.84 (m, 2H), 1.01 (m, 2H), 2.12 (s, 7H), 2.93. 3.00 (s, s, 4H), 3.25 (s, 2H), 3.60 (s, 4H), 3.79 (dd, 1H), 3.94 (m, 2H), 4.12 (t, 1H), 4.83 (s, 2H), 4.92 (m, 1H), 6.86 (d, 2H), 7.07 (t, 1H), 7.17 (m, 3H), 7.49 (dd, 1H).

Example 6

N-[((5S)-3-{4-[4-({4-[(Dimethylamino)methyl] phenoxy}acetyl)piperazin-1-yl]-3-fluorophenyl}-2-oxo-1,3-oxazolidin-5-yl)methyl]acetamide (29)

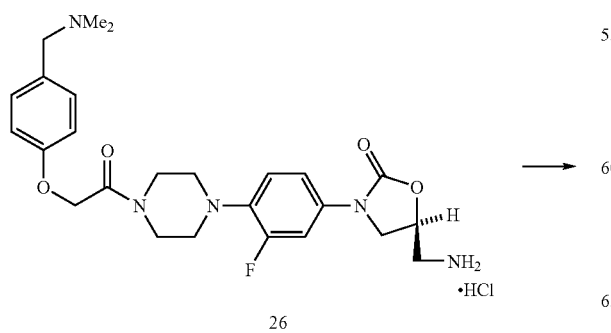

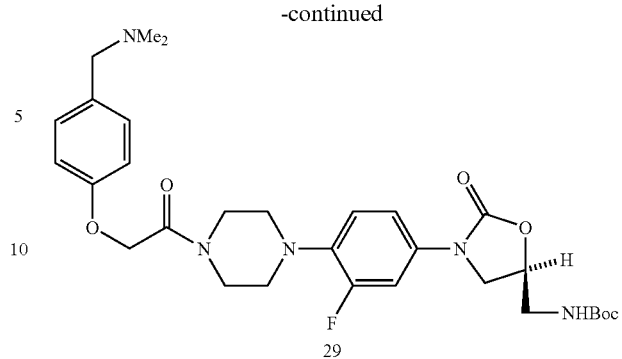

As described for the preparation of 27, the reaction of 26 (prepared from 264 mg of 25) with acetyl chloride and triethylamine gave the acetamide which was purified by silica gel chromatography with 5% MeOH-0.5%NH$_4$OH—CH$_2$Cl$_2$ followed by crystallization from Et$_2$OAc to give 73 mg of 29, a white solid; $^1$HNMR [300 MHz, (CD$_3$)$_2$SO] δ 1.81 (s, 3H), 2.45 (s, 6H), 2.93. 3.00 (s, s, 4H), 3.38 (t, 2H), 3.60 (s, 4H), 3.68 (dd, 1H), 3.85 (s, 2H), 4.06 (t, 1H), 4.69 (m, 1H), 4.88 (s, 2H), 6.94 (d, 2H), 7.06 (t, 1H), 7.16 (dd, 1H), 7.33 (d, 2H), 7.49 (dd, 1H), 8.24 (t, 1H).

Example 7

N-({(5S)-3-[3-Fluoro-4-(4-{[4-(morpholin-4-ylmethyl)phenoxy]acetyl}piperazin-1-yl)phenyl]-2-oxo-1,3-oxazolidin-5-yl}methyl)propanethioamide (32)

Step 1:

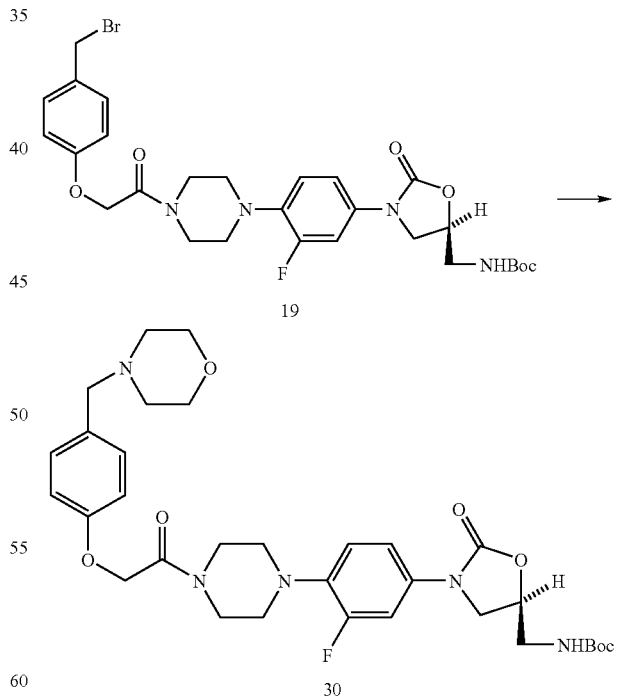

A stirred mixture of 19 (1.88 g), morpholine (1.1 ml, 12.8 mmol) sodium iodide (36 mg) and acetone (29 ml) was kept at ambient temperature for 18 h and concentrated in vacuo. A mixture of the residue in 1N HCl (15 ml) was washed with Et$_2$O and EtOAc, cooled in an ice bath and made alkaline with solid NaHCO₃. It was extracted with CH₂Cl₂ and the extract was concentrated. Chromatography of the residue on silica gel with 5% MeOH-0.5% NH₄OH—CH₂Cl₂ gave 773 mg of 30. Rechromatography of the impure fractions with 2.5% MeOH-0.25% NH₄OH—CH₂Cl₂ and trituration of the product with EtOAc-heptane gave 280 mg of additional 15: mp 166–168° C.; ¹H NMR [300 MHz, (CD₃)₂SO] δ 1.33 (s, 9H), 2.29 (s, 4H), 2.92, 2,98 (s, s, 4H), 3.24 (t, 2H), 3.35 (s, 2H), 3.53 (t, 4H), 3.60 (s, 4H), 3.74 (dd, 1H), 4.06 (t, 1H), 4.66 (m, 1H), 4.82 (s, 2H), 6.86 (d, 2H), 7.05 (t, 1H), 7.19 (m, 4H), 7.48 (dd, 1H).

Step 2:

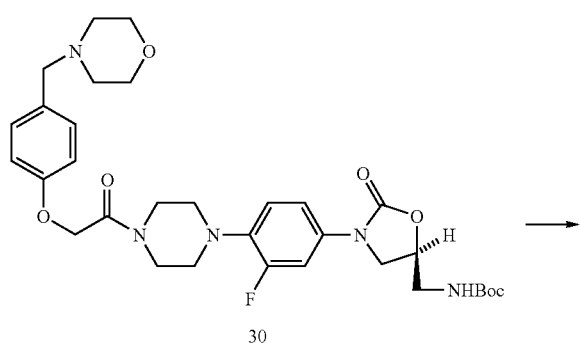

30

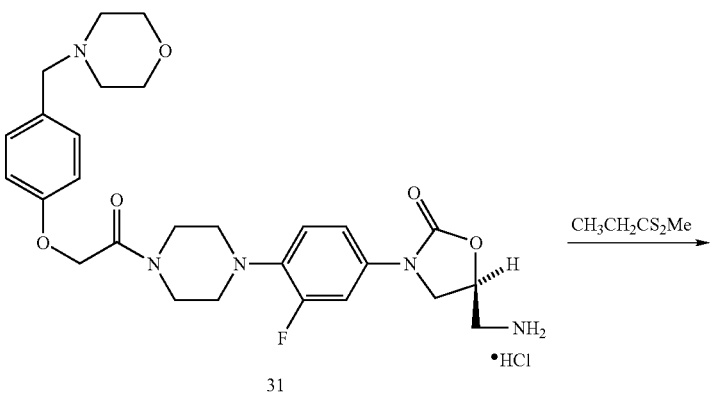

31

As described for the preparation of 26 the reaction of 30 (770 mg, 1.23 mmol) with 4N HCl in dioxane gave 31: MS (EI) m/z 527.2 (M⁺), 441.5, 334.4; IR (drift) 3330, 1758, 1666, 1626 cm⁻¹.

Step 3:

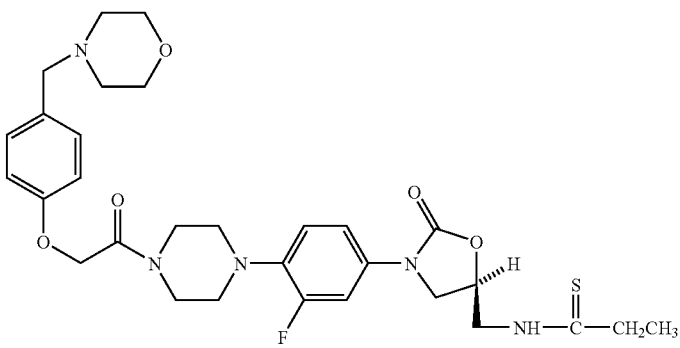

32

Example 8

N-({(5S)-3-[3-Fluoro-4-(4-{[4-(morpholin-4-ylmethyl)phenoxy]acetyl}piperazin-1-yl)phenyl]-2-oxo-1,3-oxazolidin-5-yl}methyl)cyclopropanecarbothioamide (33)

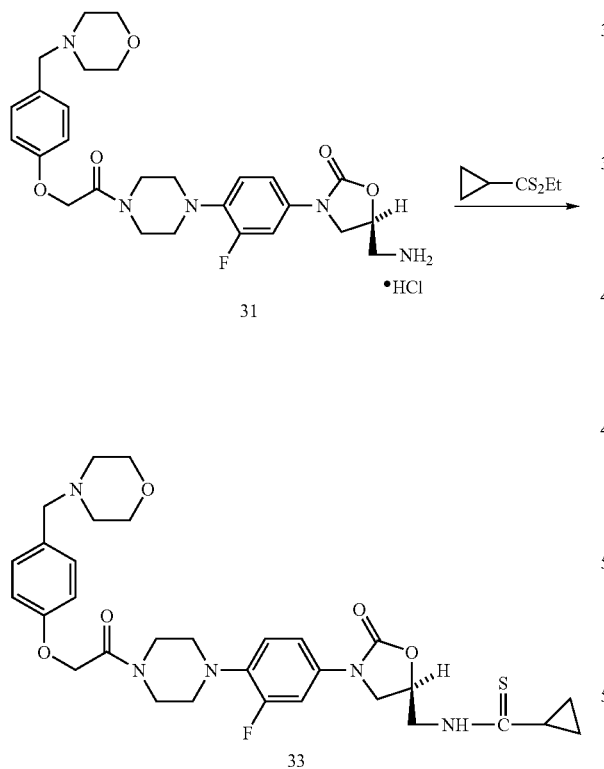

As described for the preparation of 27, the reaction of 31 (prepared from 385 mg of 25) with ethyl cyclopropanecarbodithioate and crystallization of the product from EtOAc-heptane gave 290 mg of 33: mp 138–141° C.; $^1$H NMR [300 MHz, (CD$_3$)$_2$SO] δ 0.84 (m, 2H), 1.01 (m, 2H), 2.14 (m, 1H), 2.29 (s, 4H), 2.93, 2.99 (s, s, 4H), 3.35 (s, 2H), 3.53 (t, 4H), 3.60 (s, 4H), 3.78 (dd, 1H), 3.94 (m, 2H), 4.12 (t, 1H), 4.82 (s, 2H), 4.93 (m, 1H), 6.86 (d, 2H), 7.06 (t, 1H), 7.17 (m, 3H), 7.50 (dd, 1H), 10.50 (t, 1H);

Example 9

N-({(5S)-3-[3-]Fluoro-4-(4-{[4-(morpholin-4-ylmethyl)phenoxy]acetyl(piperazin-1-yl)phenyl]-2-oxo-1,3-oxazolidin-5-yl]methyl)acetamide (34)

As described for the preparation of 24, the reaction of 31 (prepared from 260 mg of 30) with acetyl chloride and triethylamine and crystallization of the product from EtOAc-heptane gave 194 mg of 34, a white solid; mp 143–147° C.; $^1$H NMR [300 MHz, (CD$_3$)$_2$SO] δ 1.81 (s, 3H), 2.29 (s, 4H), 2.92, 2.99 (s, s, 4H), 3.36 (s, 2H), 3.38 (t, 2H), 3.53 (s, 4H), 3.60 (s, 4H), 3.68 (dd, 1H), 4.06 (t, 1H), 4.69 (m, 1H), 4.82 (s, 2H), 6.86 (d, 2H), 7.05 (t, 1H), 7.17 (m, 3H), 7.48 (dd, 1H), 8.23 (t, 1H).

Example 10

N-[((5S)-3-{3-Fluoro-4-[4-({4-[(4-methylpiperazin-1-yl)methyl]phenoxy}acetyl)piperazin-1-yl]phenyl}-2-oxo-1,3-oxazolidin-5-yl)methyl]propanethioamide (37)

Step 1:

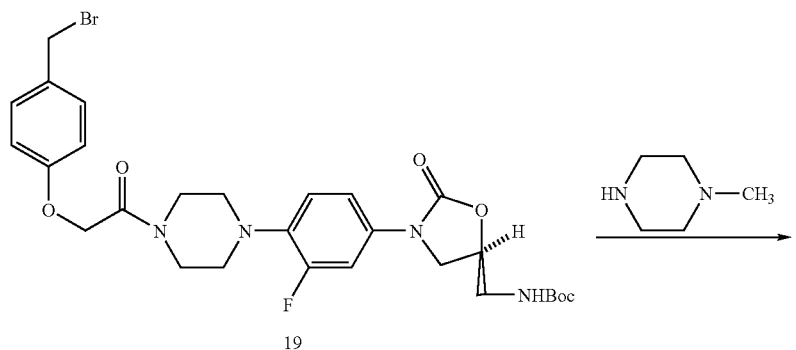

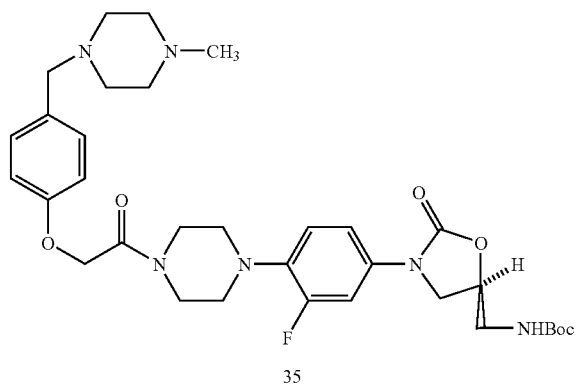

A stirred mixture of 19 (2.50 g), N-methyl-piperazine (2.10 ml, 19.1 mmol), acetone (98 ml) and a small amount of NaI was kept at ambient temperature for 18 h and concentrated in vacuo. A solution of the residue in 1N HCl (20 ml) was washed with EtOAc and then Et$_2$O (emulsions which were difficult to separate were formed in this process). The aqueous layer was adjusted to pH 10 with solid NaHCO$_3$ and extracted with CH$_2$Cl$_2$. The extract was concentrated to give 1.67 g of 35, a brown foam: MS (EI) m/z 640.1 (M$^+$), 611.0, 582.0, 540.0, 394.1, 262.5; HRMS calcd for C$_{33}$H$_{46}$FN$_6$O$_6$ (M+H$^+$) 641.3463, found 641.3455.

Step 2:

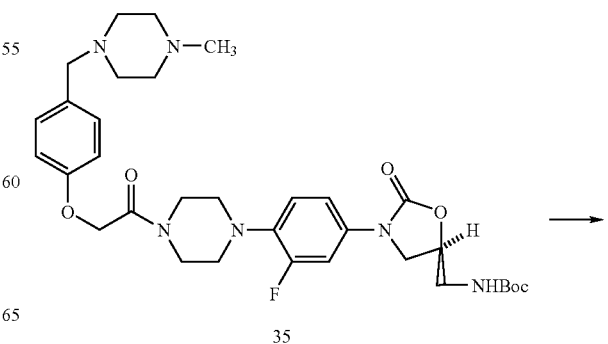

-continued

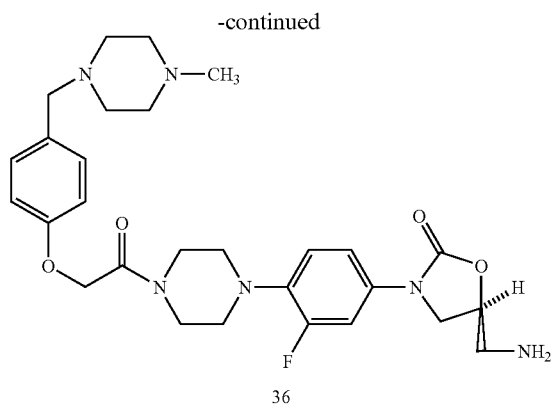

36

Compound 35 (1.67 g) was cooled in an ice bath and treated with 4N HCl in dioxane (20 ml). The stirred mixture was kept in the ice bath for 1 h and at ambient temperature for 1 h and concentrated in vacuo. The residue was triturated with three portions of CH$_2$Cl$_2$ (50 ml) with concentration after each addition. A mixture of the solid residue and saturated NaHCO$_3$ (50 ml) was extracted with CH$_2$Cl$_2$. The extract was dried (MgSO$_4$) and concentrated. Chromatography of the residue on silica gel with 10% MeOH-1% NH$_4$OH—CH$_2$Cl$_2$ and crystallization of the product from EtOAc—CH$_2$Cl$_2$-heptane gave 389 mg, mp 134–135° C. which contained a small amount of less polar impurity by TLC, and 567 mg, mp 138–141° C. of pure 36: MS (EI) m/z 540.0 (M+), 511.0, 469.1, 454.3, 441.1, 350.1; IR (drift) 3325, 3313, 1730, 1664 cm$^{-1}$.

Step 3:

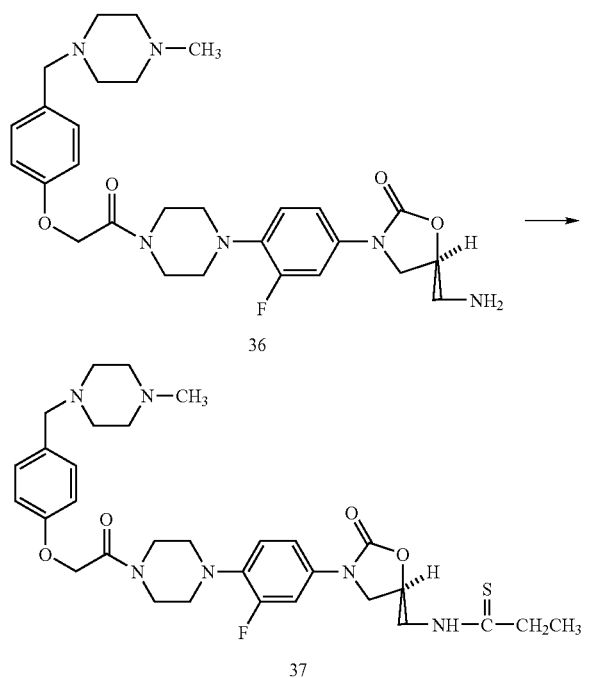

A stirred mixture of 36 (300 mg, 0.555 mmol), triethylamine (193 µL, 1.39 mmol), ethyl dithiopropionate (89 mg, 0.67 mmol) and MeOH (6 ml) was kept at ambient temperature for 18 h, treated with silica gel (2.5 g) and concentrated in vacuo. Chromatography of the residue on silica gel with 5% MeOH-0.5% NH$_4$OH—CH$_2$Cl$_2$ and crystallization of the product from Et$_2$O—CH$_2$Cl$_2$ gave 175 mg of 37, a white solid: mp 139–144° C. (dec); $^1$H NMR [300 MHz, (CD$_3$SO] δ 1.15 (t, 3H), 2.18 (s, 3H), 2.35 (broad s, 8H), 2.58 (q, 2H), 2.95, 3.00 (s, s, 4H), 3.38 (s, 2H), 3.62 (s, 4H), 3.81 (dd, 1H), 3.92 (t, 2H), 4.13 (t, 1H), 4.84 (s, 2H), 4.95 (m, 1H), 6.88 (d, 2H), 7.08 (t, 1H), 7.18 (m, 3H), 7.51 (dd, 1H), 10.35 (s, 1H).

Example 11

N-[((5S)-3-{3-]Fluoro-4-[4-({4-[(4-methylpiperazin-1-yl)methyl]phenoxy}acetyl)piperazin-1-yl]phenyl)-2-oxo-1,3-oxazolidin-5-yl)methyl]cyclopropanecarbothioamide (38)

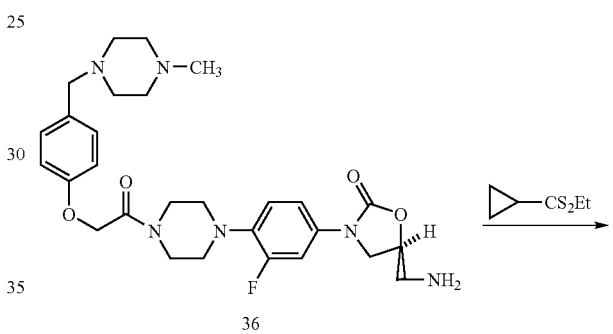

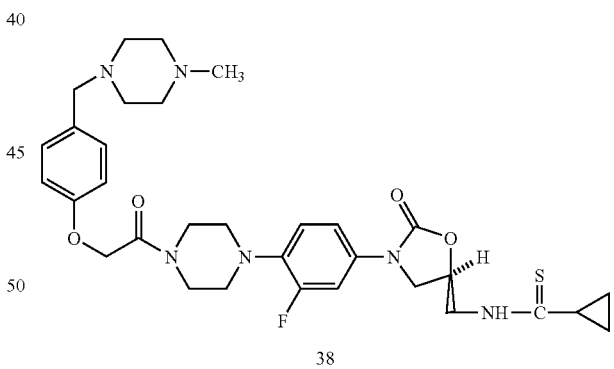

Compound 38 was prepared by the reaction of 36 (250 mg, 0.462 mmol) with ethyl cyclopropanecarbodithioate as described for the preparation of 37. Crystallization of the product from Et$_2$O—CH$_2$Cl$_2$ gave a solid which was mixed with saturated NaHCO$_3$, extracted with CH$_2$Cl$_2$: MeOH (9:1) and crystallized: IR (drift) 3302, 1739, 1638 cm–1; MS (CI) m/z 625.2 (M+H+), 581.2; HRMS (FAB) calcd for C$_{32}$H$_{42}$FN$_6$O$_4$S (M+H+) 625.2972, found 625.2961.

Example 12

N-[((5S)-3-{3-Fluoro-4-[4-({4-[(4-methylpiperazin-1-yl)methyl]phenoxy}acetyl)piperazin-1-yl]phenyl}-2-oxo-1,3-oxazolidin-5-yl)methyl]acetamide (39)

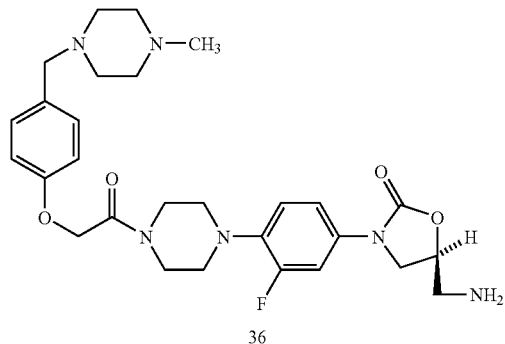

36

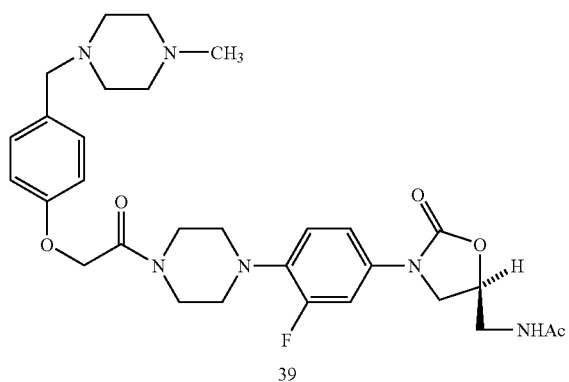

39

A stirred solution of 36 (250 mg, 0.462 mmol), triethylamine (515 μL, 3.70 mmol), CH$_2$Cl$_2$ (4.6 ml) and THF (4.6 mmol) was treated with acetyl chloride (60 μL, 0.69 mmol), kept at ambient temperature for 18 h, treated with silica gel (2.5 g) and concentrated in vacuo. Chromatography of the residue on silica gel with 5% MeOH-0.5% NH$_4$H—CH$_2$Cl$_2$ gave the product which was crystallized from Et$_2$O—CH$_2$Cl$_2$. The resulting material appeared to be a salt. It was mixed with saturated NaHCO$_3$ and extracted with 9:1 CH$_2$Cl$_2$: MeOH. The extract was dried (MgSO$_4$) and concentrated. Crystallization of the residue from EtOAc gave 39: IR (drift) 3317, 1726, 1668, 1645 cm$^{-1}$; MS (EI) m/z 582.3 (M$^+$), 538.3, 524.2, 511.2, 467.2, 439.2, 336.2, 294.1; HRMS (FAB) calcd for C$_{30}$H$_{40}$FN$_6$O$_5$ (M+H$^+$) 583.3044, found 583.3045.

Example 13

N-[((5S)-3-{4-[4-(4-{4-[(Dimethylamino)methyl]phenyl}-4-oxobutanoyl)-1-piperazinyl]-3-fluorophenyl}-2-oxo-1,3-oxazolidin-5-yl)methyl]propanethioamide (47)

Step 1:

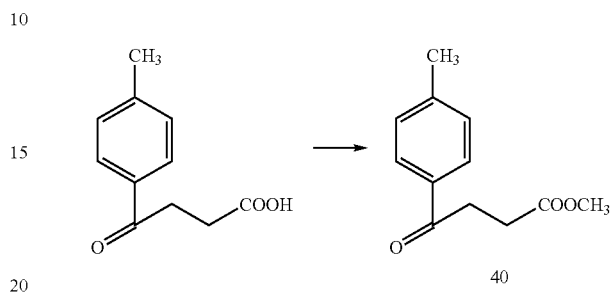

A stirred mixture of 4-(4-methylphenyl)-4-oxobutanoic acid (5.00 g, 26.0 mmol) and potassium carbonate (10.8 g, 78.0 mmol) in DMF (50 ml) was treated with methyl iodide (8.1 ml, 130 mmol) and kept at ambient temperature for 3 h. It was then mixed with water (300 ml) and extracted with Et$_2$O. The extract was washed with water, dried (MgSO$_4$) and concentrated to give 5.09 g of a light yellow solid (40): mp 40–42° C.; $^1$H NMR (300 MHz, CDCl$_3$) δ 2.41 (s, 3H), 2.75 (t, 2H), 3.30 (t, 2H), 3.70 (s, 3H), 7.26 (d, 2H), 7.88 (d, 2H); MS (EST) m/z 229 (M+Na$^+$); IR (drift) 1733, 1679 cm$^{-1}$.

Step 2:

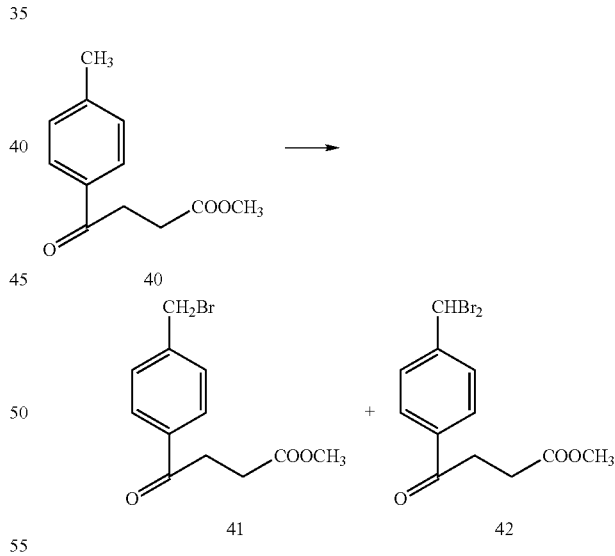

A stirred mixture of 40 (22.0 g, 107 mmol), N-bromo-succinimide (23.7 g, 133 mmol) and CHCl$_3$ (1600 ml) was kept under a bright (movie) light for 2 h; the mixture refluxed gently. Additional NBS (2.3 g) was added and stirring under the light was continued for 2 h. This mixture was concentrated in vacuo and the residue was stirred for three days with Et$_2$O (1 L) and then filtered. The solid was washed well with Et$_2$O and the filtrate was washed with water, dried (MgSO$_4$) and concentrated. The residue was triturated with 1:1 Et$_2$O-heptane at ambient temperature for 30 min and at 0° C. for 30 min and then filtered to give 22.5 g of an off-white solid that by NMR was an 85:15 mixture of 41 and 42: $^1$H NMR (300 MHz, CDCl$_3$ for 4) δ 2.77 (t, 2H), 3.31 (t, 2H), 3.71 (s, 3H), 4.50 (s, 2H), 7.49 (d, 2H), 7.96 (d, 2H); $^1$H NMR (300 MHz, CDCl$_3$ for 5) δ 2.78 (t, 2H), 3.31 (t, 2H), 3.71 (s, 3H), 6.65 (s, 1H), 7.66 (d, 2H). A sample of this mixture was purified by silica gel chromatography with 25% EtOAc-heptane to give a sample of 41 with 99.6% purity: mp 163–164° C.; IR (drift) 1729, 1680 cm$^{-1}$; MS (ESI) m/z 284, 286 (M$^+$); HRMS calcd for C$_{12}$H$_{14}$BrO$_3$ (M+H$^+$) 285.0127, found 285.0132.

Step 3:

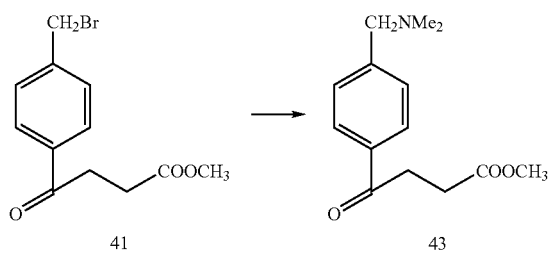

A stirred mixture of an 86:14 mixture of 41 and 42 (200 mg), 2 M dimethylamine in MeOH (1.4 ml) and sodium iodide (7 mg) in acetone (9 ml) was kept at ambient temperature for 18 h and concentrated in vacuo. A solution of the residue in 1N hydrochloric acid (5 ml) was washed with Et$_2$O, made alkaline with 2N NaOH and extracted with Et$_2$O. The extract was dried (MgSO$_4$) and concentrated to give 124 mg of 43 which was purified by silica gel chromatography with 5% MeOH—CH$_2$Cl$_2$: $^1$H NMR (300 MHz, CDCl$_3$) δ 2.24 (s, 6H), 2.76 (t, 2H), 3.32 (t, 2H), 3.47 (s, 2H), 3.70 (s, 3H), 7.41 (d, 2H), 7.94 (d, 2H).

Step 4:

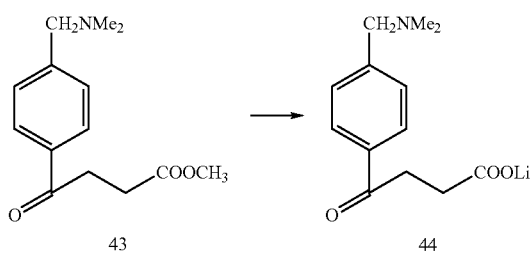

A stirred solution of 43 (632 mg, 2.53 mmol) in MeOH (17 ml) was treated with 1 M LiOH (3.3 ml) and kept at ambient temperature for 5 h. Additional LiOH (1.0 ml) was added and the mixture was kept at ambient temperature for 18 h and concentrated in vacuo. The residue was triturated with Et$_2$O, filtered, washed with Et$_2$O and dried to give 732 mg of 44, an off-white solid: mp 198–199° C.; MS (EI) m/z 234.8 (M–Li+H$^+$); MS (CI) m/z 236.3 (M–Li+2H$^+$), IR (drift) 1679 cm$^{-1}$.

Step 5:

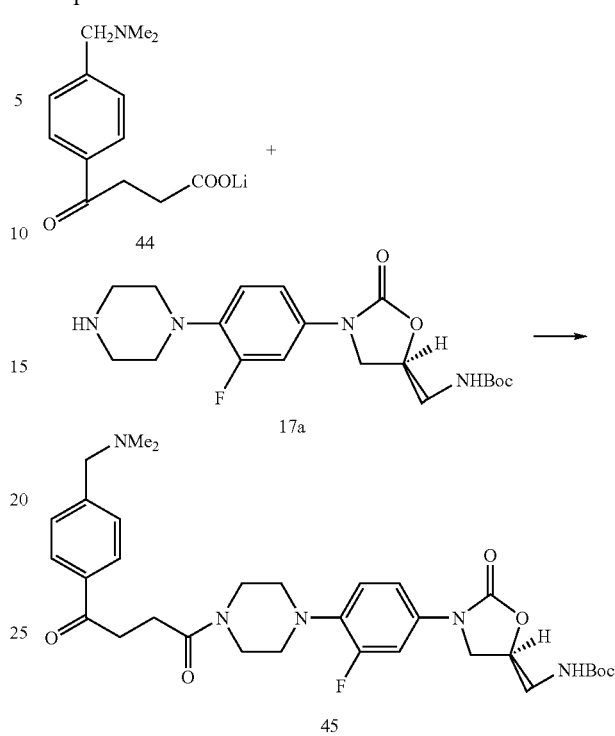

A stirred, ice cold mixture of 44 (2.5 mmol), 17a (986 mg, 2.50 mmol), triethylamine (1.05 ml, 7.50 mmol) and hydroxybenzotriazole hydrate (HOBT) (372 mg, 2.75 mmol) in DMF (22 ml) was treated with 1-(3-dimethylaminopropyl)-3-ethylcarbodiimide hydrochloride (EDC) (1.05 g, 5.50 mmol), warmed to ambient temperature and kept for 18 h. It was then mixed with water (100 ml) and Et$_2$O (75 ml). A solid precipitated. The Et$_2$O layer and solid was washed with water; the solid was collected by filtration, washed with Et$_2$O and dried to give 1.25 g of 45: mp 160–164° C.; $^1$H NMR [300 MHz, (CD$_3$)$_2$SO] δ 1.34 (s, 9H), 2.14 (s, 6H), 2.73 (t, 2H), 2.90, 3.01 (s, s, 4H), 3.22 (m, 4H), 3.44 (s, 2H), 3.58, 3.65 (s, s, 4H), 3.74 (dd, 1H), 4.07 (t, 1H), 4.66 (m, 1H), 7.08 (t, 1H), 7.19 (m, 2H), 7.42 (d, 2H), 7.49 (dd, 1H), 7.93 (d, 2H).

Step 6:

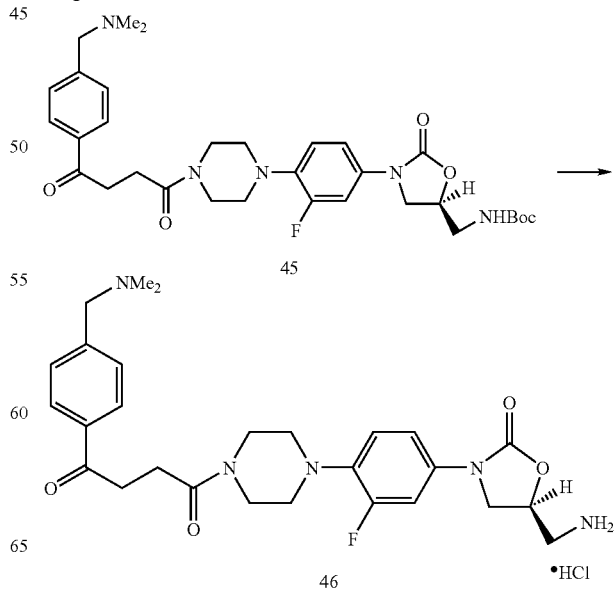

A flask containing 45 (1.20 g, 1.96 mmol) was cooled in an ice bath and treated with 4N hydrogen chloride in dioxane (10 ml). The mixture was stirred in the ice bath for 2 h and at ambient temperature for 1.5 h and then concentrated in vacuo. The residue was triturated with three 40 ml portions of $CH_2Cl_2$ with concentration after each addition to give 46, a white solid: mp>210° C.; MS (EI) m/z 511.2 ($M^+$); IR (drift) 3352, 1759, 1685, 1645, 1629 $cm^{-1}$.

Step 7:

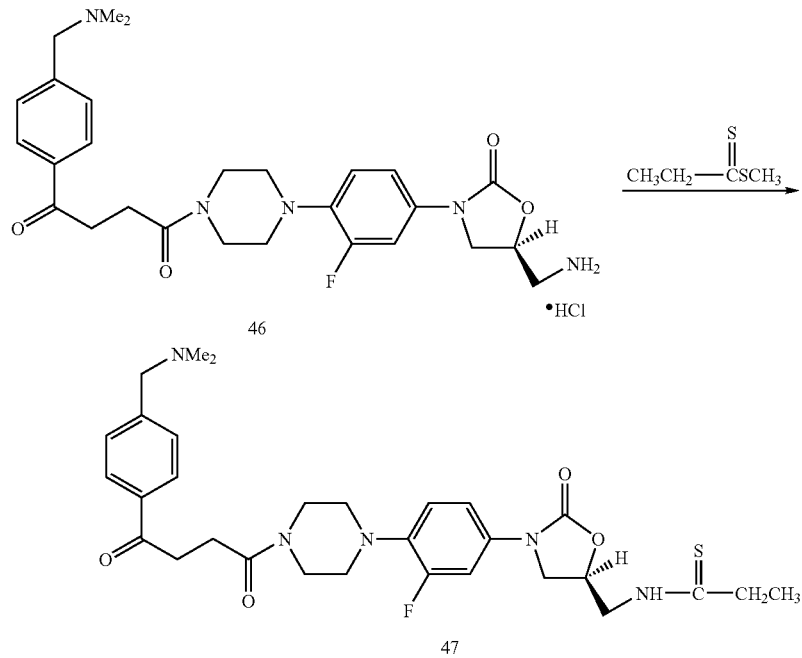

A stirred mixture of 46 (0.98 mmol), triethylamine (1.1 ml, 7.84 mmol), methyl dithiopropionate (471 mg, 3.92 mmol) and MeOH (13.6 ml) was kept at ambient temperature for 3 d and concentrated. Chromatography of the residue on silica gel with 5% MeOH-0.5% $NH_4OH$—$CH_2Cl_2$ and crystallization of the product from EtOAc gave 360 mg of 47, a white solid: mp 169° C.; $^1H$ NMR [300 MHz, $(CD_3)_2SO$] δ 1.13 (t, 3H), 2.14 (s, 6H), 2.57 (q, 2H), 2.73 (t, 2H), 2.90, 3.00 (s, s, 4H), 3.22 (t, 2H), 3.45 (s, 2H), 3.58, 3.66 (s, s, 4H), 3.80 (d, d, 1H), 3.90 (t, 2H), 4.12 (t, 1H), 4.93 (m, 1H), 7.07 (t, 1H), 7.16 (dd, 1H), 7.42 (d, 2H), 7.48 (dd, 1H), 7.93 (d, 2H), 10.30 (t, 1H);

Example 14

N-[((5S)-3-{4-[4-(4-{4-[(Dimethylamino)methyl]phenyl}-4-oxobutanoyl)-1-piperazinyl]-3-fluorophenyl}-2-oxo-1,3-oxazolidin-5-yl)methyl]cyclopropanecarbothioamide (48)

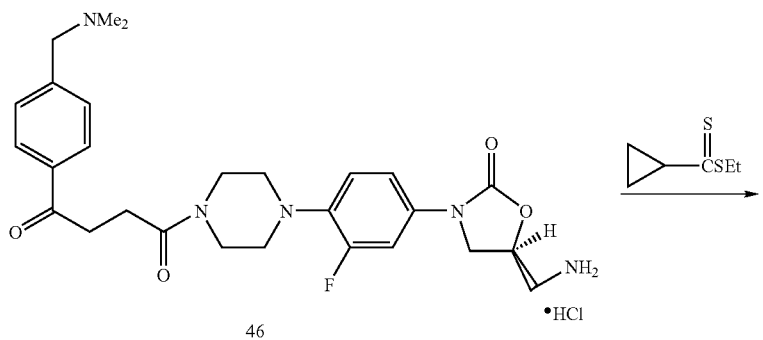

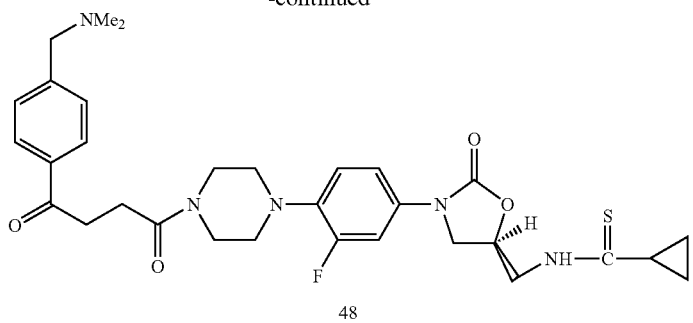

48

A stirred mixture of 46 (0.98 mmol), triethylamine (1.1 ml, 7.8 mmol) and MeOH (13.6 ml) was treated with ethyl cyclopropanecarbodithioate (573 mg, 3.92 mmol), kept at ambient temperature for 3 days and concentrated. The residue was chromatographed on silica gel and the product was crystallized from EtOAc to give 375 mg of 48, a white solid: mp 174–175° C.; $^1$H NMR [300 MHz, (CD$_3$)$_2$SO] δ 0.84 (m, 2H), 1.02 (m, 2H), 2.14 (s, 6H), 2.14 (m, 1H), 2.73 (t, 2H), 2.90, 3.00 (s, s, 4H), 3.22 (t, 2H), 3.45 (s, 2H), 3.58, 3.66 (s, s, 4H), 3.79 (dd, 1H), 3.94 (m, 2H), 4.12 (t, 1H), 4.93 (m, 1H), 7.07 (t, 1H), 7.18 (dd, 1H), 7.43 (d, 2H), 7.50 (dd, 1H), 7.93 (d, 2H), 10.47 (s, 1H); MS (CI) m/z 596 (M+H$^+$), 551.2, 536.1, 509.1, 218.1, 174.8, 161.2, 58.1.

Example 15

N-[((5S)-3-{4-[4-(4-{[(Dimethylamino)methyl]phenyl}-4-oxobutanoyl)-1-piperazinyl]-3-fluorophenyl}-2-oxo-1,3-oxazolidin-5-yl)methyl]acetamide (49)

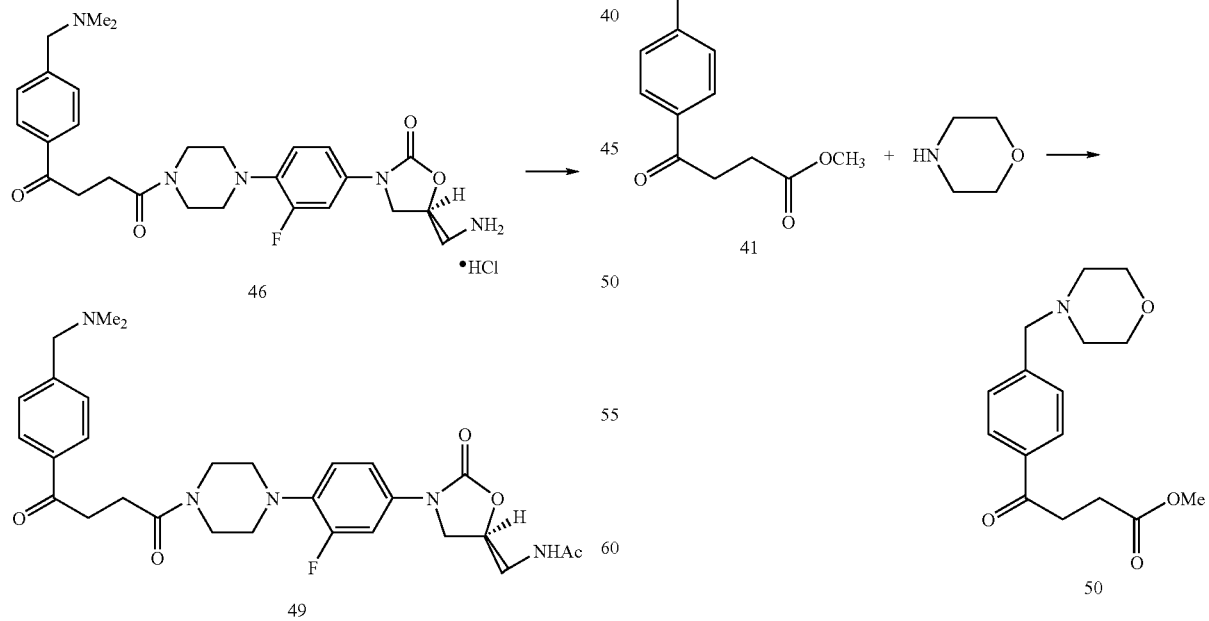

A stirred mixture of 46 (0.981 mmol), CH$_2$Cl$_2$ (10 ml), THF (10 ml) and triethylamine (1.1 ml, 7.85 mmol) was treated with acetyl chloride (128 μL, 1.47 mmol), kept at ambient temperature for 3 days and concentrated in vacuo. The residue was mixed with water and extracted with CH$_2$Cl$_2$. The extract was dried (MgSO$_4$) and concentrated. Chromatography of the residue on silica gel with 5% MeOH-0.5% NH$_4$OH—CH$_2$Cl$_2$ and crystallization of the product from EtOAc gave 369 mg of 49, and off-white solid: mp 190–192° C.; MS (EI) m/z 553.2 (M$^+$), 509.2, 467.4, 334.3, 218.2, 134.1, 84.1, 58.5; IR (drift) 3315, 1743, 1686, 1647 cm$^{-1}$. Anal. calcd for C$_{29}$H$_{36}$FN$_5$O$_5$: C, 62.91; H, 6.55; N, 12.65. Found: C, 62.60; H, 6.59; N, 12.59.

Example 16

N-({(5S)-3-[3-Fluoro-4-(4-{4-[4-(4-morpholinylmethyl)phenyl]-4-oxobutanoyl}-1-piperazinyl)phenyl]-2-oxo-1,3-oxazolidin-5-yl}methyl)propanethioamide (54)

Step 1:

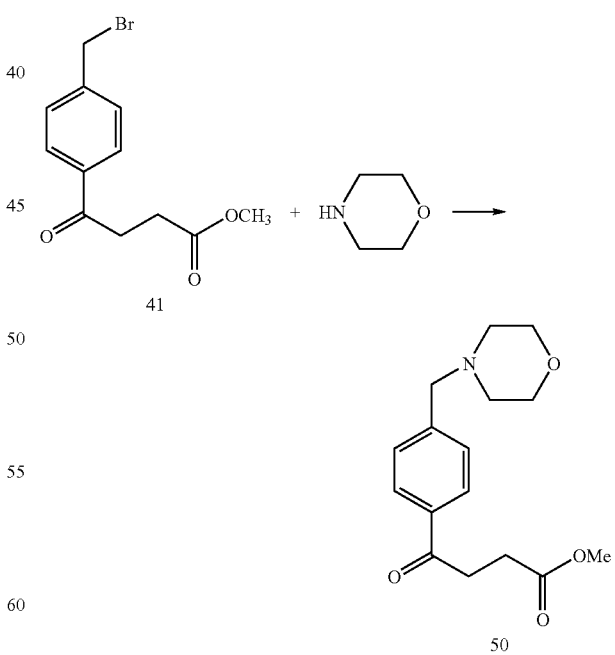

A stirred mixture of 41 (4.00 g of an 84:16 mixture of 41 and 42, 11.8 mmol of 41), morpholine (4.1 ml, 47 mmol), acetone 180 ml and a small amount of NaI was kept at ambient temperature for 18 h and concentrated in vacuo. A solution of the residue in 1N HCl was washed with Et$_2$O, adjusted to pH 9–10 with solid NaHCO$_3$ and extracted with CH$_2$Cl$_2$. The extract was dried (MgSO$_4$) and concentrated to give 3.50 g of 50, a yellow solid: mp 79–80.5° C.; MS (EI) m/z 290.6 (M$^+$), 260.1, 218.2, 204.7, 174.6, 89.4, 86.9; IR (drift) 1732, 1684 cm$^{-1}$.

Step 2:

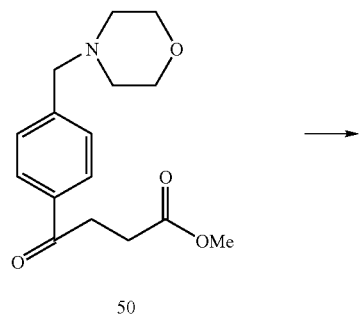

50

A stirred solution of 50 (3.44 g, 11.8 mmol) in MeOH (80 ml) was treated with 1N LiOH (15 ml), kept at ambient temperature for 18 h and concentrated in vacuo. Two 100 ml portions of Et$_2$O were added to the residue with concentration after each addition to give 51, a light brown solid: MS (EI) m/z 260.6, 218.8, 204.4, 174.6, 90.3, 57.1; IR (drift) 1668 cm$^-$.

Step 3:

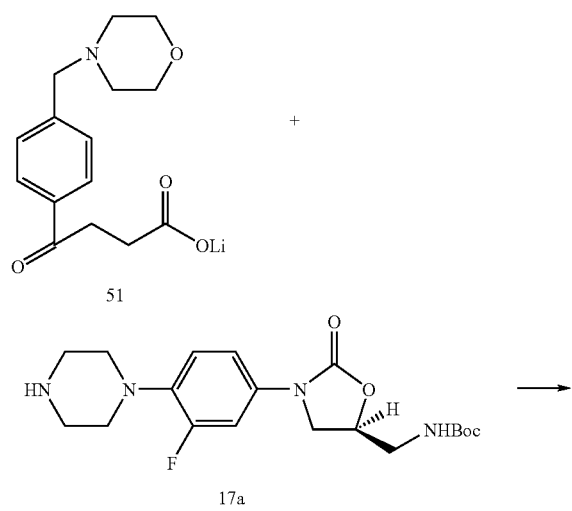

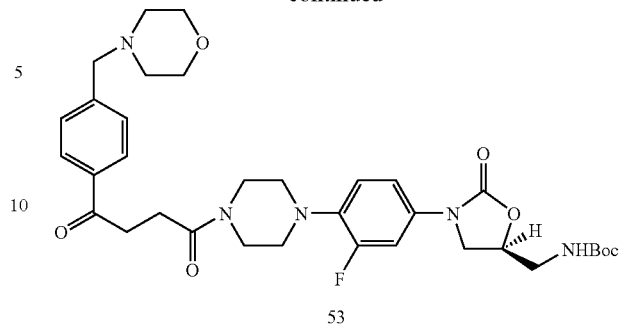

53

A stirred, ice cold mixture of 51 (11.8 mmol), 17a (4.42 g, 11.2 mmol), HOBT (1.75 g, 13.0 mmol) and DMF (75 ml) was treated with EDC (4.98 g, 26.0 mmol), allowed to warm slowly to ambient temperature and stand for 3 d. It was then mixed with water (300 ml) and Et$_2$O (500 ml), a solid formed. The Et$_2$O-solid mixture was washed with water and filtered. The solid was washed with Et$_2$O and dried to give 5.72 g of 52, an off-white solid: mp 128–131° C.; MS (FAB) m/z 654.3 (M+H$^+$), 598.3, 393.2, 260.1, 100.1, 57.1; HRMS (FAB) calcd for C$_{34}$H$_{45}$FN$_5$O$_7$ (M+H$^+$) 654.3303, found 654.3289; IR (drift) 1742, 1710, 1687, 1652 cm$^{-1}$.

Step 4:

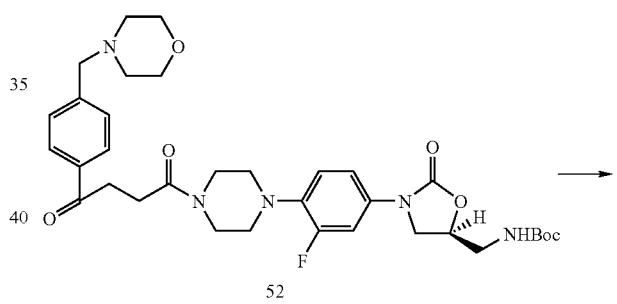

52

Solid 52 (4.00 g, 6.29 mmol) was cooled in an ice bath and treated with 4NHCl in dioxane (40 ml). The stirred mixture was kept in the ice bath for 1 h and at ambient temperature for 1 h and then concentrated in vacuo. Three 50 ml portions of CH$_2$Cl$_2$ were added to the residue with concentration after each addition to give 53, an off-white solid: MS (EI) m/z 553.0 (M$^+$), 467.2, 454.1, 377.4, 292.2, 259.3, 174.6, 86.4; IR (drift) 1759, 1685, 1646, 1627, 1608 cm$^{-1}$.

Step 5:

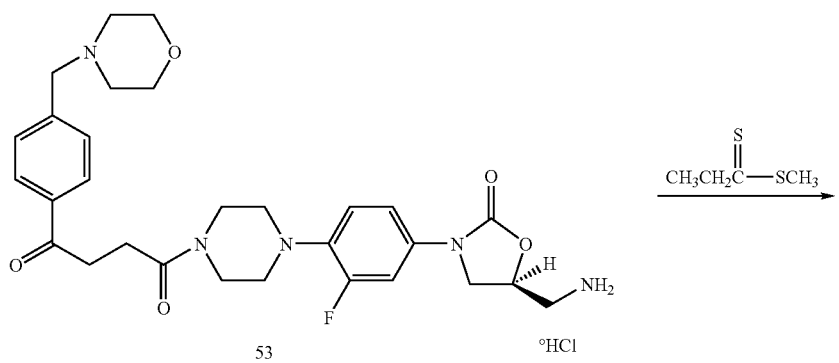

A stirred solution of 49 (one third of the product from the previous reaction—about 2.07 mmol) and triethylamine (2.31 ml, 16.6 mmol) in MeOH (28 ml) was treated with methyl dithiopropionate[5] (996 mg, 8.28 mmol) and kept at ambient temperature for 18 h. It was then concentrated in vacuo. The residue was mixed with saturated NaHCO$_3$ and extracted with CH$_2$Cl$_2$. The extract was dried (MgSO$_4$) and concentrated. Chromatography of the residue on silica gel with 2.5% MeOH-0.25% NH$_4$OH—CH$_2$Cl$_2$ and crystallization of the product first from EtOAc and then EtOH gave 727 mg of 50: mp 160° C.; $^1$H NMR [300 MHz, (CD$_3$)$_2$SO] δ 1.13 (t, 3H), 2.35 (s, 4H), 2.57 (q, 2H), 2.73 (m, 2H), 2.90, 3.00 (s, s, 4H), 3.22 (m, 2H), 3.55 (m, 8H), 3.66 (s, 2H), 3.79 (m, 1H), 3.90 (m, 2H), 4.12 (t, 1H), 4.93 (m, 1H), 7.07 (t, 1H), 7.16 (d, 1H), 7.46 (m, 3H), 7.93 (d, 2H), 10.31 (s, 1H); MS (FAB) m/z 626.3 (M+H$^+$), 260.2, 204.2, 100.1, 86.1; IR (drift) 3250, 1743, 1683, 1647 cm$^{-1}$. Anal. calcd for C$_{32}$H$_{40}$FN$_5$O$_5$S: C, 61.42; H, 6.44; N, 11.19. Found: C, 61.26; H, 6.48; N, 11.12.

Example 17

N-({(5S)-3-[3-Fluoro-4-(4-{4-[4-(4-morpholinylmethyl)phenyl]-4--oxobutanoyl}-1-piperazinyl)phenyl]-2-oxo-1,3-oxazolidin-5-yl}methyl)acetamide (55)

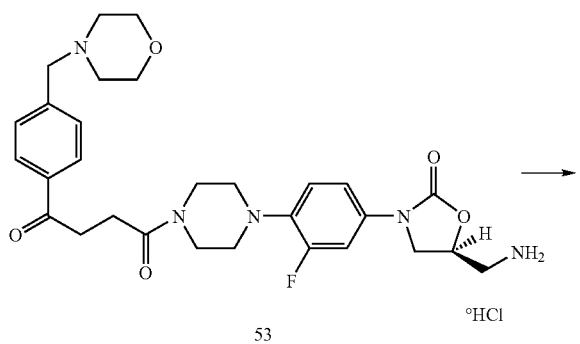

-continued

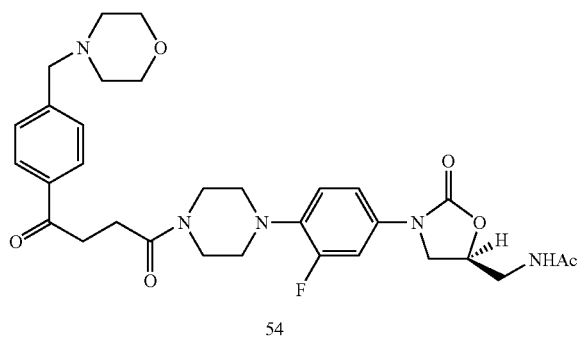

54

A stirred mixture of 53 (about 2.07 mmol), triethylamine (2.3 ml, 16.6 mmol), CH$_2$Cl$_2$ (21 ml) and THF (21 ml) was treated with acetyl chloride (270 mg, 3.11 mmol) and kept at ambient temperature for 18 h. It was concentrated in vacuo and the residue was mixed with saturated NaHCO$_3$ and extracted with CH$_2$Cl$_2$. The extract was dried (MgSO$_4$) and concentrated. Chromatography of the residue on silica gel with mixtures of MeOH—NH$_4$OH—CH$_2$Cl$_2$ containing 2.5–10% MeOH and 0.25–1% NH$_4$OH gave the product which was crystallized from EtOH to give 835 mg of 55: mp 178–179° C.; $^1$H NMR [300 MHz, (CD$_3$)$_2$SO] δ 1.82 (s, 3H), 2.34 (m, 4H), 2.73 (t, 2H), 2.90 3.00 (s, s, 4H), 3.22 (t, 2H), 3.39 (t, 2H), 3.55 (m, 8H), 3.66 (m, 3H), 4.07 (t, 1H), 4.69 (m, 1H), 7.07 (t, 1H), 7.17 (dd, 1H), 7.46 (m, 3H), 7.93 (d, 2H), 8.21 (t, 1H), Example 18

N-({(5S)-3-[3-Fluoro-4-(4-{4-[4-(4-morpholinylmethyl)phenyl]-4-oxobutanoyl}-1-piperazinyl)phenyl]-2-oxo-1,3-oxazolidin-5-yl}methyl)cyclopropanecarbothioamide (56)

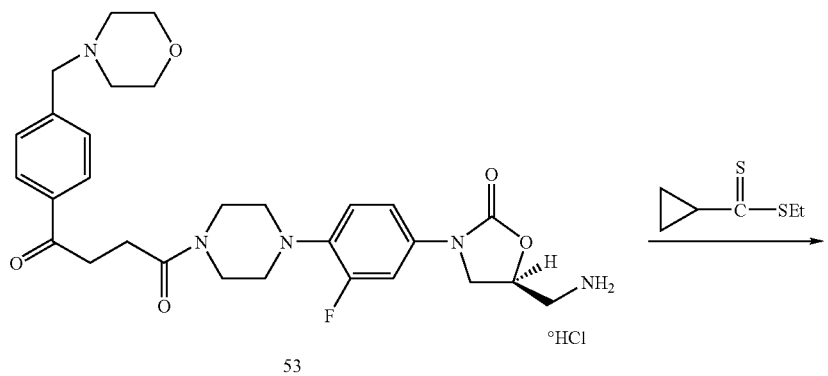

53

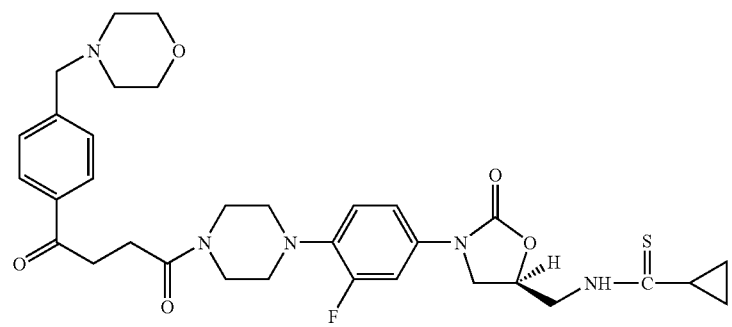

56

A stirred solution of 53 (about 2.07 mmol) and triethylamine (2.3 ml, 16.6 mmol) in MeOH (28 ml) was treated with ethyl cyclopropanecarbodithioate (1.21 g, 8.28 mmol), kept at ambient temperature for 18 h and concentrated in vacuo. A mixture of the residue in saturated NaHCO$_3$ was extracted with CH$_2$Cl$_2$. The extract was dried (MgSO$_4$) and concentrated. Chromatography of the residue on silica gel with 2.5% MeOH-0.25% NH$_4$OH—CH$_2$Cl$_2$ and crystallization of the product first from EtOAc and then from EtOH gave 713 mg of 56: mp 173–174° C.; $^1$H NMR [300 MHz, (CD$_3$)$_2$SO] δ 0.84 (m, 2H), 1.02 (m, 2H), 2.15 (m, 1H), 2.35 (m, 4H), 2.73 (t, 2H), 2.90, 3.00 (s, s, 4H), 3.22 (t, 2H), 3.55 (m, 8H), 3.66 (s, 2H), 3.79 (dd, 1H), 3.94 (m, 2H), 4.12 (t, 1H), 4.93 (m, 1H), 7.07 (t, 1H), 7.18 (dd, 1H), 7.44 (d, 2H), 7.50 (dd, 1H), 7.93 (d, 2H), 10.47 (s, 1H).

Example 19

N-[((5S)-3-{3-Fluoro-4-[4-(4-{4-[(methylamino)methyl]phenyl}-4-oxobutanoyl)piperazin-1-yl]phenyl]-2-oxo-1,3-oxazolidin-5-yl)methyl]acetamide (60)

Step 1:

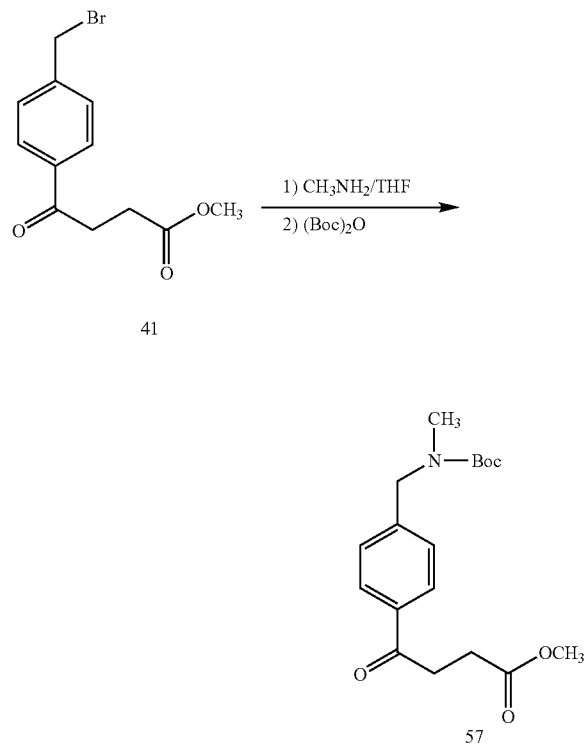

a) A solution of 4 (1.00 g of an 85:15 mixture of 4 and 5) in THF (10 ml) was added to a stirred 2M solution of methylamine in THF (35 ml), kept at ambient temperature for 1 h and concentrated in vacuo. A solution of the residue in dilute HCl (10 ml) was washed with Et$_2$O and then made alkaline with solid NaHCO$_3$.

b) The mixture of step a) was treated with THF (25 ml), cooled in an ice bath and with stirring, treated with di-(tert-butyl)dicarbonate (998 mg, 4.58 mmol). It was allowed to warm slowly to ambient temperature and stand for 4 h. It was then extracted with Et$_2$O. The extract was dried (MgSO$_4$) and concentrated. Chromatography of the residue on silica gel with 25% EtOAc-heptane gave 816 mg of 57: $^1$H NMR [300 MHz, (CD$_3$)$_2$SO] δ 1.35, 1.42 (s, s, 9H), 2.63 (t, 2H), 2.77 (s, 3H), 3.28 (t, 2H), 3.57 (s, 3H), 4.43 (s, 2H), 7.33 (d, 2H), 7.95 (d, 2H).

Step 2:

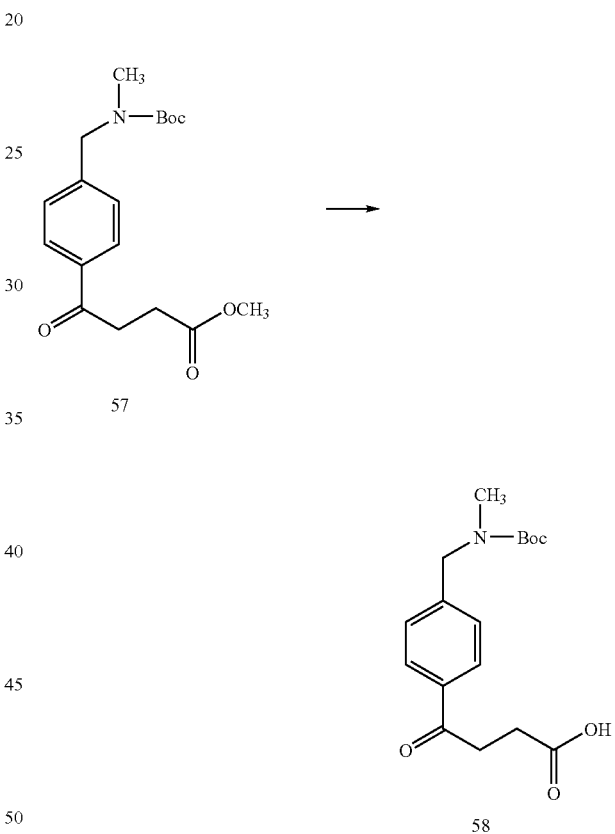

A stirred mixture of 53 (767 mg, 2.29 mmol), 1N LiOH (2.8 ml) and MeOH (15 ml) was kept at ambient temperature for 5 h, treated with additional LiOH (1 ml) and water (2.8 ml), kept at ambient temperature for 2h and concentrated in vacuo to remove MeOH. It was cooled in an ice bath, acidified with 1N HCl (4 ml) and extracted with CH$_2$Cl$_2$. The extract was washed with brine, dried (MgSO$_4$) and concentrated to give 613 mg of 15, a white foam: $^1$H NMR [300 MHz, (CD$_3$)$_2$SO) δ 1.35, 1.41 (s, s, 9H), 2.56 (t, 2H), 2.76 (s, 3H), 3.22 (t, 2H), 4.43 (s, 2H), 7.33 (d, 2H), 7.95 (d, 2H), 12.12. (s, 1H).

Step 3:

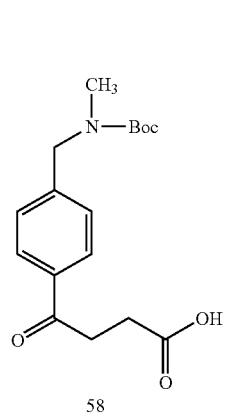

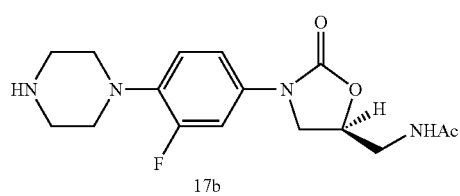

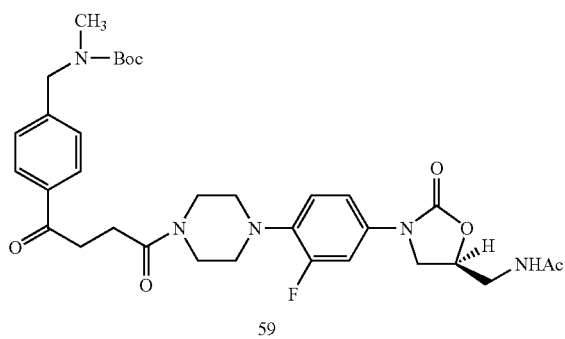

An ice cold, stirred mixture of 15 (715 mg, 2.22 mmol), 16 (748 mg, 2.22 mmol), HOBT (330 mg, 2.44 mmol) and DMF (18 ml) was treated with EDC (936 mg, 4.88 mmol) and allowed to warm slowly to ambient temperature and stand for 18 h. It was concentrated in vacuo and the residue was chromatographed on silica gel with 4% MeOH-0.4% NH$_4$OH—CH$_2$Cl$_2$ to give 878 mg of 59, a white solid: $^1$H NMR [300 MHz, (CD$_3$)$_2$SO] δ 1.35, 1.42 (s,s, 9H), 1.81 (s, 3H), 2.73 (m, 2H), 2.77 (s, 3H), 2.89, 2.99 (s, s, 4H), 3.22 (m, 2H), 3.38 (m, 2H), 3.57 (s, 2H), 3.66 (m, 3H), 4.07 (t, 1H), 4.43 (s, 2H), 4.69 (m, 1H), 7.07 (t, 1H), 7.15 (d, 1H), 7.33 (d, 2H), 7.48 (d, 1H), 7.96 (d, 2H), 8.24 (m, 1H): MS (EI) m/z 639.2 (M$^+$), 335.1, 307.1, 306.1, 249.1, 248.1, 204.1; IR (drift) 3315, 1743, 1692, 1646 cm$^{-1}$.

Step 4:

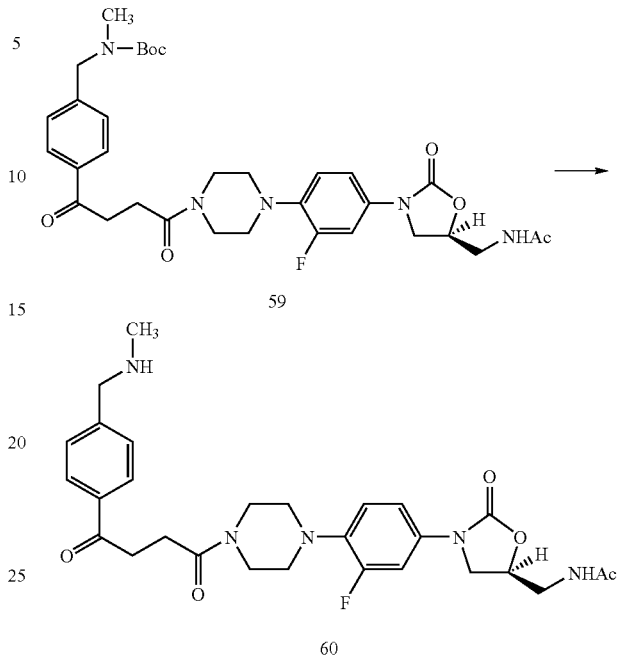

Solid 59 (616 mg, 0.963 mmol) was cooled in an ice bath and treated with 4N HCl in dioxane (10 ml). The stirred mixture was kept in the ice bath for 1 h and at ambient temperature for 30 min. It was then concentrated in vacuo. The residue was mixed with water (10 ml) and saturated NaHCO$_3$ (10 ml) and extracted with CH$_2$Cl$_2$. The extract was dried (MgSO$_4$) and concentrated. Crystallization of the residue from CH$_2$Cl$_2$-MeOH-hexane gave 427 mg of 60: $^1$H NMR [300 MHz, (CD$_3$)$_2$SO] δ 1.81 (s, 3H), 2.24 (s, 3H), 2.72 (m, 2H), 2.89, 2.99 (s, s, 4H), 3.22 (t, 2H), 3.32 (broad s), 3.38 (t, 2H), 3.57 (s, 2H), 3.68 (m, 5H), 4.07 (t, 1H), 4.69 (m, 1H), 7.07 (t, 1H), 7.17 (dd, 1H), 7.46 (m, 3H), 7.92 (d, 2H), 8.23 (t, 1H).

Example 20

N$^1$-(4-{4-[4-(4-{(5S)-5-[(Acetylamino)methyl]-2-oxo-1,3-oxazolidin-3-yl}-2-fluorophenyl)-piperazin-1-yl]-4-oxobutanoyl}benzyl-N$^1$-methylglycinamide (65)

Step 1:

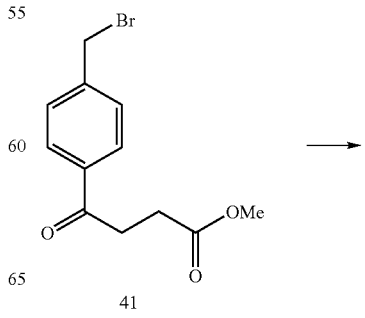

-continued

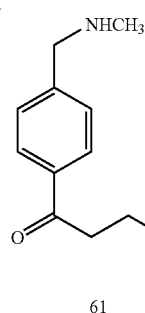

61

A solution of 41 (1.00 g of an 85:15 mixture of 41 and 42) in THF (10 ml) was added during 10 min to a stirred 2M solution of methylamine in THF (35 ml), kept at ambient temperature for 1 h and concentrated in vacuo. A solution of the residue in dilute HCl was washed with $Et_2O$ and then made alkaline with solid $NaHCO_3$. It was extracted with $CH_2Cl_2$. The extract was dried ($MgSO_4$) and concentrated to give 538 mg of 41: $^1$H NMR [300 MHz, $(CD_3)_2SO$] δ 2.23 (s, 3H), 2.63 (t, 2H), 3.27 (t, 2H), 3.57 (s, 3H), 3.69 (s, 2H), 7.44 (d, 2H), 7.91 (d, 2H); MS (EI) m/z 235.1 (M$^+$), 205.1, 204.1, 1.62.1, 148.1, 120.0; IR (drift) 3331, 1738, 1685 cm$^{-1}$.

Step 2:

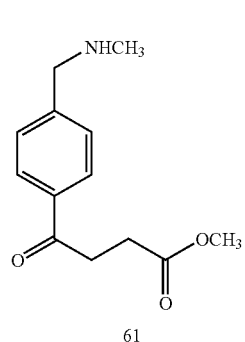

61

+ BocNHCH$_2$COOH ⟶

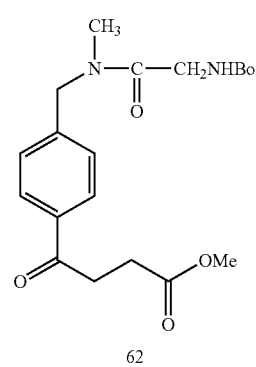

62

A stirred, ice cold solution of 61 (509 mg, 2.16 mmol), N-t-Boc-glycine (378 mg, 2.16 mmol) and HOBT (321 mg, 2.38 mmol) in DMF (18 ml) was treated with EDC (912 mg, 4.76 mmol), warmed slowly to ambient temperature and kept for 18 h. It was concentrated in vacuo and the residue was mixed with water and extracted with $Et_2O$. The extract was dried ($MgSO_4$) and concentrated. Chromatography of the residue on silica gel with 40–50% EtOAc-heptane gave 765 mg of 62, an oil: $^1$H NMR [300 MHz, $(CD_3)_2SO$] δ 1.34, 1.37 (s, s, 9H), 2.63 (t, 2H), 2.81, 2.90 (s, s, 3H), 3.28 (t, 2H), 3.57 (s, 3H), 3.76, 3.84 (d, d, 2H), 4.56, 4.62 (s, s, 2H), 6.80 (m, 1H), 7.33 (d, 2H), 7.92, 7.98 (d, d, 2H); IR (drift) 3419, 3362, 1737, 1714, 1687, 1658 cm$^{-1}$.

Step 3:

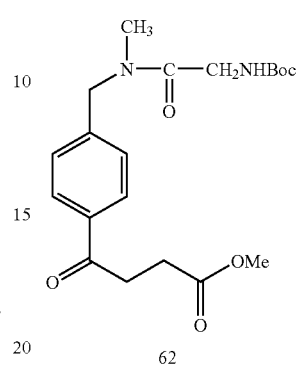

62

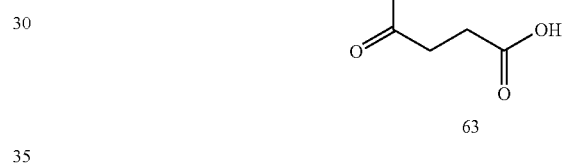

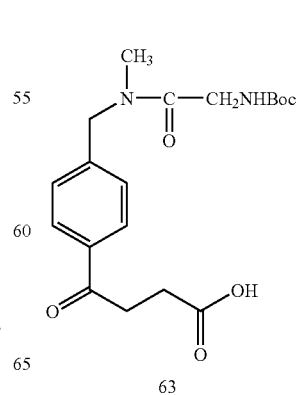

63

A stirred mixture of 62 (701 mg, 1.79 mmol) and MeOH (12 ml) was treated with 1N LiOH (2.2 ml) and kept at ambient temperature for 5 h. Additional water (2.2 ml) and LiOH (1 ml) were added and the mixture was kept at ambient temperature for about 6 h and concentrated to remove MeOH. This mixture was cooled in an ice bath, acidified with 1N HCl and extracted with $CH_2Cl_2$. The extract was washed with brine, dried ($MgSO_4$) and concentrated to give 616 mg of 63, a white foam: $^1$H NMR [300 MHz, $(CD_3)_2SO$] δ 1.34, 1.37 (s, s, 9H), 2.55 (t, 2H), 2.80, 2.90 (s, s, 3H), 3.21 (t, 2H), 3.77, 3.84 (d, d, 2H), 4.56, 4.62 (s, s, 2H), 6.81 (m, 1H), 7.33 (d, 2H), 7.92, 7.97 (d, d, 2H).

Step 4:

+

63

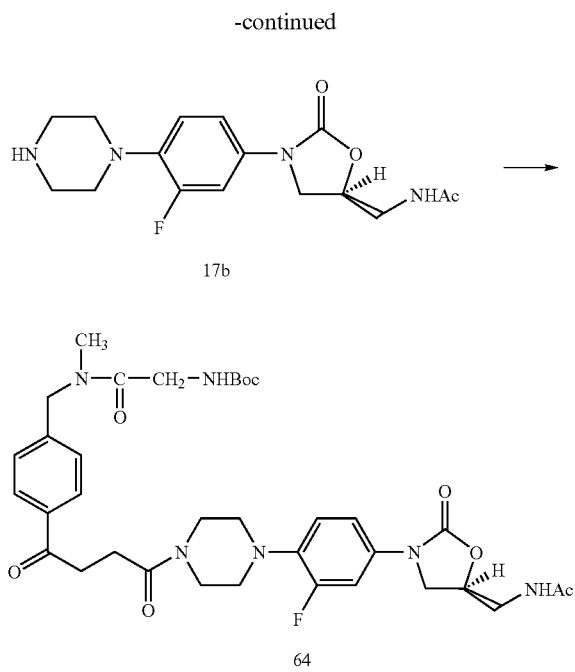

An ice cold, stirred mixture of 63 (555 mg, 1.47 mmol), 17b (493 mg, 1.47 mmol), HOBT (219 mg, 1.62 mmol) and DMF (12 ml) was treated with EDC (620 mg, 3.23 mmol), allowed to warm slowly to ambient temperature and kept for 18 h. It was concentrated in vacuo and the residue was chromatographed on silica gel with 5% MeOH-0.5% NH$_4$OH—CH$_2$Cl$_2$. The product was crystallized from CH$_2$Cl$_2$-MeOH-hexane to give 756 mg of 64: $^1$H NMR [300 MHz, (CD$_3$)$_2$SO] δ 1.34, 1.37 (s, s, 9H), 1.81 (s, 3H), 2.73 (m, 2H), 2.81, 2.90 (s, s, 3H), 2.90, 2.99 (s, s, 4H), 3.21 (m, 2H), 3.38 (t, 2H), 3.57, 3.66 (s, s, 4H), 3.68 (m, 1H), 3.78, 3.84 (d, d, 2H), 4.07 (t, 1H), 4.57, 4.63 (s, s, 2H), 4.70 (m, 1H), 6.81 (m, 1H), 7.07 (t, 1H), 7.15 (dd, 1H), 7.33 (d, 2H), 7.49 (dd, 1H), 7.93, 7.98 (d, d, 2H), 8.23 (t, 1H); MS (FAB) m/z 697 (M+H$^+$), 696 (M$^+$), 597.3, 337.1, 261.1, 204.1; HRMS (FAB) calcd for C$_{35}$H$_{45}$FN$_6$O$_8$ (M$^+$) 696.3282, found 696.3293.

Step 5:

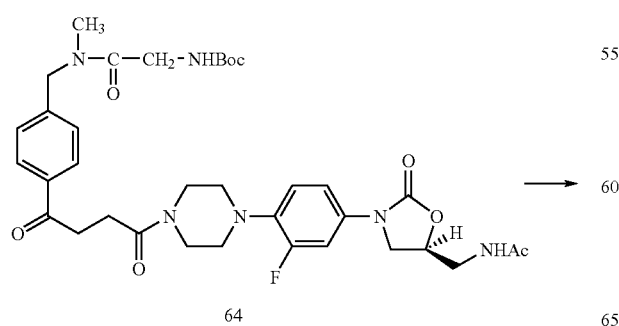

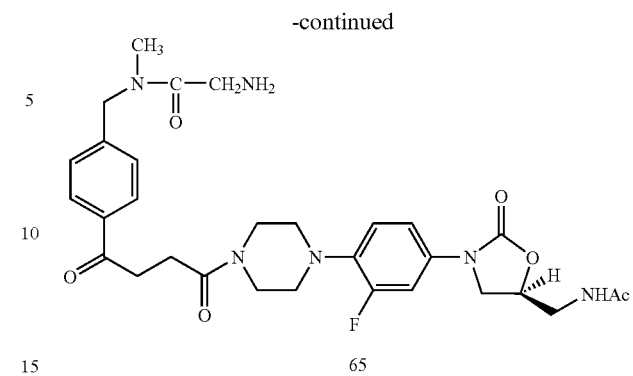

Solid 64 (400 mg, 0.574 mmol) was cooled in an ice bath and treated with 4N HCl in dioxane (10 ml). The stirred mixture was kept in the ice bath for 1 h and at ambient temperature for 30 min and then concentrated in vacuo. A mixture of the residue in water (10 ml) and saturated NaHCO$_3$ (10 ml) was extracted with CH$_2$Cl$_2$. The extract was dried (MgSO$_4$) and concentrated. Crystallization of the residue from CH$_2$Cl$_2$-EtOAc-hexane gave 281 mg of 65: MS (EI) m/z 596 (M$^+$), 552.3, 510.3, 495.3, 336.2, 306.2, 294.2, 250.3, 151.1; IR (drift) 3541, 3372, 3326, 1743, 1686, 1646 cm$^{-1}$. Anal. calcd for C$_{30}$H$_{37}$FN$_6$O$_6$: C, 60.39; H, 6.25; N, 14.09. Found: C, 60.08; H, 6.88; N, 13.75.

Example 21

N$^1$-(4-{4-[4-(4-{(5S)-5-[(Acetylamino)methyl]-2-oxo-1,3-oxazolidin-3-yl}-2-fluorophenyl)piperazin-1-yl]-4-oxobutanoyl}benzyl)-N$^1$,N$^2$,N$^2$-trimethylglycinamide (68)

Step 1:

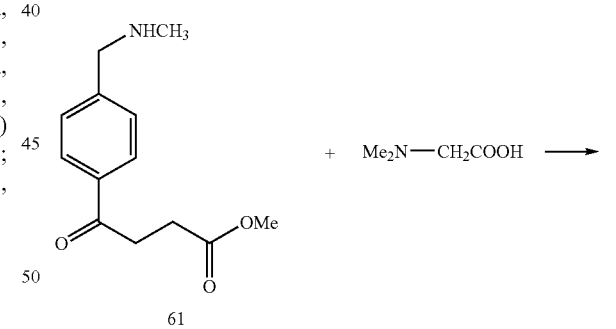

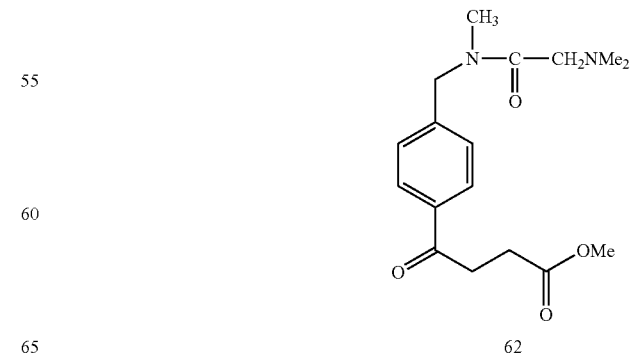

A stirred, ice cold mixture of 61 (509 mg, 2.16 mmol), HOBT (321 mg, 2.38 mmol), N,N-dimethylglycine (222 mg, 2.16 mmol) and DMF (18 ml) was treated with EDC (912 mg, 4.76 mmol) and allowed to warm slowly to ambient temperature. It was kept at this temperature for 18 h and concentrated in vacuo. The residue was chromatographed on silica gel with 4% MeOH-0.4% NH$_4$OH—CH$_2$Cl$_2$ to give 578 mg of 62, a yellow oil: $^1$H NMR [300 MHz, (CD$_3$)$_2$SO] δ 2.15, 2.20 (s, s, 6H), 2.63 (t, 2H), 2.74, 2.97 (s, s, 3H), 3.08, 3.13 (s, s, 2H), 3.27 (t, 2H), 3.57 (s, 3H), 4.54, 4.74 (s, s, 2H), 7.34 (m, 2H), 7.95 (m, 2H); MS (EI) m/z 320.1 (M$^+$), 289.1, 205.0, 146.0, 119.0, 118.0.

Step 2:

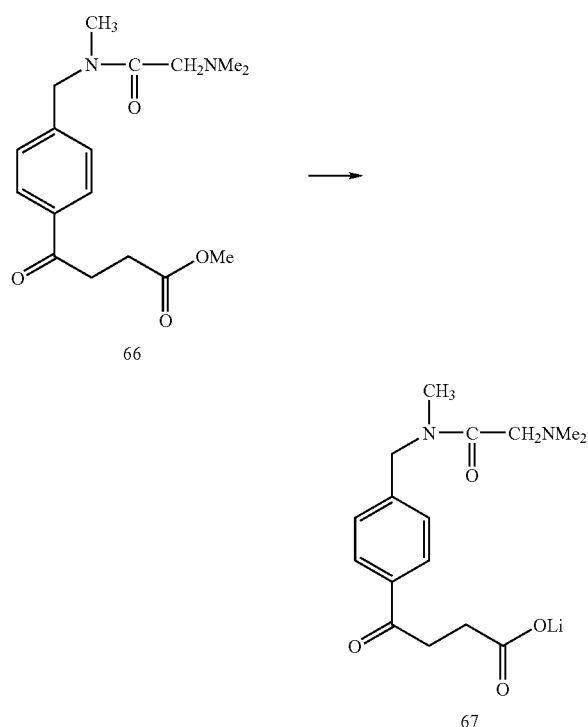

A stirred mixture of 66 (541 mg, 1.69 mmol), 1M lithium hydroxide (2.0 ml) and MeOH (11 ml) was kept at ambient temperature for 18 h, treated with additional LiOH (0.5 ml) and kept ambient temperature for 8 h. It was concentrated to dryness in vacuo and the residue was triturated with Et$_2$O to give 67 a white solid: $^1$H NMR [300 MHz, (CD$_3$)$_2$SO] δ 2.15, 2.19 (s, s, 6H), 2.24 (t, 3H), 2.73, 2.95 (s, s, 3H), 3.07 (m, 4H), 3.39 (s, 3H), 4.52, 4.72 (s, s, 2H), 7.29 (m, 2H), 7.89 (m, 2H); MS (FAB) m/z 313 (M+H$^+$); HRMS (FAB) calcd for C$_{16}$H$_{22}$LiN$_2$O$_4$ (M+H$^+$) 313.1739, found 313.1739.

Step 3:

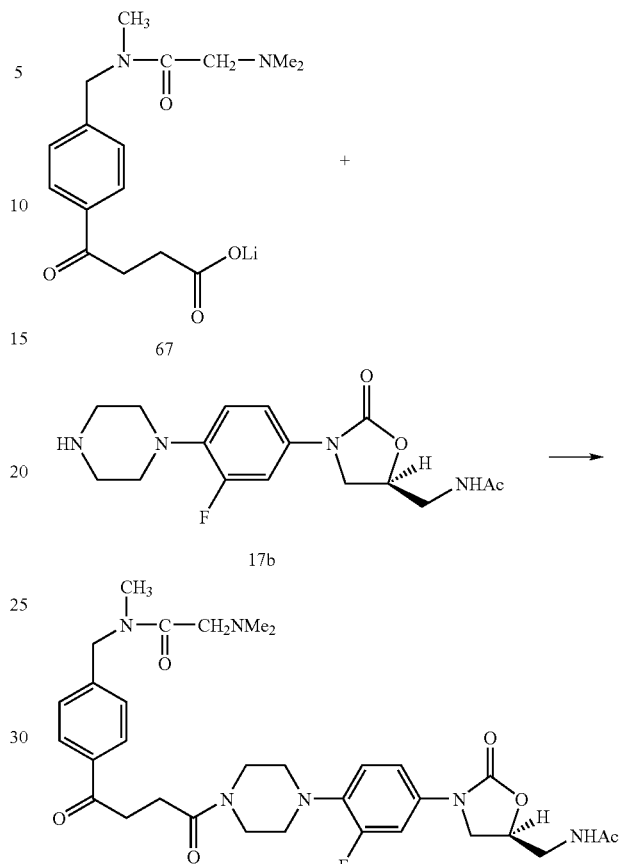

A stirred, ice cold mixture of 67 (468 mg, 1.50 mmol), 17b (505 mg, 1.50 mmol), HOBT (223 mg, 1.65 mmol) and DMF (12 ml) was treated with EDC (633 mg, 3.30 mmol) and allowed to warm slowly to ambient temperature. It was kept at this temperature for 24 h and concentrated in vacuo. The residue was mixed with water and extracted with EtOAc. The extract was dried (MgSO$_4$) and concentrated.

Chromatography of the residue on silica gel with 5% MeOH-0.5% NH$_4$OH—CHCl$_3$ and crystallization of the product from EtOAc-CH$_2$Cl$_2$-hexane gave 638 mg of 68, a white solid: MS (EI) m/z 580.4, 565.3, 552.3, 335.2, 306.2; MS (CI) m/z 625 (M+H$^+$); IR (drift) 3306, 1743, 1688, 1645 cm$^{-1}$. Anal. calcd for C$_{32}$H$_{41}$FN$_6$O$_6$: C, 61.52; H, 6.61; N, 13.45. Found: C, 61.10; H, 6.71; N, 13.32.

Example 22

N$^1$-(4-{4-[4-(4-{(5S)-5-[(Acetylamino)methyl]-2-oxo-1,3-oxazolidin-3-yl}-2-fluorophenyl)piperazin- 1-yl]-4-oxobutanoyl}benzyl)-N²,N²-dimethylglyci-
namide (75)

Step 1:

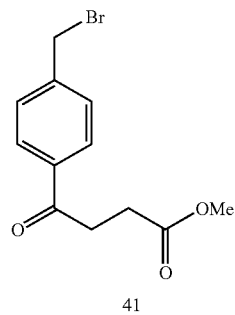  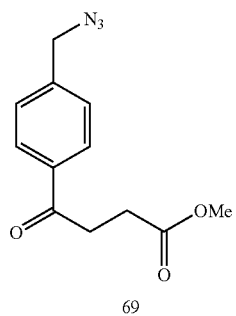

A stirred mixture of 41 (16.7 g of a 9:1 mixture of 41 and 42), sodium azide (22.3 g, 343 mmol) and DMF (84 ml) was warmed at 40–45° C. for 4 h and diluted with EtOAc (200 ml). It was washed with water, dried (MgSO₄) and concentrated. Chromatography of the residue on silica gel with 10–30% EtOAc-5% CH₂Cl₂-heptane gave 12.1 g of 69: mp 29–30° C.; ¹H NMR (300 MHz, CDCl₃) δ 2.77 (t, 2H), 3.32 (t, 2H), 3.71(s, 3H), 4.42 (s, 2H), 7.42 (d, 2H), 8.00 (d, 2H); MS (EI) m/z 247.0 (M⁺), 216.0, 205.0, 160.0, 132.0, 104.0; IR (drift) 2103, 1735, 1686 cm⁻¹.

Step 2:

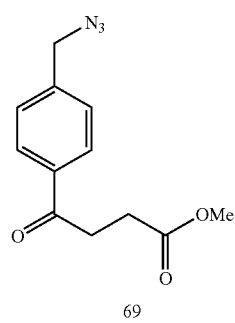 

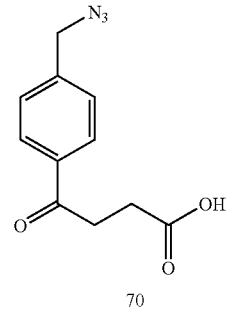

A stirred mixture of 23 (12.0 g, 48.5 mmol) and MeOH (320 ml) was treated with 1N LiOH (53.4 ml) and kept at ambient temperature for 21 h. Additional LiOH (2.6 ml) was added and the mixture was kept at ambient temperature for 4 h and concentrated in vacuo to remove MeOH. The resulting aqueous solution was acidified with 1N HCl and extracted with CH₂Cl₂. The extract was dried (MgSO₄) and concentrated. Trituration of the residue with 10% EtOAc-heptane (100 ml) gave 10.04 g of 24: ¹H NMR (300 MHz, CDCl₃) δ 2.82 (t, 2H), 3.32 (t, 2H), 4.43 (s, 2H), 7.42 (d, 2H), 8.00 (d, 2H).

Step 3:

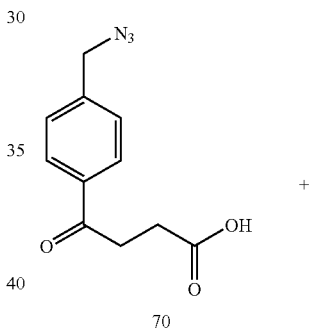

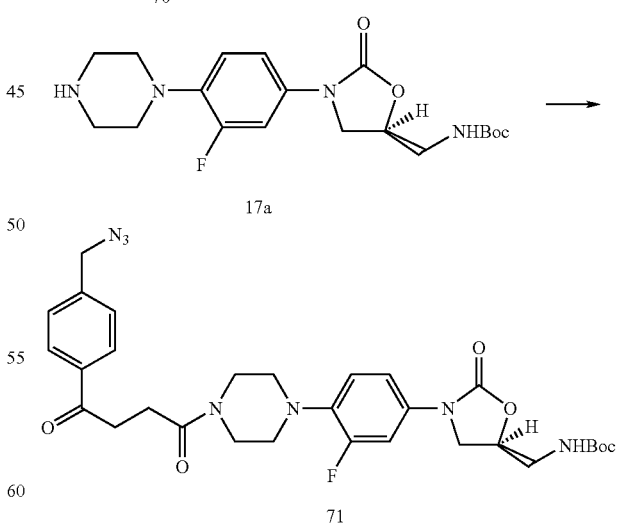

An ice cold, stirred mixture of 70 (10.0 g, 42.9 mmol), 17a (16.92 g, 42.9 mmol), HOBT (6.38 g, 47.2 mmol), and DMF (377 ml) was treated with EDC (18.1 g, 94.4 mmol) and kept for 4 h. It was diluted with water (1 L) and mixed with 1:1 Et$_2$O-heptane (500 ml). The solid was collected by filtration, washed with water and heptane and dried. Recrystalization from CH$_2$Cl$_2$-heptane gave 20.0 g of 71: mp 160–160.5° C.; $^1$H NMR [300 MHz, (CD$_3$)$_2$SO] δ 1.34 (s, 9H), 2.74 (t, 2H), 2.90, 3.00 (s, s, 4H), 3.24 (m, 4H), 3.58, 3.66 (s, s, 4H), 3.74 (dd, 1H), 4.07 (t, 1H), 4.56 (s, 2H), 4.66 (m, 1H), 7.07 (t, 1H), 7.17 (m, 2H), 7.49 (m, 3H), 8.00 (d, 2H); MS (EI) m/z 609.2 (M$^+$), 308.1, 165.0, 153.1, 138.0, 137.0; IR (drift) 3376, 2132, 2095, 1788, 1732, 1685, 1652 cm$^{-1}$.

Step 4:

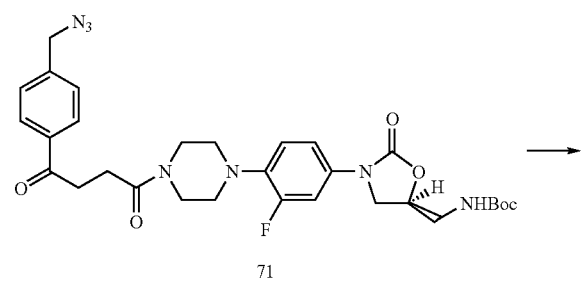

71

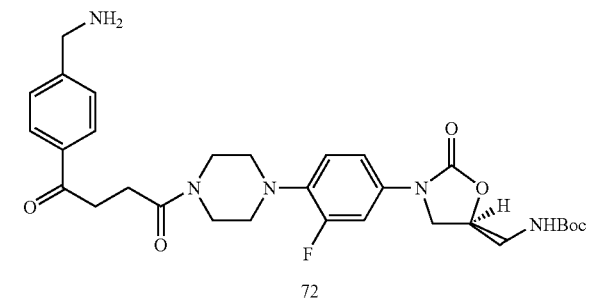

72

A mixture of 71 (4.97 g, 8.15 mmol), 10% palladium-on-carbon catalyst (1.25 g) and THF (300 ml) was hydrogenated at an initial pressure of 45 psi for 1.5 h. The flask was evacuated and refilled with hydrogen (45 psi) and the reaction was continued for 2 h. The mixture was filtered through celite; the solid was washed well with THF and the filtrate was concentrated in vacuo to give 4.95 g of 72, a white foam: IR (drift) 3320, 1753, 1710, 1684, 1645 cm$^{-1}$.

Step 5:

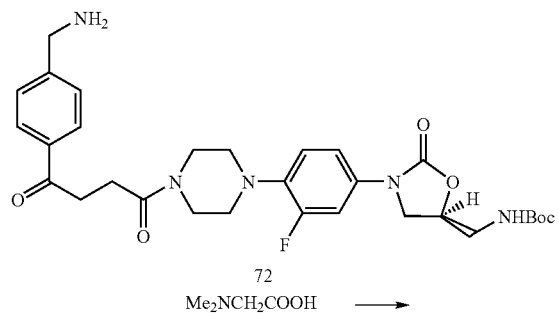

72
Me$_2$NCH$_2$COOH →

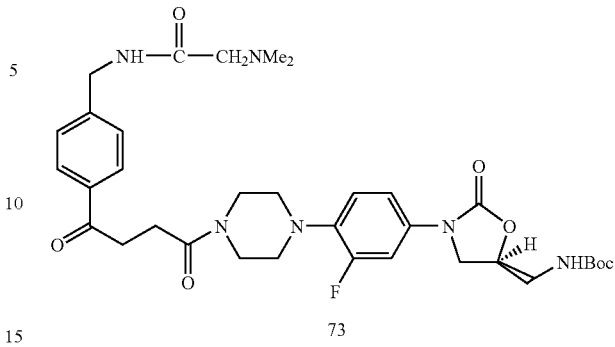

73

An ice cold, stirred mixture of 72 (2.00 g, 3.43 mmol), N,N-dimethylglycine (354 mg, 3.43 ml), HOBT (510 mg, 3.77 mmol) and DMF (30 ml) was treated with EDC (1.45 g, 7.55 mmol) and kept for 3 h. It was then diluted with water (50 ml) and extracted (emulsions) with CH$_2$Cl$_2$. The extract was dried (MgSO$_4$) and concentrated to dryness in vacuo. Chromatography of the residue on silica gel with 5% MeOH—CH$_2$Cl$_2$ gave 473 mg of 73: $^1$H NMR [300 MHz, (CD$_3$)$_2$SO] δ 1.33 (s, 9H), 2.21 (s, 6H), 2.72 (m, 2H), 2.89, 2.99 (s, s, 4H), 2.93 (s, 2H), 3.23 (m, 4H), 3.57, 3.66 (s, s, 4H), 3.74 (dd, 1H), 4.06 (t, 1H), 4.33 (d, 2H), 4.67 (m, 1H), 7.07 (t, 1H), 7.18 (m, 2H), 7.37 (d, 2H), 7.47 (dd, 1H), 7.92 (d, 2H), 8.41 (t, 1H).

Step 6:

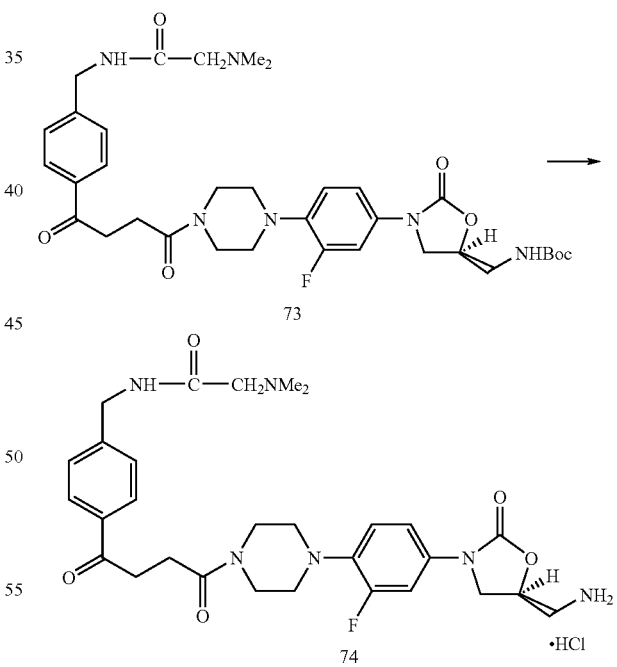

73

74 ·HCl

Solid 73 (356 mg, 0.532 mmol) was cooled in an ice bath and treated with 4N HCl in dioxane (10 ml). The stirred mixture was kept in the ice bath for 2 h and at ambient temperature for 1 h and then concentrated in vacuo. Four portions of CH$_2$Cl$_2$ (25 ml) were added to the residue with concentration after each addition to give 451 mg of 74, as an off-white solid: $^1$H NMR [300 MHz, (CD$_3$)$_2$SO] δ 2.73 (m, 2H), 2.79, 2.81 (s, s, 6H), 2.90, 3.00 (s, s, 4H), 3.22 (m, 4H), 3.54, 3.66 (s, s, 4H), 3.86 (dd, 1H), 4.01 (d, 2H), 4.14 (t, 1H), 4.41 (d, 2H), 4.95 (m, 1H), 6.22 (broad s, 4H), 7.15 (m, 2H), 7.42 (d, 2H), 7.48 (dd, 1H), 7.94 (d, 2H), 8.49 (s, 3H), 9.36 (t, 1H), 10.02 (broad s, 1H).

Step 7:

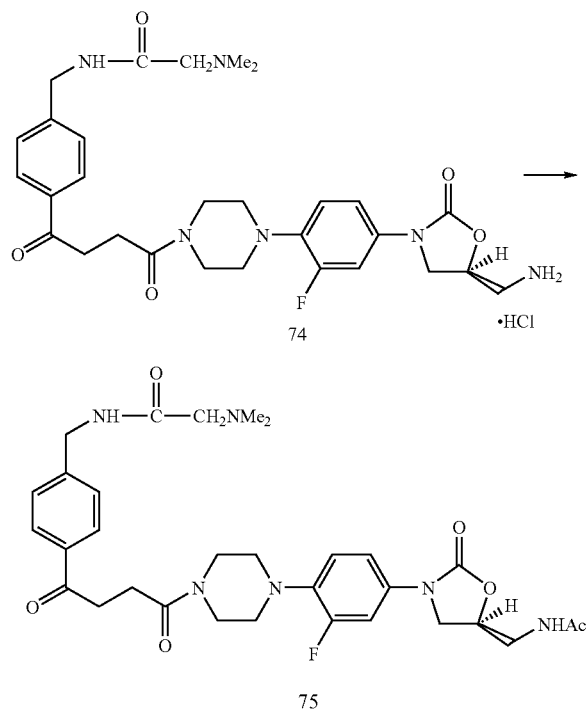

A stirred, ice cold solution of 74 (about 0.357 mmol) in pyridine (8 ml) was treated with acetic anhydride (47 μL, 0.497 mmol) and allowed to warm to ambient temperature during 1 h. It was kept at ambient temperature for 1 h and concentrated in vacuo. Chromatography of the residue on silica gel first with 5% MeOH-0.5% NH$_4$OH—CH$_2$Cl$_2$ and then with 2.5% MeOH-0.5% NH$_4$OH—CH$_2$Cl$_2$ and crystallization of the product from MeOH gave 56 mg of 75: $^1$H NMR [300 MHz, (CD$_3$)$_2$SO] δ 1.81 (s, 3H), 2.20 (s, 6H), 2.72 (t, 2H), 2.91 (m, 4H), 2.99 (s, 2H), 3.21 (t, 2H), 3.38 (t, 2H), 3.57 (s, 2H), 3.66 (m, 3H), 4.07 (t, 1H), 4.33 (d, 2H), 4.69 (m, 1H), 7.07 (t, 1H) 7.16 (dd, 1H), 7.37 (d, 2H), 7.48 (dd, 1H), 7.91 (d, 2H), 8.23 (t, 1H), 8.40 (t, 1H); MS (EI) m/z 610.2 (M$^+$), 335.1, 306.1, 106.1; HRMS calcd for C$_{31}$H$_{40}$FN$_6$O$_6$ (M+H$^+$) 611.2993, found 611.2996.

Example 23

N$^1$-(4-{4-[4-[2-Fluoro-4-{(5S)-2-oxo-5-[(propanethiolylamino)methyl]-1,3-oxazolidin-3-yl}phenyl)piperazin-1-yl]-4-oxobutanoyl}benzyl)-N$^2$,N$^2$-dimethylglycinamide (76)

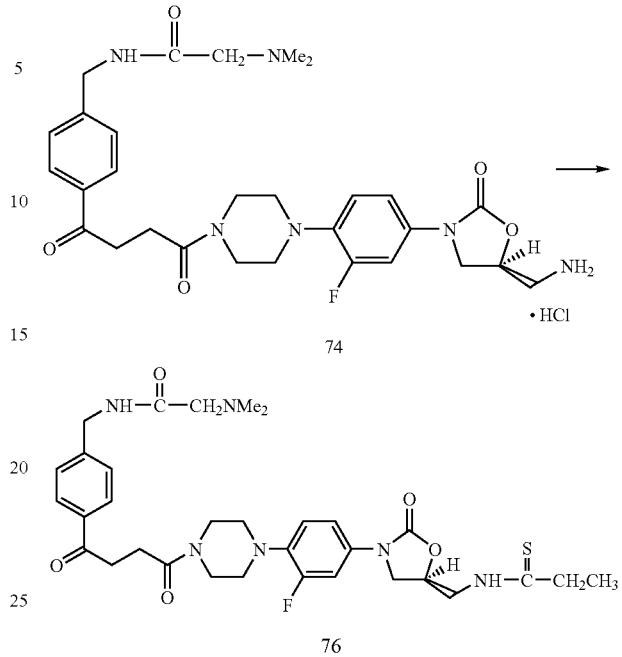

A stirred solution of 74 (270 mg, about 0.318 mmol) in MeOH (15 ml) was cooled in an ice bath and treated with Et$_3$N (0.46 ml, 3.31 mmol) and ethyl dithiopropionate (111 mg, 0.828 mmol). It was kept at ambient temperature for 18 h, adsorbed on silica gel (2 g) and chromatographed on silica gel with 5% MeOH-0.5% NH$_4$OH—CH$_2$Cl$_2$. The product was crystallized from MeOH-acetone-Et$_2$O to give 130 mg of 76, a white solid: $^1$H NMR [300 MHz, (CD$_3$)$_2$SO] δ 1.12 (t, 3H), 2.57 (q, 2H), 2.73 (t, 2H), 2.80 (s, 6H), 2.89, 3.00 (s, s, 4H), 3.22 (t, 2H), 3.57, 3.66 (s, s, 4H), 3.80 (dd, 1H), 3.89 (m, 2H), 4.00 (s, 2H), 4.11 (t, 1H), 4.42 (d, 2H), 4.94 (m, 1H), 7.07 (t, 1H), 7.18 (dd, 1H), 7.42 (d, 2H), 7.48 (dd, 1H), 7.94 (d, 2H), 9.27 (t, 1H), 9.90 (s, 1H), 10.40 (t, 1H).

Example 24a (S)—N$^1$-(4-{4-[4-(2-Fluoro-4-{(5S)-2-oxo-5-[(propanethioylamino)methyl]-1,3-oxazolidin-3-yl}phenyl)piperazin-1-yl]-4-oxobutanoyl}benzyl)alaninamide (80)

Step 1:

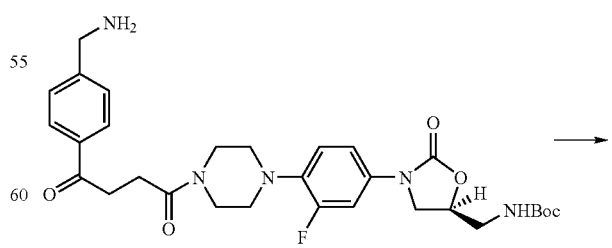

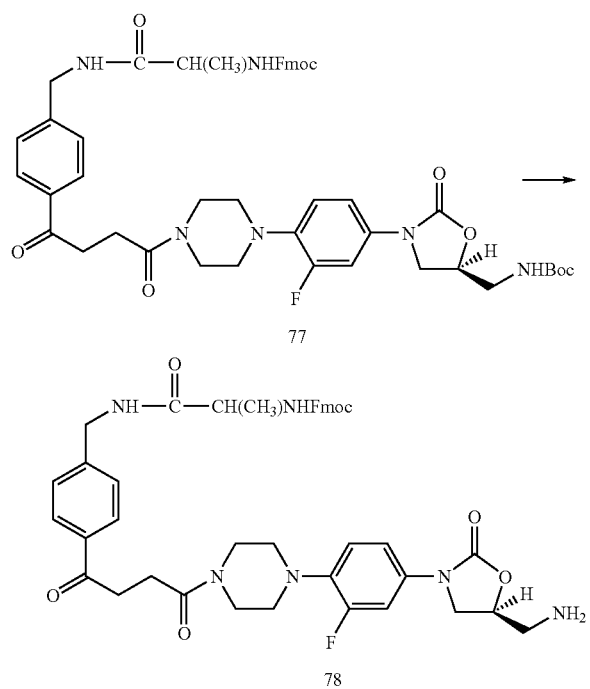

An ice cold, stirred solution of 72 (1.44 g, 2.46 mmol) and Hunig's base (0.48 ml, 2.71 mmol) in CH$_2$Cl$_2$ (25 ml) and THF (25 ml) was treated with N-Fmoc-L-alanyl chloride (894 mg, 2.71 mmol) and kept in the ice bath for 1 h. The solid mixture was mixed with additional CH$_2$Cl$_2$ (15 ml) and kept at ambient temperature for 18 h. It was then treated with about 20 ml of heptane and filtered to give 1.672 g of 29: $^1$H NMR [300 MHz, (CD$_3$)$_2$SO] δ 1.25 (d, 3H), 1.34 (s, 9H), 2.71 (t, 2H), 2.89, 2.99 (s, s, 4H), 3.23 (m, 4H), 3.57, 3.66 (s, s, 4H), 3.74 (dd, 1H), 4.06 (m, 2H), 4.24 (m, 3H), 4.34 (d, 2H), 4.66 (m, 1H), 7.07 (t, 1H), 7.18 (m, 2H), 7.35 (m, 6H), 7.48 (dd, 1H), 7.58 (d, 1H), 7.72 (m, 2H), 7.89 (m, 4H), 8.48 (t, 1H).

Step 2:

Solid 77 (940 mg, 1.07 mmol) was cooled in an ice bath and treated with 4N HCl in dioxane (10 ml). The mixture was stirred in the ice bath for 1 h and at ambient temperature for 1 h and concentrated in vacuo. The residue was mixed with four 25 ml portions of CH$_2$Cl$_2$ with concentration after each addition to give a white solid. A mixture of this material in saturated NaHCO$_3$ (20 ml) was extracted first with CH$_2$Cl$_2$ then with 5% MeOH—CH$_2$Cl$_2$ and finally with EtOAc. The extracts were dried and concentrated. Chromatography of the residue on silica gel with 5% MeOH-0.5% NH$_4$OH—CHCl$_3$ gave 562 mg of 78, a white solid: MS (ESI) m/z 777.4 (M+H$^+$), 577.1, 484.2; IR (drift) 3283, 1749, 1682, 1650, 1608 cm$^{-1}$.

Step 3:

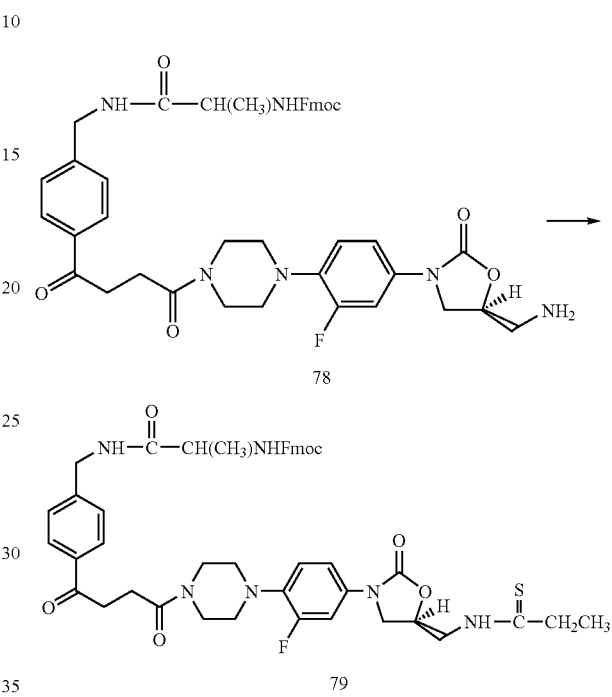

A stirred mixture of 78 (641 mg, 0.825 mmol), triethylamine (0.29 ml, 2.07 mmol), ethyl dithiopropionate (155 mg, 1.16 mmol), MeOH (15 ml) and CH$_2$Cl$_2$ (5 ml) was kept at ambient temperature for 3 h. Additional triethylamine (0.2 ml) and dithioester (100 mg) were added and the reaction was continued for an additional 2 h. The mixture was then mixed with CH$_2$Cl$_2$ (50 ml) and silica gel (2 g) and concentrated. Chromatography of the residue on silica gel with 2.5% MeOH—CH$_2$Cl$_2$ and trituration of the product with a mixture of EtOAc-MeOH—CH$_2$Cl$_2$-Et$_2$O gave 400 mg of 79, a white solid: MS (ESI) m/z 849.0 (M+H$^+$), 871.0 (M+Na$^+$), 887.0 (M+K$^+$); IR (drift) 3305, 1759, 1688, 1676, 1654, 1635 cm$^-$.

Step 4:

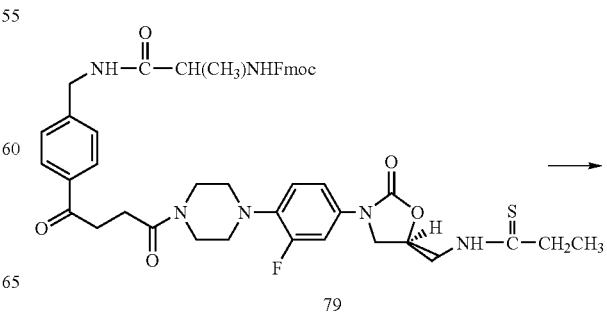

-continued

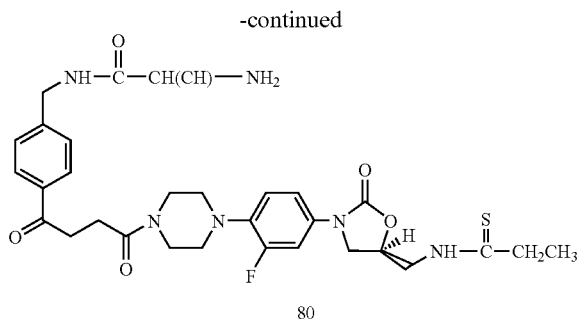
80

A stirred mixture of 79 (380 mg, 0.448 mmol), trisamine resin (400 mg, 1.6 mmol) and THF (100 ml) was refluxed for 5 d. Additional resin (250 mg) was added and the mixture was refluxed for 8 h and filtered. The filtrate was treated with silica gel (2 g) and concentrated. Chromatography of the residue on silica gel with 5% MeOH-0.5% NH₄OH—CHCl₃ and crystallization of the product from EtOAc-MeOH-heptane gave 228 mg of 80, a white solid: MS (FAB) m/z 627.3 (M+H⁺), 261.1; HRMS (FAB) calcd for $C_{31}H_{40}FN_6O_5S$ (M+H⁺) 627.2765, found 627.2767; IR (drift) 3317, 3286, 1761, 1672, 1648, 1633cm⁻¹. Anal. calcd for $C_{31}H_{39}FN_6O_5S$: C, 59.41; H, 6.27; N, 13.41. Found: C, 58.58; H, 6.18; N, 13.15.

Example 24b (S)—N¹-(4-{4-[4-(4-{(5S)-5-[(Acetylamino)methyl]-2-oxo-1,3-oxazolidin-3-yl}-2-fluorophenyl)piperazin-1-yl]-2-oxobutanoyl}benzyl)alaninamide (82)

Step 1:

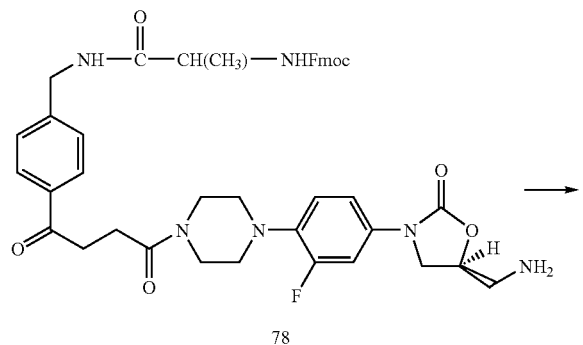
78

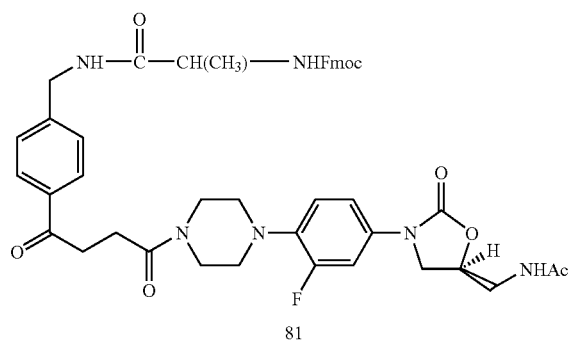
81

A stirred mixture of 78 (500 mg, 0.644 mmol), triethylamine (0.72 ml, 5.15 mmol), CH₂Cl₂ (6.5 ml) and THF (6.5 ml) was treated with acetyl chloride (84 μL, 0.966 mmol) and kept at ambient temperature for 2 h. Additional acetyl chloride (45 μL) was added and the mixture was kept at ambient temperature for 18 h. It was then treated with silica gel (1.5 g) and concentrated. Chromatography of the residue on silica gel with 2.5% MeOH—CH₂Cl₂ gave the product (370 mg) which was further purified by preparative TLC on silica gel with 2.5% MeOH—CH₂Cl₂ to give 323 mg of 81, a white solid: ¹H NMR [300 MHz, (CD₃)₂SO] δ 1.25 (d, 3H), 1.82 (s, 3H), 2.72 (m, 2H), 2.90, 3.00 (s, s, 4H), 3.14 (m, 2H), 3.38 (t, 2H), 3.62 (m, 5H), 4.07 (m, 2H), 4.25 (m, 3H), 4.33 (d, 2H), 4.70 (m, 1H), 7.30 (m, 10H), 7.72 (m, 2H), 7.89 (m, 4H), 8.21 (t, 1H), 8.47 (t, 1H).

Step 2:

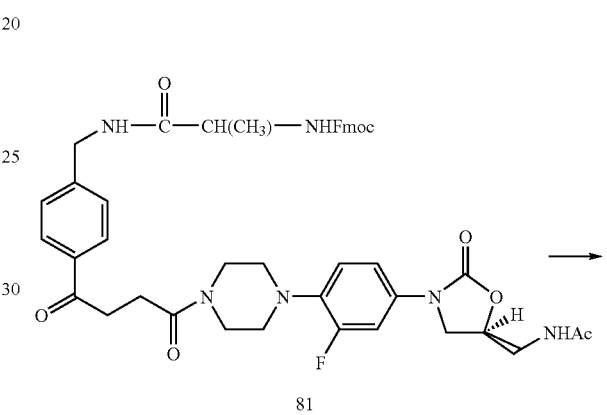
81

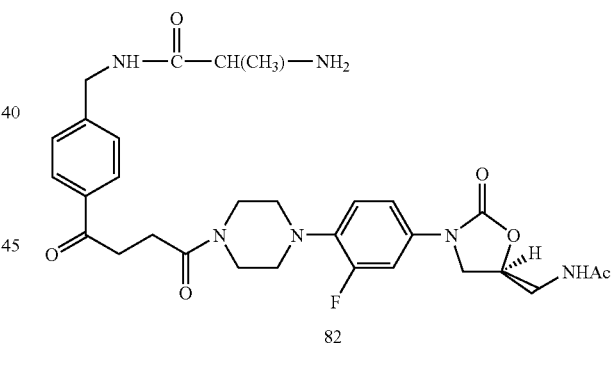
82

A stirred mixture of 81 (300 mg, 0.366 mmol), trisamine resin (91 mg) and THF (30 ml) was refluxed for 2 h and treated with additional resin (100 mg). It was refluxed for 18 h, treated with additional resin (200 mg) and refluxed for 8 h. Additional resin (200 mg) was again added and the mixture was refluxed for 18 h. The reaction was now complete; the mixture was filtered and the filtrate was concentrated. Chromatography of the residue on silica gel with 5% MeOH-0.5% NH₄OH—CHCl₃ and crystallization of the product from Et₂O-EtOAc-heptane gave 151 mg of 82: ¹H NMR [300 MHz, (CD₃)₂SO] δ 1.14 (d, 3H), 1.81 (s, 3H), 2.26 (broad s, 2H), 2.72 (t, 2H), 2.90, 3.00 (s, s, 4H), 3.21 (t, 2H), 3.00 (m, 1H), 3.38 (t, 2H), 3.63 (m, 5H), 4.07 (t, 1H), 4.33 (d, 2H), 4.68 (m, 1H), 7.07 (t, 1H), 7.15 (dd, 1H), 7.37 (d, 2H), 7.49 (dd, 1H), 7.92 (d, 2H), 8.21 (t, 1H), 8.40 (t, 1H).

Example 25

N¹-(4-{4-[4-(2-Fluoro-4-{(5S)-2-oxo-5-[(propanethioylamino)methyl]-1,3-oxazolidin-3-yl}phenyl)piperazin-1-yl]-4-oxobutanoyl}benzyl)glycinamide (85)

Step 1:

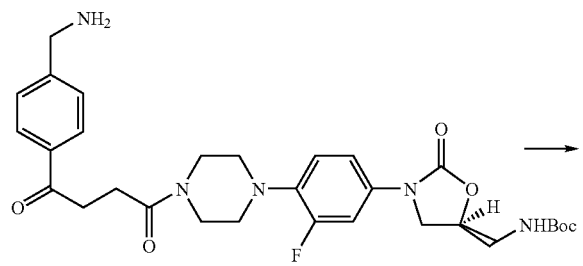

72

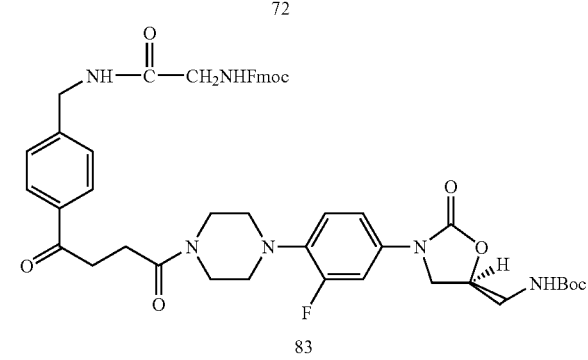

83

An ice cold, stirred mixture of 72 (957 mg, 1.64 mmol), diisopropylethylamine (Hunig's base, HB, 0.316 ml, 1.77 mmol) and THF (33 ml) was treated, portionwise during about 1 min, with Fmoc glycyl chloride (559 mg, 1.77 mmol). The mixture was allowed to warm slowly to ambient temperature and stand for 18 h. It was then concentrated in vacuo, and the residue was chromatographed on silica gel with 3% MeOH—CH$_2$Cl$_2$. Impure fractions were triturated with EtOAc-heptane and rechromatographed with 2.5% MeOH—CH$_2$Cl$_2$. The product was crystallized from EtOAc-heptane to give 600 mg of 83: MS (ESI) m/z 862.9 (M+H$^+$), 885.0 (M+Na$^+$); IR (drift) 3353, 3329, 1741, 1728, 1710, 1691, 1682, 1652 cm$^{-1}$.

Step 2:

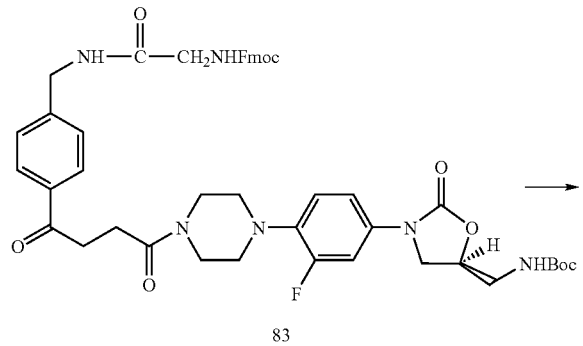

83

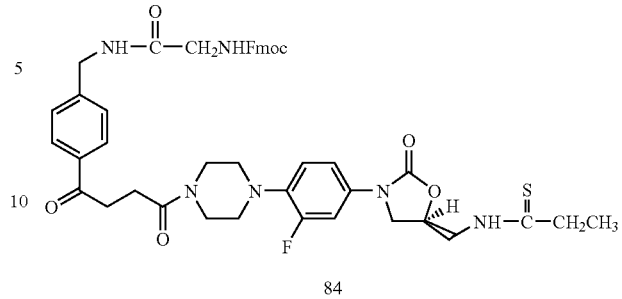

84 a) Ice cold, stirred 4N HCl in dioxane (10 ml) was treated, portionwise during 2 min with 83 (500 mg, 0.579 mmol). The mixture was kept in the ice bath for 1 h and at ambient temperature for 1 h and then concentrated in vacuo. The residue was triturated with three 50 ml portions of CH$_2$Cl$_2$ with concentration after each addition to give a white solid: MS (EI) m/z 762.5 (M$^+$); IR (drift) 3289, 3240, 1762, 1726, 1716, 1676, 1663, 1657, 1645, 1632, 1628, 1608 cm$^{-1}$.

b) A mixture of the solid of step a) (463 mg), triethylamine (242 μL, 1.74 mmol), ethyl dithiopropionate (93 mg, 0.695 mmol) and MeOH (10 ml) was stirred at ambient temperature for 18 h. Additional MeOH (5 ml), triethylamine (242 μL) and dithioester (93 mg) were added to the mixture which was stirred for an additional 24 h. It was warmed at 50° C. for 1.5 h then diluted with CH$_2$Cl$_2$ (15 ml) and stirred at ambient temperature for 4 h. This mixture was diluted with CH$_2$Cl$_2$ (100 ml) adsorbed on silica gel and chromatographed on silica gel with 3.5% MeOH—CH$_2$Cl$_2$. The product was crystallized from EtOAc—CH$_2$Cl$_2$-heptane to give 218 mg of 84, as a white powder: MS (ESI) m/z 835.0 (M+H$^+$), 857.0 (M+Na$^+$); IR (drift) 3287, 1753, 1749, 1743, 1728, 1710, 1691, 1680, 1663, 1656, 1645, 1639, 1635 cm$^{-}$.

Step 3:

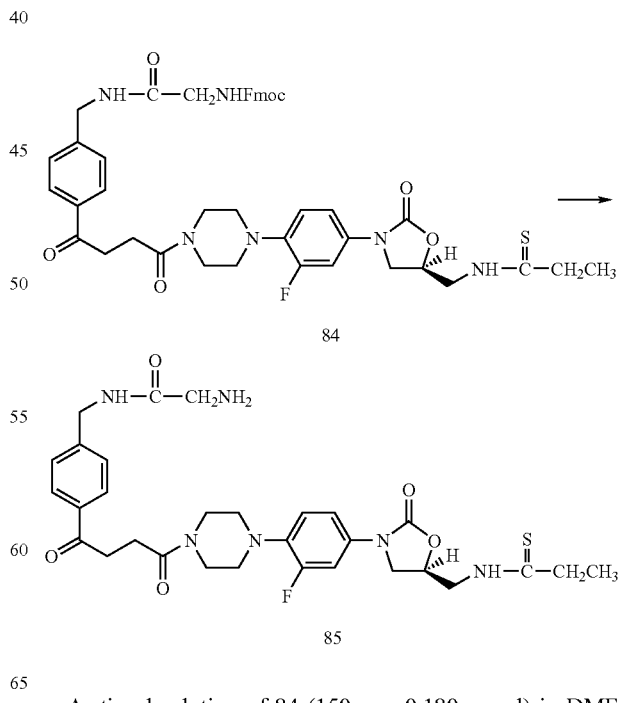

A stirred solution of 84 (150 mg, 0.180 mmol) in DMF (1.8 ml) was treated with piperidine (45 μL), kept at ambient temperature for 30 min and concentrated in vacuo. The residue was chromatographed on silica gel with 5% MeOH—CH$_2$Cl$_2$. The resulting product was combined with the product from a similar 0.0599 mmol reaction and rechromatographed on silica gel with 5% MeOH-0.5% NH$_4$OH—CHCl$_3$. Crystallization of the product from Et$_2$O—CH$_2$Cl$_2$ gave 74.8 mg of 85: MS (EI) m/z 612.5 (M$^+$), 568.3, 511.2, 321.6, 280.1, 259.1, 247.0, 208.4, 191.5, 164.4; HRMS (FAB) calcd for C$_{30}$H$_{38}$FN$_6$O$_5$S (M+H$^+$) 613.2608, found 613.2607.

Example 26

(S)-Alanyl-(S)—N$^1$-(4-{4-[4-(2-fluoro-4-{(5S)-2-oxo-5-[(propanethioylamino)methyl]-1,3-oxazolidin-3-yl]phenyl)piperazin-1-yl]-4-oxobutanoyl}benzyl)alaninamide (89)

Step 1:

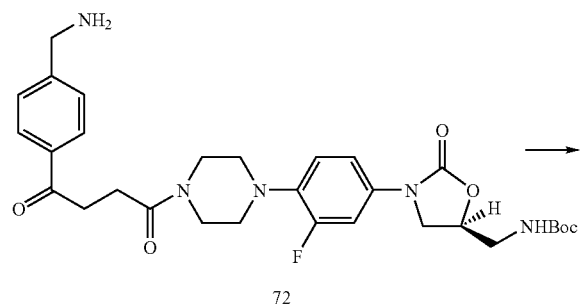

72

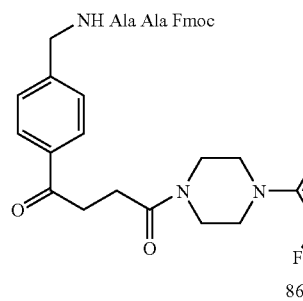

86

A stirred, ice cold mixture of 72 (2.00 g, 3.43 mmol), HOBT (510 mg, 3.77 mmol), N-Fmoc-L-alanyl-L-alanine (1.31 g, 3.43 mmol) and DMF (30 ml) was treated with EDC (1.45 g, 7.54 mmol) and allowed to warm slowly to ambient temperature. It was kept at ambient temperature for 4 h and diluted with about 500 ml of water. The resulting solid was collected by filtration, dried and chromatographed on silica gel with 5% MeOH—CH$_2$Cl$_2$ to give 2.22 g of 86: MS (ESI) m/z 948.0 (M+H$^+$), 970.0 (M+Na$^+$), 985.9 (M+K$^+$); IR (drift) 3305, 1744, 1733, 1710, 1690, 1683, 1694, 1640 cm$^{-1}$.

Step 2:

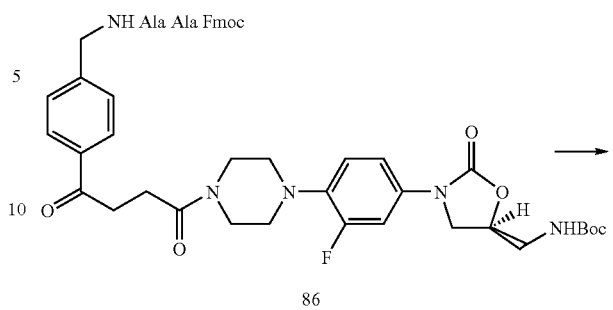

86

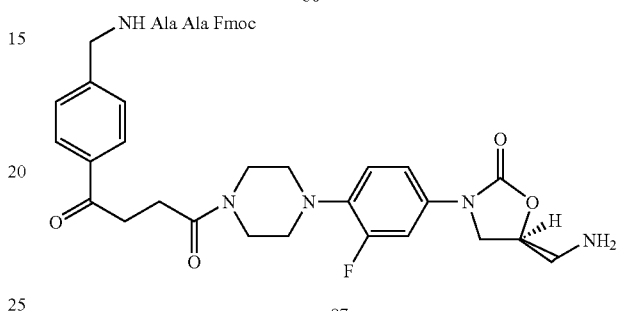

87

Stirred, ice cold 4N HCl in dioxane (20 ml) was treated with 72 (2.21 g, 2.33 mmol) and the mixture was kept in the ice bath for 2 h and at ambient temperature for 1 h. It was then concentrated in vacuo and the residue was triturated with three 50 ml portions of CH$_2$Cl$_2$ with concentration after each addition. A mixture of the residue in saturated NaHCO$_3$ was extracted with CH$_2$Cl$_2$. A solid that formed during this process was collected by filtration, washed with water and dissolved in 20% MeOH—CH$_2$Cl$_2$. The organic solutions were dried (MgSO$_4$) and concentrated to give 1.84 g of 63: MS (ESI) m/z 848.0 (M+H$^+$), 869.9 (M+Na$^+$), 886.4 (M+K$^+$), 555.0, 467.0, 295.0; IR (drift) 3288, 1749, 1746, 1686, 1661, 1645, 1642 cm$^{-1}$.

Step 3:

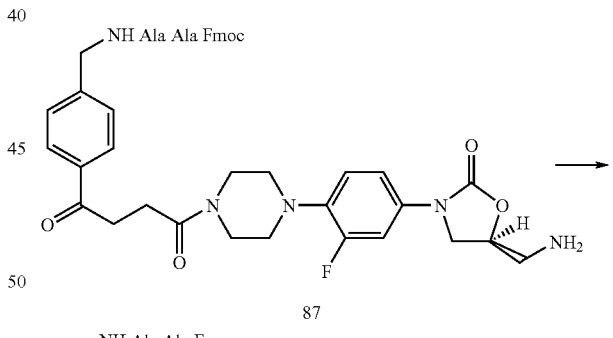

87

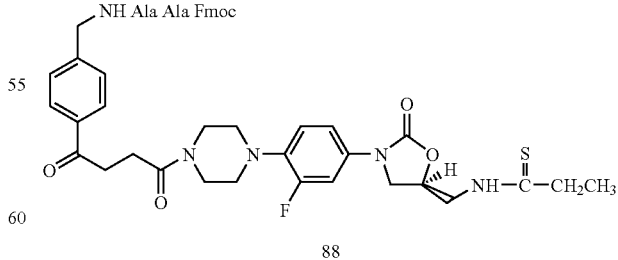

88

A stirred mixture of 87 (600 mg, 0.708 mmol), triethylamine (236 μL, 1.69 mmol) and MeOH (8 ml) was treated with ethyl dithiopropionate (133 mg, 0.991 mmol) and kept at ambient temperature for 4 d. It was then diluted with CH$_2$Cl$_2$ to dissolve the solids, mixed with silica gel (5 g) and concentrated in vacuo. Chromatography of the residue on silica gel with 5% MeOH—CH$_2$Cl$_2$ gave 367 mg of 88, a white solid: $^1$H NMR [300 MHz, (CD$_3$)$_2$SO] δ 1.13 (t, 3H), 1.22 (q, 6H), 2.57 (q, 2H), 2.72 (t, 2H), 2.90, 3.00 (s, s, 4H), 3.19 (t, 2H), 3.57, 3.66 (s, s, 4H), 3.79 (dd, 1H), 3.90 (t, 2H), 4.17 (m, 6H), 4.33 (d, 2H), 4.94 (m, 1H), 7.07 (t, 1H), 7.17 (dd, 1H), 7.42 (m, 8H), 7.69 (t, 2H), 7.88 (t, 4H), 8.02 (d, 1H), 8.41 (t, 1H), 10.28 (t, 1H).

Step 4:

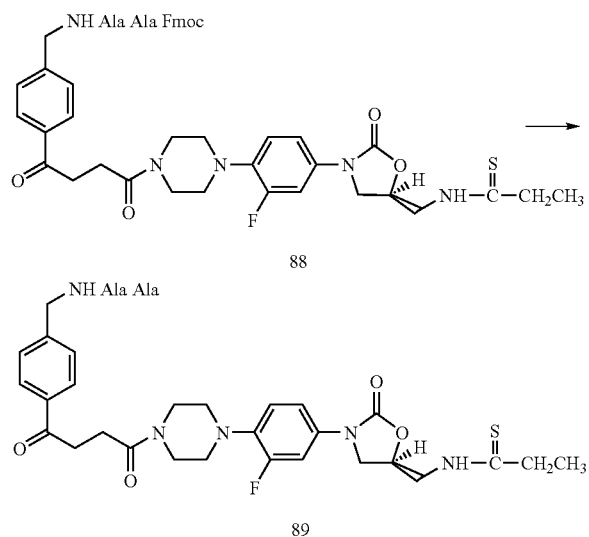

A stirred mixture of 88 (330 mg, 0.359 mmol), trisamine resin (500 mg) and THF (30 ml) was refluxed for 24 h and filtered. The filtrate was concentrated and the residue was chromatographed on silica gel with 7% MeOH-0.7% NH$_4$OH—CHCl$_3$. Crystallization of the product from MeOH—CH$_2$Cl$_2$-heptane gave 151 mg of 89: $^1$H NMR [300 MHz, (CD$_3$)$_2$SO] δ 1.14 (m, 6H), 1.25 (d, 3H), 2.27 (broad s, 2H), 2.58 (q, 2H), 2.74 (t, 2H), 2.92, 3.01 (s, s, 4H), 3.23 (t, 2H), 3.28 (m, 1H), 3.59, 3.68 (s, s, 4H), 3.81 (dd, 1H), 3.92 (t, 2H), 4.14 (t, 1H), 4.35 (m, 3H), 4.95 (m, 1H), 7.09 (t, 1H), 7.18 (dd, 1H), 7.38 (d, 2H), 7.52 (dd, 1H), 7.94 (d, 2H), 8.08 (m, 1H), 8.54 (t, 1H), 10.31 (t, 1H).

Example 27

(S)-Alanyl-(S)-N$^1$-(4-{4-[4-(4-{(5S)-5-[(acetylamino)methyl]-2-oxo-1,3-oxazolidin-3-yl}-2-fluorophenyl)piperazin-1-yl]-4-oxobutanoyl}benzyl)alaninamide (91)

Step 1:

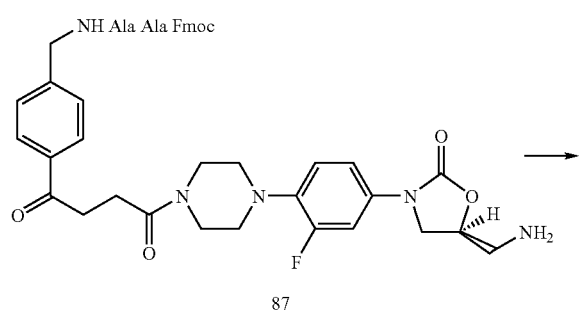

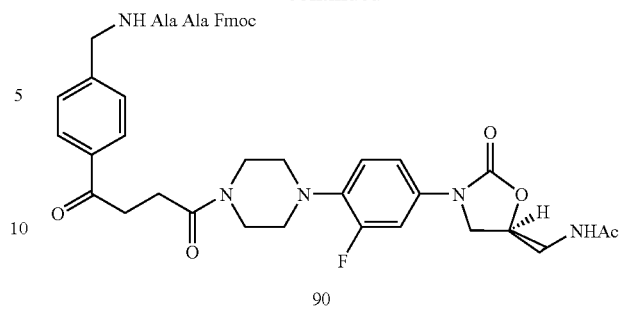

A stirred mixture of 87 (304 mg, 0.359 mmol) and pyridine (6 ml) was treated with acetic anhydride (51 μL, 0.538 mmol) and kept at ambient temperature for 4 days. It was then concentrated to dryness in vacuo. The residue was combined with the product from a similar, 0.118 mmol reaction and 105 mg (0.114 mmol) was removed for a subsequent reaction. The remaining material was chromatographed on silica gel with 10% MeOH-1% NH$^4$OH—CHCl$_3$ to give 218 mg of 90: MS (ESI) m/z 890.0 (M+H$^+$), 912.0 (M+Na$^+$), 928.0 (M+K$^+$); IR (drift) 3289, 1744, 1687, 1645 cm$^{-1}$.

Step 2:

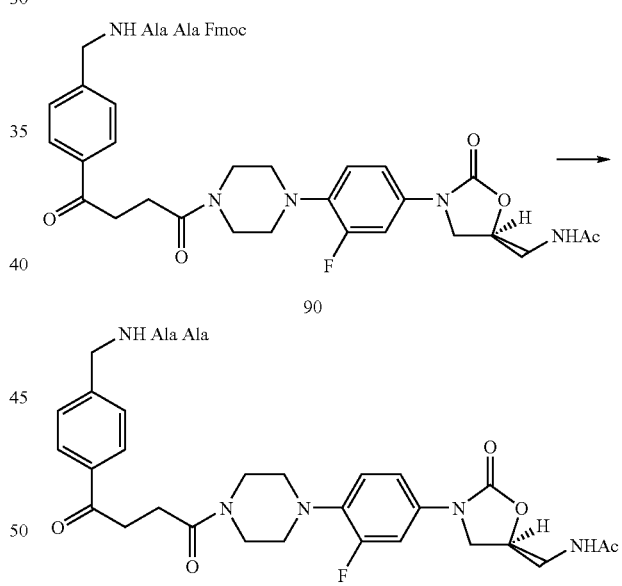

A stirred mixture of 90 (200 mg, 0.225 mmol) and trisamine resin (550 mg) in THF (25 ml) was refluxed for 4 d, treated with additional resin (250 mg) and refluxed for 1 d. It was then filtered; the filtrate was concentrated and the residue was chromatographed on silica gel with 5% MeOH-0.5% NH$_4$OH—CHCl$_3$. The product was combined with the product from a similar 0.114 mmol reaction and crystallized from MeOH—CH$_2$Cl$_2$-heptane to give 164 mg of 91: $^1$H NMR [300 MHz, (CD$_3$)$_2$SO] δ 1.12 (d, 3H), 1.23 (d, 3H), 1.81 (s, 3H), 2.72 (t, 2H), 2.89, 2.99 (s, s, 4H), 3.21 (t, 2H), 3.31 (m, 1H), 3.38 (t, 2H), 3.62 (m, 5H), 4.08 (t, 1H), 4.33

(m, 3H), 4.68 (m, 1H), 7.07 (t, 1H), 7.15 (d, 1H), 7.35 (d, 2H), 7.48 (d, 1H), 7.92 (d, 2H), 8.05 (s, 1H), 8.23 (t, 1H), 8.52 (t, 1H).

Example 28

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}benzyl)acetamide (94)

Step 1:

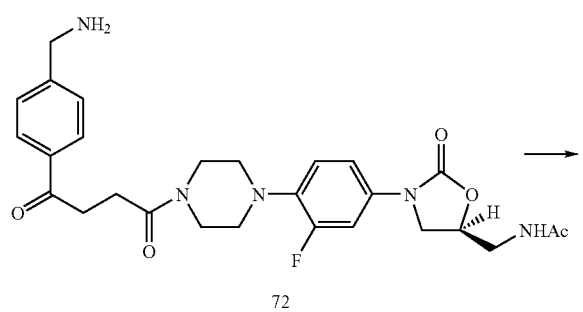

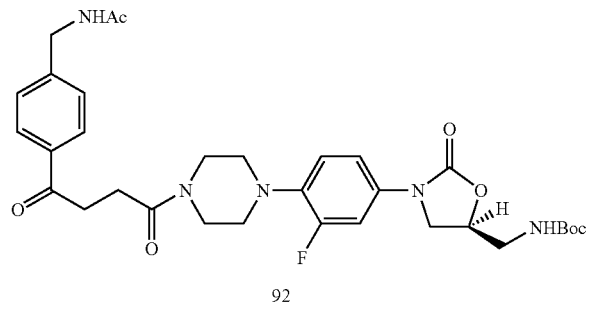

A stirred solution of 72 (100 mg, 0.171 mmol) in pyridine (2.9 ml) was treated with acetic anhydride (24 μL, 0.257 mmol) and kept at ambient temperature for 1 h. It was then concentrated to dryness in vacuo. A solution of the residue in CH$_2$Cl$_2$ was treated with heptane to give 100 mg of 92, a white solid: $^1$H NMR [300 MHz, (CD$_3$)$_2$SO] δ 1.34 (s, 9H), 1.87 (s, 3H), 2.72 (t, 2H), 2.89, 2.99 (s, s, 4H), 3.23 (m, 4H), 3.57, 3.66 (s, s, 4H), 3.74 (dd, 1H), 4.06 (t, 1H), 4.30 (d, 2H), 4.67 (m, 1H), 7.07 (t, 1H), 7.18 (m, 2H), 7.36 (d, 2H), 7.48 (dd, 1H), 7.92 (d, 2H), 8.43 (t, 1H).

Step 2:

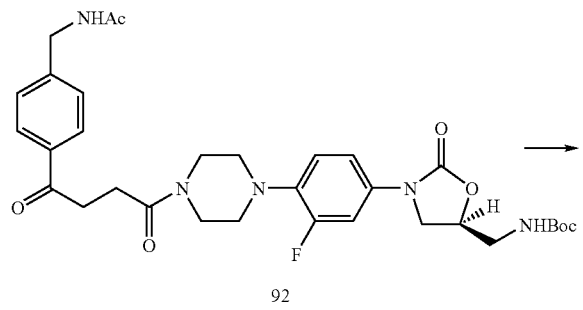

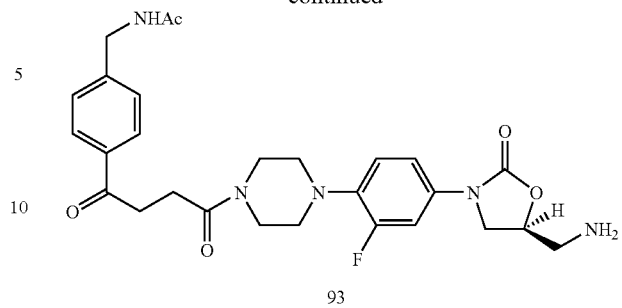

Solid 92 (2.00 g, 3.20 mmol) was cooled in an ice bath, treated with 4N HCl in dioxane (20 ml) and stirred in the ice bath for 2 h and at ambient temperature for 1 h. It was then concentrated in vacuo. A solution of the residue in water (40 ml) was made alkaline with solid NaHCO$_3$ and extracted with CH$_2$Cl$_2$. The extract was dried (MgSO$_4$) and concentrated. A solution of the residue in CH$_2$Cl$_2$-MeOH was treated with heptane and the solid that precipitated was collected by filtration and dried to give 1.45 g of 93: $^1$H NMR [300 MHz, (CD$_3$)$_2$SO] δ 1.87 (s, 3H), 2.06 (broad s, 2H), 2.72 (t, 2H), 2.80 (t, 2H), 2.89, 2.99 (s, s, 4H), 3.21 (t, 2H), 3.57, 3.66 (s, s, 4H), 3.81 (dd, 1H), 4.01 (t, 1H), 4.30 (d, 2H), 4.59 (m, 1H), 7.07 (t, 1H), 7.20 (dd, 1H), 7.36 (d, 2H), 7.51 (dd, 1H), 7.92 (d, 2H), 8.43 (t, 1H).

Step 3:

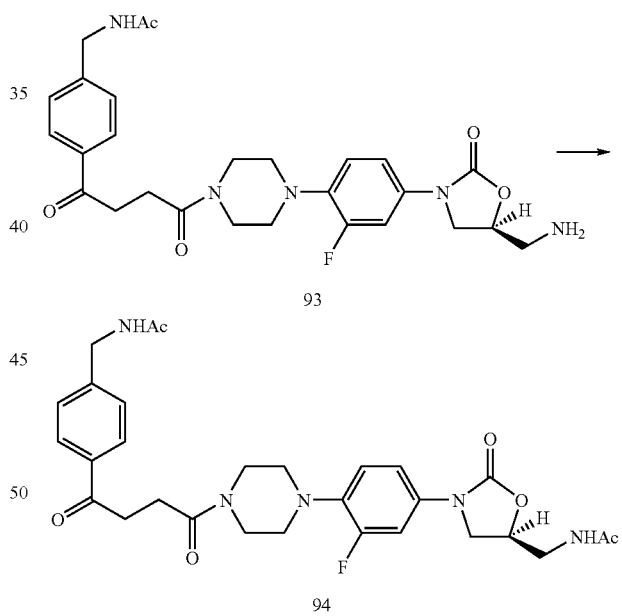

A stirred solution of 93 (500 mg, 0.951 mmol) in pyridine (16 ml) was treated dropwise with acetic anhydride (135 μL, 1.43 mmol), kept at ambient temperature for 4 h and concentrated in vacuo. A mixture of the residue and water was extracted with CH$_2$Cl$_2$. The extract was dried (MgSO$_4$) and concentrated. Crystallization of the residue from MeOH gave 450 mg of 94, a white solid: $^1$H NMR [300 MHz, (CD$_3$)$_2$SO] δ 1.81 (s, 3H), 1.87 (s, 3H), 2.72 (t, 2H), 2.89, 2.99 (s, s, 4H), 3.21 (t, 2H), 3.38 (t, 2H), 3.57 (s, 2H), 3.68 (m, 3H), 4.07 (t, 1H), 4.30 (t, 2H), 4.69 (m, 1H), 7.07 (t, 1H), 7.17 (dd, 1H), 7.36 (d, 2H), 7.49 (dd, 1H), 7.92 (d, 2H), 8.23 (t, 1H), 8.43 (t, 1H).

Example 29

N-(4-{4-[4-(2-Fluoro-4-{(5S)-2-oxo-5-[(propanethioylamino)methyl]-1,3-oxazolidin-3-yl}phenyl)-1-piperazinyl]-4-oxobutanoyl}benzyl)acetamide (95)

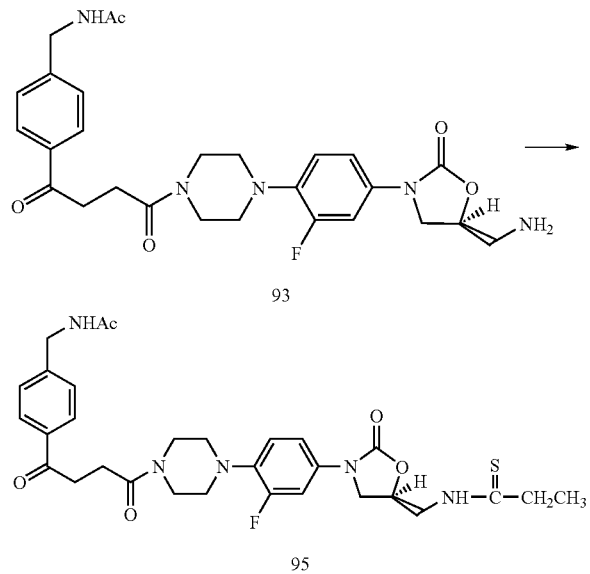

A stirred solution of 93 (500 mg, 0.951 mmol), triethylamine (662 µL, 4.76 mmol), MeOH (20 ml) and CH₂Cl₂ (10 mL) was treated with ethyl dithiopropionate (384 mg, 2.86 mmol) and kept at ambient temperature for 3 days. It was concentrated in vacuo. A solution of the residue in CH₂Cl₂ was washed with 1N HCl and saturated NaHCO₃, dried (MgSO₄) and concentrated. The solid residue was triturated with EtOAc-heptane and then crystallized from MeOH to give 466 mg of 95: $^1$H NMR [300 MHz, (CD₃)₂SO] δ 1.22 (t, 3H), 1.87 (s, 3H), 2.56 (q, 2H), 2.72 (t, 2H), 2.89, 2.99 (s, s, 4H), 3.21 (t, 2H), 3.57, 3.66 (s, s, 4H), 3.79 (dd, 1H), 3.90 (t, 2H), 4.11 (t, 1H), 4.30 (d, 2H), 4.93 (m, 1H), 7.07 (t, 1H), 7.17 (dd, 1H), 7.36 (d, 2H), 7.49 (dd, 1H), 7.92 (d, 2H), 8.43 (t, 1H), 10.29 (t, 1H).

Example 30

N-{[(5S)-3-(3-Fluoro-4-{4-[4-(4-{[(ethylsulfonyl)amino]methyl}phenyl)-4-oxobutanoyl]-1-piperazinyl}phenyl)-2-oxo-1,3-oxazolidin-5-yl]methyl}acetamide (98)

Step 1:

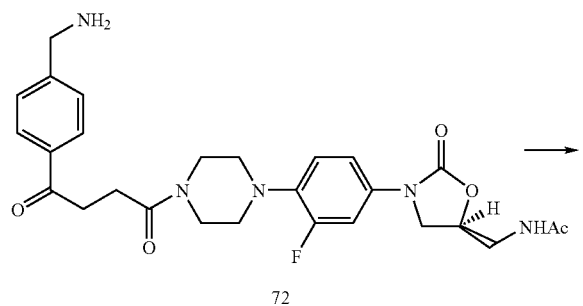

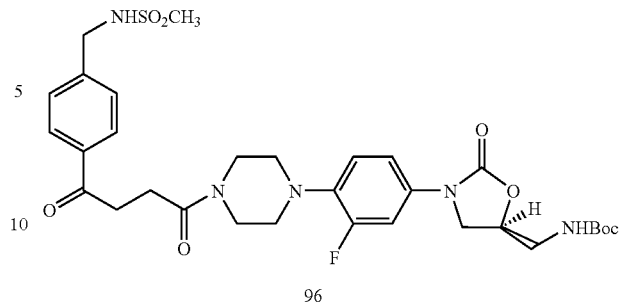

Methanesulfonyl chloride (432 µL, 3.77 mmol) was added to a stirred solution of 72 (2.00 g, 3.43 mmol) in pyridine (4.0 ml) and the mixture was kept at ambient temperature for 4 h and concentrated in vacuo. The residue was mixed with water and extracted with CH₂Cl₂. The extract was dried (MgSO₄) and concentrated. The residue was triturated with EtOAc to give 2.13 g of 96: MS (EI) m/z 661.3 (M⁺), 308.1; IR (drift) 3360, 3266, 1736, 1684, 1654 cm⁻¹.

Step 2:

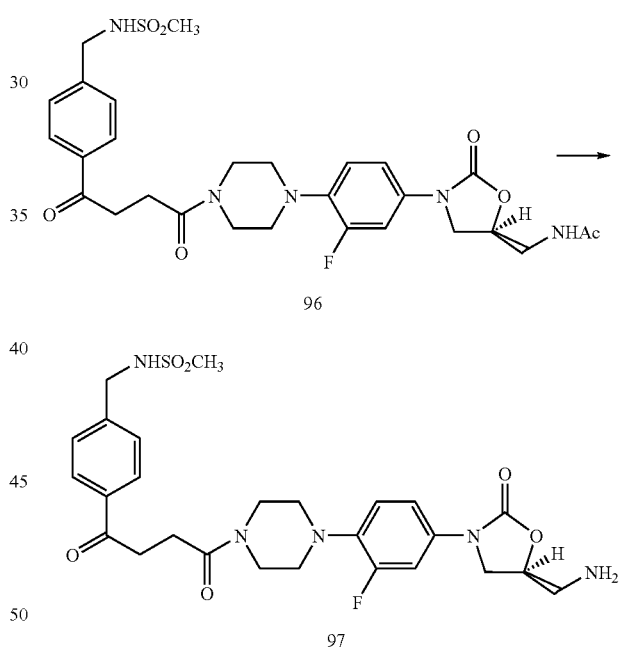

Solid 96 (1.5 g, 2.27 mmol) was cooled, under nitrogen in an ice bath and treated with 4N HCl in dioxane (15 ml). The stirred mixture was kept in the ice bath for 1.5 h and at ambient temperature for 1.5 h and then concentrated in vacuo. A solution of the residue in water (25 ml) was made alkaline with NaHCO₃ and extracted with 1:5 MeOH:CH₂Cl₂. The extract was dried (MgSO₄) and concentrated. Crystallization of the residue from MeOH gave 1.00 g of 97: $^1$H NMR [300 MHz, (CD₃)₂SO] δ 1.72 (broad s), 2.76 (m, 4H), 2.88 (s, 5H), 2.99 (s, 2H), 3.23 (t, 2H), 3.57, 3.66 (s, s, 4H), 3.81 (dd, 1H), 4.01 (t, 1H), 4.23 (s, 2H), 4.57 (m, 1H), 7.07 (t, 1H), 7.19 (dd, 1H), 7.49 (m, 3H), 7.67 (broad s, 1H), 7.96 (d, 2H).

Step 3:

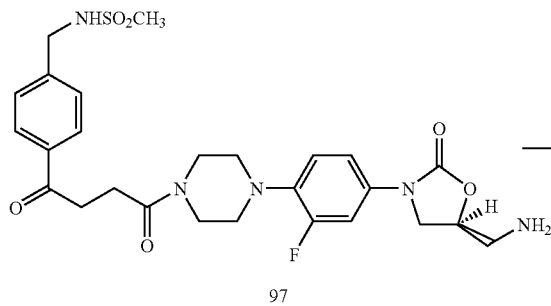

97

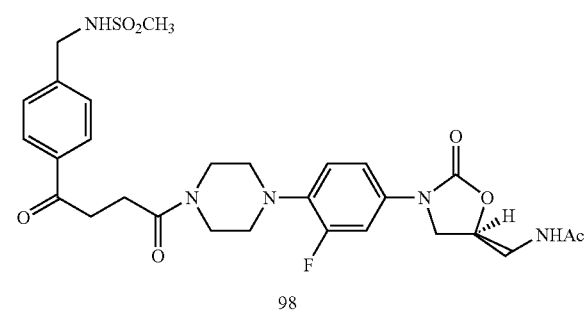

98

A stirred solution of 97 (500 mg, 0.890 mmol) in pyridine (15 ml) was treated, dropwise with acetic anhydride (126 μL, 1.34 mmol) and kept at ambient temperature for 4 h. It was then concentrated in vacuo and the residue was mixed with water and extracted with CH$_2$Cl$_2$. The extract was dried (MgSO$_4$) and concentrated. Crystallization of the residue from MeOH gave 481 mg of 98: $^1$H NMR [300 MHz, (CD$_3$)$_2$SO] δ 1.83 (s, 3H), 2.75 (t, 2H), 2.90 (s, 5H), 3.02 (s, 2H), 3.25 (t, 2H), 3.40 (t, 2H), 3.60 (s, 2H), 3.68 (m, 3H), 4.09 (t, 1H), 4.25 (d, 2H), 4.71 (m, 1H), 7.09 (t, 1H), 7.18 (dd, 1H), 7.51 (m, 3H), 7.69 (t, 1H), 7.98 (d, 2H), 8.25 (t, 1H).

Example 31

N-{[(5S)-3-(3-Fluoro-4-{4-[4-(4-{[(methylsulfonyl)amino]methyl}phenyl)-4-oxobutanoyl]-1-piperazinyl}phenyl)-2-oxo-1,3-oxazolidin-5-yl]methyl}propanethioamide (99)

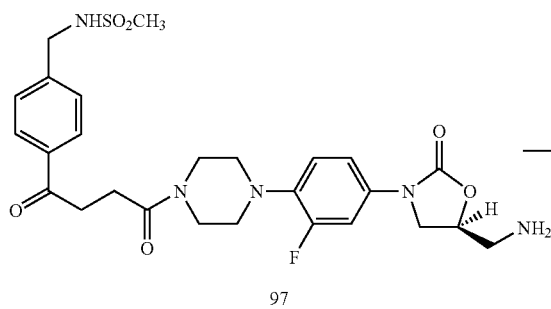

97

-continued

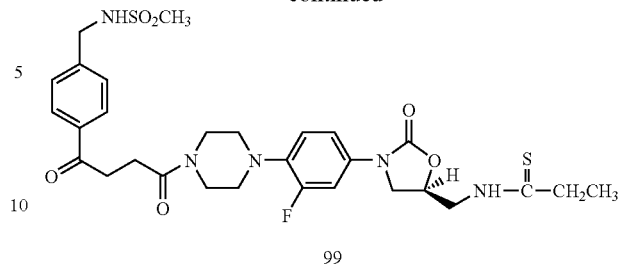

99

A stirred mixture of 97 (500 mg, 0.890 mmol), triethylamine (310 μL, 2.23 mmol), ethyl dithiopropionate (179 mg, 1.34 mmol), MeOH (20 ml) and CH$_2$Cl$_2$ (15 ml) was kept at ambient temperature for 2 h, treated with additional triethylamine (310 μL) and dithioester (179 mg) and kept at ambient temperature for 3 d. It was then treated with silica gel (5 g) and concentrated. Chromatography of the residue on silica gel with 4% MeOH—CH$_2$Cl$_2$ and crystallization of the product from MeOH gave 420 mg of 99, a white solid: $^1$H NMR [300 MHz, (CD$_3$)$_2$SO] δ 1.15 (t, 3H), 2.59 (q, 2H), 2.75 (t, 2H), 2.90 (s, 3H), 2.91 (s, 2H), 3.02 (s, 2H), 3.25 (t, 2H), 3.60, 3.68, (s, s, 4H), 3.81 (dd, 1H), 3.92 (t, 2H), 4.14 (t, 1H), 4.24 (d, 2H), 4.96 (m, 1H), 7.09 (t, 1H), 7.20 (dd, 1H), 7.51 (m, 3H), 7.69 (t, 1H), 7.98 (d, 2H), 10.32 (t, 1H).

Example 32a

N-({(5S)-3-[4-(4-{4-[4-(Aminomethyl)phenyl]-4-oxobutanoyl}-1-piperazinyl)-3-fluorophenyl]-2-oxo-1,3-oxazolidin-5-yl}methyl)propanethioamide (103)

Step 1:

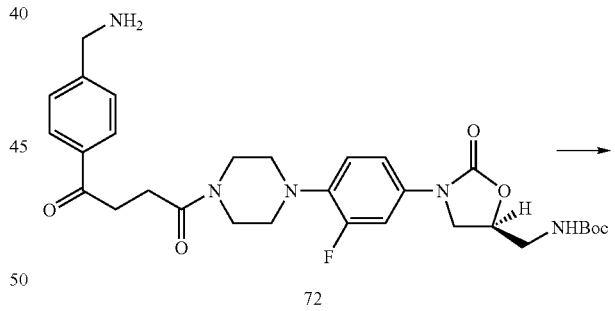

72

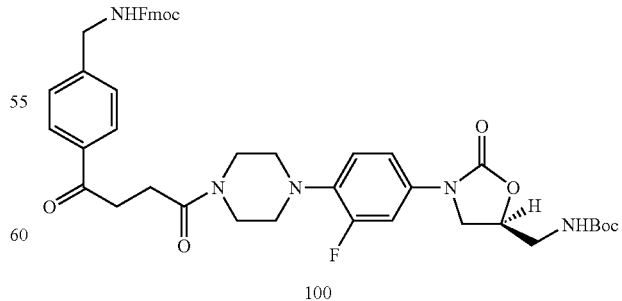

100

A stirred, ice cold mixture of 72 (2.46 mmol) and Hunig's base (0.48 ml, 2.71 mmol) in THF (49 ml) was treated with Fmoc-chloride (701 mg, 2.71 mmol) and allowed to warm slowly to ambient temperature and stand for 18 h. It was concentrated, without heating in vacuo and the residue was stirred with Et$_2$O (200 ml) and filtered. The solid was dried to give 2.10 g of 100 as an off-white solid: MS (ESI) m/z 806.1 (M+H$^+$), 827.9 (M+Na$^+$), 844.1 (M+K$^+$); IR (drift) 3353, 1731, 1694, 1685, 1651 cm$^{-1}$.

Step 2:

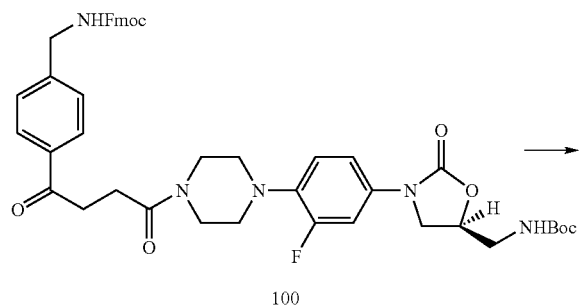

100

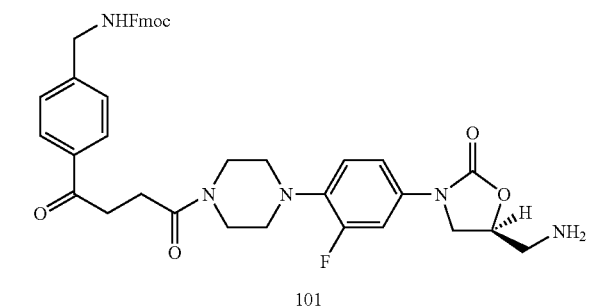

101

Ice cold 4N HCl in dioxane (10 ml) was treated with 100 (1.00 g, 1.24 mmol) and the mixture was kept in the ice bath for 1 h and at ambient temperature for 3 h. It was then concentrated in vacuo. The residue was mixed with two portions of CH$_2$Cl$_2$ (50 ml) with concentration after each addition and the resulting material was mixed with saturated NaHCO$_3$ (20 ml) and extracted with CH$_2$Cl$_2$. The extract was dried (MgSO$_4$) and concentrated to give 689 mg of 101: MS (FAB) m/z 662.3 (M–CO$_2$+H$^+$), 484.3, 356.1, 355.1, 295.2, 195.1, 179.1; HRMS (FAB) calcd for C$_{39}$H$_{41}$FN$_5$O$_4$ (M–CO$_2$+H$^+$) 662.3142, found 662.3166; IR (drift) 3288, 1749, 1682, 1645 cm$^{-1}$.

Step 3:

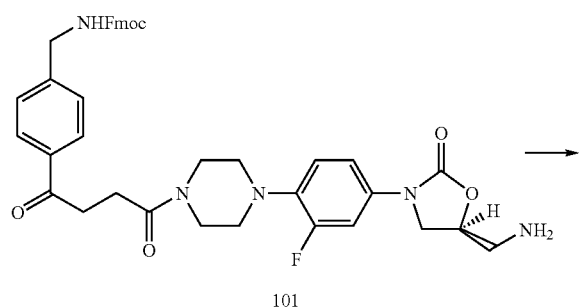

101

-continued

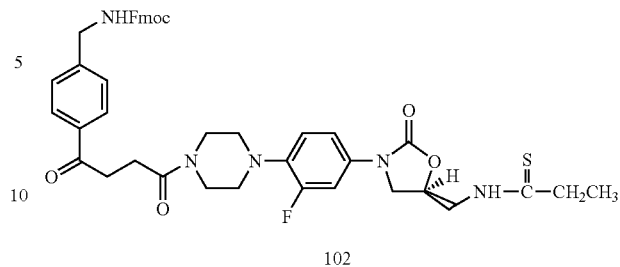

102

A stirred mixture of 101 (668 mg, 0.946 mmol), triethylamine (330 µL, 2.37 mmol) and MeOH (10 ml) was treated with ethyl dithiopropionate (152 mg, 1.14 mmol) and CH$_2$Cl$_2$ (4 ml) and the resulting solution was kept at ambient temperature for 18 h. It was then mixed with silica gel (2 g) and concentrated in vacuo. Chromatography of the residue on silica gel with 5% MeOH-0.5% NH$_4$OH—CH$_2$Cl$_2$ and crystallization of the product from EtOAc-heptane gave 445 mg of 102, a white solid: MS (CI) m/z 777.9 (M$^+$), 619.9; IR (drift) 3306, 1756, 1744, 1692, 1645 cm$^{-1}$.

Step 4:

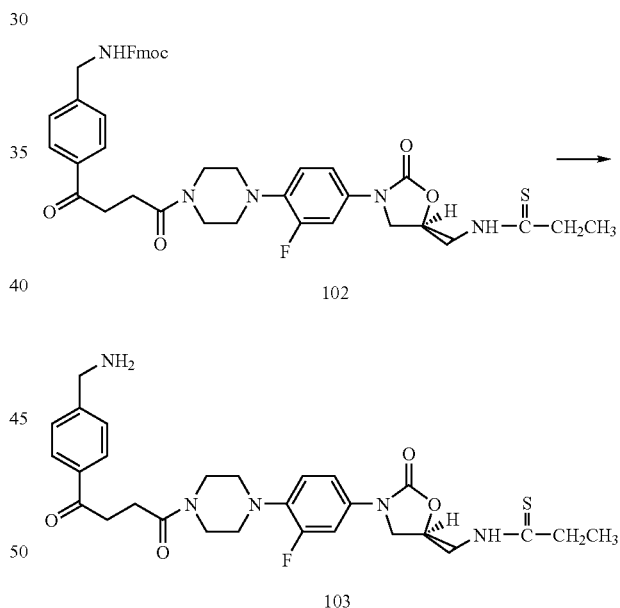

102

103

A stirred solution of 102 (340 mg, 0.437 mmol) in DMF (4.4 ml) was treated with piperidine (108 µL, 1.09 mmol), kept at ambient temperature for 30 min and concentrated in vacuo. The residue was chromatographed on silica gel with 5% MeOH-0.5% NH$_4$OH—CHCl$_3$ and the product was crystallized from EtOAc to give 192 mg of 103, a white solid: $^1$H NMR [300 MHz, (CD$_3$)$_2$SO] δ 1.12 (t, 3H), 2.13 (broad s, 2H), 2.56 (q, 2H), 2.72 (t, 2H), 2.90, 3.00 (s, s, 4H), 3.22 (t, 2H), 3.58, 3.66 (s, s, 4H), 3.77 (m, 3H), 3.90 (s, 2H), 4.11 (t, 1H), 4.93 (m, 1H), 7.07 (t, 1H), 7.17 (dd, 1H), 7.47 (m, 3H), 7.91 (d, 2H), 10.29 (s, 1H).

Example 32b

N-({(5S)-3-[4-(4-{4-[4-(Aminomethyl)phenyl]-4-oxobutanoyl}-1-piperazinyl)-3-fluorophenyl]-2-oxo-1,3-oxazolidin-5-yl}methyl)propanethioamide (103)

Step 1:

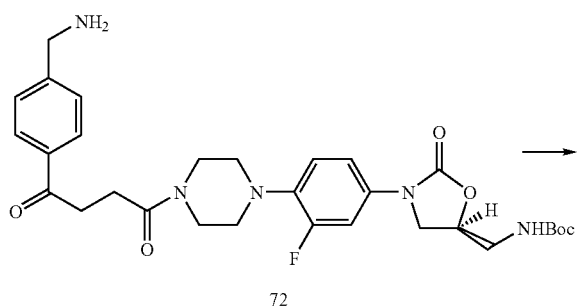
72

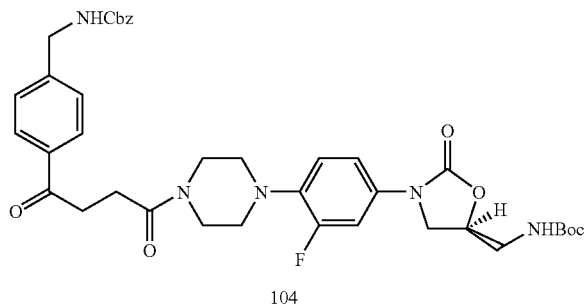
104

A stirred, ice cold mixture of 72 (70 mg, 0.12 mmol), NaHCO$_3$ (12 mg, 0.14 mmol) and 3:1 acetone:H$_2$O (1 ml) was treated with benzyl chloroformate (20 μL, 0.14 mmol) and allowed to warm slowly to ambient temperature and stand for 18 h. It was then mixed with water (15 ml) and extracted with CH$_2$Cl$_2$. The extract was dried (MgSO$_4$) and concentrated. Chromatography of the residue on silica gel with 2% MeOH—CH$_2$Cl$_2$ and crystallization of the product from EtOAc-heptane gave 51 mg of 104: mp 158–159° C.; $^1$H NMR (300 MHz, CDCl$_3$) δ 1.41 (s, 9H), 2.82 (t, 2H), 3.01, 3.09 (t, t, 4H), 3.36 (t, 2H), 3.51 (m, 2H), 3.79 (m, 5H), 4.00 (t, 1H), 4.44 (d, 2H), 4.73 (m, 1H), 4.95 (m, 1H), 5.12 (m, 1H), 5.15 (s, 2H), 6.92 (t, 1H), 7.08 (dd, 1H), 7.36 (m, 7H), 7.46 (dd, 1H), 7.98 (d, 2H).

Step 2:

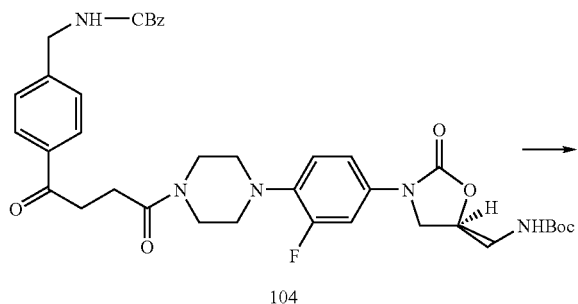
104

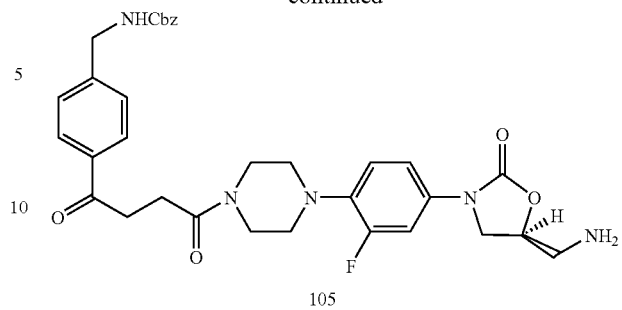
105

Solid 103 (830 mg, 1.15 mmol) was cooled in an ice bath and treated with 4N HCl in dioxane (10 ml). The stirred mixture was kept in the ice bath for 1 h and at ambient temperature for 1 h and then concentrated in vacuo. The residue was triturated with three portions of CH$_2$Cl$_2$ (50 ml) with concentration after each addition. The resulting material was mixed with saturated NaHCO$_3$ (50 ml) and extracted with CH$_2$Cl$_2$. The extract was dried (MgSO$_4$) and concentrated to give 657 mg of 105, an off-white solid: $^1$H NMR (300 MHz, CDCl$_3$) δ 2.82 (t, 2H), 3.04 (m, 6H), 3.35 (t, 2H), 3.65 (dd, 1H), 3.77 (m, 5H), 4.00 (t, 1H), 4.44 (d, 2H), 4.66 (m, 1H), 5.14 (s, 2H), 5.20 (m, 1H), 6.92 (t, 1H), 7.13 (dd, 1H), 7.36 (m, 7H), 7.49 (dd, 1H), 7.98 (d, 2H).

Step 3:

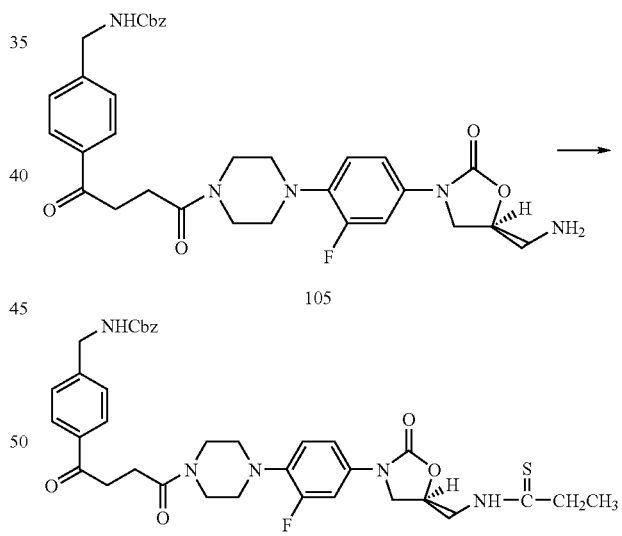
105

106

A stirred mixture of 105 (312 mg, 0.504 mmol), triethylamine (175 μL, 1.26 mmol), ethyl dithiopropionate (74 mg, 0.55 mmol) and MeOH (8 ml) was kept at ambient temperature for 18 h. Methylene chloride (5 ml) and additional dithioester (50 mg) were added and the mixture was kept at ambient temperature for 2 h and concentrated. The residue was stirred for 18 h with a mixture of water (50 ml) and 10% EtOAc-heptane. Chromatography of the resulting solid on silica gel first with 3% MeOH—CH$_2$Cl$_2$ and again with 2% MeOH—CH$_2$Cl$_2$ and crystallization of the product from EtOAc gave 241 mg of 106: MS (ESI) m/z 690.0 (M+H⁺), 711.9 (M+Na⁺), 727.9 (M+K⁺); IR (drift) 3343, 3202, 1743, 1694, 1646 cm⁻¹.

Step 4:

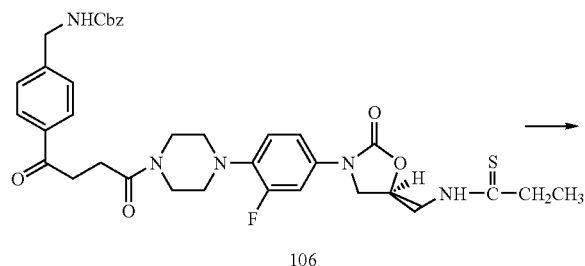

106

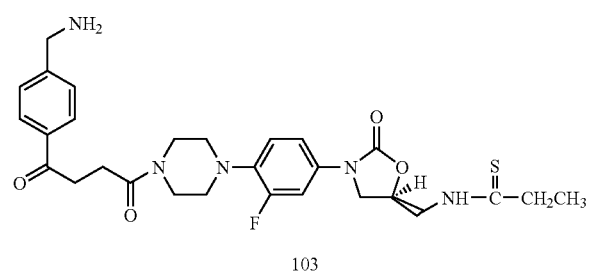

103

A stirred mixture of 106 (100 mg, 0.145 mmol) and 30% HBr in HOAc (5 ml) was kept at ambient temperature for 1 h and diluted with Et₂O (60 ml). The resulting solid was collected by filtration and washed with Et₂O. It was then mixed with water (15 ml) and saturated NaHCO₃ (15 ml) and extracted with CH₂Cl₂. The extract was dried (MgSO₄) and concentrated. Chromatography of the residue on silica gel with 2.5% MeOH-0.25% NH₄OH—CH₂Cl₂ and crystallization of the product from EtOAc gave 44 mg of 103, a white solid.

Example 33

N-({(5S)-3-[4-(4-{4-[4-(Aminomethyl)phenyl]-4-oxobutanoyl}-1-piperazinyl)-3-fluorophenyl]-2-oxo-1,3-oxazolidin-5-yl}methyl)acetamide (108)

Step 1:

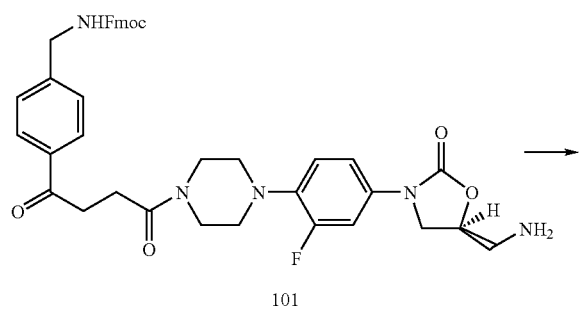

101

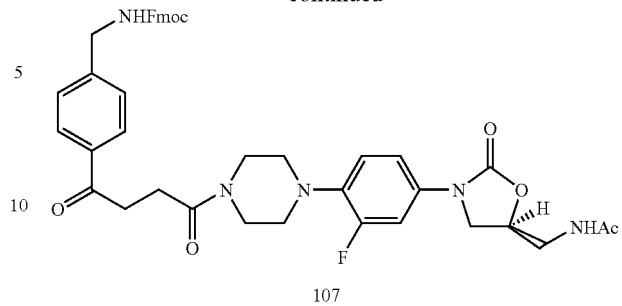

107

A stirred solution of 101 (755 mg, 1.07 mmol) and triethylamine (1.2 ml, 8.56 mmol) in THF (11 ml) and CH₂Cl₂ (11 ml) was treated with acetyl chloride (139 μL, 1.61 mmol) and kept at ambient temperature for 30 min. It was then mixed with water (30 ml) and extracted with CH₂Cl₂. The extract was washed with saturated NaHCO₃, dried (MgSO₄) and concentrated. Trituration of the solid residue with heptane that contained small amounts of acetone, Et₂O, MeOH and EtOAc gave 607 g of 107, a white solid: MS (ESI) m/z 748.0 (M+H⁺), 411.9, 231.9; IR (drift) 3305, 1744, 1687, 1646 cm⁻¹.

Step 2:

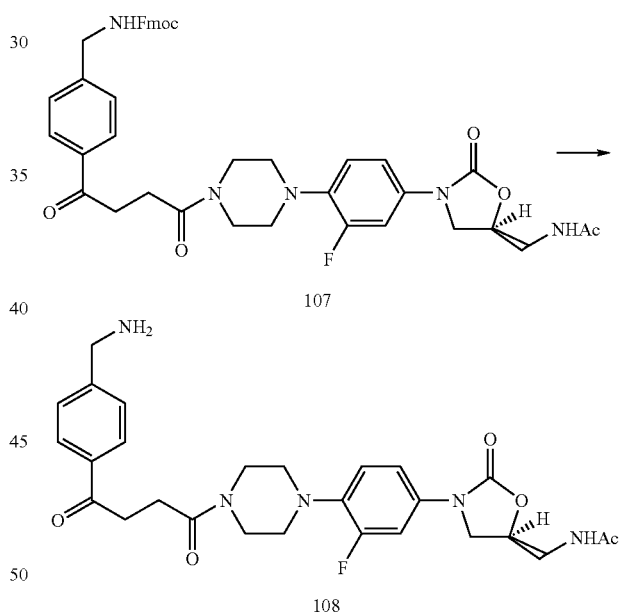

107

108

A stirred solution of 107 (576 mg, 0.770 mmol) in DMF (7.8 ml) was treated with piperidine (190 μL, 1.93 mmol), kept at ambient temperature for 30 min and concentrated in vacuo. Chromatography of the residue on silica gel with 5% MeOH-0.5% NH₄OH—CHCl₃ and crystallization of the product from MeOH—CH₂Cl₂-heptane gave a solid that turned yellow when dried at 50° C. It was dissolved in 1:1 CH₂Cl₂:MeOH (50 ml), decolorized with activated carbon and crystallized from CH₂Cl₂-MeOH-Et₂O to give 131 mg of 108: ¹H NMR [300 MHz, (CD₃)₂SO] δ 1.81 (s, 3H), 2.72 (t, 2H), 2.90, 3.00 (s, s, 4H), 3.22 (t, 2H), 3.30 (broad s), 3.38 (t, 2H), 3.58 (s, 2H), 3.66 (m, 3H), 3.81 (s, 2H), 4.07 (t, 1H), 4.68 (m, 1H), 7.07 (t, 1H), 7.16 (dd, 1H), 7.49 (m, 3H), 7.92 (d, 2H), 8.23 (t, 1H).

Example 34

N$^1$-(4-{4-[4-(4-{(5S)-5-[(Acetylamino)methyl]-2-oxo-1,3-oxazolidin-3-yl}-2-fluorophenyl)piperazin-1-yl]-4-oxobutanoyl}benzyl)glycinamide (112)

Step 1:

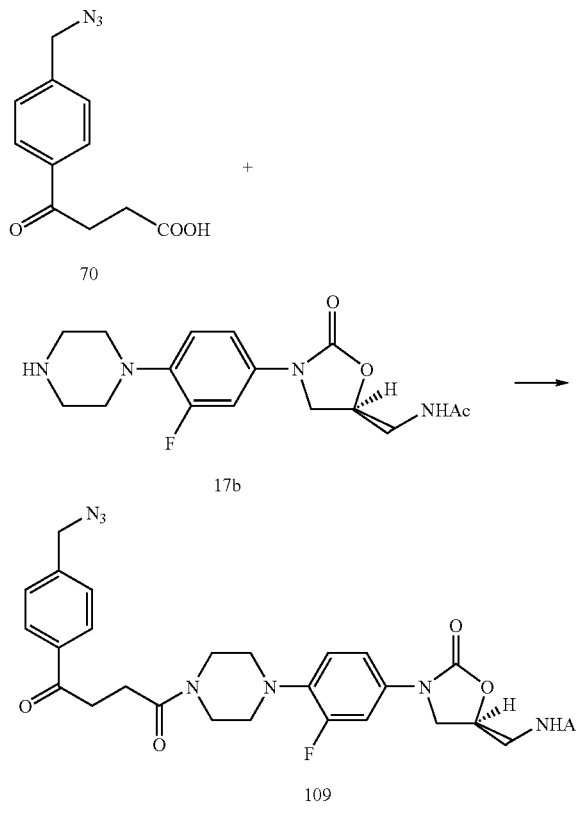

Step 2:

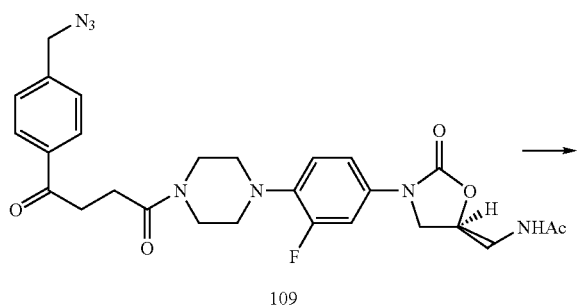

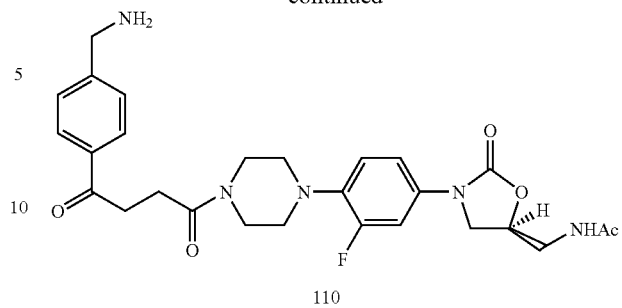

A mixture of 109 (1.50 g, 2.72 mmol), 10% palladium-on-carbon catalyst (375 mg) and THF (90 ml) was hydrogenated for 1 h at an initial pressure of 35 psi. The flask was evacuated and refilled with hydrogen and the reaction was continued for 1 h. Additional catalyst (200 mg) and CH$_2$Cl$_2$ (20 ml) were added to the mixture which was again hydrogenated for 1 h. This mixture was filtered and the filtrate was concentrated. Chromatography of the residue on silica gel with mixtures of MeOH—NH$_4$OH—CH$_2$Cl$_2$ that contained 5–10% MeOH and 0.5–1% NH$_4$OH gave 876 mg of 110, a white solid: MS (FAB) m/z 526.3 (M+H$^+$), 337.2, 190.1; IR (drift) 3323, 1743, 1685, 1647 cm$^{-1}$. Anal. calcd for C$_{27}$H$_{32}$FN$_5$O$_5$.0.5 H$_2$O: C, 60.66; H, 6.22; N, 13.10. Found: C, 60.80; H, 6.22; N, 13.04.

Step 3:

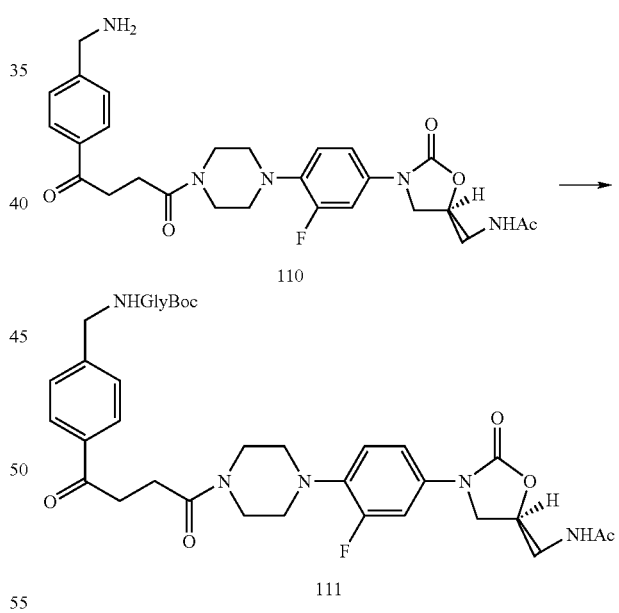

A stirred, ice cold solution of 70 (1.79 g, 7.67 mmol), 17b (2.58 g, 7.67 mmol), HOBT (1.14 g, 8.44 mmol) and DMF (67 ml) was treated with EDC (3.23 g, 16.9 mmol) and kept in the ice bath for 2 h and at ambient temperature for 2 h. It was then mixed with water (500 ml) and 1:4 Et$_2$O:heptane (250 ml). The solid was collected by filtration, dried and chromatographed on silica gel with 5% MeOH—CH$_2$Cl$_2$ to give 3.51 g of 109: MS (EI) m/z 551.2 (M$^+$), 335.1, 334.1, 307.1; IR (drift) 3307, 2100, 1743, 1688, 1647 cm$^{-1}$.

Compound 110 (852 mg, 1.62 mmol) was dissolved in warm DMF (14 ml). The stirred solution was cooled in an ice bath and treated with N-t-Boc-glycine (284 mg, 1.62 mmol), HOBT (240 mg, 1.78 mmol) and finally EDC (682 mg, 3.56 mmol). It was kept in the ice bath for 2 h and at ambient temperature for 2 h and then mixed with water (150 ml). The resulting solid was collected by filtration, washed with water and then with 1:1 Et$_2$O-heptane and dried to give 998 mg of 111: $^1$H NMR [300 MHz, (CD$_3$)$_2$SO] δ 1.37 (s, 9H), 1.81 (s, 3H), 2.72 (t, 2H), 2.89, 2.99 (s, s, 4H), 3.21 (t, 2H), 3.38 (t, 2H), 3.56 (m, 4H), 3.66 (m, 3H), 4.07 (t, 1H), 4.33 (d, 2H), 4.69 (m, 1H), 7.07 (m, 2H), 7.16 (dd, 1H), 7.37 (d, 2H), 7.49 (dd, 1H), 7.90 (d, 2H), 8.23 (t, 1H), 8.38 (t, 1H).

Step 4:

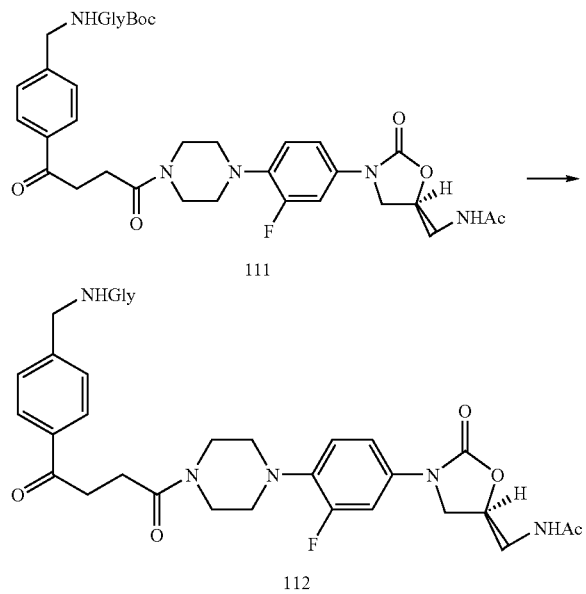

Solid 111 (830 mg, 1.22 mmol) was cooled in an ice bath under nitrogen, and treated with 4N HCl in dioxane (10 ml). The mixture was stirred in the ice bath for 1.5 h and then concentrated in vacuo. A solution of the residue in water (15 ml) was made alkaline with solid NaHCO$_3$ and freeze dried. The resulting solid was extracted with MeOH—CH$_2$Cl$_2$ and the extract was concentrated. Chromatography of the residue on silica gel with 10–20% MeOH—CH$_2$Cl$_2$ and crystallization of the product from MeOH—CH$_2$Cl$_2$-heptane gave 338 mg of 112, as an off-white solid: $^1$H NMR [300 MHz, (CD$_3$)$_2$SO] δ 1.81 (s, 3H), 2.72 (t, 2H), 2.72 (broad s, 2H), 2.89, 2.99 (s, s, 4H), 3.18 (s, 2H), 3.21 (t, 2H), 3.38 (t, 2H), 3.57 (s, 2H), 3.68 (m, 3H), 4.07 (t, 1H), 4.35 (d, 2H), 4.69 (m, 1H), 7.07 (t, 1H), 7.17 (dd, 1H), 7.38 (d, 2H), 7.49 (dd, 1H), 7.92 (d, 2H), 8.24 (t, 1H), 8.46 (t, 1H).

Example 35

2-[3-methyl-3-(4-{(5S)-2-oxo-5-[(propionylamino)methyl]-1,3-oxazolidin-3-yl}phenyl)azetidin-1-yl]-2-oxoethyl 4-(aminomethyl)benzamide (120)

Step 1:

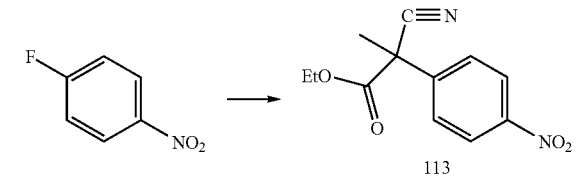

A suspension of anhydrous K$_2$CO$_3$ (13.0 g, 94.3 mmol) in CH$_3$CN (175 mL) is treated with ethyl cyanoacetate (5.0 mL, 47.1 mmol) at rt with stirring. The reaction is warmed to 75° C. for 20 min, then cooled to 0° C. with an ice bath followed by dropwise treatment with 1-fluoro-4-nitrobenzene (5.0 mL, 47.1 mmol) over 5 min. The ice bath is removed and the red suspension is warmed to 75° C. for 18 h. The dark red suspension is then cooled to rt, treated with iodomethane (26.4 mL, 424.2 mmol), K$_2$CO$_3$ (19.5 g, 141.4 mmol), acetone (60 mL), and then warmed to 60° C. for 24 h. The pink suspension is then cooled to rt and filtered through Celite (repeated EtOAc washings). After concentrating the filtrate in vacuo, the orange-brown residue is diluted with H$_2$O (300 mL) and extracted with EtOAc (2×200 mL). The combined organic extracts are washed with brine (150 mL), dried over MgSO$_4$, and concentrated in vacuo. Purification of the crude product via Biotage chromatography (eluting with 20% EtOAc/Hexane) affords 113 (4.87 g) as a white solid. $^1$H NMR (400 MHz, CDCl$_3$) δ 8.27 (d, J=8.9 Hz, 2 H), 7.73 (d, J=9.1 Hz, 2 H), 4.26 (m, 2 H), 1.99 (s, 3 H), 1.26 (t, J=7.2 Hz, 3 H).

Step 2:

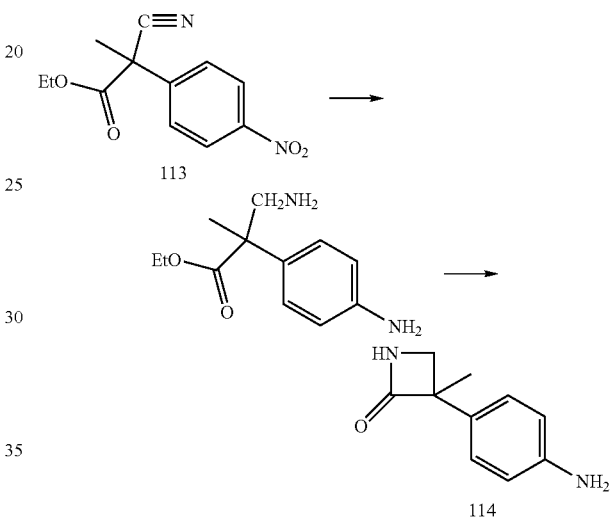

A solution 113 (15.8 g, 63.8 mmol) in absolute EtOH (650 mL) is treated with Raney nickel (34.5 g of a 50% slurry in H$_2$O) and subjected to hydrogenation in a Parr apparatus for 18 h (25–30 psi H$_2$, rt). The reaction mixture is then filtered through Celite (repeated EtOH washings) and concentrated in vacuo. Purification of the crude product via Biotage chromatography (eluting with 15% MeOH/EtOAc) affords the reduced amino-aniline compound corresponding to 113 (11.36 g) as a pale yellow oil: $^1$H NMR (400 MHz, CDCl$_3$) δ 7.04 (d, J=8.7 Hz, 2 H), 6.63 (d, J=8.7 Hz, 2 H), 4.13 (m, 2 H), 3.09 (d, J=13.3 Hz, 1 H), 2.94 (d, J=13.5 Hz, 1 H), 1.52 (s, 3 H), 1.19 (t, J=7.2 Hz, 3 H); $^{13}$C NMR (100 MHz, CDCl$_3$) δ 175.87, 145.17, 131.43, 127.06, 115.02, 60.61, 51.74, 51.14, 20.81, 14.05. A solution of this amino-aniline (8.3 g, 37.3 mmol) in THF (207 mL) is added dropwise to a 0° C. solution of methyl magnesium bromide (62.2 mL, 3.0 M in Et$_2$O) in THF (415 mL). When addition is complete, THF (30 mL) is used to rinse the addition funnel, and then the ice bath is removed and reaction stirred at rt for 3 h. The reaction contents are poured into saturated aqueous NH$_4$Cl (1000 mL) and volatiles are removed in vacuo. The aqueous phase is extracted with CHCl$_3$ (4×300 mL). The combined organic extracts are washed with H$_2$O (200 mL), brine (200 mL), dried over MgSO$_4$, and concentrated in vacuo. Purification of the crude product via Biotage chromatography (eluting with 50% EtOAc/hexane) affords 114 (4.65 g) as an off-white solid in 71% yield; $^1$H NMR (300 MHz, CDCl$_3$) δ 7.17 (d, J=8.7 Hz, 2 H), 6.65 (d, J=8.3 Hz, 2 H), 6.13 (s, 1 H), 3.48 (d, J=5.3 Hz, 1 H), 3.36 (d, J=5.3 Hz, 1 H), 1.62 (s, 3 H); $^{13}$C NMR (100 MHz, CDCl$_3$) δ 173.44, 145.30, 130.60, 126.71, 115.15, 59.41, 51.40, 23.14; MS (ESI+) for C$_{10}$H$_{12}$N$_2$O m/z 177.1 (M+H)$^{+}$ Step 3:

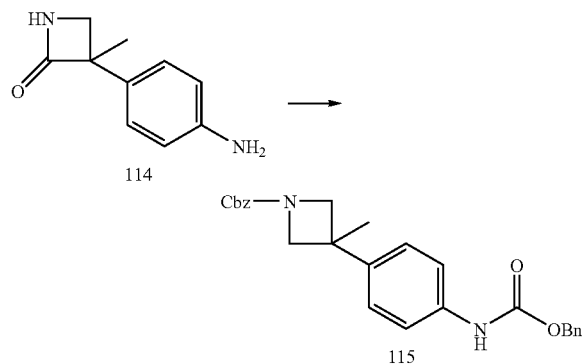

A solution of LiAlH$_4$ (79.2 mL, 1.0 M in THF) is diluted with THF (77 mL) and cooled to 0° C. To this is added a solution of 114 (4.65 g, 26.4 mmol) in THF (116 mL), with gas evolution. The ice bath is removed and the reaction was heated to reflux (75° C. oil bath) for 22 h, during which time the reaction became a white suspension. After cooling to rt, the mixture was treated successively with H$_2$O (3.01 mL), 5 N aqueous NaOH (2.71 mL), and H$_2$O (10.52 mL). The resulting suspension was diluted with EtOAc (600 mL), filtered through a pad of Celite, rinsing the Celite with additional EtOAc (400 mL). Concentration in vacuo affords the desired azetidine (4.76 g) as a yellow oil. A solution of this crude intermediate in acetone (85 mL) and H$_2$O (47 mL) was treated with sodium bicarbonate (19.96 g, 237.6 mmol). The resulting suspension was cooled to 0° C. and treated with benzylchloroformate (18.84 mL, 132.0 mmol) with gas evolution. The ice bath was removed and the reaction mixture was stirred overnight at rt. In the a.m., the reaction mixture was diluted with saturated aqueous sodium bicarbonate (200 mL) and extracted with EtOAc (3×200 mL). The combined organic extracts were washed with H$_2$O (100 mL), brine (100 mL), dried over MgSO$_4$, and concentrated in vacuo. Purification of the crude product via Biotage chromatography (eluting with 25% EtOAc/hexane) affords (4.75 g) as a pale yellow syrup; $^1$H NMR (400 MHz, CDCl$_3$) δ 7.41–7.29 (m, 12 H), 7.13 (d, J=8.7 Hz, 2 H), 6.77 (s, 1 H), 5.19 (s, 2 H), 5.10 (s, 2 H), 4.22 (d, J=8.3 Hz, 2 H), 3.97 (d, J=8.3 Hz, 2 H), 1.59 (s, 3 H); MS (ESI−) for C$_{26}$H$_{26}$N$_2$O$_4$ m/z 429.0 (M−H)$^−$ Step 4:

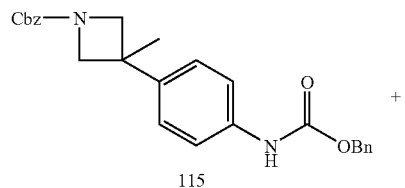

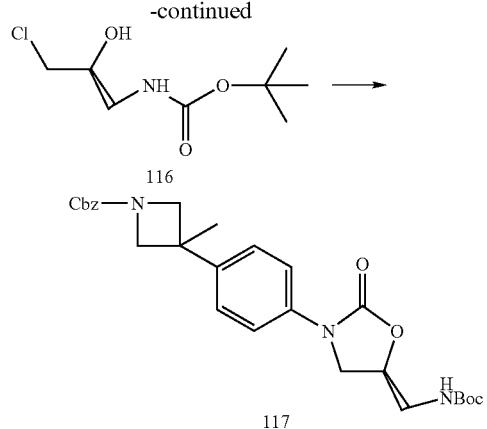

A solution of 116 (4.75 g, 11.03 mmol) in DMF (20 mL) at 0° C. is treated with LiOt-Bu (33.1 mL, 1.0 M solution in hexanes) dropwise over 25 min. After an additional 20 min, the reaction is treated with 116 (4.63 g, 22.07 mmol, U.S. patent Publication application Ser. No. 2002/0086900) and stirred 14 h with ice bath expiring. The reaction is quenched with saturated aqueous NH$_4$Cl (85 mL) and then extracted with EtOAc (3×80 mL). The combined organic extracts are washed with brine, dried over MgSO$_4$, and concentrated in vacuo. Purification of the crude product via Biotage chromatography (eluting with 50% EtOAc/hexane) affords 117 (4.16 g) as a white solid; $^1$H NMR (400 MHz, DMSO-d$_6$) δ 7.50 (d, J=8.7 Hz, 2 H), 7.39–7.30 (m, 5 H), 7.31 (d, J=8.7 Hz, 2 H), 7.22 (t, J=5.9Hz, 1 H), 5.05 (s, 2 H), 4.68 (m, 1 H), 4.14 (m, 2 H), 4.10 (t, J=9.0 Hz, 1 H), 3.95 (m, 2 H), 3.78 (dd, J=9.0, 5.9 Hz, 1 H), 3.27 (t, J=5.4 Hz, 2 H), 1.54 (s, 3 H), 1.35 (s, 9 H); $^{13}$C NMR (100 MHz, DMSO-d$_6$) δ 155.86, 154.03, 141.54, 136.73, 136.56, 128.28, 127.75, 127.52, 125.73, 117.96, 77.96, 71.28, 65.62, 47.03, 42.79, 37.69, 28.79, 28.00.

Step 5:

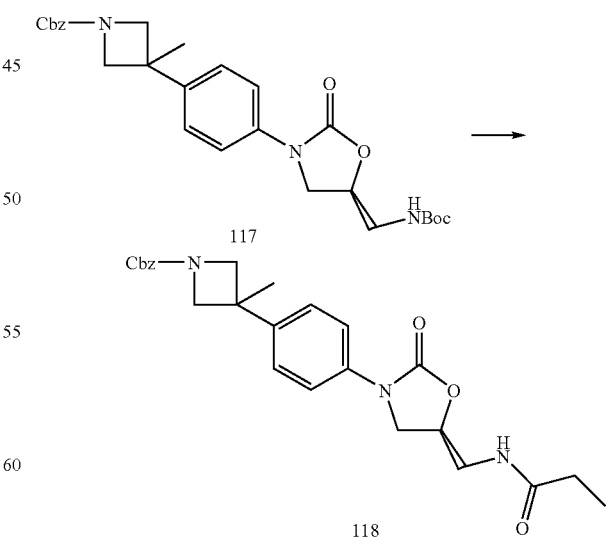

A solution of 117 (4.10 g, 8.37 mmol) in MeOH (20 mL) at 0° C. is treated with 4 M HCl-dioxane (5.0 mL) and stirred for 10 min. The ice bath is then removed, and after stirring 20 h at rt, the solution is concentrated in vacuo. The resulting pale yellow solid is subsequently treated with pyridine (12 mL) and propionic anhydride (6 mL) in CH$_2$Cl$_2$ (30 mL) at 0° C. and stirred 14 h with bath expiring. The reaction is quenched with H$_2$O (150 mL), and the layers are separated. The organic layer is washed with 1.0 M HCl (2×50 mL), brine (50 mL), dried over MgSO$_4$, and concentrated in vacuo. Trituration (Et$_2$O) affords (2.98 g) as a white solid in 79% yield; $^1$H NMR (400 MHz, DMSO-d$_6$) δ 8.18 (t, J=5.8 Hz, 1 H), 7.50 (d, J=8.7 Hz, 2 H), 7.39–7.30 (m, 5 H), 7.31 (d, J=8.5 Hz, 2 H), 5.05 (s, 2 H), 4.72 (m, 1 H), 4.13 (m, 2 H), 4.11 (t, J=8.9 Hz, 1 H), 3.96 (m, 2 H), 3.74 (dd, J=8.9, 6.2 Hz, 1 H), 3.42 (m, 2 H), 2.10 (q, J=7.7 Hz, 2 H), 1.54 (s, 3 H), 0.96 (t, J=7.7 Hz, 3 H); $^{13}$C NMR (100 MHz, DMSO-d$_6$) δ 173.65, 155.88, 154.04, 141.56, 136.74, 136.52, 128.29, 127.75, 127.53, 125.75, 117.98, 71.43, 65.64, 47.11, 41.24, 37.69, 28.78, 28.25, 9.81.

Step 6:

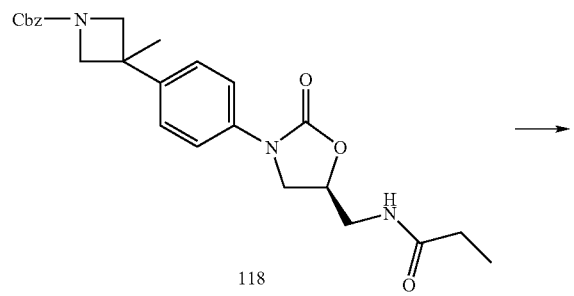

118

-continued

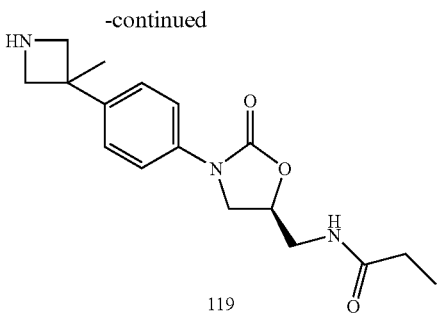

119

A solution of 118 (2.78 g, 6.16 mmol) in 5:1 MeOH:THF (60 mL) was placed under N$_2$ (g) and then treated with 10% Pd/C (278 mg). The reaction vessel was then charged with H$_2$ (g) and the reaction mixture was stirred overnight at rt. In the a.m., the mixture was filtered and concentrated in vacuo. Purification of the crude product via Biotage chromatography (eluting first with 10% MeOH/CH$_2$Cl$_2$ and then with 5–15% MeOH(NH$_3$)/CH$_2$Cl$_2$) affords (1.79 g) as a white solid; $^1$H NMR (400 MHz, DMSO-d$_6$) δ 8.18 (t, J=5.8 Hz, 1 H), 7.47 (d, J=8.9 Hz, 2 H), 7.21 (d, J=8.7 Hz, 2 H), 4.71 (m, 1 H), 4.10 (t, J=9.0 Hz, 1 H), 3.74 (t, J=6.4 Hz, 1 H), 3.73 (d, J=6.6 Hz, 2 H), 3.42 (m, 2 H), 3.38 (d, J=7.5 Hz, 2 H), 2.10 (q, J=7.5 Hz, 2 H), 1.53 (s, 3 H), 0.96 (t, J=7.6 Hz, 3 H); $^{13}$C NMR (100 MHz, DMSO-d$_6$) δ 173.65, 154.06, 144.21, 135.92, 125.29, 117.95, 71.39, 58.27, 47.15, 41.91, 41.25, 28.64, 28.25, 9.82 1.41.

Step 7:

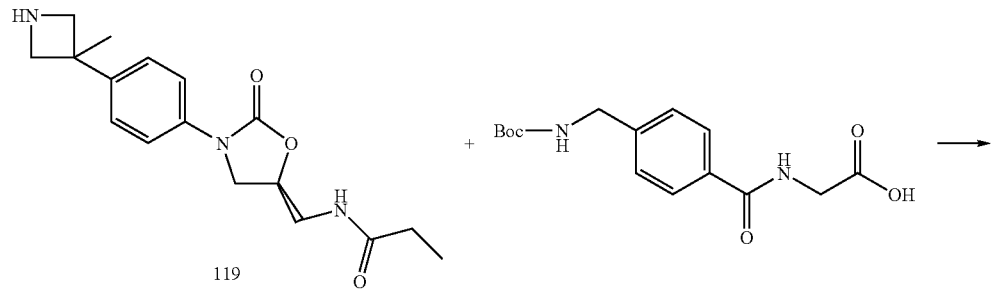

119

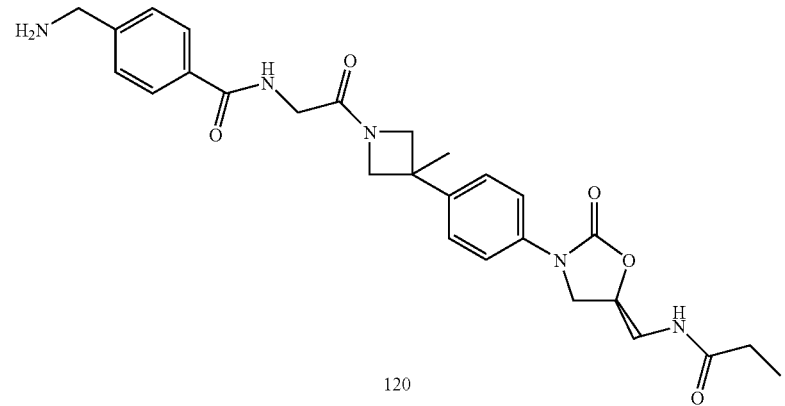

120

A solution of 119 (241 mg, 0.76 mmol) and N-(4-{[(tert-butoxycarbonyl)-amino[methyl]benzoyl)glycine (246 mg, 0.80 mmol) in CH₃CN (20 mL) at 0° C. was treated with HATU (304 mg, 0.80 mmol) followed by Hunig's base (0.70 mL, 3.99 mmol) and stirred overnight with ice bath expiring. In the a.m., the reaction mixture was concentrated in vacuo, and the residue dissolved in CH₂Cl₂ (200 mL). This organic phase was washed with H₂O, brine, dried over MgSO₄, and concentrated in vacuo to afford a yellow-brown solid. Purification via Biotage chromatography (eluting with 2–10% MeOH/CH₂Cl₂) affords the Boc-protected amine (352 mg) as a glassy film in 76% yield. This compound (300 mg) was subsequently treated with TFA (2.0 mL) in CH₂Cl₂ (7.0 mL) at 0° C. for 10 min, and then stirred an additional 2h at rt. Concentration in vacuo followed by purification via Biotage chromatography (eluting first with 10% MeOH/CH₂Cl₂ and then with 10% MeOH(NH₃)/CH₂Cl₂) affords 120 (217 mg) as a pale yellow; ¹H NMR (400 MHz, DMSO-d₆) δ 8.67 (t, J=5.7 Hz, 1 H), 8.19 (t, J=5.9 Hz, 1 H), 7.83 (d, J=8.3 Hz, 2 H), 7.53 (d, J=8.9 Hz, 2 H), 7.44 (d, J=8.3 Hz, 2 H), 7.34 (d, J=8.7 Hz, 2 H), 4.73 (m, 1 H), 4.45 (d, J=8.3 Hz, 1 H), 4.25 (d, J=8.3 Hz, 1 H), 4.12 (t, J=9.1 Hz, 1 H), 4.09 (d, J=9.1 Hz, 1 H), 3.90 (m, 3 H), 3.82 (s, 2 H), 3.76 (dd, J=9.0, 6.3 Hz, 1 H), 3.42 (m, 4 H), 2.10 (q, J=7.7 Hz, 2 H), 1.57 (s, 3 H), 0.96 (t, J=7.6 Hz, 3 H).

Example 36

N-{[(5S)-3-(4-{1-[4-(4-aminophenyl)-4-oxobutanoyl]-3-methylazetidin-3-yl}phenyl)-2-oxo-1,3-oxazolidin-5-yl]methyl}propanamide (121)

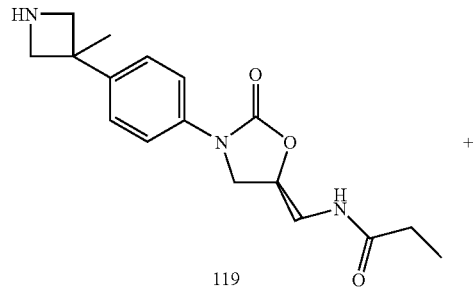

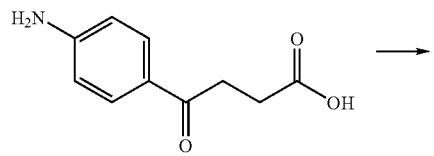

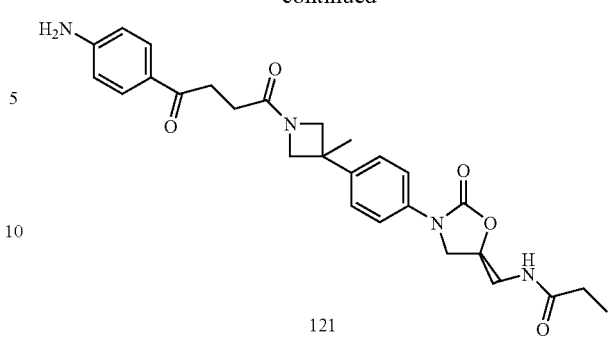

A mixture of 119 (1.50 g, 4.73 mmol), 4-(4-aminophenyl)-4-oxobutanoic acid (1.10 g, 5.67 mmol), HOBt (703 mg, 5.20 mmol), and Hunig's base (2.06 mL, 11.83 mmol) in CH₂Cl₂ (25 mL) at 0° C. was treated with EDCI (1.99 g, 10.40 mmol) and stirred 14 h with ice bath expiring. The reaction mixture was diluted with CH₂Cl₂ (50 mL) and H₂O (50 mL) and layers separated. The aqueous layer was extracted with CH₂Cl₂ (3×50 mL). The combined organic layers were washed with H₂O (50 mL), brine (50 mL), dried over MgSO₄, and concentrated in vacuo to afford a black foamy solid. Purification via Biotage chromatography (eluting with 2% MeOH(NH₃)/CH₂Cl₂) gave 121 (1.76 g) as a pale red solid in 76% yield; ¹H NMR (400 MHz, DMSO-d₆) δ 8.18 (t, J=5.5 Hz, 1 H), 7.68 (d, J=8.7 Hz, 2 H), 7.52 (d, J=8.7 Hz, 2 H), 7.34 (d, J=8.7 Hz, 2 H), 6.56 (d, J=8.7 Hz, 2 H), 6.02 (s, 2 H), 4.72 (m, 1 H), 4.41 (d, J=7.9 Hz, 1 H), 4.20 (d,J=7.9 Hz, 1 H), 4.12 (t, J=9.0 Hz, 1 H), 4.01 (d, J=9.0 Hz, 1 H), Hz, 1 H), 4.20 (d, J=7.9 Hz, 1 H), 4.12 (t, J=9.0 Hz, 1 H), 4.01 (d, J=9.0 Hz, 1 H), 3.85 (d, J=9.0 Hz, 1 H), 3.76 (dd, J=9.0, 6.4 Hz, 1 H), 3.42 (m, 2 H), 3.07 (t, J=6.4 Hz, 2 H), 2.37 (t, J=6.0 Hz, 2 H), 2.10 (q, J=7.7 Hz, 2 H), 1.57 (s, 3 H), 0.96 (t, J=7.5 Hz, 3 H); ¹³C NMR (100 MHz, DMSO-d₆) δ 195.57, 173.66, 172.10, 154.05, 47.12, 41.25, 37.01, 31.77, 28.84, 28.26, 24.84, 9.83.

Example 37

N-({(5S)-3-[4-(1-{4-[4-(glycylamino)phenyl]-4-oxobutanoyl}-3-methylazetidin-3-yl)phenyl]-2-oxo-1,3-oxazolidin-5-yl}methyl)propanamide

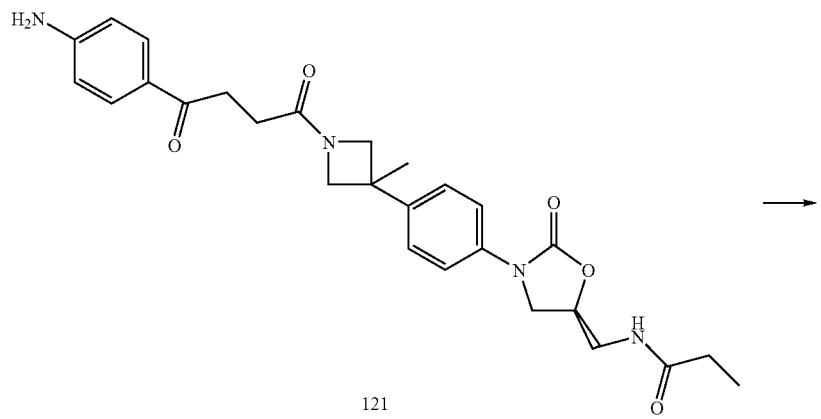

-continued

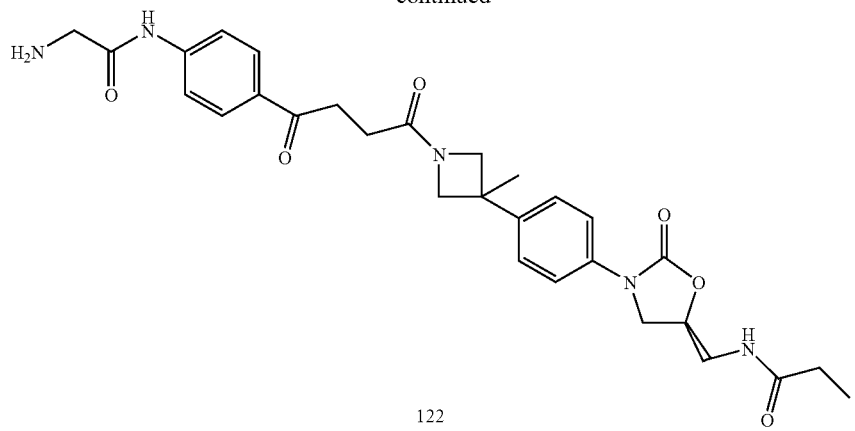

122

A solution of 121 (from Example 36)(1.00 g, 2.03 mmol) and FmocGlyCl (770 mg, 2.44 mmol) in CH$_2$Cl$_2$ (15 mL) at rt was treated with pyridine (0.82 mL, 10.15 mmol) and let stir for 90 min. The reaction was then diluted with CH$_2$Cl$_2$ (200 mL), washed with H$_2$O (75 mL), 0.1 M HCl (75 mL), brine (50 mL), dried over MgSO$_4$, and chromatography (eluting with 5% MeOH/CH$_2$Cl$_2$) affords the Fmoc-protected chromatography (eluting with 5% MeOH/CH$_2$Cl$_2$) affords the Fmoc-protected subsequently treated with piperidine (0.19 mL) in DMF (5.0 mL) at rt for 20 min, and subsequently treated with piperidine (0.19 mL) in DMF (5.0 mL) at rt for 20 min, and with 5–10% MeOH/CH$_2$Cl$_2$ and then with 10% MeOH(NH$_3$)/CH$_2$Cl$_2$ followed by trituration (Et$_2$O) affords 122 (258 mg) as a pale grey solid; $^1$H NMR (400 MHz, trituration (Et$_2$O) affords 122 (258 mg) as a pale grey solid; $^1$H NMR (400 MHz, DMSO-d$_6$) δ 8.19 (t, J=5.7 Hz, 1 H), 7.95 (d, J=8.7 Hz, 2 H), 7.78 (d, J=8.7 Hz, 2 H), 7.53 (d, J=8.7 Hz, 2 H), 7.35 (d, J=8.7 Hz, 2 H), 4.73 (m, 1 H), 4.42 (d, J=8.1 Hz, 1 H), 4.22 (d, J=8.1 Hz, 1 H), 4.13 (t, J=9.1 Hz, 1 H), 4.03 (d, J=9.1 Hz, 1 H), 3.86 (d, J=9.3 Hz, 1 H), 3.76 (dd, J=9.0, 6.3 Hz, 1 H), 3.43 (m, 3 H), 3.31 (s, 2 H), 3.21 (t, J=6.2 Hz, 2 H), 2.43 (t, J=5.6 Hz, 2 H), 2.11 (q, J=7.7 Hz, 2H), 1.58 (s, 3 H), 0.96 (t, J=7.6 Hz, 3 H); $^{13}$C NMR (100 MHz, DMSO-d$_6$) δ 197.19, 173.67, 117.99, 71.45, 61.84, 59.80, 54.81, 47.12, 45.55, 41.25, 37.07, 32.43, 28.86, 28.26, 24.69, 9.83.

Example 38

N-{[(5S)-3-(4-{1-[4-(4-aminophenyl)-4-oxobutanoyl]-3-methylazetidin-3-yl}-3-fluorophenyl)-2-oxo-1,3-oxazolidin-5-yl]methyl}acetamide (124)

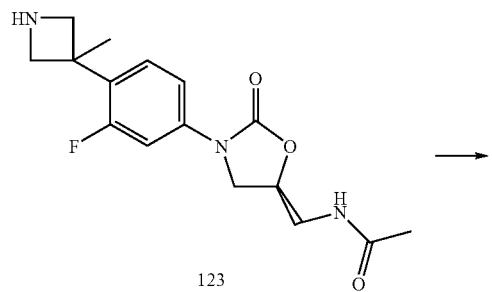

123

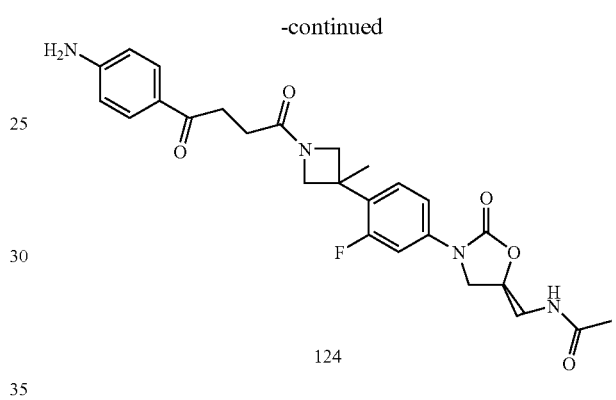

124

A solution of 123 (Prepared as described in U.S. Pat. No. 5,968,962, 1.50 g, 3.34 mmol), 4-(4-aminophenyl)-4-oxobutanoic acid (645 mg, 3.34 mmol), and Hunig's base (2.91 mL, 16.69 mmol) in CH$_3$CN (56 mL) at 0° C. was treated dropwise with a solution of HATU (1.33 g, 3.51 mmol) in CH$_3$CN (38 mL). Additional Hunig's base was stirred 14 h with ice bath expiring. The reaction mixture was concentrated in vacuo, and residue was dissolved in CH$_2$Cl$_2$. This organic layer was washed initially with 1.0 M HCl; however, back-extraction with CH$_2$Cl$_2$ was necessary to retrieve much of the desired product from the aqueous layer. The organic layers are combined, washed with brine, dried over MgSO$_4$, and concentrated in vacuo. Purification via Biotage chromatography (eluting with 4% MeOH/CH$_2$Cl$_2$) affords 124 (1.42 g) as a red solid in 86% yield; $^1$H NMR (400 MHz, DMSO-d$_6$) δ 8.25 (t, J=5.8 Hz, 1 H), 7.67 (d, J=8.5 Hz, 2 H), 7.50 (dd, J=13.5, 1.7 Hz, 1 H), 7.31 (m, 2 H), 6.55 (d, J=8.7 Hz, 2 H), 6.02 (s, 2 H), 4.74 (m, 1 H), 4.48 (d, J=8.1 Hz, 1 H), 4.21 (d, J=8.3 Hz, 1 H), 4.12 (m, 2 H), 3.85 (d, J=9.3 Hz, 1 H), 3.74 (dd, J=9.1, 6.4 Hz, 1 H), 3.42 (t, J=5.5 Hz, 2 H), 3.06 (t, J=6.4 Hz, 2 H), 2.36 (m, 2 H), 1.84 (s, 3 H), 1.56 (s, 3 H); $^{13}$C NMR (100 MHz, DMSO-d$_6$) δ 195.52, 172.19, 169.88, 161.26, 158.05, 153.88, 153.46, 138.57, 138.43, 130.07, 127.82, 127.74, 127.63, 127.43, 124.15, 113.41, 112.32, 105.66, 105.30, 71.58, 60.77, 58.62, 54.81, 47.07, 41.25, 35.07, 31.73, 28.02, 24.84, 22.34.

Example 39

N~1~-(4-{4-[3-(4-{(5S)-5-[(acetylamino)methyl]-2-oxo-1,3-oxazolidin-3-yl}-2-fluorophenyl)-3-methylazetidin-1-yl]-4-oxobutanoyl}phenyl)glycinamide (125)

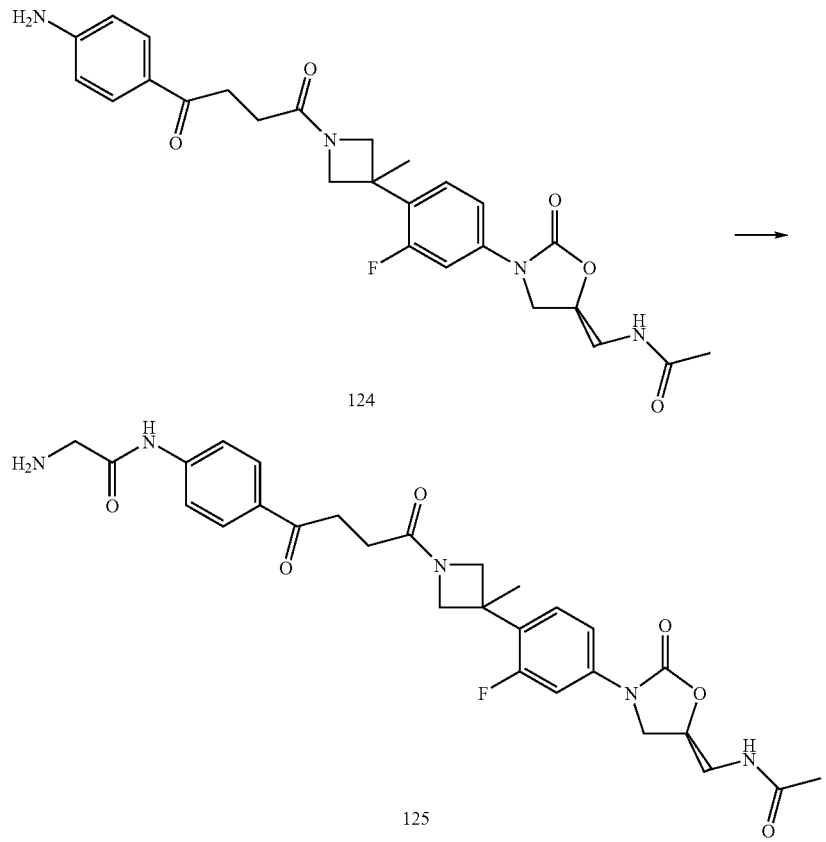

A solution of 124 (from Example 38) (790 mg, 1.59 mmol) and CbzGlyOH (349 mg, 1.67 mmol) in CH$_3$CN (40 mL) at 0° C. was treated with Hunig's base (1.39 mL, 7.96 mmol) followed by HATU (635 mg, 1.67 mmol) and stirred 14 h with ice bath expiring. The reaction mixture was concentrated in vacuo, and the residue dissolved in CH$_2$Cl$_2$ (200 mL). This organic phase was washed with 1.0 M HCl, saturated aqueous NaHCO$_3$, brine, dried over MgSO$_4$, and concentrated in vacuo. Purification via Biotage chromatography (eluting with 5% MeOH/CH$_2$Cl$_2$) affords the Cbz-protected amine (313 mg) as a pale yellow solid in 29% yield. This compound was subsequently placed under N$_2$ (g) in 10:1 THF:MeOH (11 mL) and treated with Pd/C (80 mg). The reaction vessel was then charged with H$_2$ (g) and the reaction mixture was stirred for 2 d at rt. After filtering to remove Pd/C, the filtrate was concentrated in vacuo. Purification via Biotage chromatography (eluting with 4% MeOH(NH$_3$)/CH$_2$Cl$_2$) affords 125 (99 mg) as a pale yellow-green solid: $^1$H NMR (400 MHz, DMSO-d$_6$) δ 8.26 (t, J=5.8 Hz, 1 H), 7.94 (d, J=8.9 Hz, 2 H), 7.77 (d, J=8.7 Hz, 2 H), 7.50 (dd, J=13.6, 1.6 Hz, 1 H), 7.31 (m, 2 H), 4.74 (m, 1 H), 4.49 (d, J=8.1 Hz, 1 H), 4.22 (d, J=8.1 Hz, 1 H), 4.13 (m, 2 H), 3.86 (d, J=9.3 Hz, 1 H), 3.74 (dd, J=9.0, 6.5 Hz, 1 H), 3.42 (t, J=5.4 Hz, 2 H), 3.32 (s, 2 H), 3.20 (t, J=6.3 Hz, 2 H), 2.42 (m, 2 H), 1.84 (s, 3 H), 1.57 (s, 3 H); $^{13}$C NMR (100 MHz, DMSO-d$_6$) δ 197.15, 172.49, 171.89, 169.89, 161.28, 158.06, 153.89, 142.99, 138.59, 138.45, 131.11, 129.07, 127.83, 127.71, 127.60, 127.42, 118.13, 113.42, 105.67, 105.31, 71.59, 60.81, 58.69, 48.48, 47.08, 45.47, 41.26, 35.14, 32.41, 28.03, 24.71, 22.34.

Example 40

Preparation of 2-[3-(4-{(5S)-5-[(acetylamino)methyl]-2-oxo-1,3-oxazolidin-3-yl}-2-fluorophenyl)-3-methylazetidin-1-yl]-2-oxoethyl-4-(aminoethyl)benzamide (126)

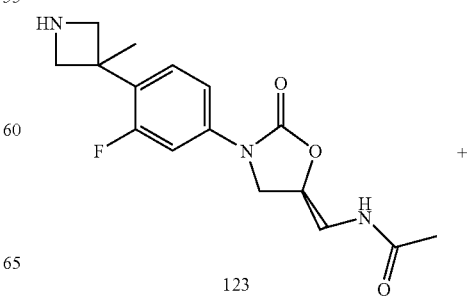

-continued

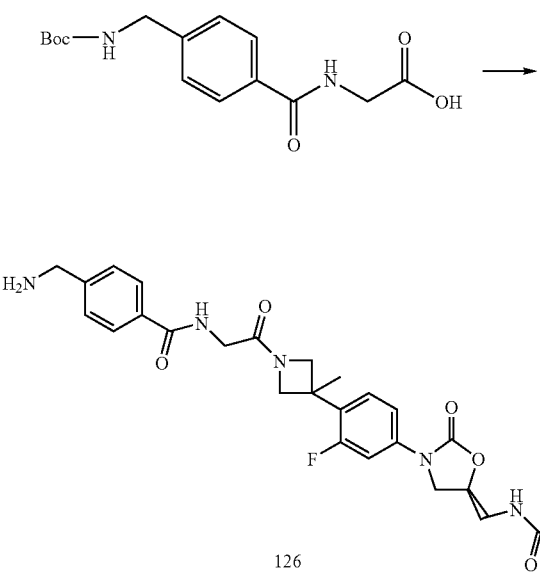

A solution of N-(4-{[(tert-butoxycarbonyl)amino] methyl}benzoyl)glycine (216 mg, 0.70 mmol) and Hunig's base (0.23 mL, 1.34 mmol) in CH₃CN (10 mL) at 0° C. was treated with HATU (266 mg, 0.70 mmol) and let stir for 35 min. A solution of 123 (300 mg, 0.67 mmol) in CH₃CN/ DMF (5 mL/1 mL) was added along with more Hunig's base (0.35 mL, 2.00 mmol). The reaction was stirred for 30 min with ice bath expiring, then concentrated in vavuo, and the amber residue was dissolved in CH₂Cl₂ (100 mL), washed with 0.1 M HCl (2×30 mL), saturated aqueous NaHCO₃ (40 mL), brine (40 mL), dried over MgSO₄, and concentrated in vacuo to afford a yellow-brown solid. Purification via Biotage chromatography (eluting with 4–5% MeOH/ CH₂Cl₂) affords the Boc-protected amine (300 mg) as a white solid in 74% yield. This compound (750 mg) was treated with TFA (3.0 mL) in CH₂Cl₂ (10 mL) at 0° C. for 20 min, and then stirred an additional 50 min at rt. Concentration in vacuo followed by purification via Biotage chromatography (eluting first with 5% MeOH/CH₂Cl₂ and then with 5% MeOH(NH₃)/CH₂Cl₂) and trituration (Et₂O) affords 126 (463 mg) as a white solid; $^1$H NMR (400 MHz, DMSO-d₆) δ 8.65 (t, J=5.6 Hz, 1 H), 8.26 (t, J=5.8 Hz, 1 H), 7.81 (d, J=8.1 Hz, 2 H), 7.51 (dd, J=13.7, 1.9 Hz, 1 H), 7.42 (d, J=8.3 Hz, 2 H), 7.31 (m, 2 H), 4.74 (m, 1 H), 4.52 (d, J=8.3 Hz, 1 H), 4.26 (d, J=8.5 Hz, 1 H), 4.18 (d, J=9.5 Hz, 1 H), 4.12 (t, J=9.0 Hz, 1 H), 3.88 (m, 3 H), 3.76 (s, 2 H), 3.74 (dd, J=9.0, 6.4 Hz, 1 H), 3.42 (t, J=5.4 Hz, 2 H), 1.84 (s, 3 H), 1.57 (s, 3 H); $^{13}$C NMR (100 MHz, DMSO-d₆) δ 169.89, 169.08, 166.12, 161.24, 158.02, 153.89, 147.67, 138.64, 138.49, 131.64, 127.78, 127.69, 127.44, 127.26, 126.98, 126.66, 113.46, 105.67, 105.31, 71.60, 60.91, 59.01, 48.48, 47.08, 45.18, 41.26, 35.72, 27.97, 22.34.

Example 41

N-{[(5S)-3-(3-Fluoro-4-{4-[4-(4-methoxyphenyl) butanoyl]piperazine-1-yl}phenyl)-2-oxo-1,3-oxazolidin-5-yl]methyl}acetamide (127). 34709-SCP-137

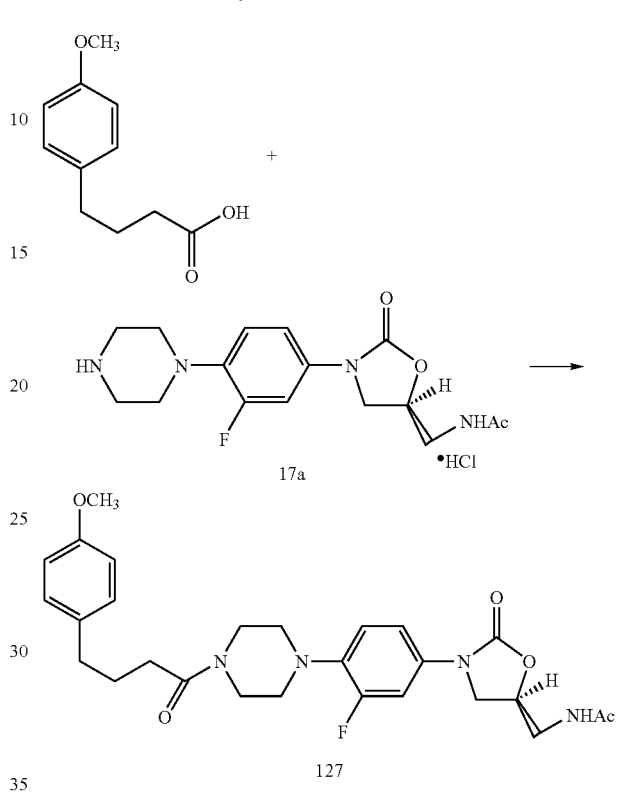

A stirred mixture of 4-(4-methoxyphenyl)butanoic acid (0.41 g, 2.11 mmol) in pyridine (10 ml), under nitrogen, was treated with EDC (0.48 g, 2.5 mmol), 3 PNU-99388 (0.78 g, 2.1 mmol) and DMAP (10 mg), kept at ambient temperature for 22 h and concentrated in vacuo. A mixture of the residue and 5% NaHCO₃ was extracted with EtOAc. The extract was washed with water and brine, dried (MgSO₄) and concentrated. Crystallization of the residue from EtOAc gave 0.75 g of 4: mp 164–165° C.; IR (drift) 3307, 1730, 1654, 1630 cm⁻¹. Anal. calcd for $C_{27}H_{33}FN_4O_5$: C, 63.27; H, 6.49; N, 10.93. Found: C, 63.20; H, 6.60; N, 10.95.

Example 42

N-{[(5S)-3-(3-Fluoro-4-{4-[4-(4-hydroxyphenyl) butanoyl]piperazin-1-yl}phenyl)-2-oxo-1,3-oxazolidin-5-yl]methyl}acetamide (128)

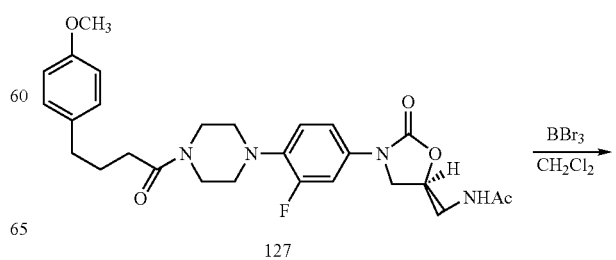

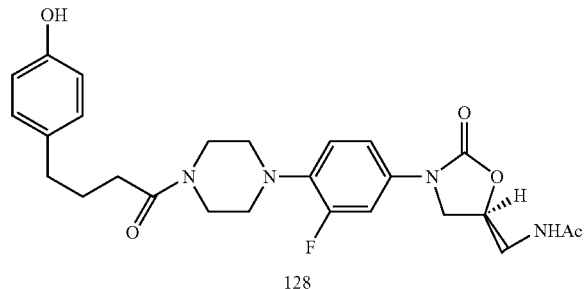

An ice cold, stirred suspension of 127 (0.25 g, 0.488 mmol) in CH$_2$Cl$_2$ (10 ml), under nitrogen, was treated, dropwise during 2 min, with a 1 M solution of boron tribromide in CH$_2$Cl$_2$ (1.02 ml). It was warmed to ambient temperature during 2 h, stirred at 0° C. for 72 h, warmed to ambient temperature for 4.5 h and mixed with ice water (20 ml). A solution of the resulting gum in CH$_2$Cl$_2$ was concentrated and the residue was chromatographed on silica gel with 7% MeOH—CH$_2$Cl$_2$. Crystallization of the product from MeOH gave 0.104 g of 128: mp 119–120° C. (dec); $^1$H NMR [400 MHz, (CD$_3$)$_2$SO] δ 1.76 (m, 2H), 1.83 (s, 3H), 2.32 (t, 2H), 2.48 (m, 2H), 2.92 (m, 4H), 3.17 (s, 3H, MeOH), 3.40 (t, 2H), 3.57 (m, 4H), 3.69 (dd, 1H), 4.08 (t, 1H), 4.08 (broad s, 1H), 4.70 (m, 1H), 6.67 (d, 2H), 6.98 (d, 2H), 7.07 (t, 1H), 7.17 (dd, 1H), 7.49 (dd, 1H), 8.25 (t, 1H), 9.13 (s, 1H); MS (ESI+) m/z 499.4 (M+H$^+$), 521 (M+Na$^+$); MS (ESI−) m/z 497.3 (M−H), 533.3 (M+Cl), 577, 579.2, (M+Br); IR (drift) 3273, 3269, 1731, 1643, 1638, cm$^{-1}$. Anal. calcd for C$_{26}$H$_{31}$FN$_4$O$_5$·CH$_3$OH: C, 61.12; H, 6.65; N, 10.56. Found: C, 60.94; H, 6.64; N, 10.56.

Example 43

2,2-Difluoro-N-{[(5S)-3-(3-fluoro-4-{4-[4-(4-methoxyphenyl)butyanoyl]piperazin-1-yl}phenyl)-2-oxo-1,3-oxazolidin-5-yl]methyl}ethanethioamide (129)

Step 1:

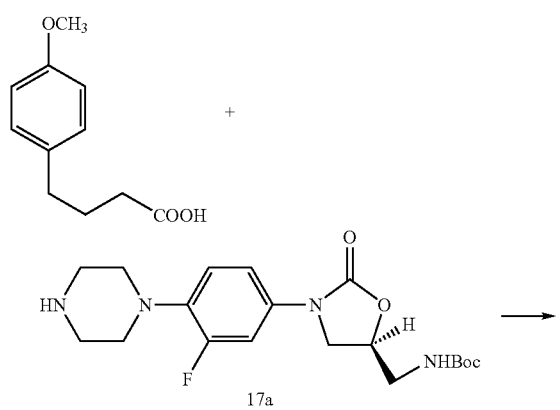

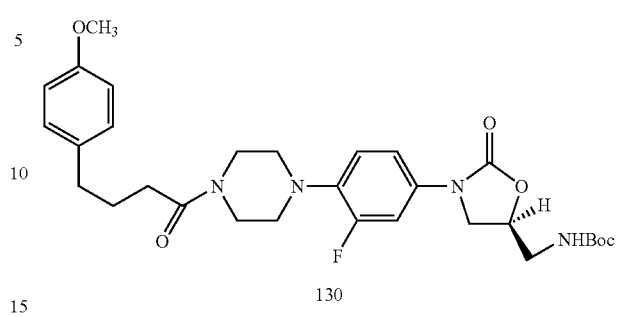

A stirred mixture of 4-(4-methoxyphenyl)butanoic acid (0.8 g, 4.1 mmol) and pyridine (20 ml), under nitrogen was treated with EDC (0.96 g, 5.0 mmol), 17a (1.69 g, 4.28 mmol) and DMAP (20 mg) and kept at ambient temperature for 22 h. It was concentrated in vacuo and the residue was mixed with 5% aqueous NaHCO$_3$ and extracted with Et$_2$O. The extract was washed with water and brine, dried (MgSO$_4$) and concentrated. Chromatography of the residue on silica gel with 2% MeOH—CH$_2$Cl$_2$ and crystallization of the product from EtOAc gave 1.26 g of 130: mp 140–141° C.; MS (ESI+) m/z 571.5 (M+H$^+$), 593.5 (M+Na$^+$); MS (ESI−) m/z 569.4 (M−H), 605 (M+Cl).

Step 2:

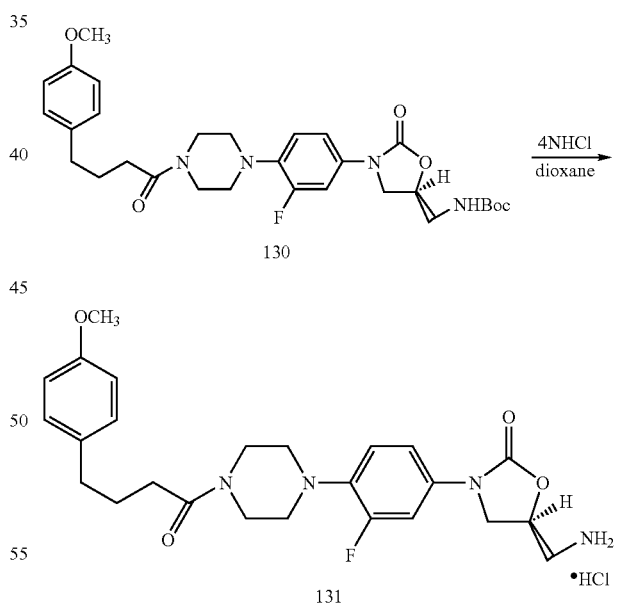

Compound 130 (0.5 g, 0.88 mmol) was cooled, under nitrogen, in an ice bath and treated, dropwise with stirring during 3 min with 4N HCl in dioxane (7 ml). It was kept in the ice bath for 45 min and at ambient temperature for 90 min. Excess hydrogen chloride was removed under a stream of nitrogen and the mixture was concentrated in vacuo to give 131, a white solid.

Step 3:

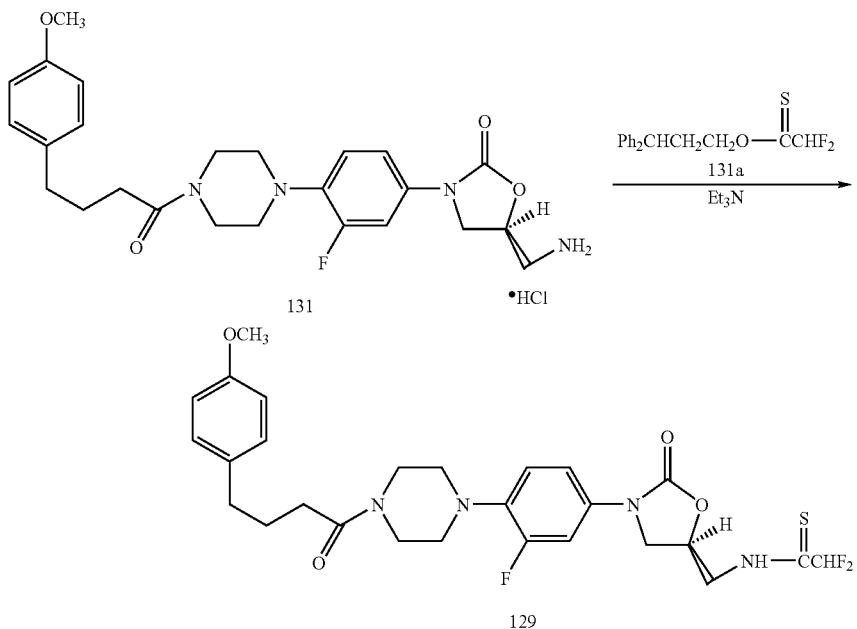

A stirred mixture of 131 (0.19 g) and CH$_2$Cl$_2$ (10 ml), under nitrogen, was treated with triethylamine (0.11 ml) and then, dropwise, with a solution of 131a (0.15 g, 0.49 mmol) in CH$_2$Cl$_2$ (2 ml). It was kept at ambient temperature for 5 h 20 min and concentrated in vacuo. Chromatography of the residue on silica gel with 1.75% MeOH—CH$_2$Cl$_2$ and crystallization of the product from EtOAc-hexane gave 0.14 g of 129: mp 128–129° C.; $^1$H NMR [400 MHz, (CD$_3$)$_2$SO] δ 1.77 (m, 2H), 2.34 (t, 2H), 2.54 (m, 2H), 2.92 (m, 4H), 3.56, 3.60 (m, m, 4H), 3.71 (s, 3H), 3.82 (dd, 1H), 3.96 (m, 2H), 4.16 (t, 1H), 5.01 (m, 1H), 6.37, 6.50, 6.64 (s, s, s, 1H), 6.85 (d, 2H), 7.10 (m, 3H), 7.18 (dd, 1H), 7.50 (dd, 1H), 11.18 (t, 1H); MS (ESI+) m/z 365.3 (M+H$^+$); MS (ESI−) m/z 563.3 (M−H), 599 (M+Cl); IR (drift) 3274, 1744, 1633, 1617 cm$^{-1}$. Anal. calcd for C$_{27}$H$_{31}$F$_3$N$_4$O$_4$S: C, 57.44; H, 5.53; N, 9.92. Found: C, 57.02; H, 5.52; N, 9.83.

Example 44

N-{[(5S)-3-(4-{4-[4-(4-Bromophenyl)-4-oxobutanoyl]-1-piperazinyl}-3-fluorophenyl)-2-oxo-1,3-oxazolidin-5-yl]methyl}acetamide (132)

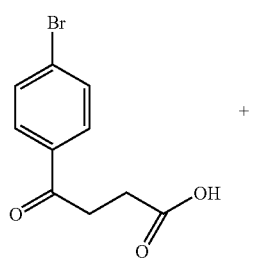

+

-continued

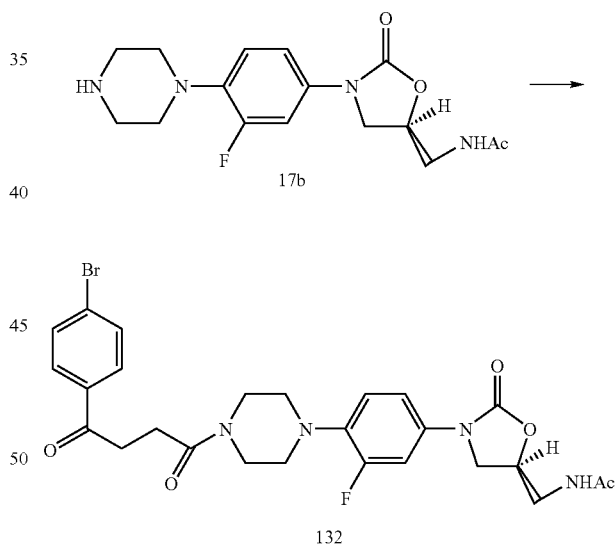

A stirred mixture of 3-(4-bromobenzoyl)propionic acid (0.186 g, 0.723 mmol) and pyridine (6 ml), under nitrogen, was treated with EDC (0.13 g, 0.68 mmol), DMAP (10 mg) and 17b$^{12}$ (0.24 g, 0.72 mmol), kept at ambient temperature for 18 h and concentrated in vacuo. Chromatography of the residue on silica gel with 3% MeOH—CHCl$_3$ and crystallization of the product from CH$_3$CN gave 0.17 g of 132: mp 197–198° C.; MS (ESI+) mn/z 597, 599 (M+Na$^+$); MS (ESI−) m/z 573, 575 (M−H), 609.2, 611.2 (M+Cl); IR (drift) 3311, 1742, 1687, 1647 cm$^{-1}$. Anal. calcd for C$_{26}$H$_{28}$BrFN$_4$O$_5$: C, 54.27; H, 4.90; N, 9.74. Found: C, 54.29; H, 4.97; N, 9.75.

Example 45

N-{[(5S)-3-(4-{4-[4-(4-Bromophenyl)-4-oxobutanoyl]-1-piperazinyl}-3-fluorophenyl)-2-oxo-1,3-oxazolidin-5-yl]methyl}ethanethioamide (133)

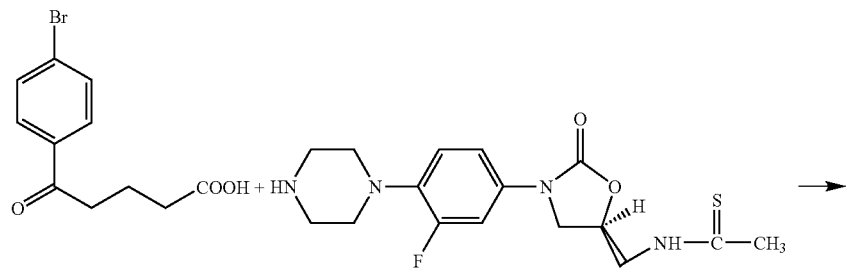

17c

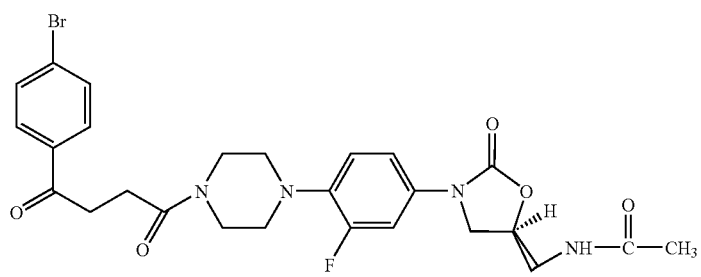

133

A stirred mixture 3-(4-bromobenzoyl)propionic acid (0.186 g, 0.723 mmol) and pyridine (6 ml), under nitrogen, was treated with EDC (0.13 g, 0.68 mmol), DMAP (10 mg) and 17c[6] (0.25 g, 0.71 mmol), kept at ambient temperature for 18 h and concentrated in vacuo. Chromatography of the residue on silica gel with 3% MeOH—CHCl$_3$ and crystallization of the product from CH$_3$CN gave 0.23 g of 133: mp 219–220° C. (dec); MS (ESI+) m/z 613, 615 (M+Na$^+$); MS (ESI−) m/z 589, 591 (M−H), 625.2, 627.2 (M+Cl); IR (drift) 3238, 1755, 1680, 1645, 1620 cm$^{-1}$. Anal. calcd for C$_{26}$H$_{28}$BrFN$_4$O$_4$S: C, 52.79; H, 4.77; N, 9.47. Found: C, 52.82; H, 4.86; N, 9.86.

Example 46

N-{[(5S)-3-(4-{4-[4-(4-Cyanophenyl)-4-oxobutanoyl]-1-piperazinyl}-3-fluorophenyl-2-oxo-1,3-oxazolidin-5-yl]methyl}acetamide (135)

Step 1:

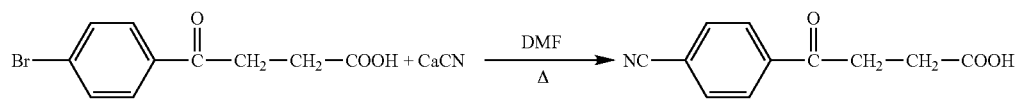

134

According to the method of Curran and Ross[8] a stirred mixture of 3-(4-bromobenzoyl)propionic acid (4.57 g, 0.0178 mol), copper (I) cyanide (1.84 g, 0.0205 mol) and DMF (12 ml) was refluxed, under nitrogen, for 4 h, cooled for 5 min, combined with a mixture of water (12 ml), FeCl$_3$.6 H$_2$O (7.8 g) and concentrated HCl (1 ml) and warmed on the steam bath for 20 min. This mixture was poured into water (100 ml) and cooled in an ice bath. The solid was collected by filtration, washed with cold water, and dried in vacuo. A portion of this material was chromatographed on silica gel with 2.5% MeOH-0.25% HOAc-CH$_2$Cl$_2$ to give 0.7 g of 134: MS (ESI−) m/z 201.9 (M−H). The remaining product was crystallized from CHCl$_3$ to give 1.23 g of additional 134.

Step 2:

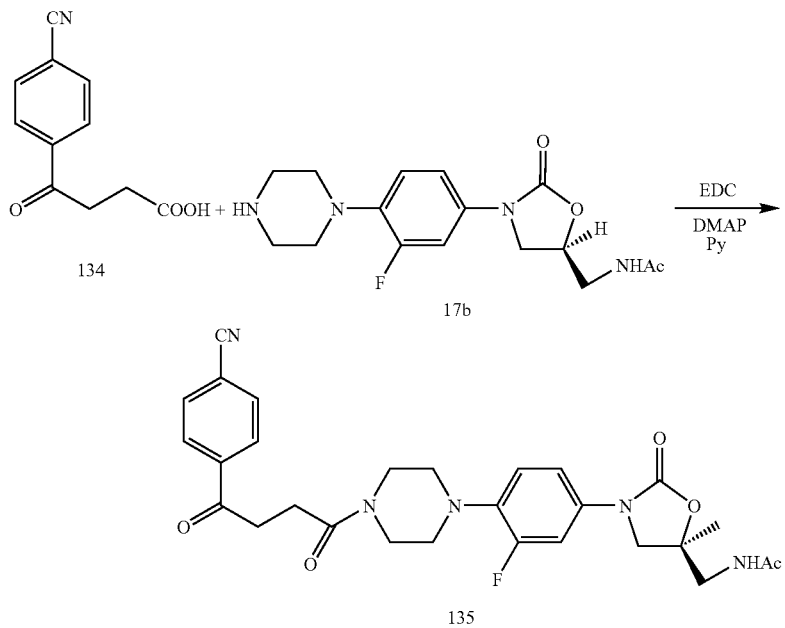

A stirred mixture of 3-(4-cyanobenzoyl)propionic acid 134 (0.178 g, 0.88 mmol) and pyridine (6 ml), under nitrogen was treated with EDC (0.16 g, 0.83 mmol) and 4-dimethylaminopyridine (10 mg), kept at ambient temperature for 5 min, treated with 61[12] (0.29 g, 0.862 mmol) and kept at ambient temperature for 3 h and at 10° C. for 18 h. It was concentrated in vacuo and the residue was chromatographed on silica gel with 2–5% MeOH—$CH_2Cl_2$. Crystallization of the product from $CH_3CN$ gave 0.261 g of 135: mp 197–198° C.; MS (ESI+) m/z 522.2 (M+H$^+$), 544 (M+Na$^+$); MS (ESI−) m/z 520.1 (M−H), 556.0 (M+Cl); IR (drift) 3296, 2234, 1757, 1693, 1640 cm$^{-1}$; $^1$H NMR [300 MHz, (CD$_3$)$_2$SO] δ 1.81 (s, 3H), 2.06 (s, 1.4H, CH$_3$CN), 2.77 (t, 2H), 2.89, 2.99 (s, s, 4H), 3.25 (t, 2H), 3.38 (t, 2H), 3.57 (s, 2H), 3.66 (m, 3H), 4.07 (t, 1H), 4.68 (m, 1H), 7.07 (t, 1H), 7.17 (dd, 1H), 7.49 (dd, 1H), 8.00 (d, 2H), 8.11 (d, 2H), 8.23 (t, 1H); HRMS (FAB) calcd for C$_{27}$H$_{29}$FN$_5$O$_5$ (M+H$^+$) 522.2153, found 522.2139. Anal. calcd for C$_{27}$H$_{28}$FN$_5$O$_5$·0.5 CH$_3$CN: C, 62.04; H, 5.48; N, 14.21. Found: C, 61.31; H, 5.57; N, 13.95.

A mixture of boron trifluoride-acetic acid complex (0.74 ml, 5.3 mmol) and water (0.09 ml, 5.0 mmol) was added, under nitrogen with stirring to 134 (0.20 g, 0.98 mmol) and the resulting mixture was warmed in an oil bath at 130° C. for 10 min, kept at ambient temperature for 1 h and rewarmed at 130° C. for 5 min. It was then concentrated under a stream of nitrogen. The residue was mixed with $CH_2Cl_2$ and MeOH to give 0.17 g of 136, a white solid: MS (ESI+) m/z 221.9 (M+H$^+$), 244.0 (M+Na$^+$); MS (ESI−) m/z 220 (M−H).

Example 47

4-{4-[4-(4-{(5S)-5-[(Acetylamino)methyl]-2-oxo-1,3-oxazolidin-3-yl}-2-fluorophenyl)-1-piperazinyl]-4-oxobutanoyl}benzamide (137)

Step 1:

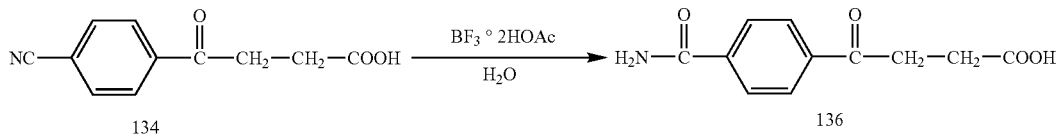

Step 2:

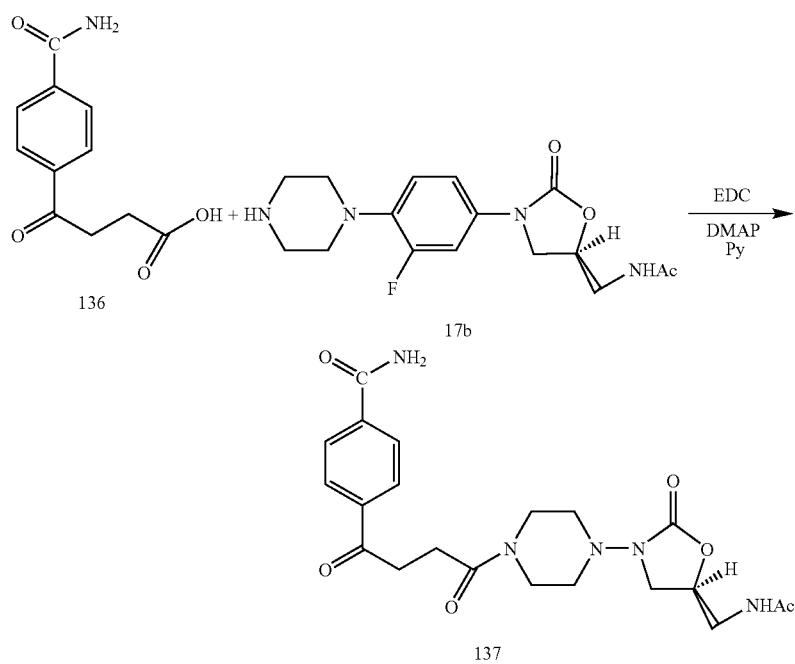

A stirred mixture of 136 (0.16 g, 0.72 mmol) and pyridine (6 ml) under nitrogen was treated with EDC (0.13 g, 0.68 mmol), DMAP (10 mg) and 17b[12] (0.24 g, 0.71 mmol) and kept at ambient temperature for 20 h. It was then concentrated in vacuo and the residue was chromatographed on silica gel with 7–10% MeOH—$CH_2Cl_2$. Crystallization of the product from MeOH—$CH_2Cl_2$ gave 0.219 g of 137: mp>250° C.; IR (drift) 3394, 3335, 3199, 1746, 1727, 1697, 1676, 1630 $cm^{-1}$. Anal. calcd for $C_{27}H_{30}FN_5O_6$: C, 60.10; H, 5.60; N, 12.98. Found: C, 59.60, 59.78; H, 5.64, 5.64; N, 12.77, 12.91.

Example 48

4-{4-[4-(4-{(5S)-5-[(Ethanethiolylamino)methyl]-2-oxo-1,3-oxazolidin-3-yl}-2-fluorophenyl)-1-piperazinyl]-4-oxobutanoyl}benzamide 138

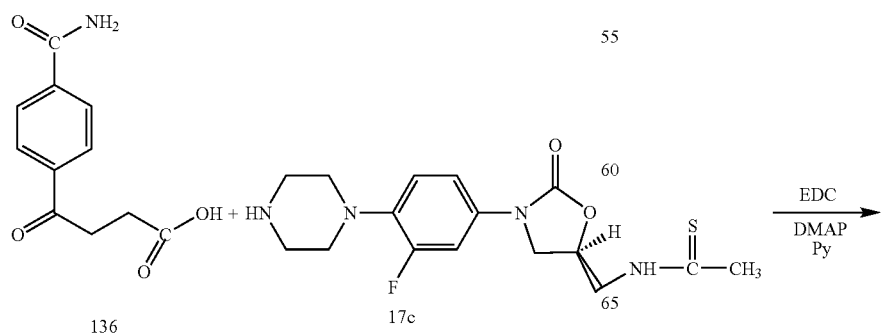

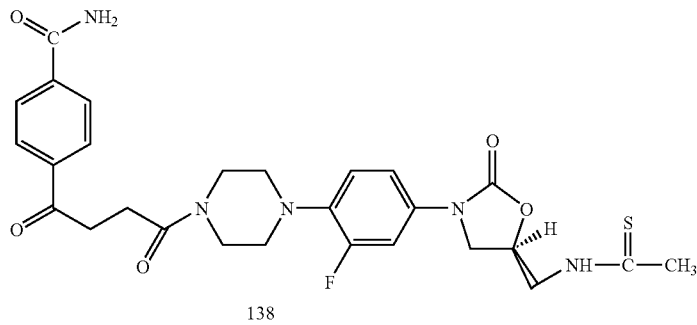

138

A stirred mixture of 136 (0.16 g, 0.72 mmol) in pyridine (6 ml) under nitrogen, was treated with EDC (0.13 g, 0.68 mmol) and DMAP (10 mg), kept at ambient temperature for 5 min and treated with 17c[6] (0.25 g, 0.71 mmol). It was kept at ambient temperature for 2.5 h and concentrated in vacuo. Chromatography of the residue on silica gel with 6% MeOH—$CH_2Cl_2$ and crystallization of the product from $CH_3CN$ gave 0.11 g, mp 219–220° C. (dec) and 0.13 g, mp 223–224° C. (dec) of 138: IR (drift) 3374, 3301, 3290, 3253, 3195, 1738, 1679, 1661, 1620 $cm^{-1}$. Anal. calcd for $C_{27}H_{30}FN_5O_5S$: C, 58.37; H, 5.44; N, 12.60. Found: C, 58.22; H, 5.46; N, 12.70.

A stirred mixture of 3-(4-chlorobenzoyl)propionic acid (0.153 g, 0.72 mmol) in pyridine (6 ml), under nitrogen, was treated with EDC (0.14 g, 0.73 mmol), DMAP (10 mg) and 17b[12] (0.24 g, 0.72 mmol), kept at ambient temperature for 20 h and concentrated in vacuo. Chromatography of the residue on silica gel with 5% MeOH—$CHCl_3$ and crystallization of the product from $CH_3CN$ gave 0.256 g of 139: mp 208–209° C.; IR (drift) 3328, 1741, 1672, 1645, 1625 $cm^{-1}$. Anal. calcd for $C_{26}H_{28}ClFN_4O_5$: C, 58.81; H, 5.32; N, 10.55. Found: C, 58.78; H, 5.36; N, 10.54.

Example 49

N-{[(5S)-3-(4-{4-[4-(4-Chlorophenyl)-4-oxobutanoyl]-1-piperazinyl}-3-fluorophenyl)-2-oxo-1,3-oxazolidin-5-yl]methyl}acetamide 139

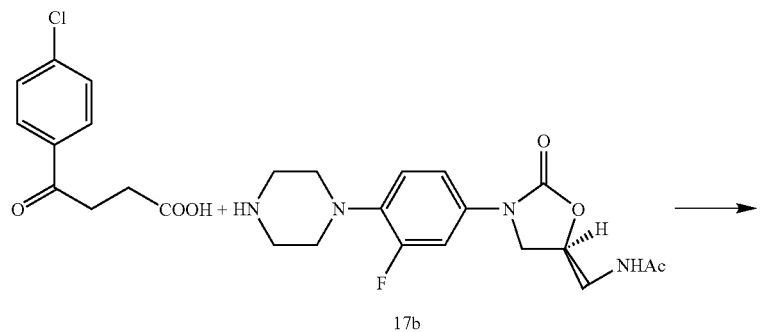

17b

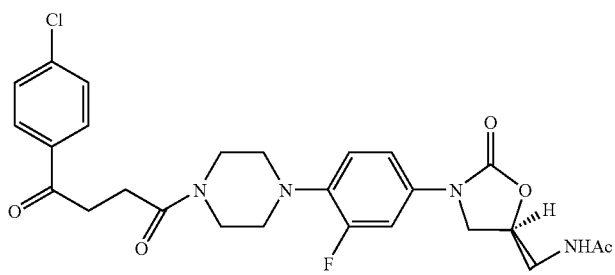

139

Example 50

N-{[(5S)-3-(4-{4-[4-(4-chlorophenyl)-4-oxobutanoyl]-1-piperazinyl}-3-fluorophenyl)-2-oxo-1,3-oxazolidin-5-yl]methyl}ethanethioamide 140

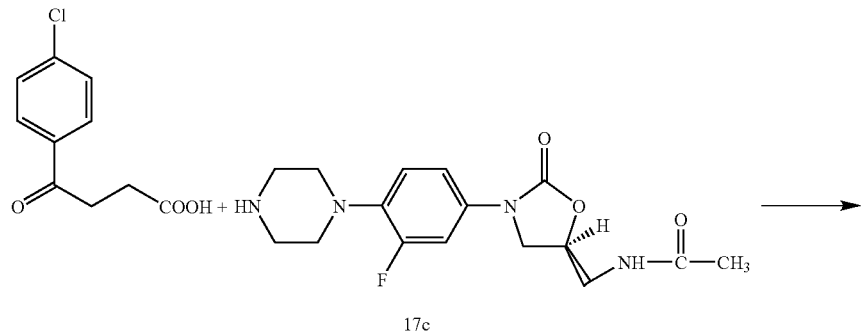

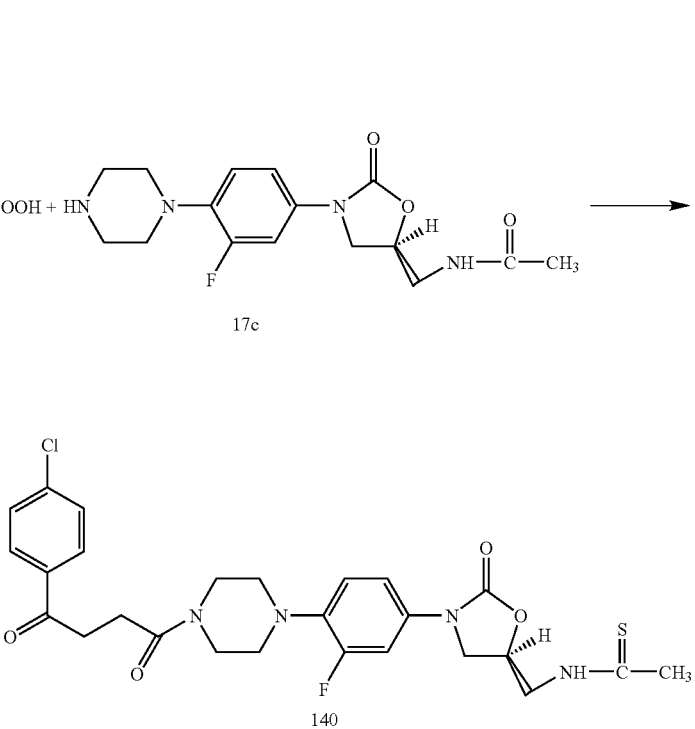

A stirred mixture of 3-(4-chlorobenzoyl)propionic acid (0.153 g, 0.720 mmol) in pyridine (6 ml), under nitrogen was treated with EDC (0.13 g, 0.68 mmol), DMAP (10 mg) and 17c[6] (0.25 g, 0.71 mmol), kept at ambient temperature for 20 h and concentrated in vacuo. Chromatography of the residue on silica gel with 2% MeOH—$CH_2Cl_2$ and crystallization of the product from $CH_3CN$ gave 0.226 g of 140: mp 215–216° C. (dec); IR (drift) 3235, 1755, 1679, 1620 $cm^{-1}$. Anal. calcd for $C_{26}H_{28}ClFN_4O_4S$: C, 57.08; H, 5.16; N, 10.24. Found: C, 57.09; H, 5.24; N, 10.43.

Example 51

N-[((5S)-3-{3-Fluoro-4-[4-(4-{4-[(methylsulfonyl)amino]phenyl}-4-oxobutanoyl)-1-piperazinyl]phenyl}-2-oxo-1,3-oxazolidin-5-yl)methyl]propanethioamide 141

Step 1:

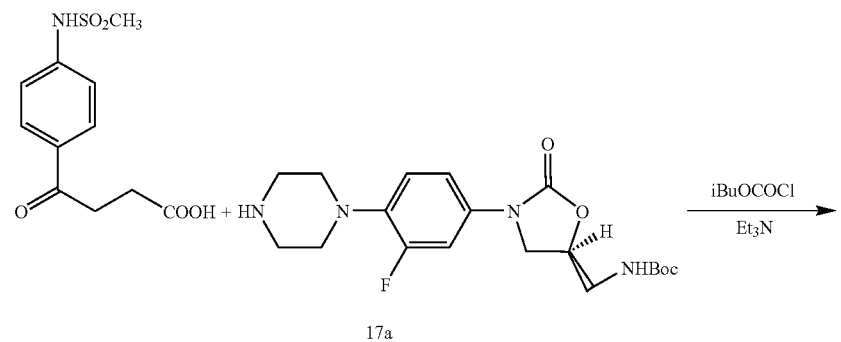

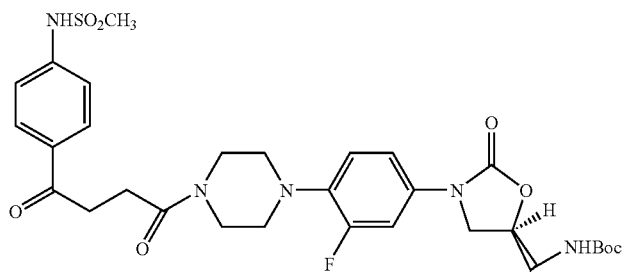

142

A stirred mixture of PNU-68849 4-[(methylsulfonyl)amino]-□-oxo-Benzenebutanoic acid, (0.583 g, 2.15 mmol) and triethylamine (0.35 ml) in THF (20 ml), under nitrogen, was cooled in an ice-MeOH bath and treated, dropwise with isobutyl chloroformate (0.33 ml). It was kept in the bath for 30 min and then treated with a mixture of 17a[5] (0.85 g, 2.15 mmol), triethylamine (0.35 ml) and THF (15 ml). This mixture was kept at 0° C. for 90 min and concentrated in vacuo. Chromatography of the residue on silica gel with 2% MeOH—CH$_2$Cl$_2$ and crystallization of the product from CH$_3$CN gave 0.64 g, mp 171–173° C. (dec) and 0.151 g, mp 173–175° C. (dec) of 142: MS (ESI) 670.3 (M+Na$^+$).

Step 2:

A stirred solution of 142 (0.42 g, 0.65 mmol) in dioxane (8 ml) was cooled in an ice bath and treated, dropwise during 4 min, with ice cold 4N HCl in dioxane (6 ml). The mixture was kept in the ice bath for 1 h, at ambient temperature for 3 h and at 4° C. for 18 h. It was then concentrated in vacuo to give 0.4 g of 143: MS (ESI) m/z 548.2 (M+H$^+$).

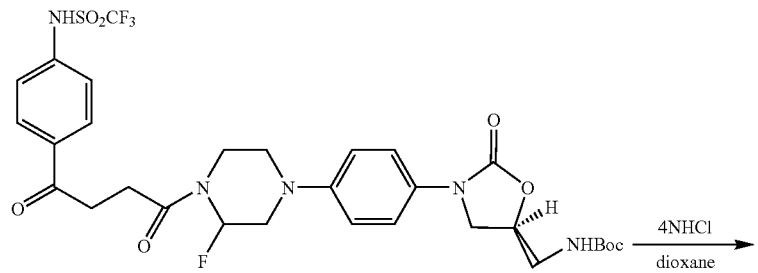

142

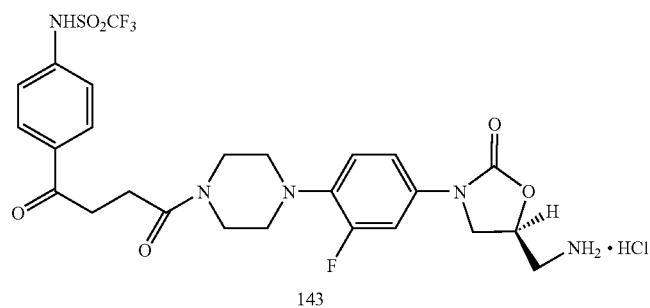

143

Step 3:

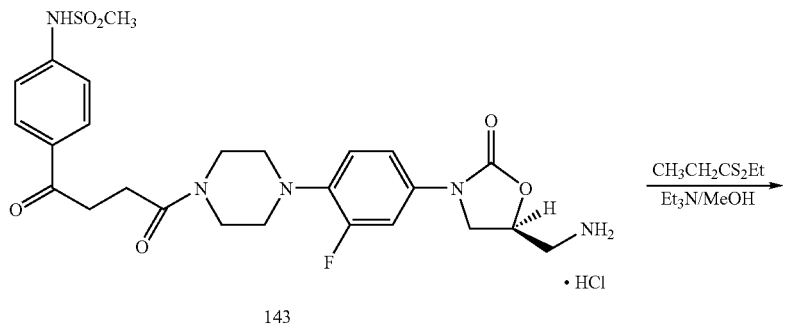

A stirred mixture of 143 (0.16 g), triethylamine (0.15 ml, 1.08 mmol) and MeOH (10 ml), under nitrogen, was treated with ethyl dithiopropionate (0.05 ml, 0.39 mmol), kept at ambient temperature for 3 h and concentrated in vacuo. The residue was found to be a mixture of starting material and product. It was mixed with MeOH (6 ml), triethylamine (0.1 ml) and ethyl dithiopropionate (0.04 ml) and stirred at ambient temperature for 6 h. This mixture was concentrated and the residue was chromatographed on silica gel with 2% MeOH—CH$_2$Cl$_2$. Crystallization of the product from MeOH gave 0.07 g of 141: mp 201–202° C. (dec) with softening at 198° C.; $^1$H NMR [300 MHz, (CD$_3$)$_2$SO] δ 1.13 (t, 3H), 2.57 (q, 2H), 2.71 (t, 2H), 2.90, 3.00 (s, s, 4H), 3.09 (s, 3H), 3.18 (t, 2H), 3.57, 3.64 (s, s, 4H), 3.78 (dd, 1H), 3.90 (t, 2H), 4.12 (t, 1H), 4.92 (m, 1H), 7.08 (t, 1H), 7.17 (dd, 1H), 7.28 (d, 2H), 7.50 (dd, 1H), 7.95 (d, 2H), 10.31 (s, 1H); MS (ESI) m/z 642.2 (M+Na$^+$); HRMS (FAB) calcd for C$_{28}$H$_{35}$FN$_5$O$_6$S$_2$ (M+H$^+$) 620.2012, found 620.2006; IR (drift) 3301, 3177, 3159, 1747, 1674, 1630 cm$^{-1}$.

Example 52

N-[((5S)-3-{3-Fluoro-4-[4-(4-{4-[(methylsulfonyl)amino]phenyl}-4-oxobutanoyl-1-piperazinyl]phenyl}-2-oxo-1,3-oxazolidin-5-yl)methyl]acetamide 144

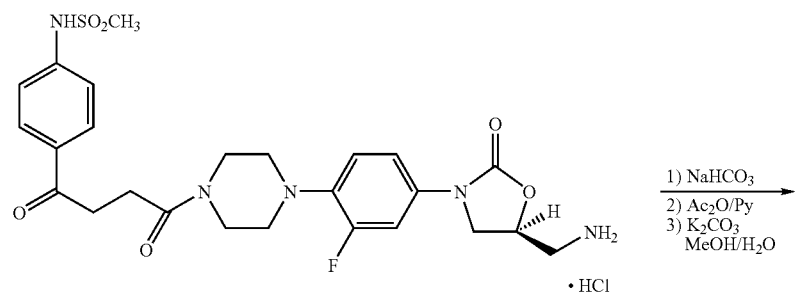

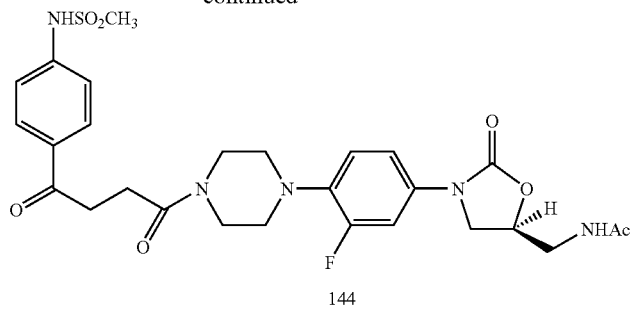

144

A sample of 143 (prepared from 0.35 g, 0.54 mmol of 17a) was stirred with a mixture of Et$_2$O (5 ml) and 5% NaHCO$_3$ (10 ml) and concentrated under a stream of nitrogen. The resulting solid was collected by filtration, washed with water and dried to give 0.23 g of the free base. A stirred suspension of this material in pyridine (3 ml), under nitrogen, was cooled in an ice bath and treated with acetic anhydride (0.16 ml). It was kept in the ice bath for 1 h and at ambient temperature for 2.5 h and then concentrated in vacuo. The product was found to be a mixture of 144 and a compound in which both the amine and the sulfonamide nitrogen had been acetylated. A solution of the residue in MeOH was therefore hydrolyzed with 10% aqueous K$_2$CO$_3$ (2 ml). When the reaction was complete the mixture was concentrated and the residue was mixed with water, neutralized with 10% KHSO$_4$ and extracted with CH$_2$Cl$_2$. The extract was dried (Na$_2$SO$_4$) and concentrated. Chromatography of the residue on silica gel with 3–5% MeOH—CH$_2$Cl$_2$ and crystallization of the product from MeOH gave 0.102 g of 144: mp 220–222° C. (dec); MS (ESI) m/z 590.3 (M+H$^+$), 612 (M+Na$^+$); IR (drift) 3374, 3348, 3168, 3154, 1759, 1674, 1623, 1602 cm$^{-1}$; HRMS (FAB) calcd for C$_{27}$H$_{33}$FN$_5$O$_7$S (M+H$^+$) 590.2084, found 590.2098. Anal. calcd for C$_{27}$H$_{32}$FN$_5$O$_7$S: C, 55.00; H, 5.47; N, 11.88. Found: C, 54.72; H, 5.55; N, 11.78.

Example 53

N-(4-{4-[4-(2-Fluoro-4-{(5S)-2-oxo-5-[(propanethi-olylamino)methyl]-1,3-oxazolidin-3-yl}phenyl)-1-piperazinyl]-4-oxobutanoyl}phenyl)acetamide 145

Step 1:

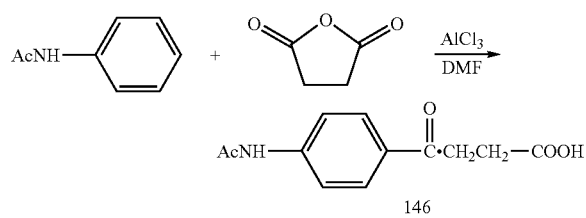

Dimethylformamide (19.1 ml) was added, dropwise during 30 min, under nitrogen with stirring to aluminum chloride (116.5 g). The addition was exothermic and gave a semiliquid mass. This mixture was warmed in an oil bath at 70° C. and treated, portionwise during 10 min, with a mixture of acetanilide (12.5 g, 0.0925 mol) and succinic anhydride (8.35 g, 0.0834 mol). It was kept at 70–72° C. for 1 h and then poured into ice (800 g). The resulting solution was treated with a mixture of concentrated HCl (50 ml) and ice (50 g) to give a precipitate which was collected by filtration washed with cold water and dried. Crystallization of the solid from acetonitride gave 10.7 g of 146: MS (ESI) m/z 236.1 (M+H$^+$), 258.1 (M+Na$^+$).

Step 2:

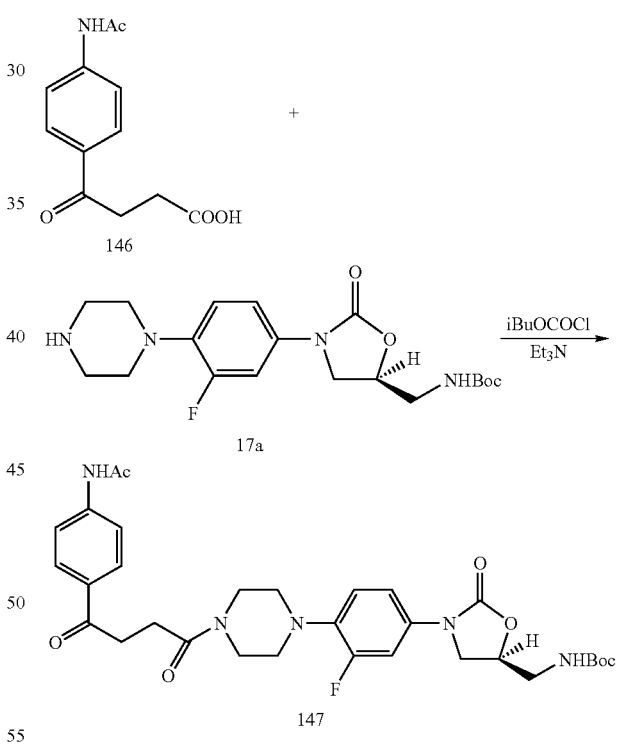

A stirred mixture of 146 (1.01 g, 4.29 mmol) and triethylamine (0.69 ml, 4.96 mmol) in THF (20 ml), under nitrogen was cooled in an ice-MeOH bath and treated, dropwise with isobutyl chloroformate (0.66 ml, 5.1 mmol). It was kept in the bath for 30 min and then treated, in portions during 4 min, with a mixture of 17a$^5$ (1.69 g, 4.28 mmol), triethylamine (0.69 ml, 4.96 mmol) and THF (15 ml). The mixture was allowed to warm to 10° C. during 2 h when it was concentrated in vacuo. A mixture of the residue and CH$_2$Cl$_2$ was washed with saturated NaHCO$_3$, water and brine, dried (Na$_2$SO$_4$) and concentrated. Chromatography of the residue on silica gel with 5% MeOH—CHCl$_3$ gave 1.84 g of 147: $^1$H NMR [300 MHz, (CD$_3$)$_2$SO] δ 1.34 (s, 9H), 2.07 (s, 3H), 2.71 (t, 2H), 2.89, 2.99 (s, s, 4H), 3.18 (t, 2H), 3.25 (t, 2H), 3.57, 3.66 (s, s, 4H), 3.75 (dd, 1H), 4.06 (t, 1H), 4.66 (m, 1H), 7.07 (t, 1H), 7.18 (m, 2H), 7.48 (dd, 1H), 7.69 (d, 2H), 7.93 (d, 2H), 10.28 (s, 1H); MS (ESI) m/z 612.3 (M+H$^+$), 634.2 (M+Na$^+$).

Step 3:

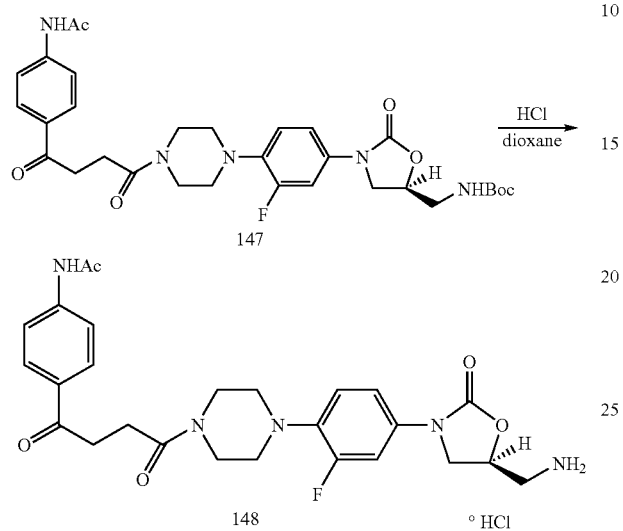

A stirred mixture of 147 (1.0 g, 1.63 mmol) in dioxane (25 ml), under nitrogen was cooled in an ice bath and treated with ice-cold 4N hydrogen chloride in dioxane (10 ml). It was kept in the ice bath for 1.5 h, at ambient temperature for 4 h and at 0° C. for 14 h. It was then kept at ambient temperature for 2 h and concentrated in vacuo to give 1.04 g of 148, a white powder.

Step 4:

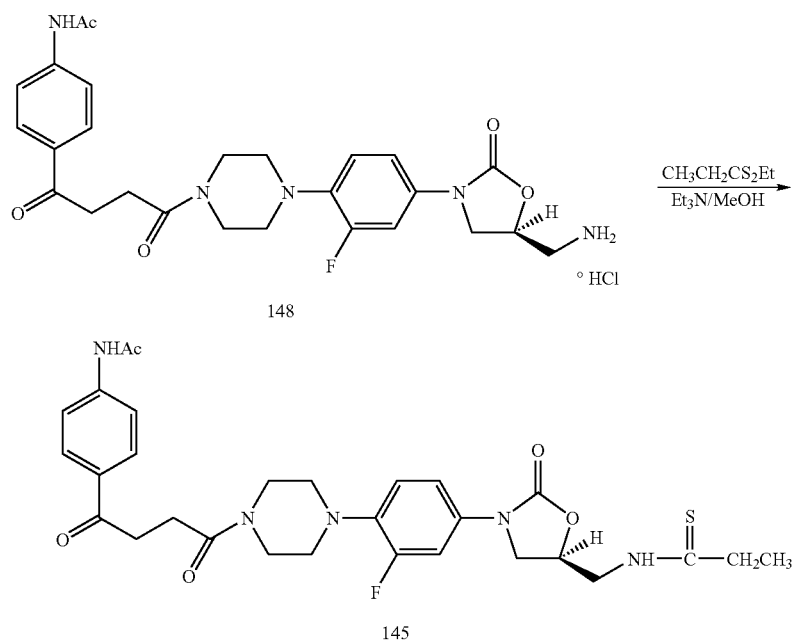

A stirred mixture of 148 (0.51 g), triethylamine (0.37 ml, 2.7 mmol) and MeOH (20 ml), under nitrogen, was treated with ethyl dithiopropionate (0.13 ml, 1.02 mmol), kept at ambient temperature for 4 h and concentrated under a stream of nitrogen for 1 h. The solid product was collected by filtration, and the filtrate was concentrated under a stream of nitrogen. Trituration of the residue with MeOH gave additional product. Chromatography of the combined product on silica gel with 2.5% MeOH—CH$_2$Cl$_2$ and crystallization from MeOH gave 0.326 g of 145: mp 198–199° C. (dec) with softening at 195° C.; MS (ESI) m/z 584.3 (M+H$^+$), 606.3 (M+Na$^+$); IR (drift) 3258, 3193, 1742, 1697, 1678, 1615 cm$^{-1}$. Anal. calcd for C$_{29}$H$_{34}$FN$_5$O$_5$S: C, 59.68; H, 5.87; N, 12.00. Found: C, 59.45; H, 5.94; N, 11.94.

Example 54

2-Amino-N-(4-{4-[4-(2-fluoro-4-{(5S)-2-oxo-5-[(propanethiolylamino)methyl]1,3-oxazolidin-3-yl}phenyl)-1-piperazinyl]-4-oxobutanoyl}phenyl)acetamide 149

Step 1:

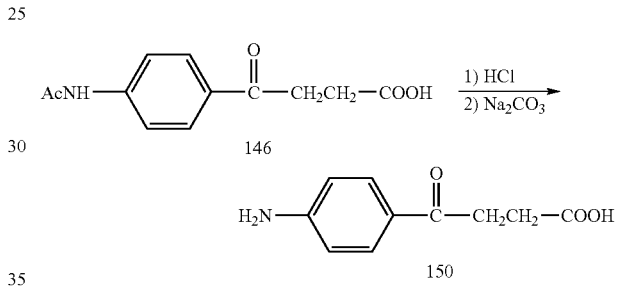

A mixture of 146 (4.97 g, 0.021 mol) and concentrated HCl (35 ml) was warmed on the steam bath for 20 min and the resulting solution was placed under a stream of nitrogen for 30 min. The resulting mixture was diluted with water (50 ml) and adjusted to pH 4 with solid Na₂CO₃. The solid product was collected by filtration, washed with water and dried in vacuo at 50° C. to give 3.95 g of 150 which could be recrystallized from acetonitrile. A second crop, 0.31 g of 150 was obtained from the aqueous filtrate.

Step 2:

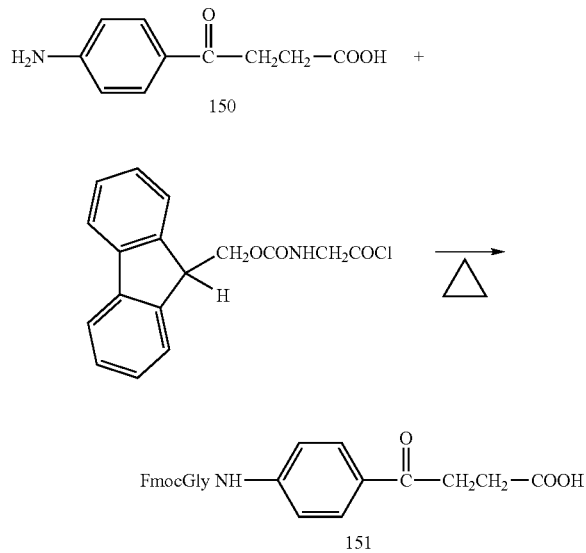

A stirred mixture of 150 (0.47 g, 0.00243 mol), N-Fmoc-glycyl chloride (0.85 g, 0.0027 mol) and THF (50 ml) was refluxed, under nitrogen for 4 h and cooled to ambient temperature. The solid was collected by filtration to give 0.18 g of 151. Concentration of the mother liquor gave an additional 1.14 g of 151: MS (ESI+) m/z 495 (M+Na); MS (ESI−) m/z 471 (M−H).

Step 3:

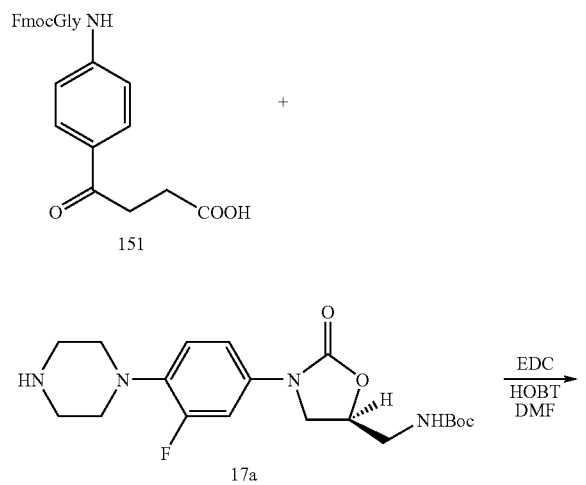

-continued

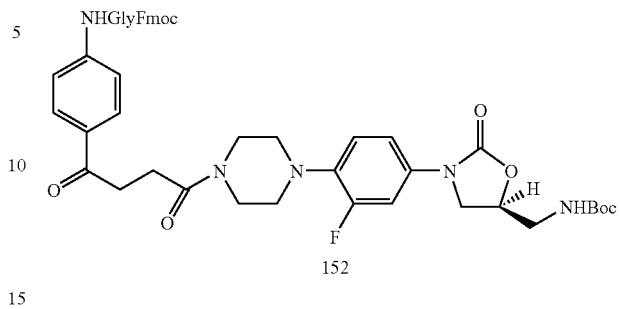

An ice cold, stirred mixture of 151(0.17 g, 0.36 mmol) and DMF (3 ml), under nitrogen was treated with 1-(3-dimethylaminopropyl)-3-ethylcarbodiimide hydrochloride (0.08 g, 0.42 mmol) and 1-hydroxybenzotriazole hydrate (0.05 g, 0.37 mmol), kept for 20 min and then treated with 17a[5] (0.14 g, 0.35 mmol) in portions during 10 min. The mixture was kept in the ice bath for 1 h 45 min and at ambient temperature for 45 min and then concentrated in vacuo. Chromatography of the semisolid residue on silica gel with 2% MeOH—CH₂Cl₂ gave 0.18 g of 152: MS (ESI−) m/z 883.2 (M+Cl); ¹H NMR (300 MHz, CDCl₃) δ 1.42 (s, 9H), 2.81 (m, 2H), 3.16 (s, s, 2H), 3.38 (m, 4H), 3.54 (m, 4H), 3.79 (m, 3H), 4.04 (m, 4H), 4.16 (s, 3H), 4.25 (t, 1H), 4.50 (d, 2H), 4.78 (m, 1H), 5.03 (m, 1H), 5.64 (m, 1H), 7.04 (m, 1H), 7.32 (m, 3H), 7.42 (m, 3H), 7.61 (m, 5H), 7.77 (m, 3H), 7.96 (m, 3H), 8.57 (m, 1H). Step 4:

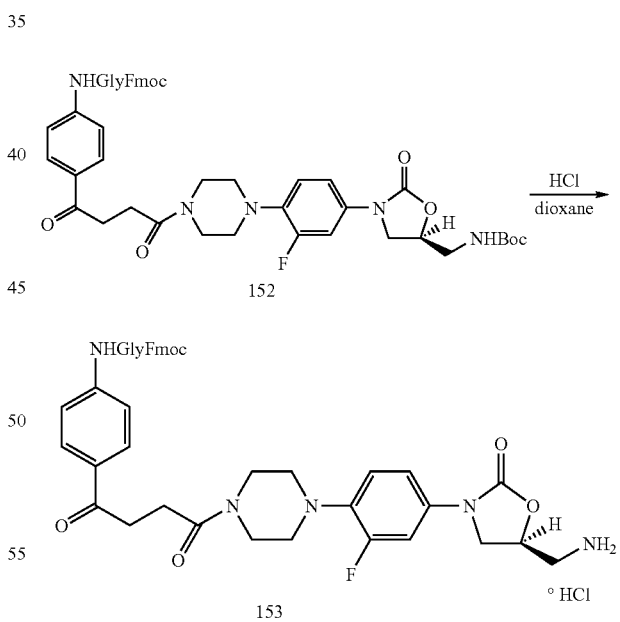

A stirred suspension of 152 (0.34 g, 0.4 mmol) in dioxane (24 ml), under nitrogen was treated with ice cold 4N HCl in dioxane (6 ml) with cooling in an ice bath. It was kept in the ice bath for 1.25 h, at ambient temperature for 3 h, at 0° C. for 18 h and at ambient temperature for 6 h. It was then placed under a stream of nitrogen for 30 min and concentrated in vacuo to give 7153.

Step 5:

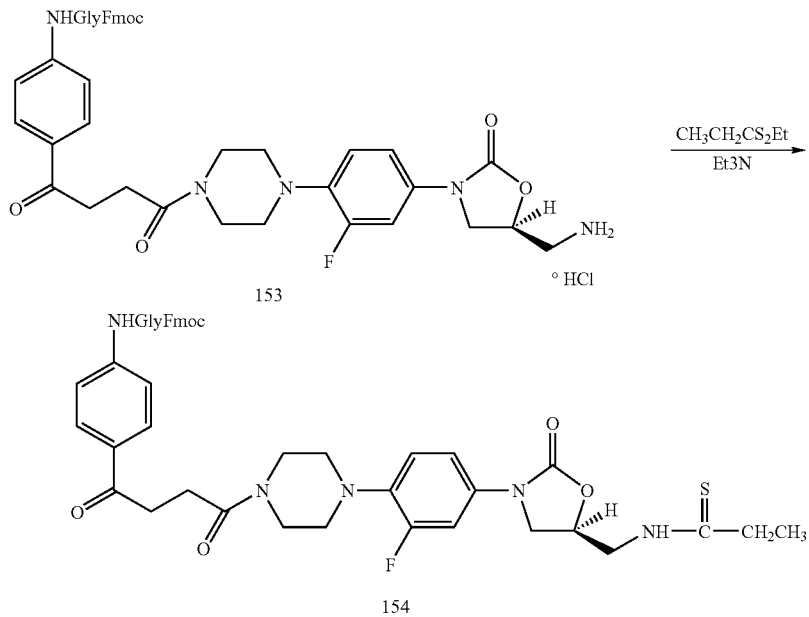

A stirred mixture of 153 from the previous reaction, ethyl dithiopropionate (0.073 ml) and triethylamine (0.22 ml) in MeOH (15 ml), under nitrogen, was kept at ambient temperature for 2 h, treated with additional MeOH (15 ml) and kept at ambient temperature for 21 h. The reaction was still not complete. The mixture was treated with additional triethylamine (0.1 ml) and kept for 24 h; it was then treated with additional ethyl dithiopropionate (0.07 ml) and kept at ambient temperature for 6 h and at 0° C. for 72 h. It was concentrated under a stream of nitrogen for 7 h and then in vacuo. Chromatography of the residue on silica gel with 1.5–3% MeOH—$CH_2Cl_2$ gave 0.09 g of 154: MS (ESI–) m/z 819 (M–H), 855 (M+Cl).

Step 6:

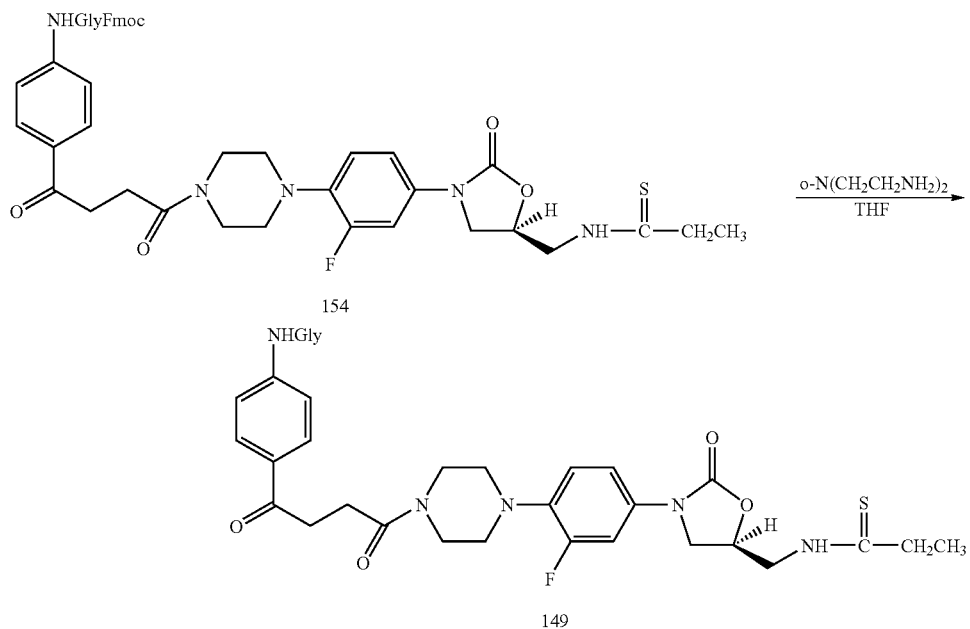

A stirred mixture of 154 (0.10 g, 0.12 mmol), "trisamine" resin (0.12 g, 0.48 mmol) and THF (10 ml) was refluxed, under nitrogen for 5 h, kept at ambient temperature for 18 h and refluxed for 4 h. It was filtered, the solid was washed with THF and MeOH and the filtrate was concentrated in vacuo. Chromatography of the residue over silica gel with 4% MeOH-0.25% NH₄OH—CH₂Cl₂ and crystallization of the product from MeOH-EtOAc gave 0.0516 g of 149, mp 197–198° C. (dec): MS (ESI+) m/z 599.3 (M+H⁺); MS (ESI−) m/z 633.0 (M+Cl⁻); IR (drift) 3283, 1736, 1680, 1644, 1630 cm⁻¹; HRMS (FAB) calcd for $C_{29}H_{36}FN_6O_5S$ (M+H⁺) 599.2452, found 599.2471.

Example 55

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}phenyl)-2-aminoacetamide 155

Step 1:

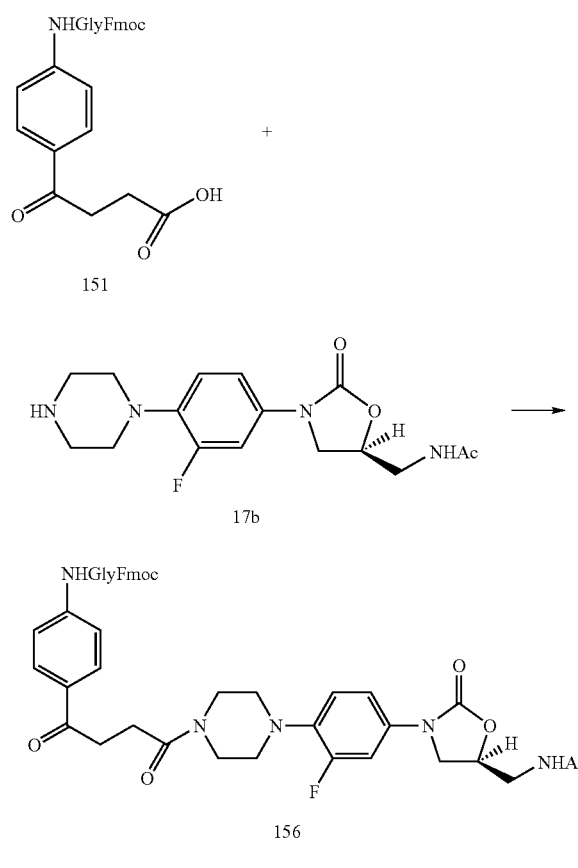

Step 2:

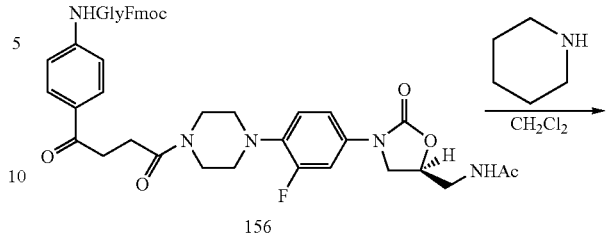

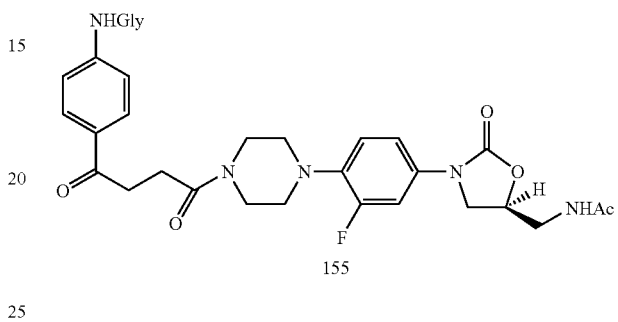

A stirred mixture of 156 (0.15 g, 0.19 mmol) and CH₂Cl₂ (5 ml), under nitrogen was treated with piperidine (0.06 ml, 0.61 mmol) and kept at ambient temperature for 3.5 h. Additional piperidine (0.2 ml) was added and the mixture was kept at ambient temperature for 24 h and concentrated in vacuo. Chromatography of the residue on silica gel with 8% MeOH-0.5% NH₄OH—CH₂Cl₂ and crystallization of the product from MeOH-EtOAc gave 0.0459 g of 155: mp 221–222° C. (dec); MS (ESI+) m/z 569.3 (M+H⁺); MS (ESI−) m/z 603.2 (M+Cl⁻); IR (drift) 3322, 3297, 1742, 1687, 1645 cm⁻¹; ¹H NMR [300 MHz, (CD₃)₂SO] δ 1.81 (s, 3H), 2.71 (t, 2H), 2.89, 2.99 (s, s, 4H), 3.19 (t, 2H), 3.30 (m, 5H), 3.38 (t, 2H), 3.57 (s, 2H), 3.66 (m, 3H), 4.07 (t, 1H), 4.69 (m, 1H), 7.07 (t, 1H), 7.16 (dd, 1H), 7.48 (dd, 1H), 7.77 (d, 2H), 7.95 (d, 2H), 8.23 (t, 1H); HRMS (FAB) calcd for $C_{28}H_{34}FN_6O_6$ (M+H⁺) 569.2524, found 569.2529.

Example 56

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}phenyl)-(2S)-2-aminopropanamide 157

A stirred mixture of 151 (0.19 g, 0.40 mmol), EDC (0.08 g, 0.42 mmol) and HOBT (0.05 g, 0.37 mmol) in DMF (3 ml), under nitrogen, was kept at ambient temperature for 30 min and treated with 17b¹² (0.12 g, 0.36 mmol). It was kept at ambient temperature for 18 h, treated with additional EDC (0.08 g) and HOBT (0.05 g), and kept at ambient temperature for 72 h. This mixture was concentrated in vacuo and the residue was chromatographed on silica gel with 2.5–4% MeOH—CH₂Cl₂ to give 0.06 g of 156: MS (ESI−) m/z 825.2 (M+Cl⁻); ¹H NMR [300 MHz, (CD₃)₂SO] δ 1.81 (s, 3H), 2.71 (t, 2H), 2.90, 3.00 (s, s, 4H), 3.19 (t, 2H), 3.38 (t, 2H), 3.55 (s, 2H), 3.66 (m, 3H), 3.82 (d, 2H), 4.07 (t, 1H), 4.27 (m, 3H), 4.67 (m, 1H), 7.08 (t, 1H), 7.18 (dd, 1H), 7.40 (m, 6H), 7.70 (m, 5H), 7.95 (m, 4H), 8.21 (t, 1H).

Step 1:

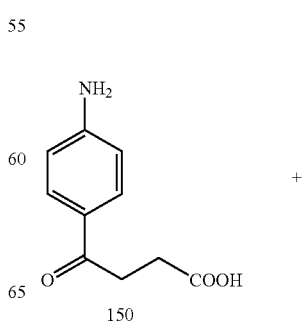

-continued

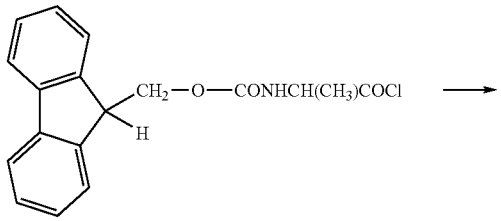

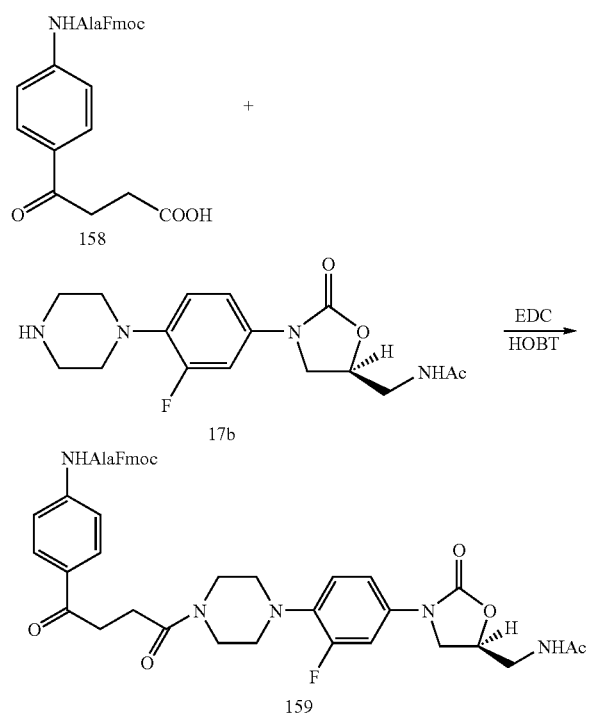

A stirred mixture of 22 (0.50 g, 2.59 mmol) and (S)-N-Fmoc-alanyl chloride (0.939 g, 2.85 mmol) in THF (50 ml) was refluxed under nitrogen for 2 h, cooled and filtered. The filtrate was concentrated and the residue was crystallized from acetonitrile to give 0.78 g, mp 211–212° C. and 0.20 g, mp 210–211° C. of 24: MS (ESI+) m/z 309.2 (M+Na$^+$); MS (ESI−) m/z 485.1 (M−H), 521.0 (M+Cl).

Step 2:

A mixture of 158 (0.35 g, 0.72 mmol), EDC (0.15 g, 0.78 mmol), HOBT (0.10 g, 0.74 mmol) and DMF (6 ml) was stirred under nitrogen for 15 min, treated with 17b$^{12}$ (0.24 g, 0.71 mmol) and kept at ambient temperature for 22 h. By TLC a considerable amount of 17b remained in the reaction mixture. It was treated with a mixture of 158 (0.175 g), EDC (0.075 g), HOBT (0.05 g) and DMF (2 ml) that had been prepared, under nitrogen, in a separate flask and stirred for 30 min. The resulting mixture was kept at ambient temperature for 72 h and concentrated in vacuo. Chromatography of the residue on silica gel with 3% MeOH—CH$_2$Cl$_2$ gave 0.14 g of 159: MS (ESI−) m/z 839.2 (M+Cl).

Step 3:

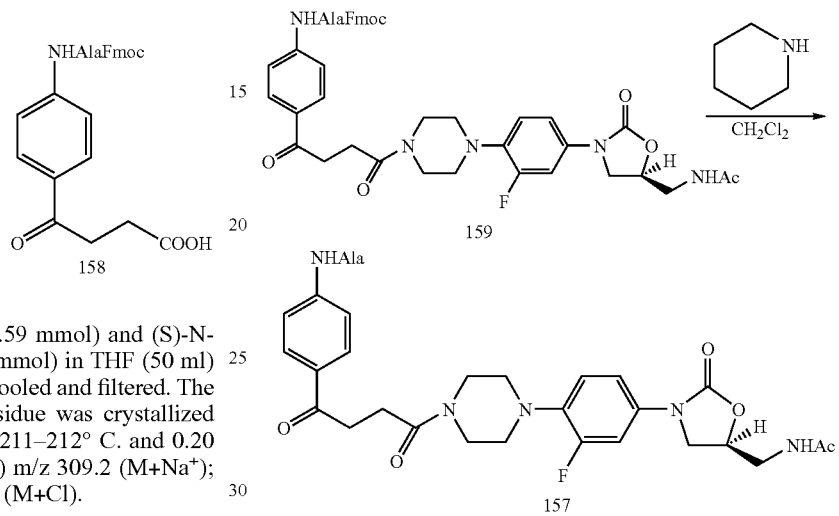

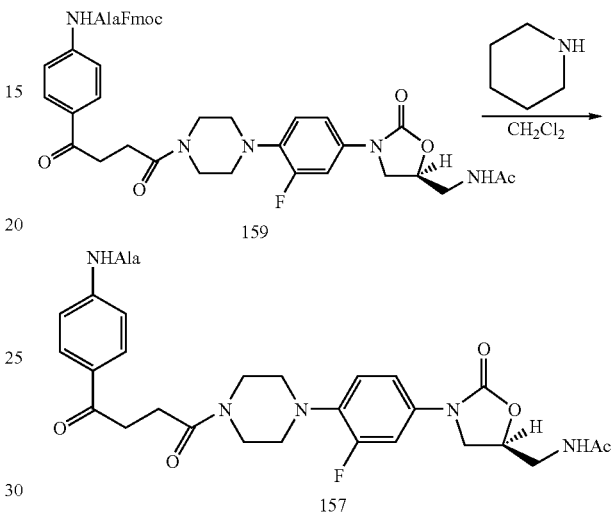

A stirred suspension of 159 (0.11 g, 0.14 mmol) in CH$_2$Cl$_2$ (20 ml), under nitrogen was treated with piperidine (0.3 ml) and kept at ambient temperature for 18 h. The resulting solution was concentrated in vacuo and the residue was chromatographed on silica gel with 4% MeOH-0.25% NH$_4$OH—CH$_2$Cl$_2$. A solution of the product in MeOH—CH$_2$Cl$_2$ was concentrated in vacuo to give 0.048 g of 157 as a foam: MS (ESI+) m/z 583.3 (M+H$^+$); MS (ESI−) m/z 617.1 (M+Cl$^−$); IR (drift) 3300, 1751, 1749, 1677, 1647 cm$^{-1}$; HRMS (FAB) calcd for C$_{29}$H$_{36}$FN$_6$O$_6$ (M+H$^+$) 583.2680, found 583.2682.

Example 57

N-1-(4-{4-[4-(4-{(5S)-5-[(Ethanethiolylamino)methyl]-2-oxo-1,3-oxazolidin-3-yl}-2-fluorophenyl)piperazin-1-yl]-4-oxobutanoyl}phenyl)-(S)-alaninamide 160

Step 1:

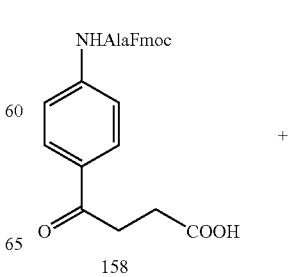

-continued

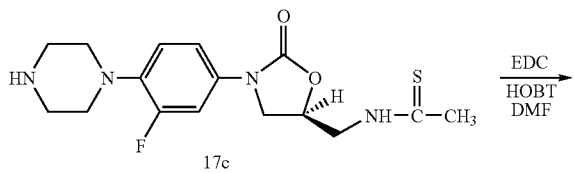

17c

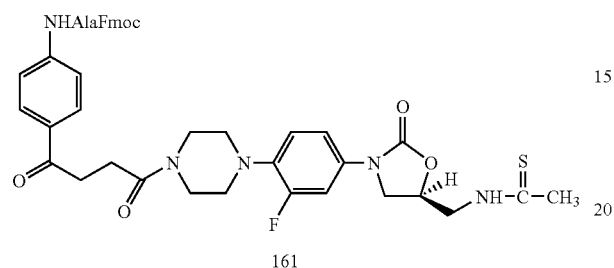

161

A stirred mixture of 158 (0.213 g, 0.438 mmol) in DMF (2.5 ml), under nitrogen, was treated with EDC (0.084 g, 0.438 mmol) and HOBT (0.05 g, 0.375 mmol), kept at ambient temperature for 10 min and treated with 17c⁶ (0.123 g, 0.349 mmol). It was kept at ambient temperature for 18 h and concentrated in vacuo. Chromatography of the residue on silica gel with 3% MeOH—CH₂Cl₂ gave 0.29 g of 161: MS (ESI–) m/z 855.3 (M+Cl).

Step 2:

A stirred mixture of 161 (0.29 g, 0.35 mmol) and CH₂Cl₂ (45 ml), under nitrogen was treated with piperidine (0.8 ml) and kept at ambient temperature for 22 h. It was concentrated in vacuo and the residue was crystallized from CH₃CN. The solid was collected by filtration and the filtrate was concentrated. Chromatography of the residue on silica gel with 2.5% MeOH—CH₂Cl₂ and crystallization from CH₃CN gave 0.0675 g of 160: MS (ESI+) mn/z 599.4 (M+H⁺); MS (ESI–) m/z 597.4 (M–H), 633.3 (M+Cl); IR (drift) 3243, 3280, 3176, 1753, 1750, 1685, 1681, 1645, 1630 cm⁻¹; HRMS (FAB) calcd for C₂₉H₃₆FN₆O₅S (M+H⁺) 599.2452, found 599.2454.

Example 58

N¹-[4-(5-{4-[4-((5S)-5-{[(2,2-Difluoroethanethioyl)amino]methyl}-2-oxo-1,3-oxazolidin-3-yl)-2-fluorophenyl]piperazin-1-yl}-5-oxopentanoyl)phenyl]glycinamide 162

Step 1:

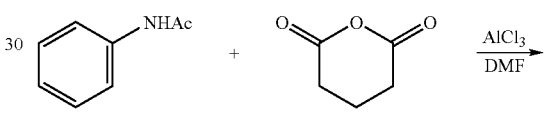

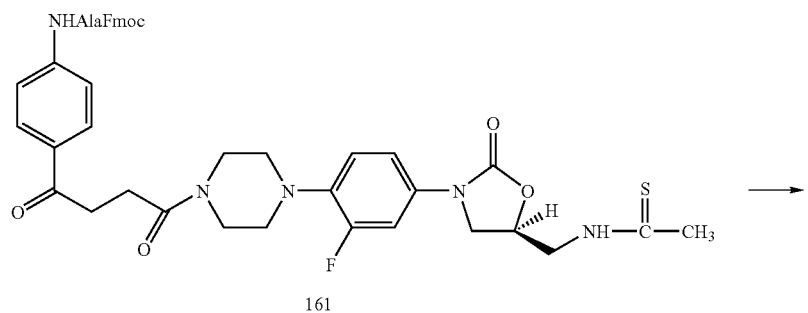

161

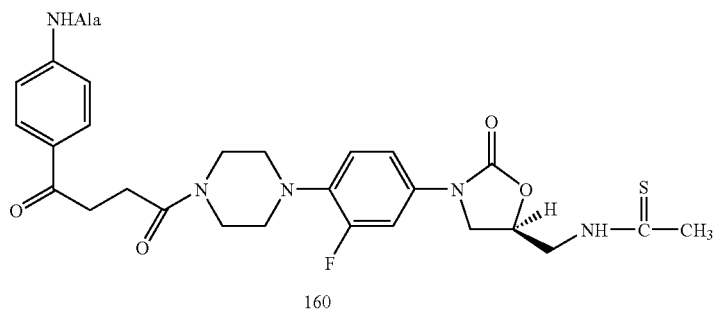

160

-continued

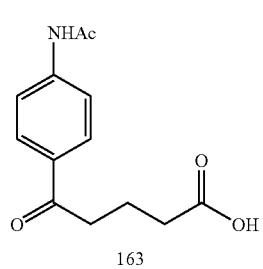
163

Dimethylformamide (9.6 ml) was added, dropwise with stirring under nitrogen during 30 min to aluminum chloride (58.25 g) and the resulting mixture was warmed in a bath at 75° C. and treated, portionwise during 8 min, with a mixture of acetanilide (6.25 g, 0.0462 mol) and glutaric anhydride (4.75 g, 0.0417 mol). The mixture was kept at 72–75° C. for 1 h and then mixed with ice. The resulting stirred mixture was treated with a mixture of concentrated hydrochloric acid (25 ml) and ice (25 g). The product was collected by filtration, washed with cold water, dried and crystallized from acetonitrile to give 2.0 g of 163, mp 185–186° C. MS (ESI+) m/z 250.2 (M+H$^+$), 272.2 (M+Na$^+$), 288.1 (M+K$^+$); MS (ESI−) m/z 248.1 (M−H), 284.1 (M+Cl).

Step 2:

A mixture of 163 (2.0 g, 8.0 mmol) and concentrated hydrochloric acid (10 ml) was warmed on the steam bath for 20 min and cooled under a stream of nitrogen for 20 min. It was then diluted with water (20 ml) and adjusted to pH 5 with solid Na$_2$CO$_3$. The mixture was cooled and the solid product was collected by filtration, washed with cold water and dried in vacuo to give 164: MS (ESI+) m/z 208.1 (M+H), 230.2 (M+Na$^+$); MS (ESI−) m/z 206.1 (M−H), 242.1 (M+Cl).

Step 3:

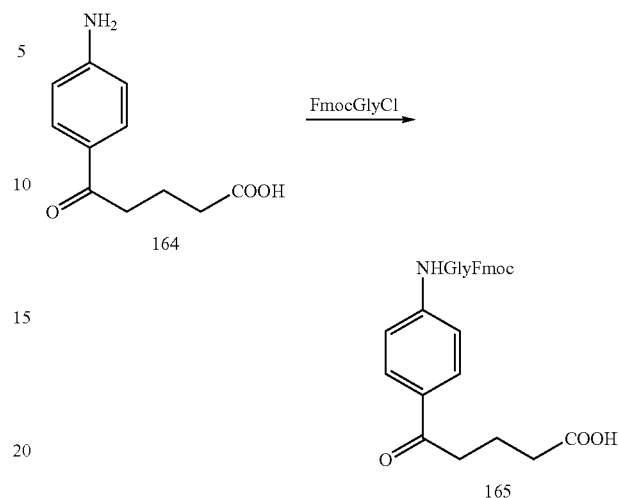

A stirred mixture of 23 (0.50 g, 2.4 mmol) and N-Fmoc-glycyl chloride (0.85 g, 2.7 mmol) in THF (50 ml) was refluxed, under nitrogen, for 4 h, cooled and diluted with CH$_2$Cl$_2$ (50 ml). The white precipitate was collected by filtration to give 0.93 g of 25: mp 217–218° C.; MS (ESI−) m/z 485.2 (M−H), 521.2 (M+35). The filtrate was concentrated and the residue was mixed with Et$_2$O and filtered to give 0.20 g of additional 83, mp 215–216° C.

Step 4:

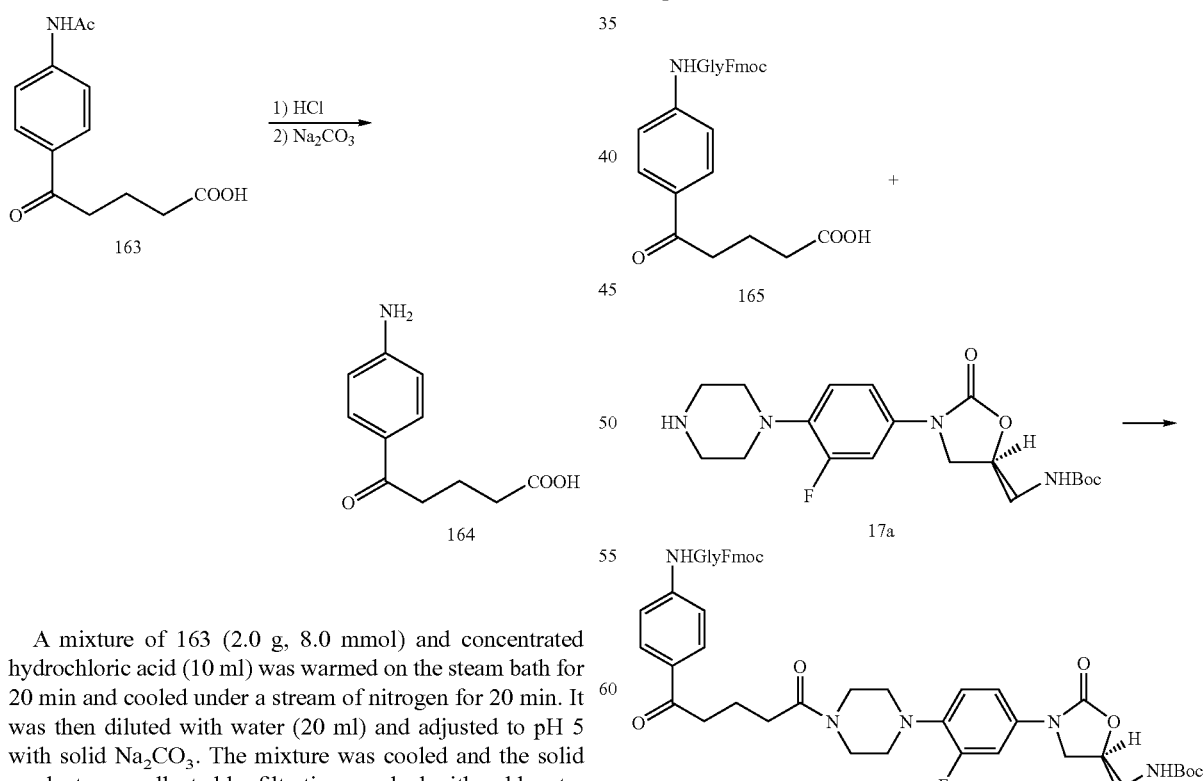

A stirred mixture of 165 (0.486 g, 0.999 mmol), 17a (0.4 g, 1.0 mmol) and pyridine (7 ml), under nitrogen, was treated with EDC (0.25 g, 1.3 mmol) and DMAP (10 mg) and kept at ambient temperature for 24 h. It was concentrated in vacuo and the residue was stored under a stream of nitrogen for 2 d. During this period it appeared (MS) that a considerable amount of the Fmoc protecting group had been removed. The residue was mixed with water and extracted with CH$_2$Cl$_2$. The extract was washed with water and brine, dried (Na$_2$SO$_4$) and concentrated to give 0.45 g of a mixture of 166 and the Fmoc deprotected material. A stirred mixture of this material in THF (20 ml), under nitrogen, was treated with diisopropylethylamine (0.13 ml, 0.77 mmol) and Fmoc chloride (0.14 g, 0.54 mmol) and kept at ambient temperature for 2.5 h. It was concentrated in vacuo and the residue was chromatographed on silica gel with 4% MeOH—CH$_2$Cl$_2$ to give 0.39 g of 166: MS (ESI+) m/z 863.5 (M+H$^+$), 885.5 (M+Na$^+$); MS (ESI−) m/z 897.5 (M+Cl).

Step 5:

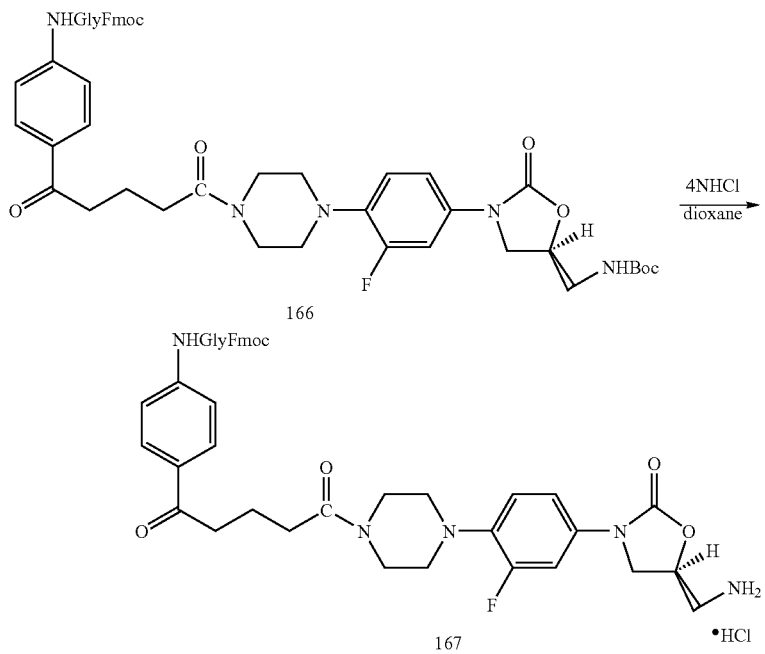

The product 166 from the previous reaction was cooled in an ice bath, under nitrogen, and, with stirring, treated dropwise during 1.5 min with 4N HCl in dioxane (3 ml). It was kept in the ice bath for 45 min and at ambient temperature for 130 min. Excess hydrogen chloride was then removed under a stream of nitrogen and the resulting mixture was concentrated in vacuo to give 0.30 g of 167.

Step 6:

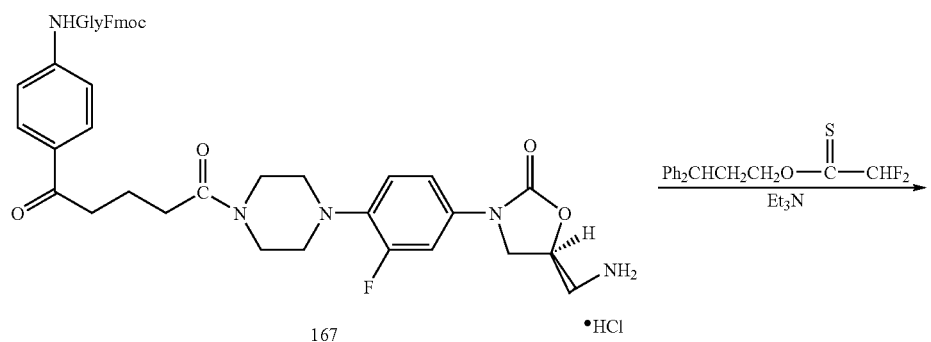

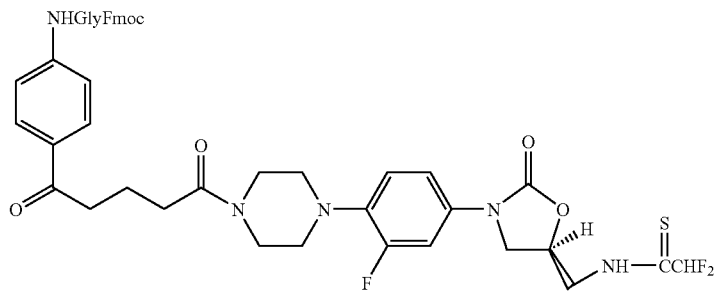

168

A stirred mixture of 167 (0.30 g) from the previous reaction in CH$_2$Cl$_2$ (25 ml), under nitrogen, was treated with triethylamine (0.11 ml) and then dropwise with a solution of O-(3,3-diphenylpropyl) difluoroethanethioate (0.15 g, 0.49 mmol) in CH$_2$Cl$_2$ (2 ml). It was kept at ambient temperature and treated with additional portions of O-(3,3-diphenylpropyl) difluoroethanethioate (0.05 g in 1 ml of CH$_2$Cl$_2$) after 2 h and 4 h. The resulting mixture was kept at ambient temperature for 18 h and concentrated in vacuo. The residue was triturated with 3% MeOH—CH$_2$Cl$_2$ and the resulting solid was crystallized from CH$_2$Cl$_2$—Et$_2$O to give 0.29 g of 168: MS (ESI+) m/z 879.6 (M+Na$^+$); MS (ESI−) m/z 855.3 (M−H), 891.2 (M+Cl).

Step 7:

A stirred mixture of 168 (0.29 g) from the previous reaction in DMF (2 ml), under nitrogen, was treated dropwise with piperidine (0.07 ml), kept at ambient temperature for 30 min and concentrated in vacuo. Chromatography of the residue on silica gel with 4% MeOH-0.2% NH$_4$OH—CH$_2$Cl$_2$ and crystallization of the product from MeOH gave 0.08 g of 162: mp 196–197° C. (dec); $^1$H NMR [400 MHz, (CD$_3$)$_2$SO] δ 1.85 (m, 2H), 2.43 (t, 2H), 292, 2.96 (m, m, 4H), 3.03 (t, 2H), 3.35 (s, 3H), 3.60 (m, 4H), 3.83 (dd, 1H), 3.94 (m, 2H), 4.15 (t, 1H), 5.00 (m, 1H), 6.32, 6.46, 6.59 (s, s, s, 1H), 7.07 (t, 1H), 7.19 (dd, 1H), 7.51 (d, 1H), 7.77 (d, 2H), 7.95 (d, 2H); MS (ESI+) m/z 635.4 (M+H$^+$); MS (ESI−) m/z 633.3 (M−H), 669.3 (M+Cl); IR (drift) 3394, 3258, 1743, 1693, 1672, 1645 cm$^{-1}$. Anal. calcd for C$_{29}$H$_{33}$F$_3$N$_6$O$_5$S; C, 54.88; H, 5.24; N, 13.24. Found: C, 54.46; H, 5.27; N, 13.09.

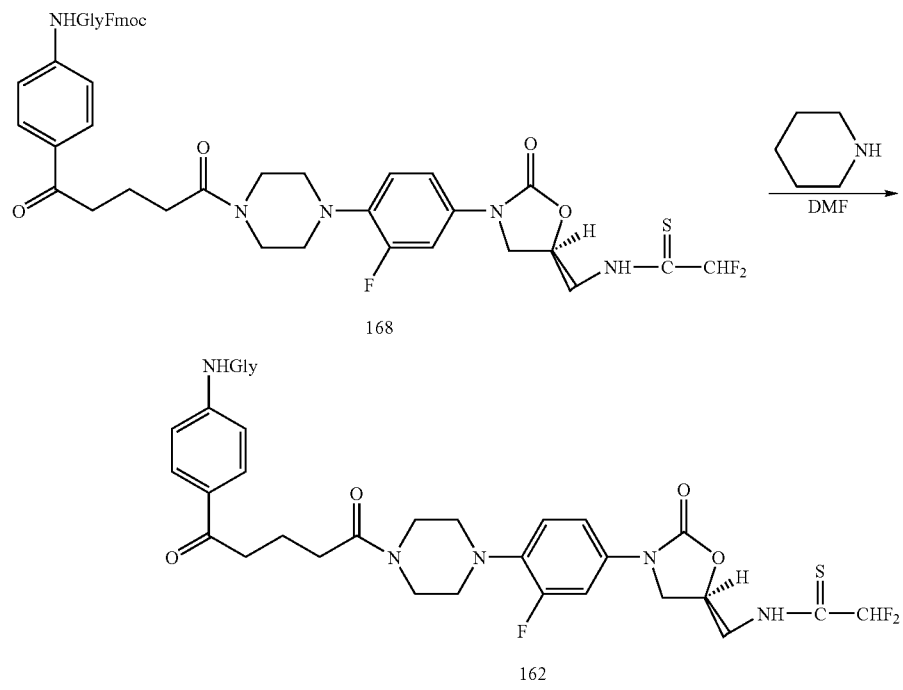

Example 59

N[1]-(4-{5-[4-(4-{(5S)-5-[(Acetylamino)methyl]-2-oxo-1,3-oxazolidin-3-yl}-2-fluorophenyl)piperazin-1-yl]-5-oxopentanoyl}phenyl)glycinamide 169

Step 1:

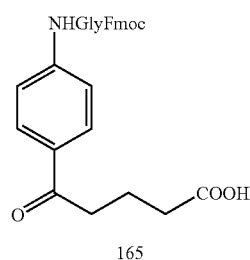

165

+

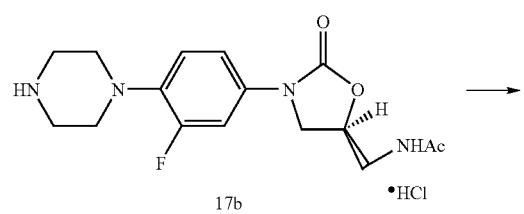

17b •HCl

→

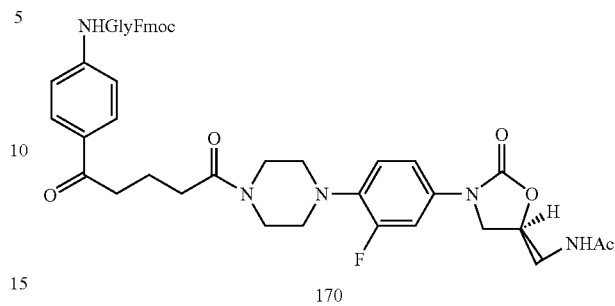

170

A stirred mixture of 165 (0.486 g, 0.999 mmol) and 17b (0.4 g, 1.1 mmol) in pyridine (8 ml), under nitrogen, was treated with EDC (0.25 g, 1.3 mmol) and DMAP (10 mg), kept at ambient temperature for 24 h and concentrated in vacuo. A mixture of the residue in water was extracted with $CH_2Cl_2$; the extract was washed with saturated $NaHCO_3$ and brine and concentrated to give 0.6 g of 170, a yellow solid: MS (ESI−) m/z 839.4 (M+Cl).

Step 2:

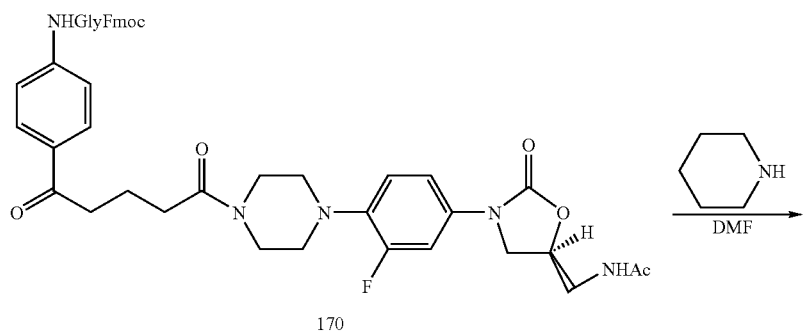

170

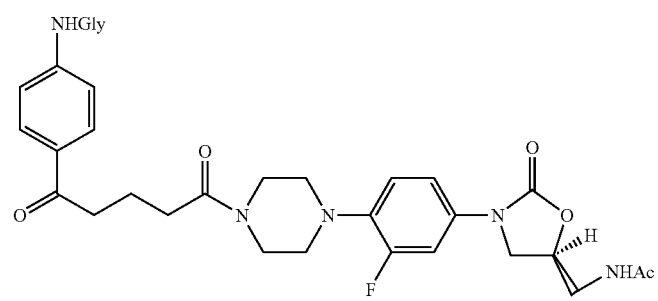

169

A stirred suspension of 170 (0.6 g, 0.75 mmol) in DMF (5 ml), under nitrogen, was treated with piperidine (0.15 ml), kept at ambient temperature for 30 min and concentrated in vacuo. Chromatography of the solid residue on silica gel with 4% MeOH-0.2% NH$_4$OH—CH$_2$Cl$_2$ to 10% MeOH-0.5% NH$_4$OH—CH$_2$Cl$_2$ and crystallization of the product from MeOH gave 0.24 g, mp 189–190° C. and 0.06 g, mp 178–181° C. of 169: $^1$H NMR [400 MHz, (CD$_3$)$_2$SO] δ 1.83 (s, 3H), 1.84 (m, 2H), 2.42 (t, 2H), 2.91, 2.95 (m, m, 4H), 3.03 (t, 2H), 3.31 (s, 2H), 3.35 (s), 3.40 (t, 2H), 3.60 (m, 4H), 3.70 (dd, 1H), 4.08 (t, 1h), 4.71 (m, 1H), 7.06 (t, 1H), 7.18 (dd, 1H), 7.50 (dd, 1H), 7.78 (d, 2H), 7.95 (d, 2H), 8.26 (t, 1H); IR (drift) 3336, 3258, 1725, 1678, 1651, 1631 cm$^{-1}$; MS (ESI+) m/z 583.3 (M+H$^+$); MS (ESI−) m/z 617.3 (M+Cl). Anal. calcd for C$_{29}$H$_{35}$FN$_6$O$_6$: C, 59.78; H, 6.05; N, 14.42. Found: C, 59.14; H, 6.10; N, 14.22.

Example 60

N-(4-{4-[4-(4-{(5S)-5-[(Acetylamino)methyl]-2-oxo-1,3-oxazolidin-3-yl}-2-fluorophenyl)-1-piperazinyl]-4-oxobutyl}phenyl)-2-aminoacetamide 171

Step 1:

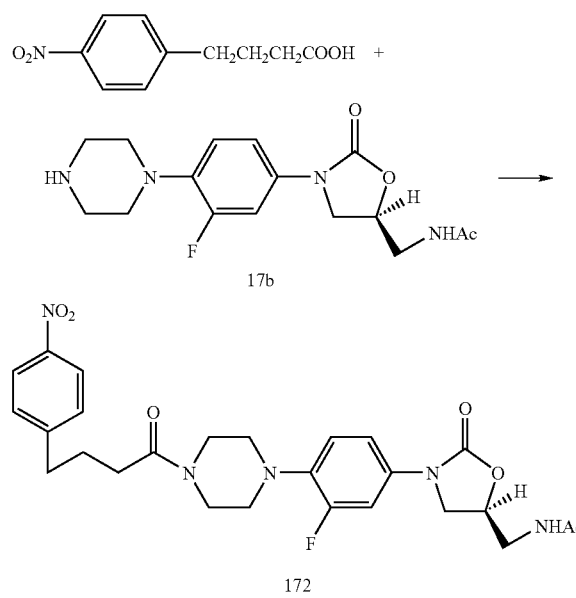

A stirred mixture of 4-(4-nitrophenyl)butanoic acid (0.9 g, 4.3 mmol) and triethylamine (0.69 ml) in THF (20 ml), under nitrogen, was cooled in an ice-MeOH bath and treated, dropwise during 15 min, with isobutyl chloroformate (0.66 ml). It was kept in the bath for 50 min and the resulting thick suspension was treated with a mixture of 17b (1.44 g, 4.28 mmol), triethylamine (0.69 ml) and THF (20 ml). This mixture was kept in the ice-MeOH bath for 3 h and then mixed with EtOAc to give a mixture which contained solid product. It was washed with saturated NaHCO$_3$ and water and filtered to give 1.11 g of 172. The organic solution was concentrated to about 50 ml to give 0.94 g of additional product (26): MS (ESI) m/z 550.4 (M+Na$^+$).

Step 2:

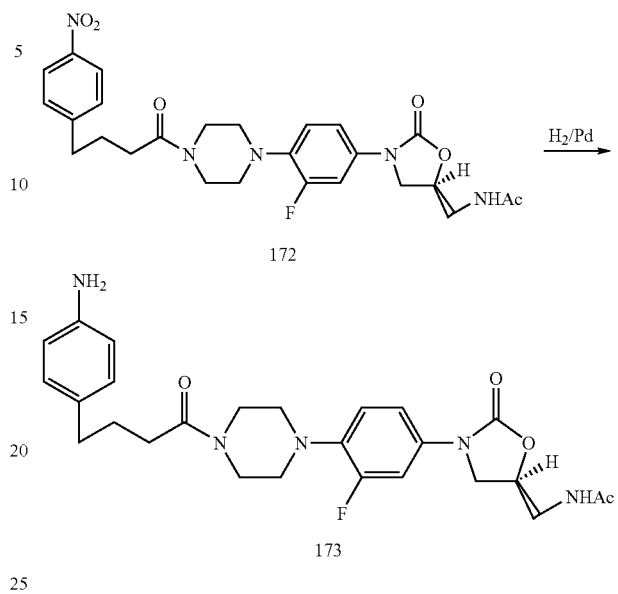

A mixture of 172 (1.1 g, 2.08 mmol), CH$_2$Cl$_2$ (75 ml), MeOH (75 ml) and 10% palladium-on-carbon catalyst (0.65 g) was hydrogenated for 90 min at an initial pressure of 19 psi which was raised to 50 psi during 35 min. The catalyst was removed by filtration through celite, the solid was washed with 50% MeOH—CH$_2$Cl$_2$, and the filtrate was concentrated to give 0.74 g of product. A sample of this material was chromatographed on silica gel with 5% MeOH—CHCl$_3$ and crystallized from MeOH-EtOAc to give 173: mp 141–143° C. (dec); MS (ESI) m/z 498.4 (M+H$^+$), 520.4 (M+Na$^+$); IR (drift) 3340, 3302, 3231, 1733, 1645, 1628 cm$^{-1}$. Anal. calcd for C$_{26}$H$_{32}$FN$_5$O$_4$: C, 62.76; H, 6.48; N, 14.07. Found: C, 62.29; H, 6.50; N, 13.85.

Step 3:

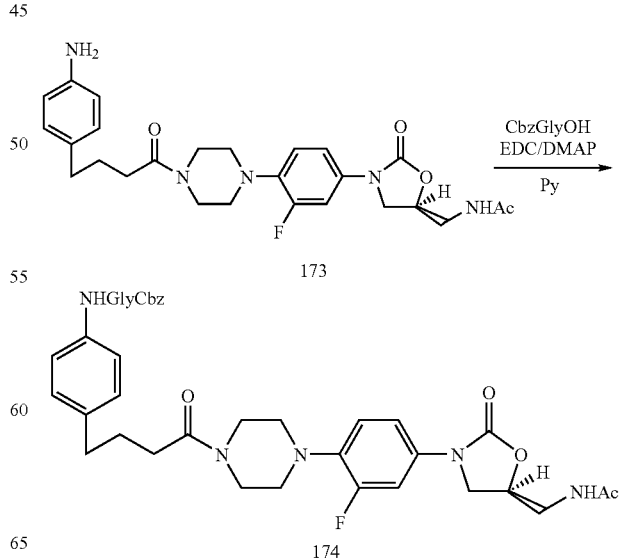

A stirred mixture of N-carbobenzyloxyglycine (0.19 g, 0.91 mmol), 1-(3-dimethylaminopropyl)-3-ethylcarbodiimide hydrochloride (EDC, 0.19 g, 0.99 mmol) and pyridine (5 ml), under nitrogen, was treated with 173 (0.43 g, 0.86 mmol) and 4-dimethylaminopyridine (DMAP, 10 mg) and kept at ambient temperature for 6 h. By TLC (0.5% NH₄OH-7.5% MeOH—CH₂Cl₂) there had been little reaction. Additional Cbz glycine (0.19 g) and EDC (0.19 g) were added and the mixture was kept at ambient temperature for 18 h. By TLC with the solvent system that contained ammonium hydroxide there still had been no reaction but TLC with 10% MeOH—CH₂Cl₂ demonstrated that the reaction was complete. The mixture was concentrated in vacuo and the residue was mixed with CH₂Cl₂ and 1N HCl to give a mixture which contained solid product. It was extracted with CH₂Cl₂ and filtered to give 0.37 g of product. The extract was washed with water and brine and concentrated. The residue was chromatographed on silica gel with 7.5% MeOH—CHCl₃ to give 0.20 g of additional product 174: MS (ESI) m/z 689.5 (M+H⁺), 711.4 (M+Na⁺).

Step 4:

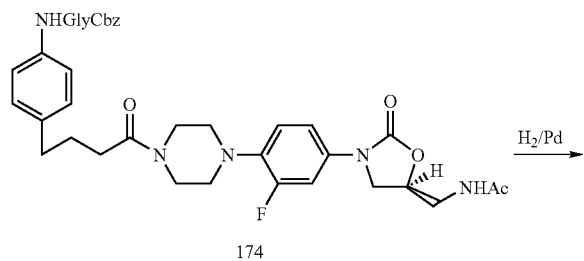

174

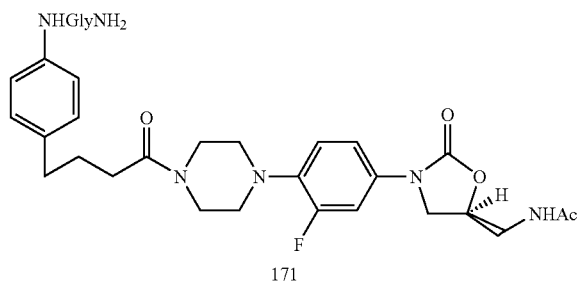

171

A mixture of 174 (0.53 g, 0.77 mmol), MeOH (90 ml), CH₂Cl₂ (60 ml) and 10% palladium-on-carbon catalyst (0.28 g) was hydrogenated at an initial pressure of 36 psi for 7 h and filtered through celite. The solid was washed with 60% MeOH—CH₂Cl₂ and the filtrate was concentrated. Chromatography of the residue on silica gel with 0.5% NH₄OH-10% MeOH—CHCl₃ and crystallization of the product from MeOH gave 0.199 g of 171: mp 199–200° C. (dec); MS (ESI) m/z 555.4 (M+H⁺); IR (drift) 3302, 1732, 1653, 1628 cm⁻¹. Anal. calcd for $C_{28}H_{35}FN_6O_5$: C, 60.64; H, 6.38; N, 15.15. Found: C, 60.59; H, 6.46; N, 15.07.

Example 61

2-Amino-N-(4-{4-[4-(2-fluoro-4-{(5S)-2-oxo-5-[(propanethiolylamino)methyl]-1,3-oxazolidin-3-yl}phenyl)-1-piperazinyl]-4-oxobutyl}phenyl)acetamide 175

Step 1:

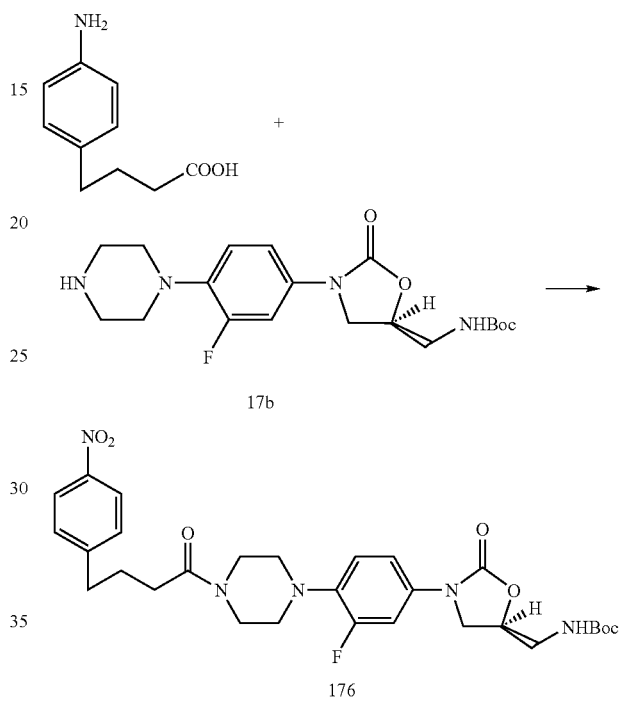

A stirred mixture of 4-(4-nitrophenyl)butanoic acid (0.9 g, 4.3 mmol), triethylamine (0.69 ml) and THF (20 ml), under nitrogen, was cooled in an ice-MeOH bath and treated, dropwise during 30 sec, with isobutyl chloroformate (0.66 ml). It was kept in the bath for 50 min and then treated, portionwise during 5 min, with a mixture of 17b (1.69 g, 4.28 mmol), triethylamine (0.69 ml) and THF (13 ml). This mixture was kept in the ice-methanol bath for 90 min when it was concentrated in vacuo. A mixture of the residue in CH₂Cl₂ was washed with saturated NaHCO₃, water and brine, dried (Na₂SO₄) and concentrated to give 2.54 g of 176: MS (ESI) m/z 586.5 (M+H⁺), 608.4 (M+Na⁺).

Step 2:

-continued

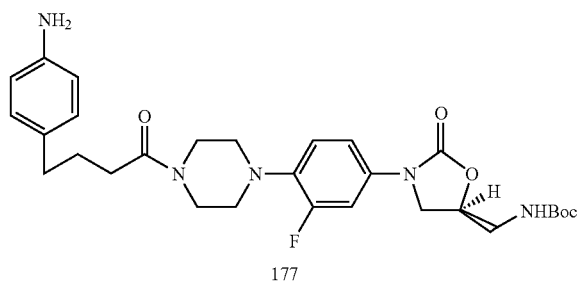

177

A mixture of 176 (1.25 g, 2.13 mmol), 10% palladium-on-carbon catalyst (0.7 g), MeOH (75 ml) and CH$_2$Cl$_2$ (75 ml) was hydrogenated at an initial pressure of 50 psi for 80 min and filtered through celite. The solid was washed with 50% MeOH—CH$_2$Cl$_2$ and the filtrate was concentrated in vacuo to give 1.17 g of 177: MS (ESI) m/z 556.5 (M+H$^+$), 578.5 (M+Na$^+$), 594.5 (M+K$^+$).

Step 3:

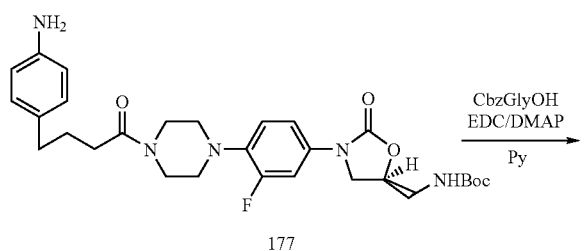

177

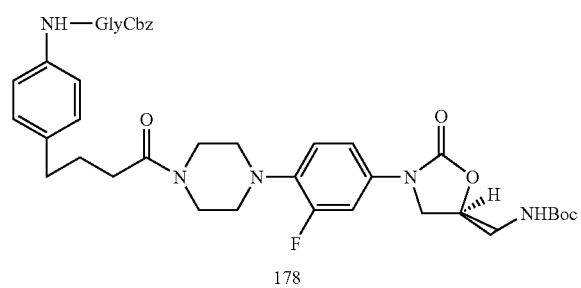

178

A stirred mixture of N-Cbz glycine (0.50 g, 2.39 mmol) and EDC (0.46, 2.4 mmol) in pyridine (15 ml), under nitrogen, was kept at ambient temperature for 10 min and treated with 177 (0.97 g, 1.75 mmol) and DMAP (15 mg). It was kept at ambient temperature for 22 h and concentrated in vacuo. Chromatography of the residue on silica gel with 2–4% MeOH—CH$_2$Cl$_2$ gave 0.73 g (56%) of 178: MS (ESI) m/z 747.6 (M+H$^+$), 769.5 (M+Na$^+$).

Step 4:

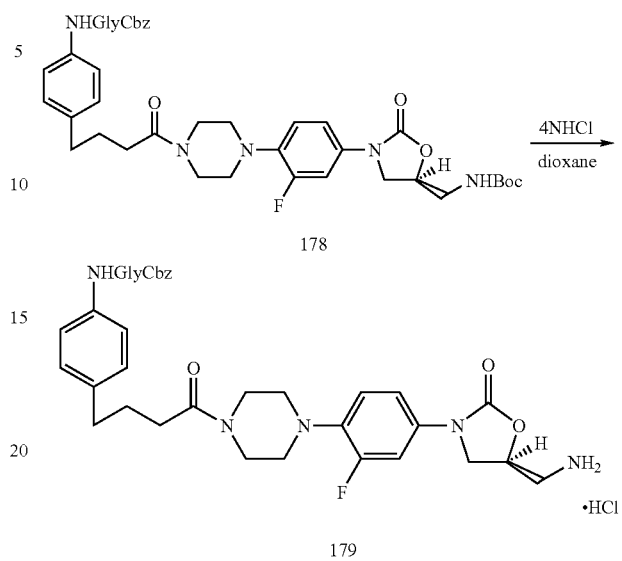

178

179

A stirred suspension of 178 (0.5 g, 0.67 mmol) in dioxane (10 ml) was treated, dropwise during 4 min, with ice-cold 4N HCl in dioxane (5 ml). The mixture was cooled in an ice bath during the addition and kept in the bath for 1 h, at ambient temperature for 2 h and at 4° C. for 18 h. It was then concentrated in vacuo to give 0.50 g of 179: MS (ESI) m/z 647.6 (M+H$^+$).

Step 5:

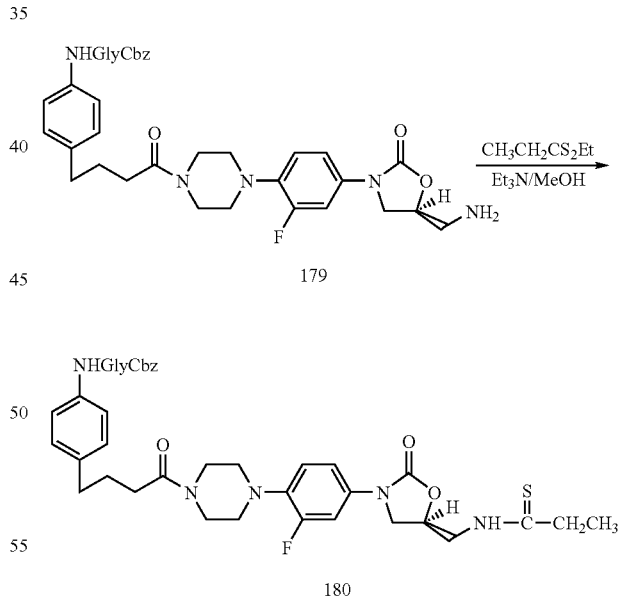

179

180

A stirred suspension of 179 (0.50 g) in MeOH (20 ml), under nitrogen, was treated with triethylamine (0.37 ml, 2.66 mmol) and ethyl dithiopropionate (0.13 ml, 1.0 mmol) and kept at ambient temperature for 22 h. It was then concentrated under a stream of nitrogen for 30 min and filtered. The solid was washed with cold MeOH and dried to give 0.30 g of 180: MS (ESI) m/z 719.6 (M+H$^+$), 741.6 (M+Na$^+$).

Step 6:

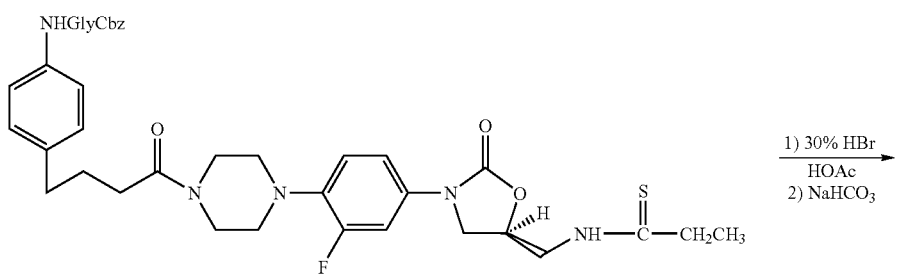

Solid 180 (0.28 g, 0.39 mmol) was mixed with 30% hydrogen bromide in acetic acid (3.9 ml) and stirred at ambient temperature for 30 min. The resulting solution was diluted with Et$_2$O (50 ml) and the liquid was decanted from the solid. This was repeated twice and the solid was then collected by filtration, washed with Et$_2$O, dissolved in water and made alkaline with saturated NaHCO$_3$. The resulting solid was collected by filtration, washed with water and dried to give 0.18 g of crude product. Additional product (0.01 g) was obtained by extracting the aqueous filtrate with CH$_2$Cl$_2$. Chromatography of the combined product on silica gel with 0.4% NH$_4$OH-8% MeOH—CHCl$_3$ and crystallization from EtOAc-MeOH gave 0.0688 g of 175: mp 161–163° C. (dec) with softening at 148° C.; MS (ESI) m/z 585.5 (M+H$^+$), 607.4 (M+Na$^+$); IR (drift) 3322, 3256, 1753, 1749, 1744, 1727, 1681, 1631 cm$^{-1}$. Anal. calcd for C$_{29}$H$_{37}$FN$_6$O$_4$S: C, 59.57; H, 6.38; N, 14.37. Found: C, 58.19; H, 6.48; N, 13.85.

Example 62

(S)-2-Amino-N-(4-{4-[4-(2-fluoro-4-{(5S)-2-oxo-5-[(propanethiolylamino)methyl]-1,3-oxazolidin-3-yl}phenyl)-1-piperazinyl]-4-oxobutyl}phenyl)propanamide 181

Step 1:

-continued

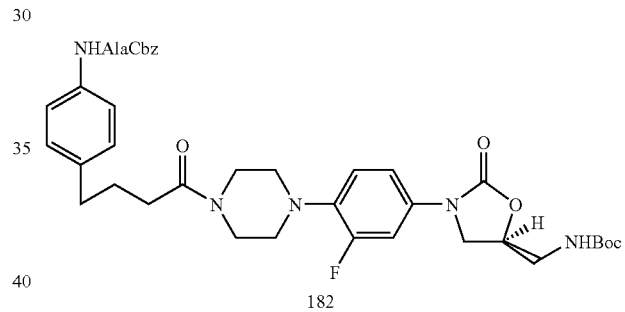

A stirred mixture of N-carbobenzyloxy-L-alanine (0.47 g, 2.1 mmol) and EDC (0.43 g, 2.2 mmol) in pyridine (15 ml), under nitrogen, was treated with 177 (0.91 g, 1.64 mmol) and DMAP (15 mg), kept at ambient temperature for 20 h and concentrated in vacuo. Chromatography of the residue on silica gel with 2–4% MeOH—CHCl$_3$ gave 0.70 g of 182: MS (ESI) m/z 783.7 (M+Na$^+$).

Step 2:

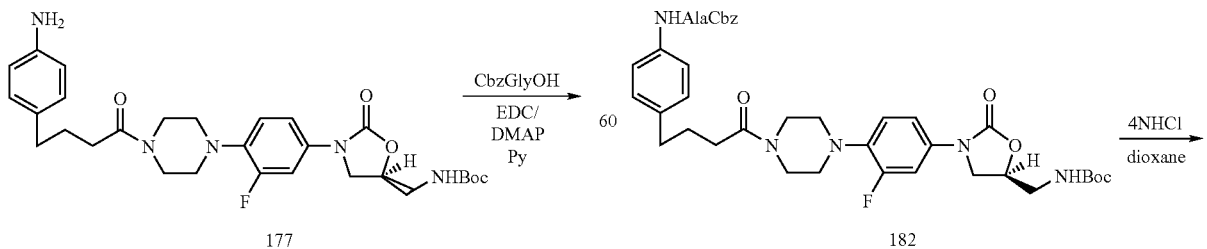

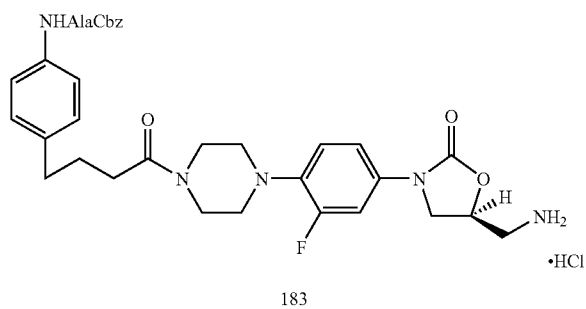

183

A stirred solution of 182 (0.57 g, 0.75 mmol) in dioxane (14 ml), under nitrogen, was treated, dropwise during 2.5 min, with ice cold 4N hydrogen chloride in dioxane (7.5 ml). The mixture was cooled in an ice bath during the addition and kept in the bath for 90 min, at ambient temperature for 4 h and at 4° C. for 16 h. Hydrogen chloride was removed under a stream of nitrogen and the resulting mixture was concentrated in vacuo to give 183, a white solid.

Step 3:

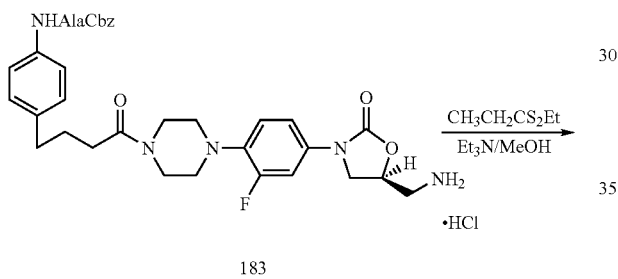

183

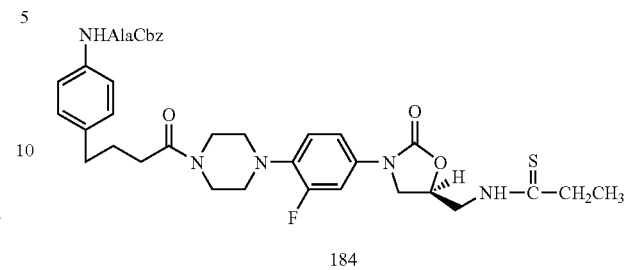

184

A stirred mixture of 183 from the previous reaction and triethylamine (0.37 ml) in MeOH (20 ml), under nitrogen, was treated with ethyl dithiopropionate (0.13 ml), kept at ambient temperature for 72 h and concentrated. Chromatography of the residue on silica gel with 2–3% MeOH—CHCl$_3$ gave 0.42 g of 184: $^1$H NMR [300 MHz, (CD$_3$)$_2$SO] δ 1.12 (t, 3H), 1.26 (d, 3H), 1.77 (m, 2H), 2.32 (t, 2H), 2.55 (m, 4H), 2.90 (m, 4H), 3.56 (m, 4H), 3.78 (dd, 1H), 3.89 (t, 2H), 4.13 (m, 2H), 4.94 (m, 1H), 5.01 (s, 2H), 7.05 (t, 1H), 7.13 (m, 3H), 7.33 (m, 5H), 7.47 (m, 3H), 7.57 (d, 1H), 9.91 (s, 1H), 10.31 (t, 1H); MS (ESI) m/z 733.5 (M+H$^+$), 755.5 (M+Na$^+$).

Step 4:

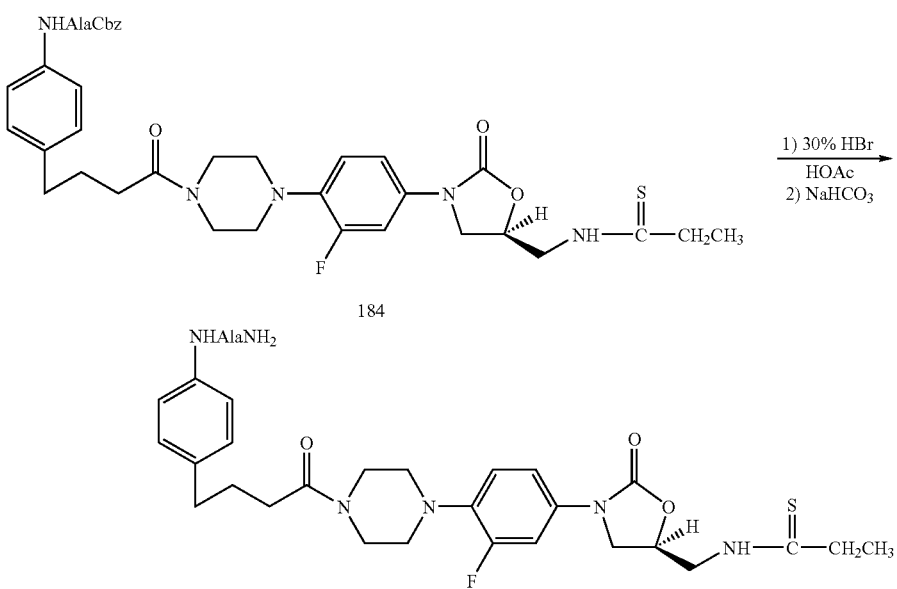

A mixture of 184 (0.40 g, 0.55 mmol) and 30% hydrogen bromide in acetic acid (5.0 ml) was stirred for 35 min at ambient temperature and then diluted with $Et_2O$ (100 ml). The liquid was decanted from the resulting solid which was washed twice with $Et_2O$, collected by filtration and washed with $Et_2O$. The solid was dissolved in water (20 ml) and neutralized (pH 9–10) with saturated $NaHCO_3$ to give a solid which was collected by filtration, dried and chromatographed on silica gel with 0.2% $NH_4OH$-4% MeOH—$CHCl_3$. The product was crystallized from MeOH to give 0.24 g of 181: MS (ESI) m/z 599.3 (M+H$^+$); IR (drift) 3263, 1753, 1751, 1744, 1727, 1676, 1662, 1645, 1639, 1633 cm$^{-1}$; HRMS (FAB) calcd for $C_{30}H_{40}FN_6O_4S$ (M+H$^+$) 599.2816, found 599.2824. Anal. calcd for $C_{30}H_{39}FN_6O_4S \cdot 0.5$ $H_2O$: C, 59.29; H, 6.63; N, 13.83. Found: C, 59.10; H, 6.79; N, 13.59.

Example 63

N-(4-{4-[4-(4-{(5S)-5-[(Acetylamino)methyl]-2-oxo-1,3-oxazolidin-3-yl}-2-fluorophenyl)piperazin-1-yl]-4-oxobutyl)phenyl)-2-(dimethylamino)acetamide 185

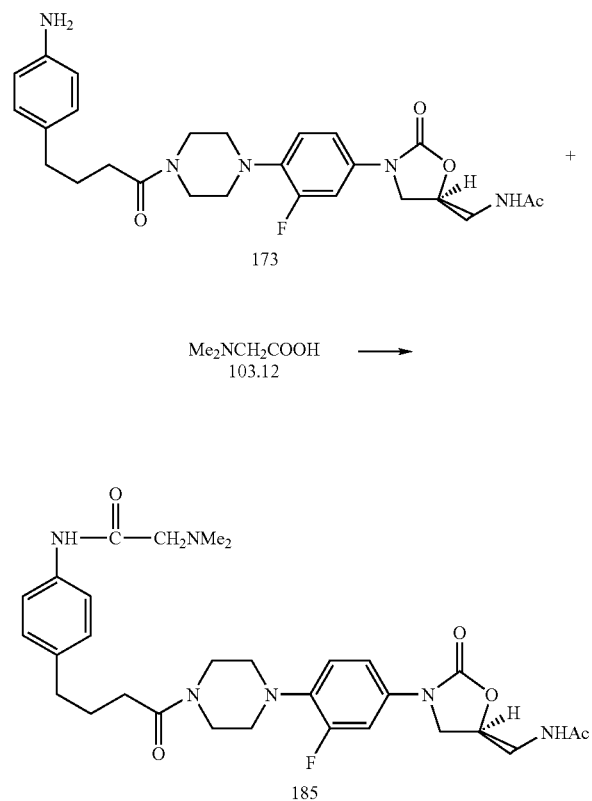

A stirred mixture of N,N-dimethylglycine (0.0263 g, 0.255 mmol) in pyridine (4 ml), under nitrogen, was treated with EDC (0.049 g), DMAP (5 mg) and 173 (0.127 g, 0.255 mmol), kept at ambient temperature for 3 h 10 min and concentrated in vacuo. Chromatography of the residue on silica gel with 2–6% MeOH—$CH_2Cl_2$ gave the product which was dissolved in $CH_2Cl_2$ and concentrated to give 185, a foam: MS (ESI+) m/z 583.5 (M+H$^+$), 605.4 (M+Na$^+$); MS (ESI–) m/z 581.4 (M–H), 617.4 (M+Cl); IR (drift) 3287, 1743, 1676, 1645 cm$^{-1}$; HRMS (FAB) calcd for $C_{30}H_{40}FN_6O_5$ (M+H$^+$) 583.3044, found 583.3058.

Example 64

N-(4-{4-[4-(4-{(5S)-5-[(Ethanethiolylamino)methyl]-2-oxo-1,3-oxazolidin-3-yl}-2-fluorophenyl)piperazin-1-yl]-4-oxobutyl}phenyl)-2-(dimethylamino)acetamide 186

Step 1:

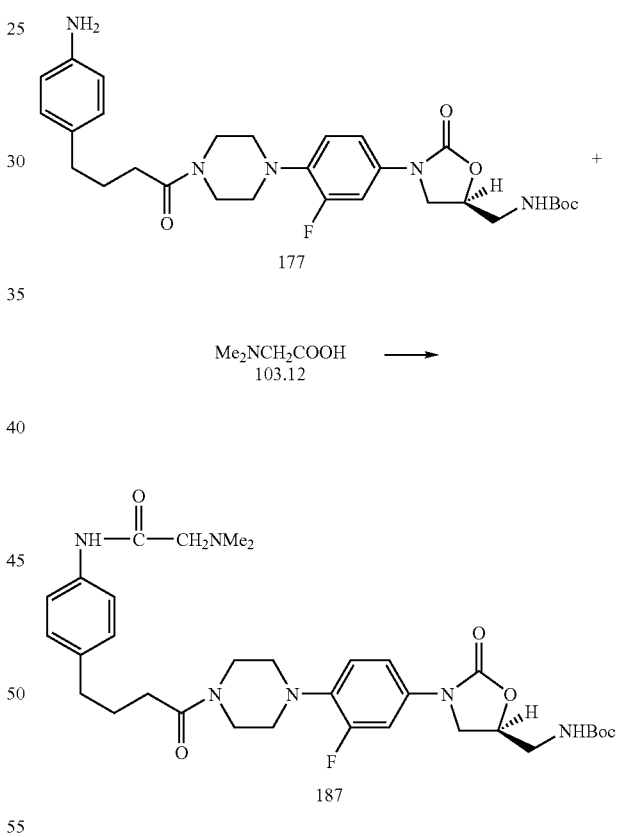

A stirred mixture of N,N-dimethylglycine (0.028 g, 0.27 mmol) in pyridine (4 ml), under nitrogen was treated with EDC (0.052 g, 0.27 mmol), DMAP (5 mg) and 177 (0.15 g, 0.27 mmol), kept at ambient temperature for 5 h and concentrated in vacuo. Chromatography of the residue on silica gel with 2–3% MeOH—$CH_2Cl_2$ gave 0.09 g of 187: MS (ESI+) m/z 641.5 (M+H$^+$); MS (ESI–) m/z 639.4 (M–H), 675.4 (M+Cl).

Step 2:

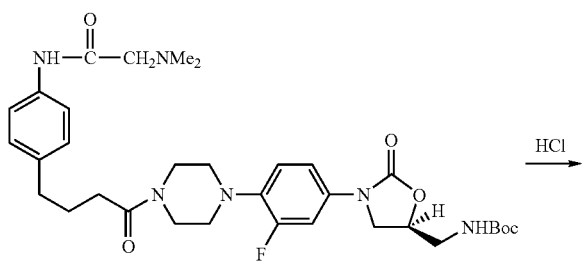

187

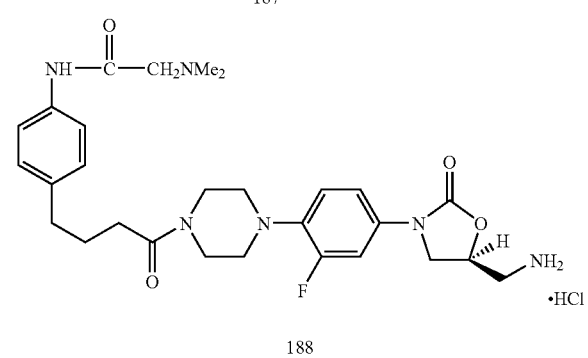

188

Compound 187 (0.21 g, 0.33 mmol) was cooled in an ice bath, under nitrogen and treated, dropwise with 4N HCl in dioxane (3.0 ml). The mixture was kept in the ice bath for 1 h and at ambient temperature for 30 min with occasional swirling. It was placed under a stream of nitrogen for 30 min and then concentrated in vacuo to give 188, a white powder: MS (ESI+) m/z 541.4 (M+H$^+$); MS (ESI−) m/z 575.4 (M+Cl).

Step 3:

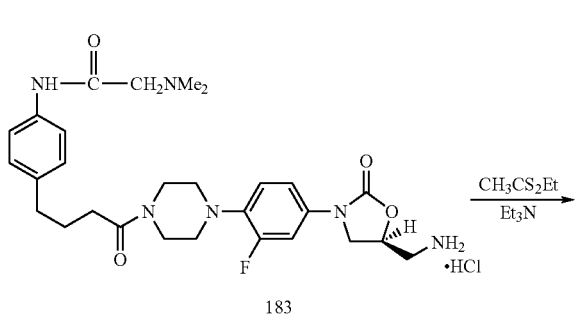

183

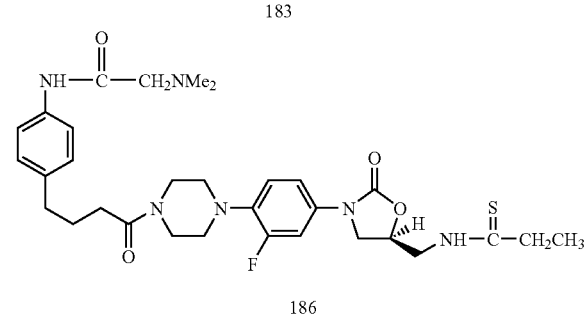

186

A stirred mixture of 188 from the previous reaction and MeOH (2.5 ml), under nitrogen was treated with triethylamine (0.4 ml) and ethyl dithioacetate (0.088 ml), kept at ambient temperature for 1 h and concentrated in vacuo. Chromatography of the residue on silica gel with 2.5–4% MeOH—CH$_2$Cl$_2$ gave 0.13 g of 186: MS (ESI+) m/z 599.4 (M+H$^+$); MS (ESI−) m/z 597.3 (M−H), 633.3 (M+Cl); IR (drift) 3251, 1754, 1680, 1663, 1645, 1638 cm$^{-1}$; HRMS (FAB) calcd for C$_{30}$H$_{40}$FN$_6$O$_4$S (M+H$^+$) 599.2816, found 599.2827.

Example 65

N$^1$-(3-{4-[4-(4-{(5S)-5-[(Acetylamino)methyl]-2-oxo-1,3-oxazolidin-3-yl}-2-fluorophenyl)piperazin-1-yl]-1-hydroxy-4-oxobutyl}phenyl)glycinamide
189

Step 1:

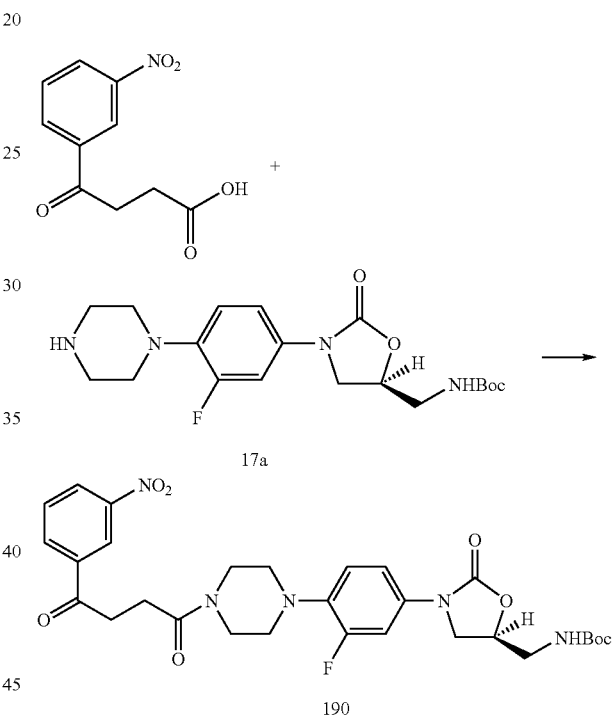

17a

190

A stirred mixture of 3-nitro-□-oxo-benzenebutanoic acid, $^{13}$ (0.9 g, 4.1 mmol) and pyridine (20 ml), under nitrogen was treated with EDC (0.96 g, 5.0 mmol), kept at ambient temperature for 2 min and treated with 17a (1.69 g, 4.29 mmol) and DMAP (20 mg). It was kept at ambient temperature for 46 h and concentrated in vacuo. A solution of the residue in CH$_2$Cl$_2$ was washed with dilute KHSO$_4$ and water and concentrated in vacuo. Chromatography of the residue on silica gel with 1 to 2% MeOH—CH$_2$Cl$_2$ gave 2.2 g of 190. A sample was recrystallized from EtOAc-hexane: mp 124–126° C.; $^1$H NMR (300 MHz, CDCl$_3$) δ 1.40 (s, 9H), 2.90 (t, 2H), 3.04, 3.13 (m, m, 4H), 3.39 (t, 2H), 3.52 (m, 2H), 3.79 (m, 5H), 4.00 (t, 1H), 4.75 (m, 1H), 4.96 (m, 1H), 6.98 (t, 1H), 7.09 (dd, 1H), 7.49 (dd, 1H), 7.69 (t, 1H), 8.35 (d, 1H), 8.43 (d, 1H), 8.86 (m, 1H); MS (ESI+) m/z 599.8 (M+H$^+$), 621.8 (M+Na$^+$); MS (ESI−) m/z 597.8 (M−H), 633.7 (M+Cl).

Step 2:

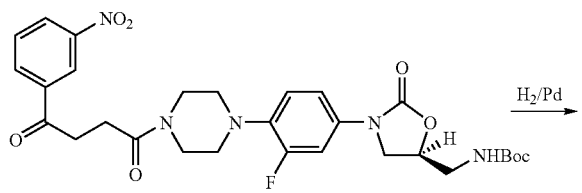
190

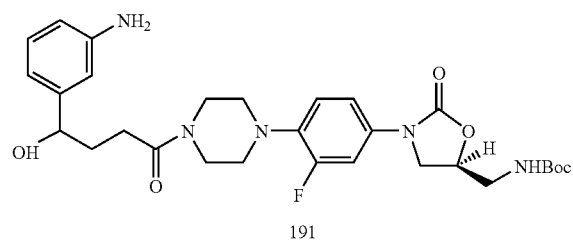
191

A mixture of 190 (0.4 g, 0.67 mmol), MeOH (35 ml), CH$_2$Cl$_2$ (35 ml) and 10% palladium-on-carbon catalyst (0.2 g) was hydrogenated at an initial pressure of 29 psi for 25 min. Complete reduction of the ketone and nitro groups with little of the over reduced, deshydroxy material was obtained. The mixture was filtered through celite and the filtrate was concentrated. Chromatography of the residue over silica gel with 2 to 4% MeOH—CH$_2$Cl$_2$ gave 0.26 g of 1912: MS (ESI+) m/z 572.4 (M+H$^+$), 564.4 (M+Na$^+$); MS (ESI−) m/z 570.3 (M−H), 606.3 (M+Cl).

Step 3:

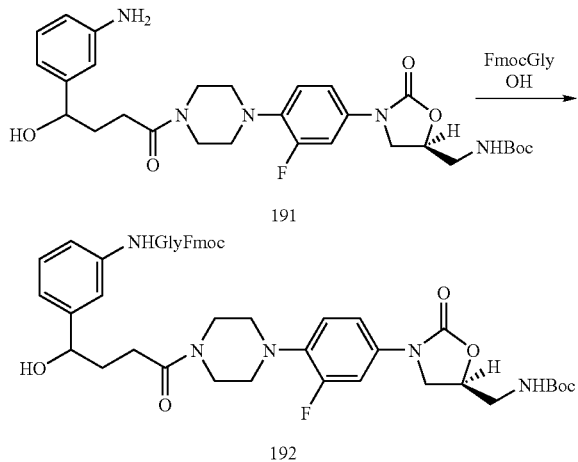
191

192

A stirred mixture of N-Fmoc glycine (0.45 g, 1.5 mmol) and DMF (8 ml), under nitrogen, was treated with HOBT (0.254 g) and 0.5 M DCC in CH$_2$Cl$_2$ (4.65 ml), kept at ambient temperature for 50 min and treated, dropwise, with a solution of 191 (0.88 g, 1.5 mmol) in DMF (2 ml). It was kept at ambient temperature for 90 min and concentrated in vacuo. Chromatography of the residue on silica gel with 2.5% MeOH—CH$_2$Cl$_2$ gave 0.63 g of 192: MS (ESI+) m/z 851.5 (M+H$^+$), 873.5 (M+Na$^+$).

Step 4:

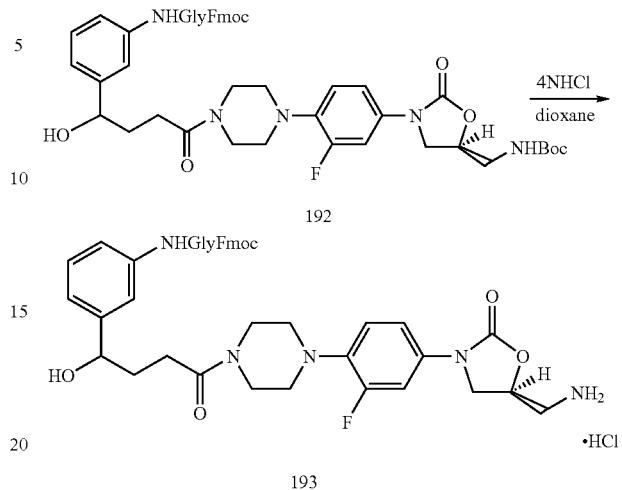
192

193

Ice cold 4N hydrogen chloride in dioxane (4.5 ml) was added, dropwise under nitrogen, to 192 (0.65 g, 0.765 mmol) which had been cooled in an ice bath. The mixture was kept in the ice bath for 30 min and at ambient temperature for 90 min. It was then placed under a stream of nitrogen for 10 min and concentrated in vacuo to give 193, a white solid: MS (ESI+) m/z 751.5 (M+H$^+$); MS (ESI−) m/z 785.2 (M+Cl).

Step 5:

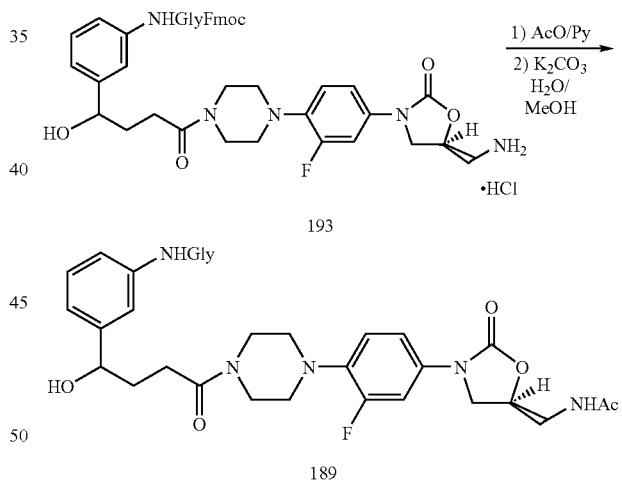
193

189

An ice cold, stirred mixture of the product 193 from the previous reaction in pyridine (5 ml), under nitrogen, was treated, dropwise with a solution of acetic anhydride (1.25 ml) in pyridine (1.5 ml). It was kept in the ice bath for 40 min and at ambient temperature for 50 min and then concentrated in vacuo. A mixture of the residue in CH$_2$Cl$_2$ was washed with saturated NaHCO$_3$, water and brine. Concentration of the CH$_2$Cl$_2$ solution gave 0.78 g of a mixture of mono and diacylated products. A stirred mixture of this material (0.53 g) in MeOH (15 ml), under nitrogen was treated with 10% aqueous K$_2$CO$_3$ (1.8 ml) and kept at ambient temperature for 18 h. It was concentrated in vacuo. Chromatography of the residue on silica gel with 12% MeOH-0.6% NH$_4$OH—CH$_2$Cl$_2$ and crystallization of the product from MeOH gave 0.102 g of 189: ¹H NMR [300 MHz, (CD₃)₂SO] δ 1.81 (s, 3H), 1.81 (m, 2H), 2.37 (t, 2H), 2.88 (m, 4H), 3.23 (s, 2H), 3.32 (broad s, 3H), 3.38 (t, 2H), 3.54 (m, 4H), 3.68 (dd, 1H), 4.06 (t, 1H), 4.52 (m, 1H), 4.69 (m, 1H), 5.26 (d, 1H), 6.98–7.25 (m, 4H), 7.45–7.56 (m, 3H), 8.23 (t, 1H); MS (ESI+) m/z 571.3 (M+H⁺), 593.3 (M+Na⁺); MS (ESI−) m/z 569.1 (M−H), 605.1 (M+Cl); IR (drift) 3444, 3372, 3342, 3307, 1749, 1680, 1663 cm⁻¹. Anal. calcd for C₂₈H₃₅FN₆O₆·2H2O: C, 55.44; H, 6.48; N, 13.85. Found: C, 54.84; H, 6.48; N, 13.60.

Example 66

N¹-[3-(4-{4-[4-((5S)-5-{[(2,2-Difluoroethanethiolyl)amino]methyl}-2-oxo-1,3-oxazolidin-3-yl)-2-fluorophenyl]piperazin-1-yl}-4-oxobutanoyl)phenol] glycinamide 194

Step 1:

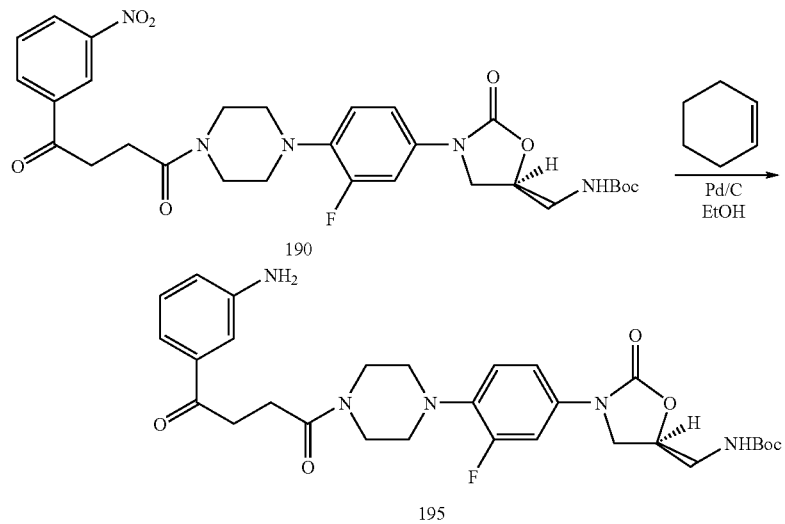

A stirred mixture of 190 (2.1 g, 3.5 mmol), cyclohexene (4 ml), 10% palladium-on-carbon catalyst (0.5 g) and EtOH (50 ml) was refluxed, under nitrogen for 2.5 h, kept at ambient temperature for 20 h, refluxed for 4 h and kept at ambient temperature for 3 d. It was then diluted with CH₂Cl₂ and filtered through celite. The solid was washed with 10% EtOAc—CH₂Cl₂ and the combined filtrate was concentrated in vacuo. Chromatography of the residue on silica gel with 3% MeOH—CH₂Cl₂ gave 195: MS (ESI+) m/z 570.4 (M+H), 592.4 (M+Na⁺).

Step 2:

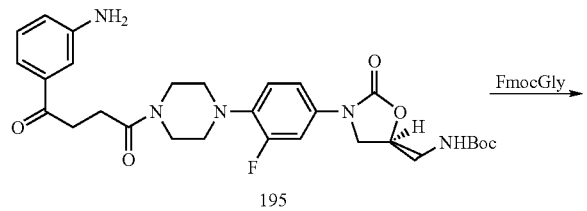

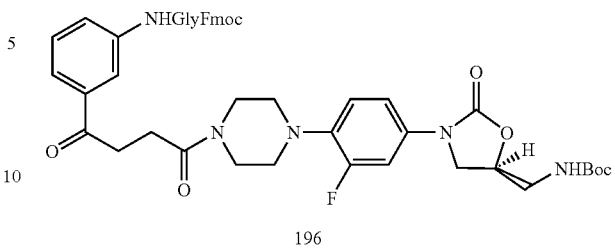

A stirred mixture of N-Fmoc glycine (0.155 g, 0.521 mmol), HOBT (0.09 g) and DMF (3 ml) was treated, dropwise during 1.5 min, with 0.5 M DCC in CH₂Cl₂ (1.6 ml) and kept at ambient temperature for 50 min. It was then treated, dropwise during 2 min, with a solution of 195 (0.30 g, 0.53 mmol) in DMF (2 ml) and kept at ambient temperature for 20 h. The mixture was concentrated in vacuo and the residue was mixed with water to give a solid which was collected by filtration, washed with water and dried in vacuo. Chromatography of this material on silica gel with 7.5% MeOH—CH₂Cl₂ gave 0.42 g of 196: MS (ESI+) m/z 849.4 (M+H⁺), 871.4 (M+Na⁺); MS (ESI−) m/z 847.3 (M−H), 883.2 (M+Cl⁻).

Step 3:

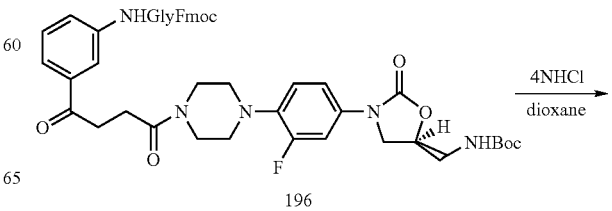

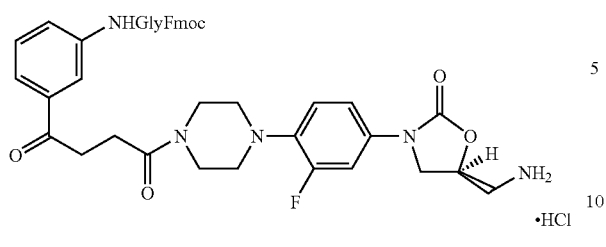

197

Ice cold 196 (0.74 g, 0.87 mmol), under nitrogen, was treated, dropwise with ice cold 4N HCl in dioxane (6.2 ml) and the mixture was stirred in the ice bath for 30 min and at ambient temperature for 90 min. It was concentrated to give 0.72 g of 197: MS (ESI+) m/z 749.4 (M+H$^+$); MS (ESI−) m/z 783.2 (M+Cl).

Step 4:

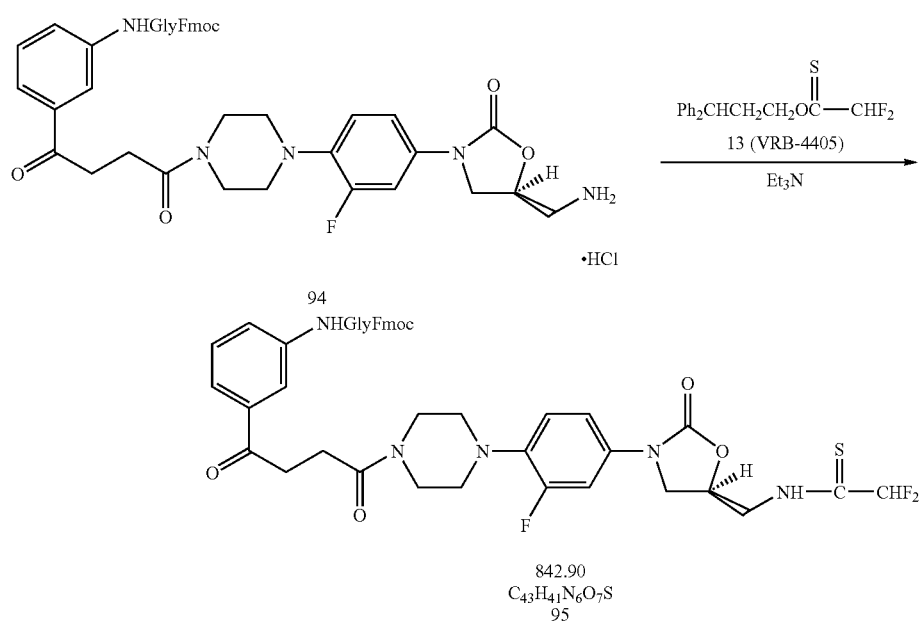

A stirred mixture of 197 (0.22 g) and triethylamine (0.08 ml) in CH$_2$Cl$_2$ (20 ml), under nitrogen, was treated, dropwise, with a solution of O-(3,3-diphenylpropyl) difluoroethanethioate (0.11 g, 0.36 mmol) in CH$_2$Cl$_2$ (0.5 ml) and kept at ambient temperature for 18 h. It was then concentrated in vacuo and the residue was chromatographed on silica gel with 3% MeOH—CH$_2$Cl$_2$ to give 198: MS (ESI+) m/z 865.3 (M+Na$^+$); MS (ESI−) m/z 841.3 (M−H), 877.4 (M+Cl).

Step 5:

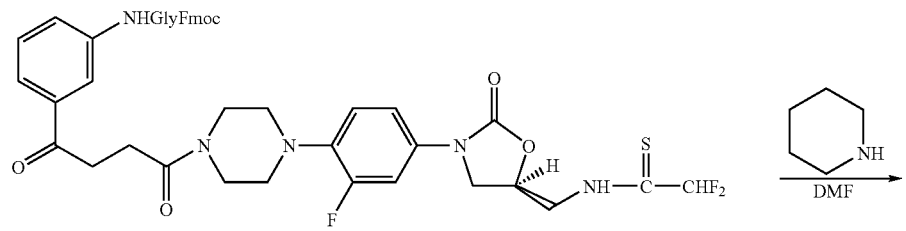

198

-continued

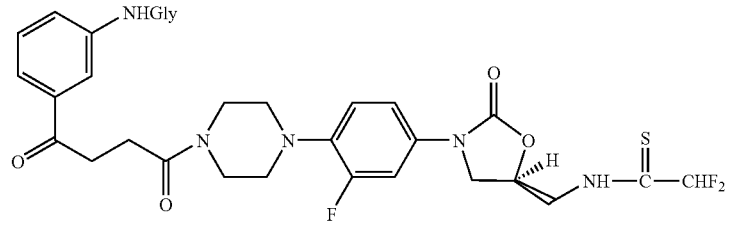

194

A stirred mixture of 198, prepared from 0.49 g of 197, in DMF (3 ml), under nitrogen, was treated with piperidine (0.10 ml), kept at ambient temperature for 40 min and concentrated in vacuo. Chromatography of the residue on silica gel with 7.5% MeOH-0.5% NH$_4$OH—CH$_2$Cl$_2$ and crystallization of the product from MeOH-EtOAc gave 0.030 g of 194: $^1$H NMR [400 MHz, (CD$_3$)$_2$SO] δ 2.76 (t, 2H), 2.92, 3.02 (s, s, 4H), 3.23 (t, 2H), 3.34 (broad s), 3.40 (s, 2H), 3.60, 3.69 (s, s, 4H), 3.84 (dd, 1H), 3.95 (m, 2H), 4.16 (t, 1H), 5.01 (m, 1H), 6.34, 6.48, 6.62 (s, s, s, 1H), 7.10 (t, 1H), 7.20 (dd, 1h), 7.48 (m, 2H), 7.70 (d, 1H), 7.89 (d, 1H), 8.25 (s, 1H); MS (ESI+) m/z 621.3 (M+H$^+$); MS (ESI−) m/z 619.3 (M−H), 655.3 (M+Cl); IR (drift) 3268, 1753, 1691, 1685, 1682, 1645, 1638, 1636, 1628 cm$^{-1}$; HRMS (FAB) calcd for C$_{28}$H$_{32}$F$_3$N$_6$O$_5$S (M+H$^+$) 621.2107, found 621.2117.

Example 67

N-{[(5S)-3-(3-Fluoro-4-{4-[4-(3-nitrophenyl)-4-oxobutanoyl]piperazin-1-yl}phenyl)-2-oxo-1,3-oxazolidin-5-yl]methyl}actamide 199

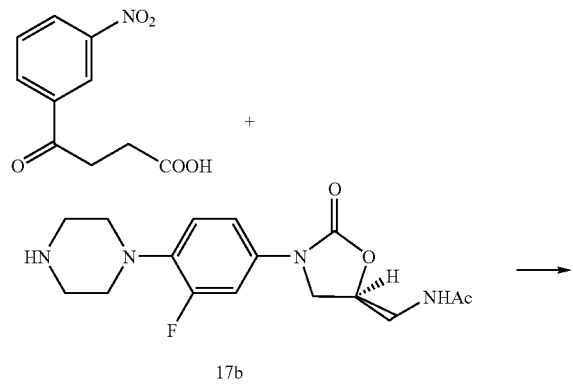

17b

-continued

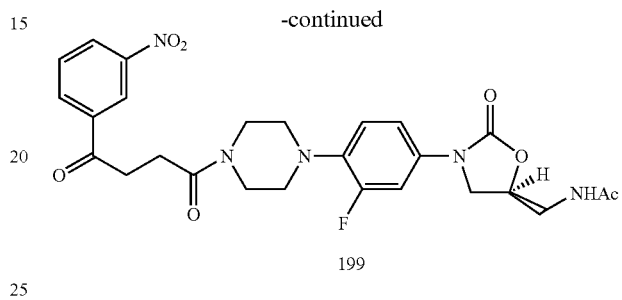

199

A stirred mixture of 3-nitro-□-oxo-benzenebutanoic acid, $^{13}$ (0.9 g, 4.0 mmol) and triethylamine (0.69 ml) in THF (20 ml) was cooled, under nitrogen, in an MeOH-ice bath and treated, dropwise, with isobutyl chloroformate (0.66 ml). It was kept in the bath for 45 min and then treated, portionwise during 10 min, with a mixture of 17b$^{12}$ (1.44 g, 4.28 mmol), triethylamine (0.69 ml) and THF. The mixture was kept in the bath for 2 h and at ambient temperature for 90 min and then concentrated in vacuo. Chromatography of the residue on silica gel with 2.5% MeOH—CH$_2$Cl$_2$ and crystallization of the product from CH$_3$CN gave 0.69 g of 199: mp 178–179° C.; IR (drift) 3280, 1736, 1691, 1672, 1650 cm$^{-1}$; MS (ESI+) m/z 541.8 (M+H$^+$), 563.8 (M+Na$^+$); MS (ESI−) m/z 540.8 (M−H), 575.8 (M+Cl). Anal. calcd for C$_{26}$H$_{28}$FN$_5$O$_7$: C, 57.67; H, 5.21; N, 12.93. Found: C, 57.86; H, 5.33; N, 12.84.

Example 68

N$^1$-(3-{4-[4-(4-{(5S)-5-[(Acetylamino)methyl]-2-oxo-1,3-oxazolidin-3-yl}-2-fluorophenyl)piperazin-1-yl]-4-oxobutanoyl}phenyl)glycinamide 200

Step 1:

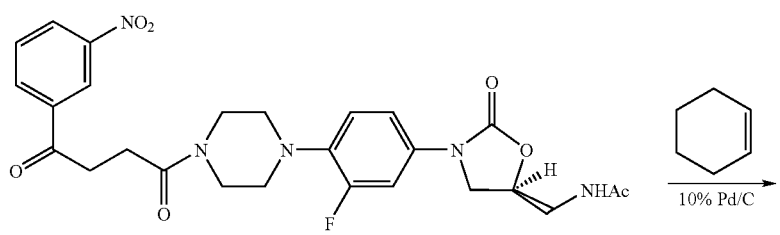

199

-continued

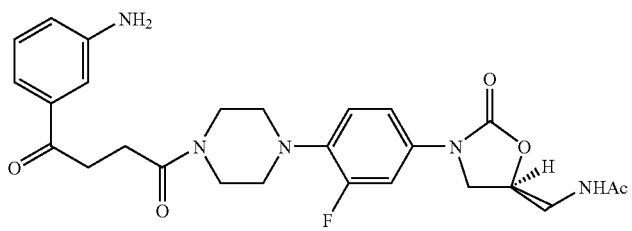

201

A stirred mixture of 199 (0.77 g, 1.42 mmol), cyclohexene (1.0 ml), 10% palladium-on-carbon catalyst (0.21 g) and EtOH (30 ml) was refluxed, under nitrogen for 1 h and kept at ambient temperature for 18 h. Additional catalyst (0.15 g) and cyclohexene (1 ml) were added and the mixture was refluxed for 3.5 h, cooled and filtered through celite. The solid was washed with EtOH and the filtrate was concentrated to give 0.26 g of recovered 199. The solid was then washed with 50% MeOH—CH$_2$Cl$_2$ (300 ml); the filtrate was concentrated and the residue was chromatographed over silica gel with 2–4% MeOH—CH$_2$Cl$_2$. Trituration of the product with MeOH—CH$_2$Cl$_2$ gave 0.18 g of 201 as the hydrochloride salt: MS (ESI+) m/z 512.2 (M+H$^+$), 534.2 (M+Na$^+$); MS (ESI–) m/z 510.1 (M–H), 546.0 (M+Cl), 556.0 (M+HCO$_2$); IR (drift) several bands 3600–3400, 3355, 3281, 1738, 1682, 1662, 1632 cm$^{-1}$. Anal. calcd for C$_{26}$H$_{31}$ClFN$_5$O$_5$: C, 56.99; H, 5.70; N, 12.78. Found: C, 57.12; H, 6.00; N, 12.63.

Step 2:

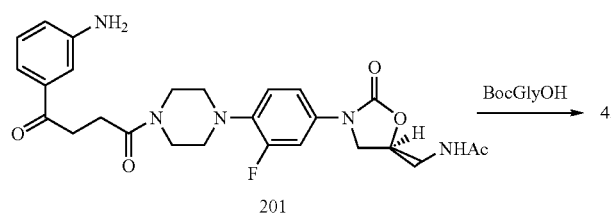

201

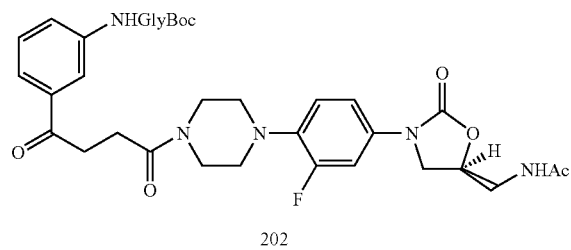

202

A stirred mixture of N-Boc glycine (0.052 g, 0.29 mmol), HOBT (0.05 g), 0.5 M dicyclohexylcarbodiimide (DCC) in CH$_2$Cl$_2$ (0.9 ml) and DMF (4 ml) was kept at ambient temperature, under nitrogen, for 45 min and treated, dropwise, with a solution of 201 (0.15 g, 0.29 mmol) in DMF (2 ml). It was kept at ambient temperature for 22 h and concentrated in vacuo. Chromatography of the residue on silica gel with 5% MeOH—CHCl$_3$ gave 0.15 g of 202: MS (ESI+) m/z 669.3 (M+H$^+$), 691.3 (M+Na$^+$); MS (ESI–) m/z 667.2 (M–H).

Step 3:

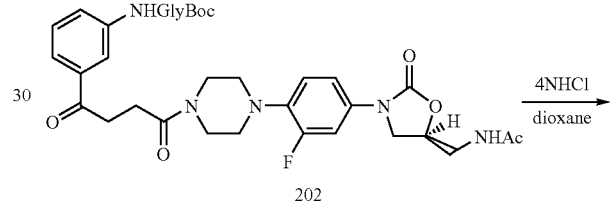

202

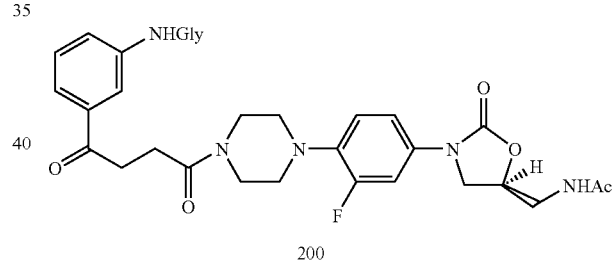

200

Ice cold 4N HCl in dioxane (1.3 ml) was added, dropwise with stirring under nitrogen, to ice cold 202 (0.15 g, 0.22 mmol). The mixture was kept in the ice bath for 1 h and at ambient temperature for 1 h and then concentrated under a stream of nitrogen to give a white solid. This was mixed with 5% aqueous NaHCO$_3$ and Et$_2$O to give a solid. Nitrogen was bubbled through the mixture to remove the Et$_2$O and the solid was collected by filtration and washed with cold water. The solid was triturated with hot MeOH and recrystallized from CH$_2$Cl$_2$-MeOH to give 200: $^1$H NMR [300 MHz, (CH$_3$)$_2$SO] δ 1.81 (s, 3H), 2.74 (t, 2H), 2.90, 3.00 (s, s, 4H), 3.15 (t, 2H), 3.28 (m, 4H), 3.38 (t, 2H), 3.58 (s, 2H), 3.66 (m, 3H), 4.07 (t, 1H), 4.69 (m, 1H), 7.07 (t, 1H), 7.16 (dd, 1H), 7.45 (m, 2H), 7.66 (d, 1H), 7.88 (d, 1H), 8.25 (m, 2H); IR (drift) 3316, 3287, 1748, 1702, 1682, 1662, 1630 cm$^{-1}$; HRMS (ESI+) calcd for C$_{28}$H$_{34}$FN$_6$O$_6$ (M+H$^+$) 569.2524, found 569.2510.

Example 69

N-{[(5S)-3-(4-{4-[4-(2-Aminophenyl)-4-oxobutanoyl]piperazin-1-yl}-3-fluorophenyl)-2-oxo-1,3-oxazolidin-5-yl]methyl}acetamide 203

Step 1:

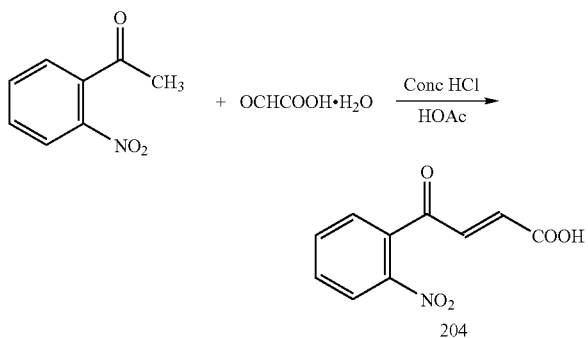

According to the method of Bianchi et.al. (*Eur. J. Med. Chem.* 1988, 23, 45–52) a stirred mixture of o-nitroacetophenone (2.48 g, 0.0150 mol), glyoxylic acid hydrate (1.53 g, 0.0166 mol) and acetic acid (25 ml) was treated with concentrated hydrochloric acid (2.5 ml) and warmed, under nitrogen at 125° C. for 22 h. It was then concentrated in vacuo and the residue was mixed with ice and adjusted to pH 9–10 with 10% aqueous Na$_2$CO$_3$. This mixture was washed with Et$_2$O, cooled and adjusted to pH 3–4 with cold dilute hydrochloric acid. The residual Et$_2$O was removed under a stream of nitrogen and the resulting solid was collected by filtration, washed with water, dried and crystallized from EtOH (Darco) to give 0.49 g of 204, mp 171–172° C. (lit.[14] mp 169–171° C.): $^1$H NMR[300 MHz, (CD$_3$)$_2$SO] δ 6.36 (d, 1H), 7.20 (d, 1h), 7.69 (dd, 1H), 7.81 (m, 1H), 7.91 (m, 1H), 8.22 (d, 1H), 13.33 (s, 1H); MS (ESI+) m/z 223.1 (M+H$^+$); MS (ESI−) m/z 219.9 (M−H).

Step 2:

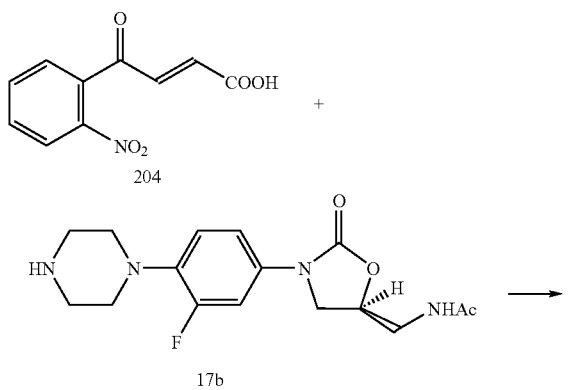

A stirred mixture of 204 (0.29 g, 1.3 mmol) and DMF (5 ml), under nitrogen, was treated with EDC (0.25 g, 1.3 mmol) and HOBT (0.17 g, 1.3 mmol), kept at ambient temperature for 2 min and treated with 17b (0.436 g, 1.29 mmol). It was kept at ambient temperature for 1 h and concentrated in vacuo. The residue was kept under a stream of nitrogen for 18 h and then chromatographed on silica gel with 5% MeOH—CH$_2$Cl$_2$. Crystallization of the product from EtOAc gave 0.36 g of 205: MS (ESI+) m/z 540.1 (M+H$^+$), 562.1 (M+Na$^+$); MS (ESI−) m/z 538.0 (M−H), 574.0 (M+Cl), 584.0 (M+CHO$_2$).

Step 3:

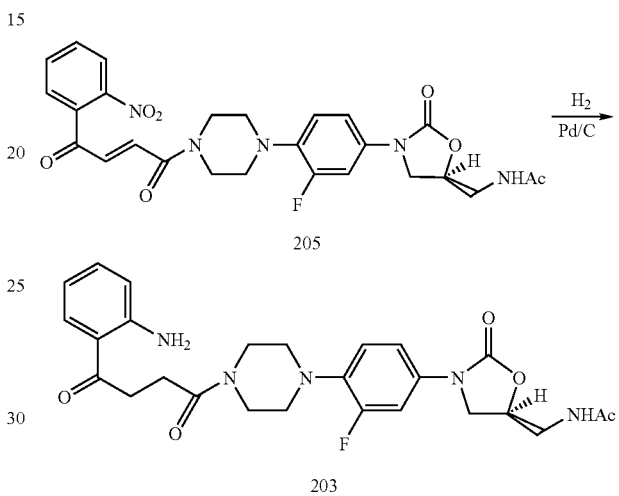

A mixture of 205 (1.18 g, 2.18 mmol), 50% MeOH—CH$_2$Cl$_2$ and 10% palladium-on-carbon catalyst was hydrogenated at an initial pressure of 40 psi for 2.25 h and filtered. The solid was washed with 50% MeOH—CH$_2$Cl$_2$ and the filtrate was concentrated to give 0.92 g, of 203. A sample which was chromatographed on silica gel with 5% MeOH-0.2% NH$_4$OH—CH$_2$Cl$_2$ and crystallized from MeOH had: MS (ESI+) m/z 512.4 (M+H$^+$), 534.3 (M+Na$^+$); MS (ESI−) m/z 510.3 (M−H), 546.2 (M+Cl); IR (drift) 3455, 3340, 3287, 1744, 1644, 1638 cm$^{-1}$; HRMS (FAB) calcd for C$_{26}$H$_{31}$FN$_5$O$_5$ (M+H$^+$) 512.2309, found 512.2308.

Example 70

N-{[(5S)-3-(4-{4-[(5-Amino-1,3-dioxo-1,3-dihydro-2H-isoindol-2-yl)acetyl]piperazin-1-yl}-3-fluorophenyl)-2-oxo-1,3-oxazolidin-5-yl]methyl}acetamide 208

Step 1:

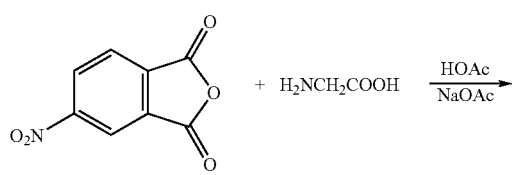

-continued

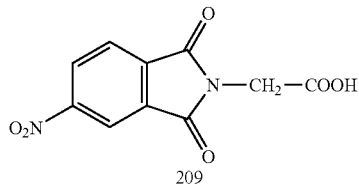

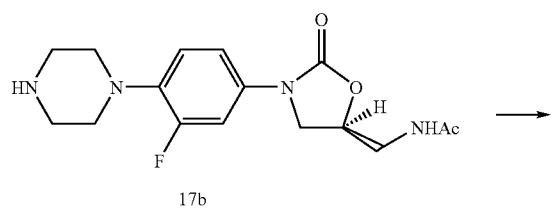

A stirred mixture of 4-nitrophthalic anhydride (1.4 g, 0.0072 mol), glycine (0.55 g, 0.0073 mol), sodium acetate (0.66 g, 0.0080 mol) and acetic acid (10 ml) was immersed in a bath that had been preheated to 100° C., warmed to 130° C. and kept at that temperature for 90 min. It was then kept at ambient temperature for 3 h and the thick suspension was diluted with EtOH and filtered. The solid was washed with EtOH and then crystallized from EtOH to give 2.16 g of 209: MS (ESI−) m/z 249.1 (M−H).

Step 2:

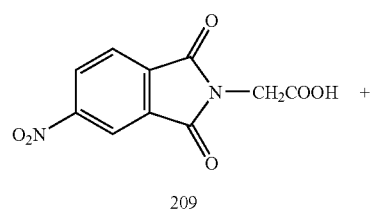

A stirred mixture of 209 (0.25 g, 1.0 mmol) and pyridine (7 ml), under nitrogen, was treated with 17b (0.34 g, 1.0 mmol), EDC (0.3 g, 1.6 mmol) and DMAP (10 mg), kept at ambient temperature for 3 h and concentrated in vacuo. Chromatography of the residue on silica gel with 5% MeOH—$CH_2Cl_2$ gave 0.22 g of 210: MS (ESI+) m/z 591.3 (M+Na$^+$); MS (ESI−) m/z 568.2 (M−H), 603.2 (M+Cl).

Step 3:

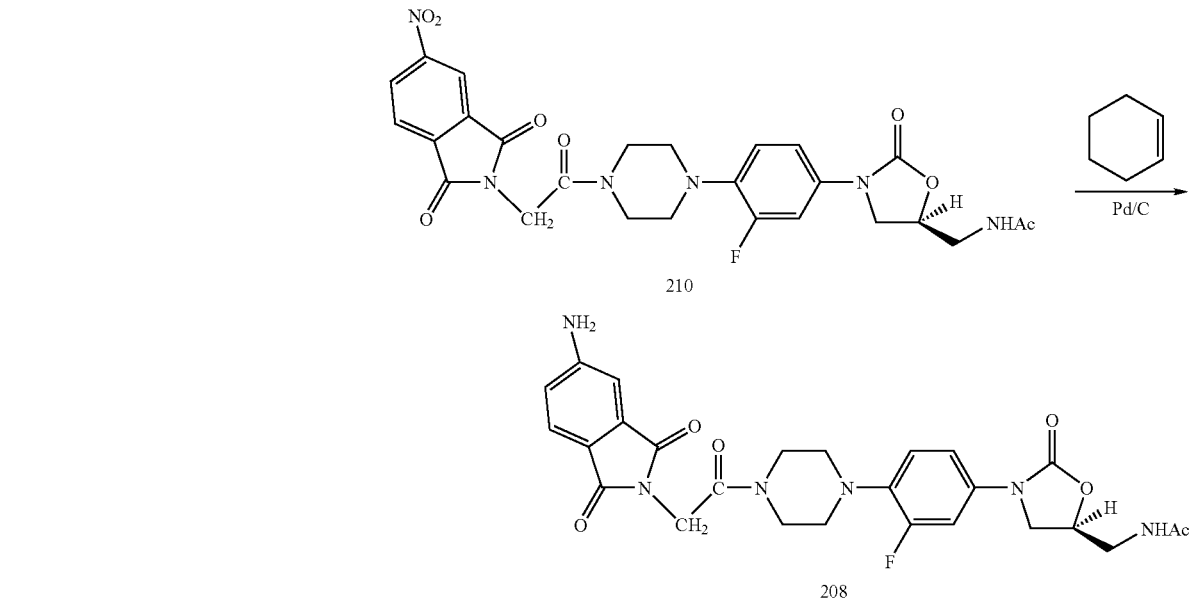

A stirred mixture of 210 (0.5 g, 0.88 mmol), ethanol (20 ml), cyclohexene (1 ml) and 10% palladium-on-carbon catalyst (0.12 g) was refluxed, under nitrogen, for 3.5 h, diluted with $CH_2Cl_2$ and filtered through celite. The filtrate was concentrated in vacuo to give 0.42 g of product. A sample of this material was crystallized from MeOH-EtOAc-hexane to give 208: mp 241–243° C. (dec); MS (ESI+) m/z 539.3 (M+H$^+$), 561.2 (M+Na$^+$); MS (ESI−) m/z 537.2 (M−H), 573.2 (M+Cl); IR (drift) 3421, 3382, 3364, 3341, 3234, 1763, 1743, 1701, 1661 cm$^{-1}$; HRMS (ESI) calcd for $C_{26}H_{28}FN_6O_6$ (M+H$^+$) 539.2054, found 539.2071.

Example 71

N$^1$-(2-{2-[4-(4-{(5S)-5-[(Acetylamino)methyl]-2-oxo-1,3-oxazolidin-3-yl}-2-fluorophenyl)piperazin-1-yl]-2-oxoethyl}-1,3-dioxo-2,3-dihydro-1H-isoindol-5-yl)glycinamide (210)

Step 1:

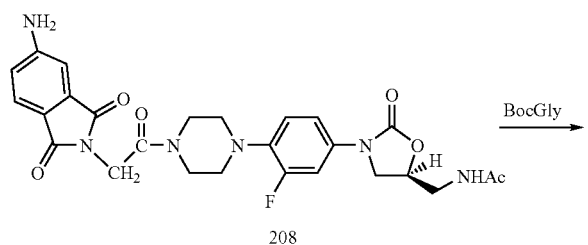

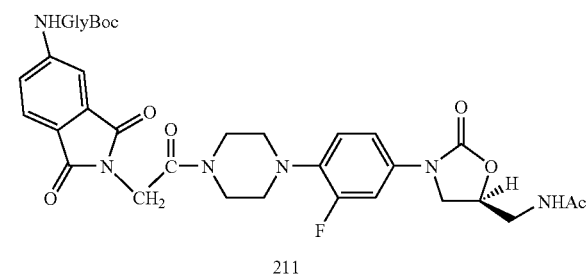

A stirred mixture of 208 (0.42 g, 0.78 mmol), N-Boc glycine (0.143 g, 0.817 mmol) and pyridine (6 ml), under nitrogen, was treated with EDC (0.22 g, 1.15 mmol) and DMAP (10 mg), kept at ambient temperature for 2 h 35 min and concentrated in vacuo. Chromatography of the residue on silica gel with 5% MeOH—$CH_2Cl_2$ gave 0.4 g of 211: $^1$H NMR (300 MHz, CDCl$_3$) δ 1.49 (s, 9H), 2.05 (s, 3H), 3.15, 3.24 (s, s, 4H), 3.70 (m, 2H), 3.80 (m, 3H), 3.89 (s, 2H), 3.94 (d, 2H), 4.06 (t, 1H), 4.56 (s, 2H), 4.82 (m, 1H), 5.42 (m, 1H), 6.44 (t, 1H), 7.10 (m, 2H), 7.50 (d, 1H), 7.61 (d, 1H), 7.77 (d, 1H), 7.93 (s, 1H), 9.45 (s, 1H); MS (ESI+) m/z 696.3 (M+H$^+$), 718.3 (M+Na$^+$); MS (ESI−) m/z 694.2 (M−H), 730.1 (M+Cl).

Step 2:

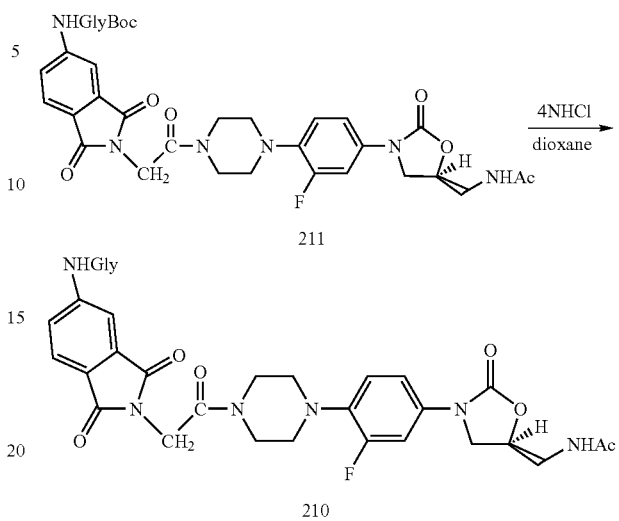

A sample of 211 (0.4 g, 0.57 mmol) was cooled in an ice bath, under nitrogen and, with stirring, treated, dropwise, with 4N hydrogen chloride in dioxane (3.5 ml). It was kept in the ice bath for 30 min and at ambient temperature for 3 h and the concentrated under a stream of nitrogen. The residue was mixed with 5% NaHCO$_3$ and extracted with $CH_2Cl_2$. The extract was washed with water and brine and concentrated. Chromatography of the residue on silica gel with 6% MeOH-0.3% NH$_4$OH—$CH_2Cl_2$ to 10% MeOH-0.5% NH$_4$OH—$CH_2Cl_2$ and crystallization of the product from MeOH gave 0.133 g of 210: mp 153° C. (dec); $^1$H NMR [300 MHz, (CD$_3$)$_2$SO] δ 1.84 (s, 3H), 2.96, 3.06 (s, s, 4H), 3.17 (s, 1.5H, MeOH), 3.38 (s, 2H), 3.41 (t, 2H), 3.61 (s, 2H), 3.72 (m, 3H), 4.10 (t, 1H), 4.10 (0.5H), 4.56 (s, 2H), 4.72 (m, 1H), 5.09 (broad s, 1H), 7.11 (t, 1H), 7.18 (dd, 1H), 7.52 (dd, 1H), 7.87 (d, 1 H), 7.97 (dd, 1H), 8.24 (t, 1H), 8.32 (d, 1H); IR (drift) 3369, 3300, 3217, 1758, 1744, 1714, 1712, 1662, 1646 cm$^{-1}$; MS (ESI+) m/z 596.3 (M+H$^+$); MS (ESI−) m/z 630.1 (M+Cl). Anal. calcd for $C_{28}H_{30}FN_7O_7$·CH$_3$OH: C, 55.49; H, 5.46; N, 15.62. Found: C, 55.33; H, 5.44; N, 15.93.

Example 72

N$^1$-[2-(3-{4-[4-((5S)-5-{[(2,2-Difluoroethanethiolyl)amino]methyl}-2-oxo-1,3-oxazolidin-3-yl)-2-fluorophenyl]piperazin-1-yl}-3-oxopropyl)-1,3-dioxo-2,3-dihydro-1H-isoindol-5-yl]glycinamide 212

Step 1:

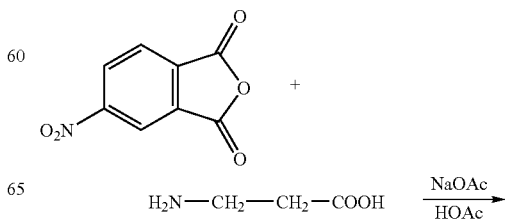

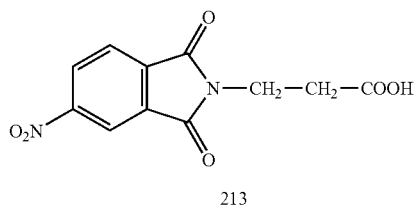

213

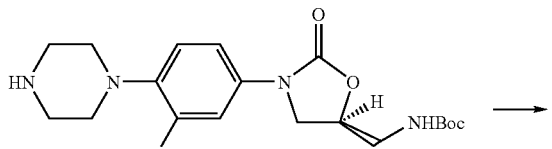

17a

A stirred mixture of 4-nitrophthalic anhydride (2.8 g, 0.0145 mol), β-alanine (1.3 g, 0.0146 mol), sodium acetate (1.32 g, 0.0161 mol) and acetic acid (20 ml) was warmed, under nitrogen to 135° C. during 90 min, kept at this temperature for 2 h and cooled to ambient temperature. It was mixed with EtOH (50 ml) and the solid was collected by filtration, washed with EtOH and dried at 55–60° C. in vacuo. Crystallization from acetonitrile gave 2.34 g, mp 210–211° C. and 0.27 g, mp 208–209° C. of 213: $^1$H NMR [400 MHz, $(CD_3)_2SO$] δ 2.64 (t, 2H), 3.83 (t, 2H), 8.13 (d, 1H), 8.50 (d, 1H), 8.62 (dd, 1H), 12.44 (s, 1H); MS (ESI+) m/z 287.1 (M+Na$^+$); MS (ESI−) m/z 263.1 (M−H).

Step 2:

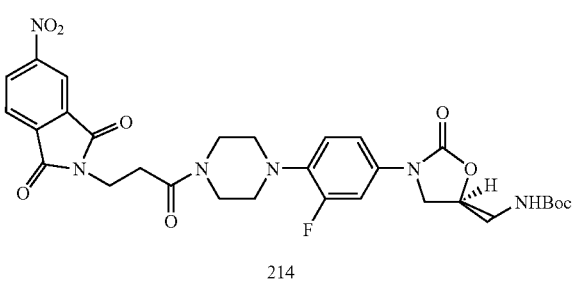

214

A stirred mixture of 213 (1.17 g, 4.43 mmol) and pyridine (20 ml), under nitrogen was treated with EDC (1.27 g, 6.62 mmol), 17a$^5$ (1.75 g, 4.44 mmol) and DMAP (20 mg), kept at ambient temperature for 19 h and concentrated in vacuo. A mixture of the residue and water was extracted with EtOAc and $CH_2Cl_2$. The extracts were washed with 5% $NaHCO_3$ and brine, dried ($MgSO_4$) and concentrated. Chromatography of the residue on silica gel with 2% MeOH—$CH_2Cl_2$ gave 2.02 g of 214: MS (ESI+) m/z 641.5 (M+H$^+$), 663.5 (M+Na$^+$); MS (ESI−) m/z 639.3 (M−H), 671.4 (M+$CH_3O$), 675.3 (M+Cl).

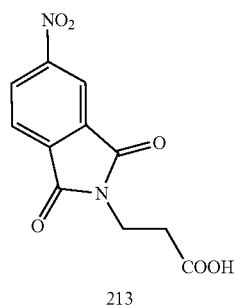

213

Step 3:

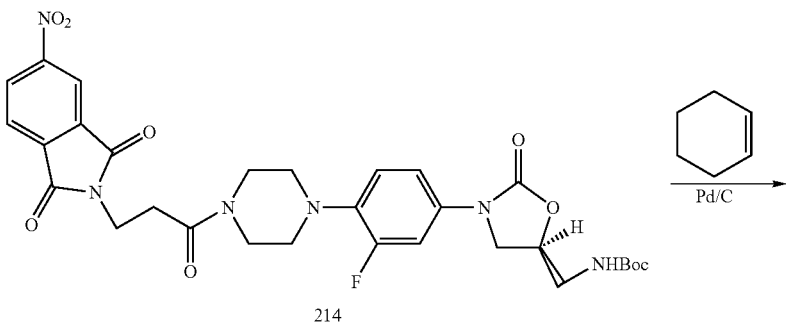

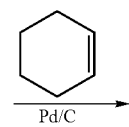

214

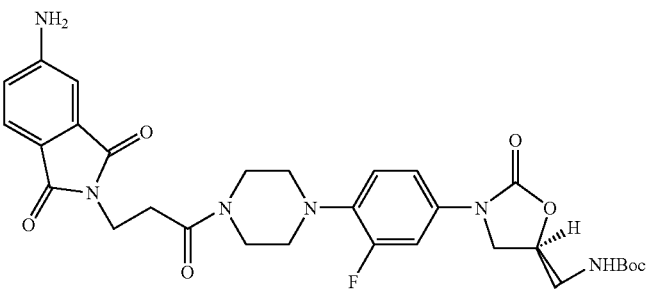

215

A stirred mixture of 214 (1.0 g, 1.56 mmol), cyclohexene (1.8 ml), 10% palladium-on-carbon catalyst (0.21 g) and EtOH (40 ml) was refluxed, under nitrogen for 3.25 h, cooled, diluted with CH$_2$Cl$_2$ and filtered through celite. The solid was washed with 20% EtOH—CH$_2$Cl$_2$ and the filtrates were concentrated. The residue was combined with the crude product from a second identical reaction and chromatographed on silica gel with 5% MeOH—CH$_2$Cl$_2$ to give 1.66 g of 215: $^1$H NMR (400 MHz, CDCl$_3$) δ 1.44 (s, 9H), 2.80 (t, 2H), 3.04 (m, 4H), 3.55 (m, 2H), 3.65, 3.81 (m, m, 4H), 3.85 (m, 1H), 4.04 (m, 3H), 4.43 (s, 2H), 4.79 (m, 1H), 5.03 (m, 1H), 6.85 (dd, 1H), 6.92 (t, 1H), 7.06 (d, 1H), 7.12 (dd, 1H), 7.48 (dd, 1H), 7.63 (d, 1H); MS (ESI+) m/z 611 (M+H$^+$), 633.5 (M+Na$^+$); MS (ESI−) m/z 609.3 (M−H), 645.3 (M+Cl).

Step 4:

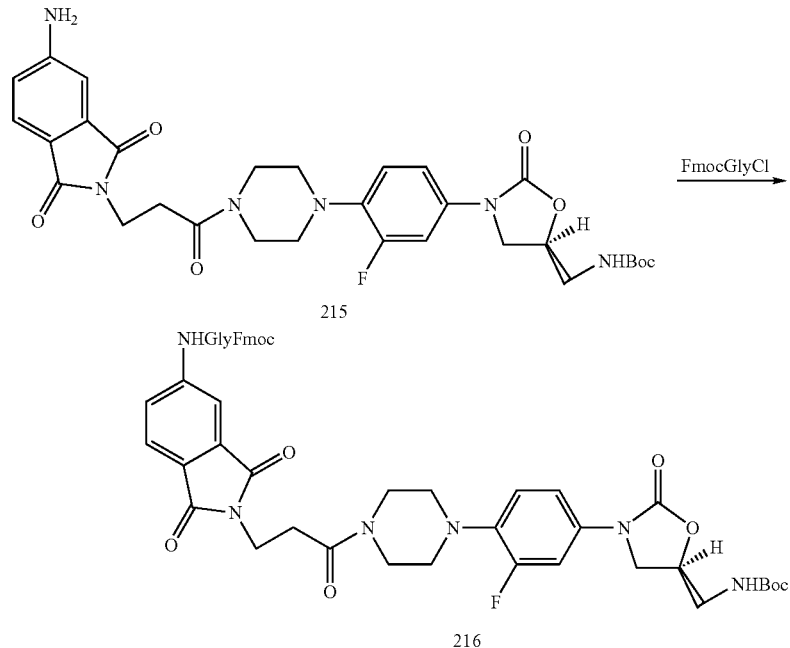

A stirred mixture of 215 (0.31 g, 0.507 mmol) and N-Fmoc glycyl chloride (0.167 g, 0.529 mmol) in THF (30 ml) was refluxed, under nitrogen for 3.5 h, cooled and concentrated in vacuo. Crystallization of the residue from MeOH-EtOAc gave 0.41 g of 216: mp 175–177° C. (dec); MS (ESI−) m/z 888.5 (M−H), 924.4 (M+35).

Step 5:

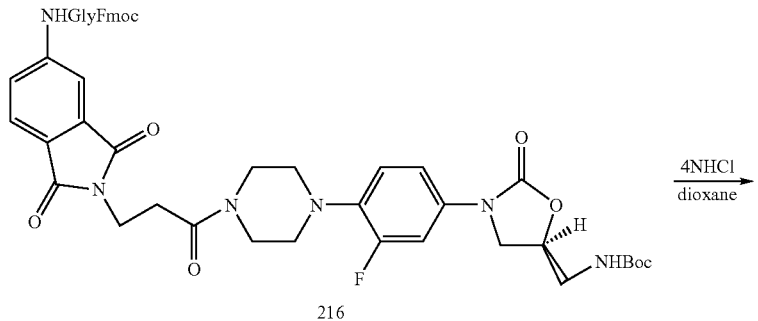

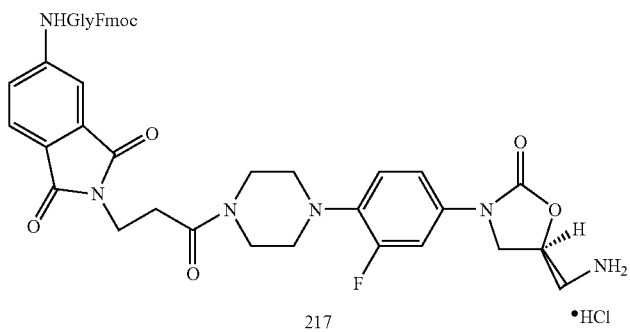

217 •HCl

A sample of 216 (0.77 g, 0.866 mmol) was cooled in an ice bath under nitrogen and treated, dropwise with stirring during 1.5 min, with 4N hydrogen chloride in dioxane (7 ml). It was kept in the ice bath for 40 min and at ambient temperature for 110 min. Excess hydrogen chloride was removed with a stream of nitrogen and the resulting mixture was concentrated in vacuo to give 0.71 g of 217.

Step 6:

A stirred mixture of 217 (0.32 g) and triethylamine (0.11 ml) in CH$_2$Cl$_2$ (30 ml), under nitrogen was treated, dropwise, with a solution of O-(3,3-diphenylpropyl) difluoroethanethioate (0.15 g, 0.49 mmol) in CH$_2$Cl$_2$ (2 ml) and kept at ambient temperature for 4.5 h. Additional O-(3,3-diphenylpropyl) difluoroethanethioate (0.05 g) in CH$_2$Cl$_2$ (1 ml) was added and the mixture was kept at ambient temperature for 18 h and concentrated in vacuo. The residue was triturated with 3% MeOH—CH$_2$Cl$_2$ to give 0.27 g of 218: MS (ESI−) m/z 918.4 (M+Cl).

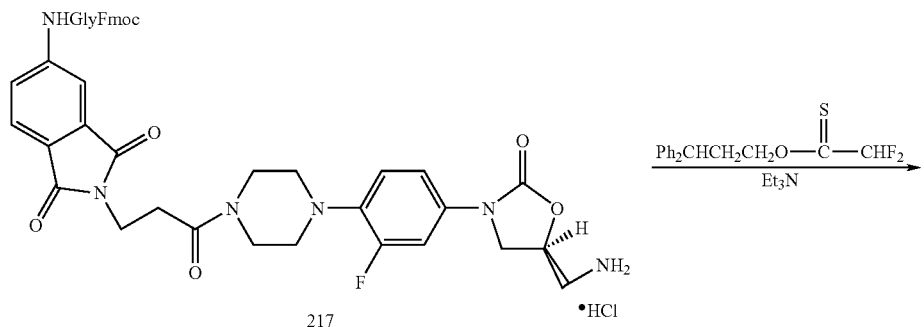

217 •HCl

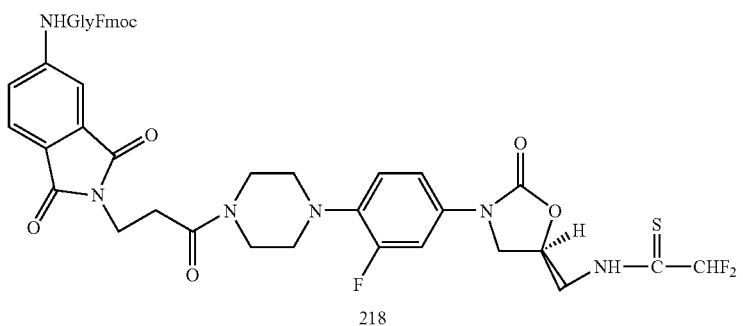

218

Step 7:

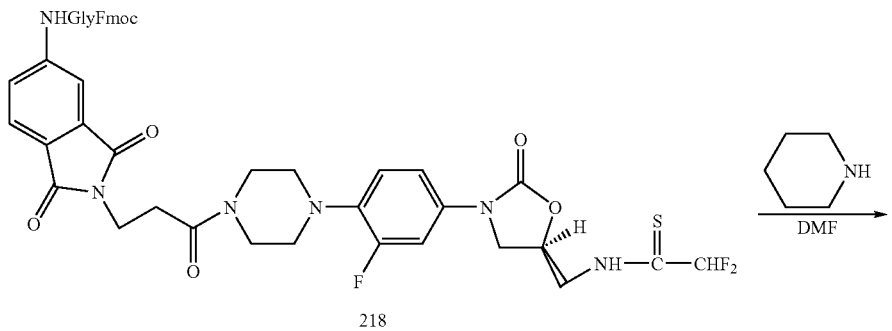

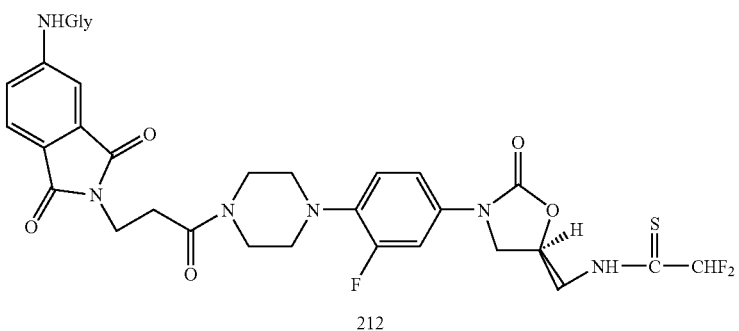

A stirred mixture of 14 (0.26 g, 0.294 mmol) in DMF (2 ml), under nitrogen, was treated with piperidine (0.06 ml), kept at ambient temperature for 30 min and concentrated in vacuo. Chromatography of the residue on silica gel with 5% MeOH-0.3% $NH_4OH$—$CH_2Cl_2$ to 7.5% MeOH-0.5% $NH_4OH$—$CH_2Cl_2$ gave 0.032 g of 101: MS (ESI+) m/z 662.3 (M+H$^+$); MS (ESI-) m/z 696.3 (M+Cl); IR (drift) 3241, 1749, 1744, 1710, 1677, 1663, 1645, 1628; HRMS calcd for $C_{29}H_{31}F_3N_7O_6S$ (M+H$^+$) 662.2008, found 662.2029.

Example 73

MIC Test Method

The in vitro MICs of test compounds were determined by a standard agar dilution method. A stock drug solution of each analog was prepared in the preferred solvent, usually DMSO:H$_2$O (1:3). Serial 2-fold dilutions of each sample are made using 1.0 ml aliquots of sterile distilled water. To each 1.0 ml aliquot of drug was added 9 ml of molten Mueller Hinton agar medium. The drug-supplemented agar was mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension was made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC μg/ml), the lowest concentration of drug that inhibits visible growth of the organism, was read and recorded. The data is shown in Table I.

TABLE 1

| Compound No. | Structure | MIC Data[a] | | | | | | | | |
|---|---|---|---|---|---|---|---|---|---|---|
| | | SAUR[b] 9213 | SAUR 31583 | SEPI[c] 30593 | EFAE[d] 9217 | EFAE[e] 12712 | SPNE[f] 9912 | SPYO[g] 152 | HINF[h] 30063 | HINF 31810 | MCAT[i] 30607 |
| 2 | | 2 | 4 | 1 | 1 | 1 | 0.125 | 0.125 | 16 | 8 | 2 |
| 8 | | 32 | >64 | 8 | 32 | 32 | 2 | 2 | >64 | >64 | 32 |
| 9 | | 4 | 32 | 2 | 2 | 2 | 0.25 | 0.25 | 32 | 32 | 4 |

TABLE 1-continued

MIC Data[a]

| Compound No. | Structure | SAUR[b] 9213 | SAUR 31583 | SEPI[c] 30593 | EFAE[d] 9217 | EFAE[e] 12712 | SPNE[f] 9912 | SPYO[g] 152 | HINF[h] 30063 | HINF 31810 | MCAT[i] 30607 |
|---|---|---|---|---|---|---|---|---|---|---|---|
| 10 | 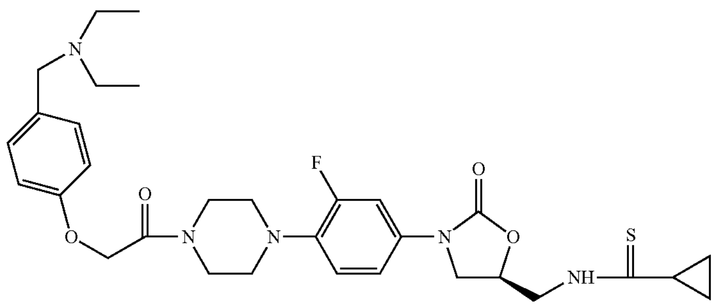 | 2 | 8 | 1 | 2 | 2 | 0.25 | 0.25 | 32 | 32 | 2 |
| 13 | 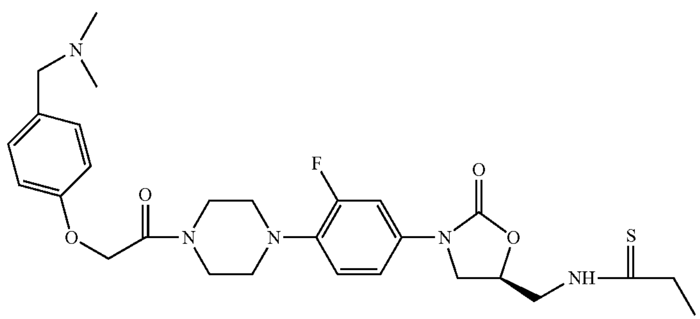 | 8 | 16 | 1 | 1 | 2 | 0.125 | 0.25 | 16 | 16 | 4 |
| 14 | 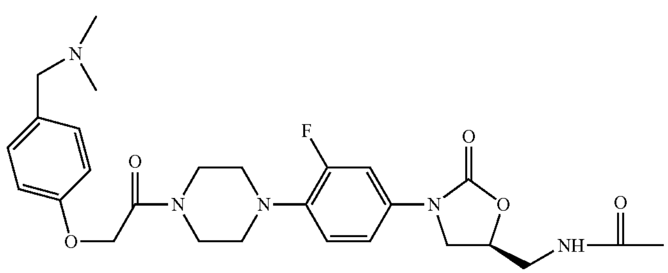 | 16 | >64 | 8 | 8 | 8 | 0.5 | 0.5 | 64 | 32 | 32 |

TABLE 1-continued

| Compound No. | Structure | MIC Data[a] | | | | | | | | |
|---|---|---|---|---|---|---|---|---|---|---|
| | | SAUR[b] 9213 | SAUR 31583 | SEPI[c] 30593 | EFAE[d] 9217 | EFAE[e] 12712 | SPNE[f] 9912 | SPYO[g] 152 | HINF[h] 30063 | HINF 31810 | MCAT[i] 30607 |
| 17 | | 8 | 32 | 2 | 1 | 2 | 0.25 | 0.5 | 64 | 32 | 4 |
| 18 | | 4 | 16 | 1 | 1 | 2 | 0.25 | 0.25 | 64 | 32 | 2 |
| 19 | | 16 | >64 | 8 | 4 | 8 | 1 | 1 | >64 | 64 | 64 |

TABLE 1-continued

MIC Data[a]

| Compound No. | Structure | SAUR[b] 9213 | SAUR 31583 | SEPI[c] 30593 | EFAE[d] 9217 | EFAE[e] 12712 | SPNE[f] 9912 | SPYO[g] 152 | HINF[h] 30063 | HINF 31810 | MCAT[i] 30607 |
|---|---|---|---|---|---|---|---|---|---|---|---|
| 22 | 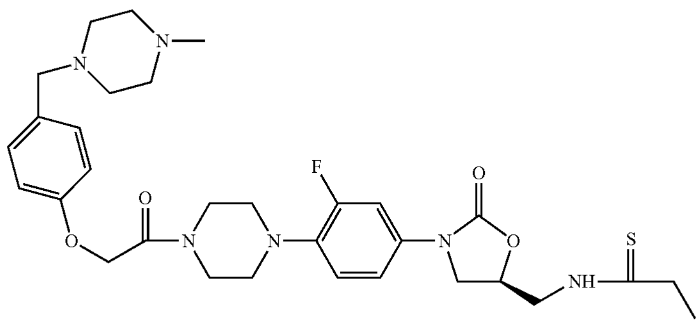 | 8 | 32 | 2 | | 2 | 0.125 | 0.25 | 32 | 16 | 2 |
| 23 | 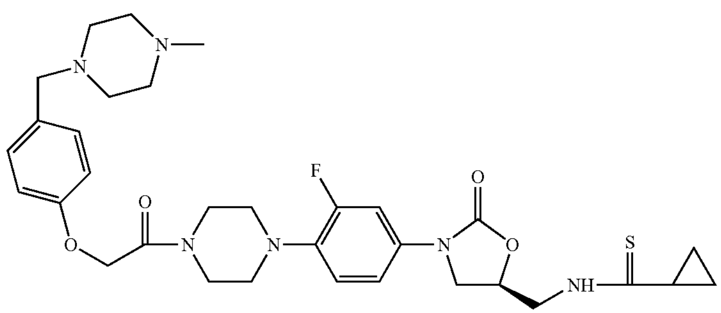 | 16 | >64 | 8 | | 8 | 0.5 | 0.5 | 64 | 64 | 32 |

TABLE 1-continued

| Compound No. | Structure | MIC Data[a] | | | | | | | | |
|---|---|---|---|---|---|---|---|---|---|---|
| | | SAUR[b] 9213 | SAUR 31583 | SEPI[c] 30593 | EFAE[d] 9217 | EFAE[e] 12712 | SPNE[f] 9912 | SPYO[g] 152 | HINF[h] 30063 | HINF 31810 | MCAT[i] 30607 |
| 24 | | 4 | 16 | 2 | | 2 | 0.125 | 0.25 | 32 | 16 | 2 |

[a]Minimum inhibitory concentration (μg/mL).
[b]*S. aureus*
[c]*S. epidermidis*
[d]*E. Faecalis*
[e]*E. Faecium*
[f]*S. pneumonia*
[g]*S. pyogenes*
[h]*H. influenzae*
[i]*M. catarrhalis*

We claim:
1. A compound of formula I

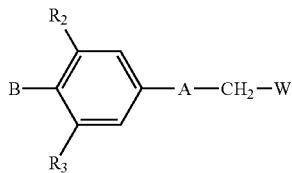

or pharmaceutically acceptable salts thereof wherein:
A is a structure i, ii, iii, or iv;

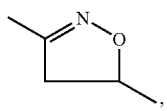

i

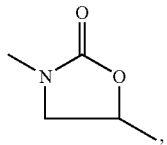

ii

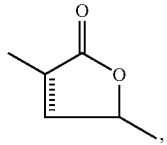

iii

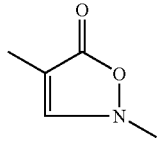

iv

B is

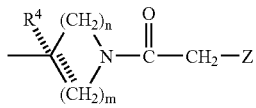

(a)

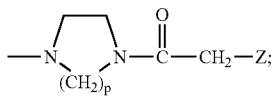

(b)

W is —N(H)C(X)—$R_1$, Het, or —Y-HET, in which the Het or —Y-HET is optionally substituted with =S or =O, provided that when A is structure iv, W is not —Y-HET or Het;
X is O or S;
Y is NH, O, or S;
Z is

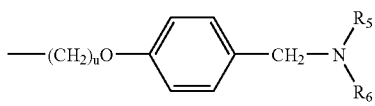

(a)

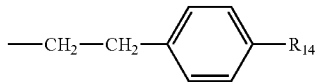

(b)

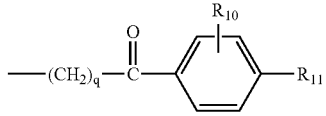

(c)

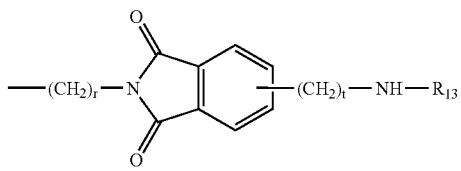

(d)

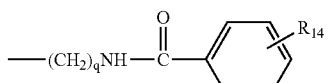

(e)

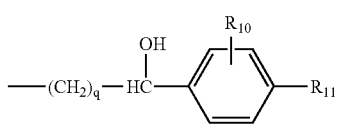

(f)

$R_1$ is a) H,
b) $NH_2$,
c) $NHC_{1-4}$alkyl,
d) $C_{1-4}$ alkyl,
e) $C_{2-4}$ alkenyl,
f) O—$C_{1-4}$ alkyl,
i) S-$C_{1-4}$ alkyl, or
j) $(CH_2)_s$ $C_{3-6}$ cycloalkyl, in which each occurrence of alkyl or cycloalkyl in $R_1$ is optionally substituted by one, two or three halogens (F or Cl);
each $R_2$ and $R_3$ is independently hydrogen, halogen (F or Cl), methyl or ethyl;
$R_4$ is H, $CH_3$ or F;
$R_5$ is H or $C_{1-4}$ alkyl;
$R_6$ is H, $C_{1-4}$ alkyl, or

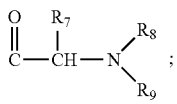

or $R_5$ and $R_6$ together form an optionally substituted saturated heterocycle;
$R_7$ is H, or $C_{1-4}$ alkyl which can be optionally substituted by —OH, —$NH_2$, —NH—C(=NH)—$NH_2$, —SH, —$SCH_3$, —COOH, —C(O)$NH_2$, phenyl which can be optionally substituted with —OH;
$R_8$ is H or $CH_3$;
$R_9$ is H, $CH_3$, —C(O)—CH($R_7$)—$NR_8R_8$,

$R_{10}$ or $R_{11}$ is halo, $C_{1-4}$alkyl, $CF_3$, —CN, —$NO_2$, —OH, —O—$C_{1-4}$alkyl, —NH—S(O)$_w$$C_{1-4}$alkyl;

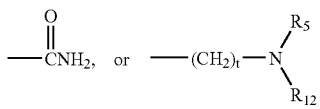

$R_{12}$ is H, $C_{1-4}$alkyl, —S(O)$_2$—$C_{1-4}$alkyl,

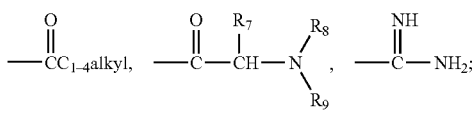

or $R_5$ and $R_{12}$ together form a saturated heterocycle;
$R_{13}$ is H, or

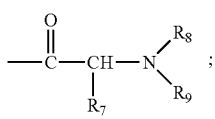

$R_{14}$ is —(CH$_2$)$_r$NHR$_{13}$, —OH, —OC$_{1-4}$alkyl;
m is 0, 1, 2, 3, 4;
n is 0, 1, 2, 3, 4 with the proviso that m plus n is 2, 3, 4, or 5;
p is 2, 3;
q is 1, 2;
r, s and t are independently 0, 1;
u and w are independently 0, 1, 2; and
provided that W is not Het or —Y-HET when Z is a, b, or d, and further provided that Z is not b when A is formula iii.

2. The compound of claim 1, wherein B is

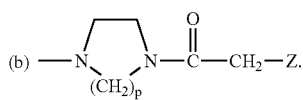

3. The compound of claim 2, wherein p is 2.
4. The compound of claim 1, wherein B is

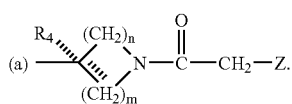

5. The compound of claim 4, wherein n and m are both 2.
6. The compound of claim 4, wherein n and m are both 1.
7. The compound of claim 4, wherein $R_4$ is —CH$_3$.
8. The compound of claim 2, wherein Z is (a).
9. The compound of claim 8, wherein $R_5$ and $R_6$ are $C_{1-4}$ alkyl.
10. The compound of claim 8, wherein $R_5$ and $R_6$ together form an optionally substituted saturated heterocycle.
11. The compound of claim 10, wherein $R_5$ and $R_6$ form an optionally substituted morpholinyl and piperazinyl.
12. The compound of claim 11, wherein $R_5$ and $R_6$ form a morpholinyl and piperazinyl each of which are substituted with $C_{1-4}$ alkyl.

13. The compound of claim 8, wherein u=0.
14. The compound of claim 4, wherein Z is (a).
15. The compound of claim 14, wherein $R_5$ and $R_6$ are $C_{1-4}$alkyl.
16. The compound of claim 14, wherein $R_5$ and $R_6$ together form an optionally substituted saturated heterocycle.
17. The compound of claim 16, wherein $R_5$ and $R_6$ form an optionally substituted morpholinyl and piperazinyl.
18. The compound of claim 17, wherein $R_5$ and $R_6$ form a morpholinyl and piperazinyl each of which are substituted with $C_{1-4}$ alkyl.
19. The compound of claim 14, wherein u=0.
20. The compound of claim 2, wherein Z is (c).
21. The compound of claim 20, wherein $R_{10}$ is H.
22. The compound of claim 20, wherein $R_{11}$ is —C(O)—NH$_2$, —NHS(O)$_u$C$_{1-4}$alkyl, or —(CH$_2$)$_t$—NR$_5$R$_{12}$.
23. The compound of claim 22, wherein $R_{11}$ is —CH$_2$N(C$_{1-4}$alkyl)$_2$, —CH$_2$— satrurated heterocycle, —CH$_2$—NH—C$_{1-4}$alkyl, —CH$_2$—N(C1-4alkyl)-C(O)—CHR$_7$—NR$_8$R$_9$, —CH$_2$—NH—C(O)—C$_{1-4}$alkyl, —CH$_2$—NH—SO$_2$—(C1-4alkyl), —CH$_2$—NH$_2$, or —NH—C(O)—CHR$_7$—NR$_8$R$_9$.
24. The compound of claim 20, wherein $R_{10}$ is ortho to $R_{11}$.
25. The compound of claim 20, wherein q is 1.
26. The compound of claim 4, wherein Z is (c).
27. The compound of claim 26, wherein $R_{10}$ is H.
28. The compound of claim 26, wherein $R_{11}$ is —C(O)—NH$_2$, —NHS(O)$_u$C$_{1-4}$alkyl, or —(CH$_2$)$_t$—NR$_5$R$_{12}$.
29. The compound of claim 28, wherein $R_{11}$ is —CH$_2$N(C$_{1-4}$alkyl)$_2$, —CH$_2$— satrurated heterocycle, —CH$_2$—NH—C$_{1-4}$alkyl, —CH$_2$—N(C1-4alkyl)-C(O)—CHR$_7$—NR$_8$R$_9$, —CH$_2$—NH—C(O)—C$_{1-4}$alkyl, —CH$_2$—NH—SO$_2$—(C1-4alkyl), —CH$_2$—NH$_2$, or —NH—C(O)—CHR$_7$-NR$_8$R$_9$.
30. The compound of claim 26, wherein q is 1.
31. The compound of claim 2, wherein Z is (b).
32. The compound of claim 31, wherein $R_{14}$ is —OC$_{1-4}$ alkyl, —OH, or —NH—C(O)—CH(R$_7$)—NR$_8$R$_9$.
33. The compound of claim 4, wherein Z is (b).
34. The compound of claim 33, wherein $R_{14}$ is —OC$_{1-4}$ alkyl, —OH, or —NH—C(O)—CH(R$_7$)—NR$_8$R$_9$.
35. The compound
N-[((5S)-3-{4-[4-({4-[(Diethylamino)methyl]phenoxy}acetyl)piperazin-1-yl]-3-fluorophenyl}-2-oxo-1,3-oxazolidin-5-yl)methyl]propanethioamide;
N-[((5S)-3-{4-[4-({4-[(Diethylamino)methyl]phenoxy}acetyl)piperazin-1-yl]-3-fluorophenyl}-2-oxo-1,3-oxazolidin-5-yl)methyl]cyclopropanecarbothioamide;
N-[((5S)-3-{4-[4-({4-[(Diethylamino)methyl]phenoxy}acetyl)piperazin-1-yl]-3-fluorophenyl}-2-oxo-1,3-oxazolidin-5-yl)methyl]acetamide;
N-[((5S)-3{4-[4-({4-[(Dimethylamino)methyl]phenoxy}acetyl)piperazin-1-yl]-3-fluorophenyl}-2-oxo-1,3-oxazolidin-5-yl)methyl]propanethioamide;
N-[((5S)-3-{4-[4-({4-[(Dimethylamino)methyl]phenoxy}acetyl)piperazin-1-yl]-3-fluorophenyl}-2-oxo-1,3-oxazolidin-5-yl)methyl]cyclopropanecarbothioamide;
N-[((5S)-3-{4-[4-({4-[(Dimethylamino)methyl]phenoxy}acetyl)piperazin-1-yl]-3-fluorophenyl}-2-oxo-1,3-oxazolidin-5-yl)methyl]acetamide;
N-({(5S)-3-[3-Fluoro-4-(4-{[4-(morpholin-4-ylmethyl)phenoxy]acetyl}piperazin-1-yl)phenyl]-2-oxo-1,3-oxazolidin-5-yl}methyl)propanethioamide;

N-({(5S)-3-[3-Fluoro-4-(4-{[4-(morpholin-4-ylmethyl)
phenoxy]acetyl}piperazin-1-yl)phenyl]-2-oxo-1,3-ox-
azolidin-5-yl}methyl)cyclopropanecarbothioamide;
N-({(5S)-3-[3-Fluoro-4-(4-{[4-(morpholin-4-ylmethyl)
phenoxy]acetyl}piperazin-1-yl)phenyl]-2-oxo-1,3-ox-
azolidin-5-yl}methyl)acetamide;
N-[((5S)-3-{3-Fluoro-4-[4-({4-[(4-methylpiperazin-1-yl)
methyl]phenoxy}acetyl)piperazin-1-yl]phenyl}-2-oxo-
1,3-oxazolidin-5-yl)methyl]propanethioamide;
N-[((5S)-3-{3-Fluoro-4-[4-({4-[(4-methylpiperazin-1-yl)
methyl]phenoxy}acetyl)piperazin-1-yl]phenyl}-2-oxo-
1,3-oxazolidin-5-yl)methyl]cyclopropanecarbothioam-
ide;
N-[((5S)-3-{3-Fluoro-4-[4-({4-[(4-methylpiperazin-1-yl)
methyl]phenoxy}acetyl)piperazin-1-yl]phenyl}-2-oxo-
1,3-oxazolidin-5-yl)methyl]acetamide;
N-[((5S)-3-{4-[4-(4-{4-[(Dimethylamino)methyl]phe-
nyl}-4-oxobutanoyl)-1-piperazinyl]-3-fluorophenyl}-
2-oxo-1,3-oxazolidin-5-yl)methyl]propanethioamide;
N-[((5S)-3-{4-[4-(4-{4-[(Dimethylamino)methyl]phe-
nyl}-4-oxobutanoyl)-1-piperazinyl]-3-fluorophenyl}-
2-oxo-1,3-oxazolidin-5-yl)methyl]cyclopropanecar-
bothioamide;
N-[((5S)-3-{4-[4-(4-{4-[(Dimethylamino)methyl]phe-
nyl}-4-oxobutanoyl)-1-piperazinyl]-3-fluorophenyl}-
2-oxo-1,3-oxazolidin-5-yl)methyl]acetamide;
N-({(5S)-3-[3-Fluoro-4-(4-{4-[4-(4-morpholinylmethyl)
phenyl]-4-oxobutanoyl}-1-piperazinyl)phenyl]-2-oxo-
1,3-oxazolidin-5-yl}methyl)propanethioamide;
N-({(5S)-3-[3-Fluoro-4-(4-{4-[4-(4-morpholinylmethyl)
phenyl]-4-oxobutanoyl}-1-piperazinyl)phenyl]-2-oxo-
1,3-oxazolidin-5-yl}methyl)acetamide;
N-({(5S)-3-[3-Fluoro-4-(4-{4-[4-(4-morpholinylmethyl)
phenyl]-4-oxobutanoyl}-1-piperazinyl)phenyl]-2-oxo-
1,3-oxazolidin-5-yl}methyl)cyclopropanecarbothioa-
mide;
N-[((5S)-3-{3-Fluoro-4-[4-(4-{4-[(methylamino)methyl]
phenyl}-4-oxobutanoyl)piperazin-1-yl]phenyl}-2-oxo-
1,3-oxazolidin-5-yl)methyl]acetamide;
$N^1$-(4-{4-[4-(4-{(5S)-5-[(Acetylamino)methyl]-2-oxo-1,
3-oxazolidin-3-yl}-2-fluorophenyl)-piperazin-1-yl]-4-
oxobutanoyl}benzyl-$N^1$-methylglycinamide;
$N^1$-(4-{4-[4-(4-{(5S)-5-[(Acetylamino)methyl]-2-oxo-1,
3-oxazolidin-3-yl}-2-fluorophenyl)piperazin-1-yl]-4-
oxobutanoyl}benzyl)-$N^1,N^2,N^2$-trimethylglycinamide;
$N^1$-(4-{4-[4-(4-{(5S)-5-[(Acetylamino)methyl]-2-oxo-1,
3-oxazolidin-3-yl}-2-fluorophenyl)piperazin-1-yl]-4-
oxobutanoyl}benzyl)-$N^2,N^2$-dimethylglycinamide;
$N^1$-(4-{4-[4-[2-Fluoro-4-{(5S)-2-oxo-5-[(propanethioly-
lamino)methyl]-1,3-oxazolidin-3-yl}phenyl)piperazin-
1-yl]-4-oxobutanoyl}benzyl)-$N^2,N^2$-dimethylglycina-
mide;
(S)-$N^1$-(4-{4-[4-(2-Fluoro-4-{(5S)-2-oxo-5-[(propaneth-
ioylamino)methyl]-1,3-oxazolidin-3-yl}phenyl)piper-
azin-1-yl]-4-oxobutanoyl}benzyl)alaninamide;
(S)-$N^1$-(4-{4-[4-(4-{(5S)-5-[(Acetylamino)methyl]-2-
oxo-1,3-oxazolidin-3-yl}-2-fluorophenyl)piperazin-1-
yl]-2-oxobutanoyl}benzyl)alaninamide;
$N^1$-(4-{4-[4-(2-Fluoro-4-{(5S)-2-oxo-5-[(propanethioy-
lamino)methyl]-1,3-oxazolidan-3-yl}phenyl)piper-
azin-1-yl]-4-oxobutanoyl}benzyl)glycinamide;
(S)-Alanyl-(S)-$N^1$-(4-{4-[4-(2-fluoro-4-{(5S)-2-oxo-5-
[(propanethioylamino)methyl]-1,3-oxazolidin-3-
yl}phenyl)piperazin-1-yl]-4-oxobutanoyl}benzyl)
alaninamide;

(S)-Alanyl-(S)-$N^1$-(4-{4-[4-(4-{(5S)-5-[(acetylamino)
methyl]-2-oxo-1,3-oxazolidin-3-yl}-2-fluorophenyl)
piperazin-1-yl]-4-oxobutanoyl}benzyl)alaninamide;
N-(4-{4-[4-(4-{(5S)-5-[(Acetylamino)methyl]-2-oxo-1,
3-oxazolidin-3-yl}-2-fluorophenyl)-1-piperazinyl]-4-
oxobutanoyl}benzyl)acetamide;
N-(4-{4-[4-(2-Fluoro-4-{(5S)-2-oxo-5-[(propanethioy-
lamino)methyl]-1,3-oxazolidin-3-yl}phenyl)-1-piper-
azinyl]-4-oxobutanoyl}benzyl)acetamide;
N-{[(5S)-3-(3-Fluoro-4-{4-[4-(4-{[(methylsulfonyl)
amino]methyl}phenyl)-4-oxobutanoyl]-1-
piperazinyl}phenyl)-2-oxo-1,3-oxazolidin-5-yl]
methyl}acetamide;
N-{[(5S)-3-(3-Fluoro-4-{4-[4-(4-{[(methylsulfonyl)
amino]methyl}phenyl)-4-oxobutanoyl]-1-
piperazinyl}phenyl)-2-oxo-1,3-oxazolidin-5-yl]
methyl}propanethioamide;
N-({(5S)-3-[4-(4-{4-[4-(Aminomethyl)phenyl]-4-oxobu-
tanoyl}-1-piperazinyl)-3-fluorophenyl]-2-oxo-1,3-ox-
azolidin-5-yl}methyl)propanethioamide;
N-({(5S)-3-[4-(4-{4-[4-(Aminomethyl)phenyl]-4-oxobu-
tanoyl}-1-piperazinyl-3-fluorophenyl]-2-oxo-1,3-ox-
azolidin-5-yl}methyl)acetamide;
$N^1$-(4-{4-[4-(4-{(5S)-5-[(Acetylamino)methyl]-2-oxo-1,
3-oxazolidin-3-yl}-2-fluorophenyl)piperazin-1-yl]-4-
oxobutanoyl}benzyl)glycinamide;
2-[3-methyl-3-(4-{(5S)-2-oxo-5-[(propionylamino)me-
thyl]-1,3-oxazolidin-3-yl}phenyl)azetidin-1-yl]-2-oxo-
ethyl 4-(aminomethyl)benzamide;
N-{[(5S)-3-(4-{1-[4-(4-aminophenyl)-4-oxobutanoyl]-3-
methylazetidin-3-yl}phenyl)-2-oxo-1,3-oxazolidin-5-
yl]methyl}propanamide;
N-({(5S)-3-[4-(1-{4-[4-(glycylamino)phenyl]-4-oxobu-
tanoyl}-3-methylazetidin-3-yl)phenyl]-2-oxo-1,3-ox-
azolidin-5-yl}methyl)propanamide;
N-{[(5S)-3-(4-{1-[4-(4-aminophenyl)-4-oxobutanoyl]-3-
methylazetidin-3-yl}-3-fluorophenyl)-2-oxo-1,3-ox-
azolidin-5-yl]methyl}acetamide;
N~1~-(4-{4-[3-(4-{(5S)-5-[(acetylamino)methyl]-2-oxo-
1,3-oxozolidin-3-yl}-2-fluorophenyl)-3-methylazeti-
din-1-yl]-4-oxobutanoyl}phenyl)glycinamide;
2-[3-(4-{(5S)-5-[(acetylamino)methyl]-2-oxo-1,3-oxazo-
lidin-3-yl}-2-fluorophenyl)-3-methylazetidin-1-yl]-2-
oxoethyl-4-(aminomethyl)benzamide;
N-{[(5S)-3-(3-Fluoro-4-{4-[4-(4-methoxyphenyl)bu-
tanoyl]piperazine-1-yl}phenyl)-2-oxo-1,3-oxazolidin-
5-yl]methyl}acetamide;
N-{[(5S)-3-(3-Fluoro-4-{4-[4-(4-hydroxyphenyl)bu-
tanoyl]piperazin-1-yl}phenyl)-2-oxo-1,3-oxazolidin-5-
yl]methyl}acetamide;
2,2-Difluoro-N-{[(5S)-3-(3-fluoro-4-{4-[4-(4-methox-
yphenyl)butanolyl]piperazin-1-yl}phenyl)-2-oxo-1,3-
oxazolidin-5-yl]methyl}ethanethioamide;
N-{[(5S)-3-(4-{4-[4-(4-Bromophenyl)-4-oxobutanoyl]-
1-piperazinyl}-3-fluorophenyl)-2-oxo-1,3-oxazolidin-
5-yl]methyl}acetamide;
N-{[(5S)-3-(4-{4-[4-(4-Bromophenyl)-4-oxobutanoyl]-
1-piperazinyl}-3-fluorophenyl)-2-oxo-1,3-oxazolidin-
5-yl]methyl}ethanethioamide;
N-{[(5S)-3-(4-{4-[4-(4-Cyanophenyl)-4-oxobutanoyl]-1-
piperazinyl}-3-fluorophenyl-2-oxo-1,3-oxazolidin-5-
yl]methyl}acetamide;
4-{4-[4-(4-{(5S)-5-[(Acetylamino)methyl]-2-oxo-1,3-
oxazolidin-3-yl}-2-fluorophenyl)-1-piperazinyl]-4-
oxobutanoyl}benzamide;

4-{4-[4-(4-{(5S)-5-[(Ethanethiolylamino)methyl]-2-oxo-1,3-oxazolidin-3-yl}-2-fluorophenyl)-1-piperazinyl]-4-oxobutanoyl}benzamide;

N-{[(5S)-3-(4-{4-[4-(4-Chlorophenyl)-4-oxobutanoyl]-1-piperazinyl}-3-fluorophenyl)-2-oxo-1,3-oxazolidin-5-yl]methyl}acetamide;

N-{[(5S)-3-(4-{4-[4-(4-chlorophenyl)-4-oxobutanoyl]-1-piperazinyl}-3-fluorophenyl)-2-oxo-1,3-oxazolidin-5-yl]methyl}ethanethioamide;

N-[((5S)-3-{3-Fluoro-4-[4-(4-{4-[(methylsulfonyl)amino]phenyl}-4-oxobutanoyl)-1-piperazinyl]phenyl}-2-oxo-1,3-oxazolidin-5-yl)methyl]propanethioamide;

N-[((5S)-3-{3-Fluoro-4-[4-(4-{4-[(methylsulfonyl)amino]phenyl}-4-oxobutanoyl-1-piperazinyl]phenyl}-2-oxo-1,3-oxazolidin-5-yl)methyl]acetamide, N-(4-{4-[4-(2-Fluoro-4-{(5S)-2-oxo-5-[(propanethiolylamino)methyl]-1,3-oxazolidin-3-yl}phenyl)-1-piperazinyl]-4-oxobutanoyl}phenyl)acetamide;

2-Amino-N-(4-{4-[4-(2-fluoro-4-{(5S)-2-oxo-5-[(propanethioylamino)methyl]1,3-oxazolidin-3-yl}phenyl)-1-piperazinyl]-4-oxobutanoyl}phenyl)acetamide;

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}phenyl)-2-aminoacetamide;

N-(4-{4-[4-(4-{(5S)-5-[(Acetylamino)methyl]-2-oxo-1,3-oxazolidin-3-yl}-2-fluorophenyl)-1-piperazinyl]-4-oxobutanoyl}phenyl)-(2S)-2-aminopropanamide;

N-1-(4-{4-[4-(4-{(5S)-5-[(Ethanethiolylamino)methyl]-2-oxo-1,3-oxazolidin-3-yl}-2-fluorophenyl)piperazin-1-yl]-4-oxobutanoyl}phenyl)-(S)-alaninamide;

N$^1$-[4-(5-{4-[4-((5S)-5-{[(2,2-Difluoroethanethioyl)amino]methyl}-2-oxo-1,3-oxazolidin-3-yl)-2-fluorophenyl]piperazin-1-yl}-5-oxopentanoyl)phenyl]glycinamide;

N$^1$-(4-{5-[4-(4-{(5S)-5-[(Acetylamino)methyl]-2-oxo-1,3-oxazolidin-3-yl}-2-fluorophenyl)piperazin-1-yl]-5-oxopentanoyl}phenyl)glycinamide;

N-(4-{4-[4-(4-{(5S)-5-[(Acetylamino)methyl]-2-oxo-1,3-oxazolidin-3-yl}-2-fluorophenyl)-1-piperazinyl]-4-oxobutyl}phenyl)-2-aminoacetamide;

2-Amino-N-(4-{4-[4-(2-fluoro-4-{(5S)-2-oxo-5-[(propanethiolylamino)methyl]-1,3-oxazolidin-3-yl}phenyl)-1-piperazinyl]-4-oxobutyl}phenyl)acetamide;

(S)-2-Amino-N-(4-{4-[4-(2-fluoro-4-{(5S)-2-oxo-5-[(propanethiolylamino)methyl]-1,3-oxazolidin-3-yl}phenyl)-1-piperazinyl]-4-oxobutyl}phenyl)propanamide;

N-(4-{4-[4-(4-{(5S)-5-[(Acetylamino)methyl]-2-oxo-1,3-oxazolidin-3-yl}-2-fluorophenyl)piperazin-1-yl]-4-oxobutyl}phenyl)-2-(dimethylamino)acetamide;

N-(4-{4-[4-(4-{(5S)-5-[(Ethanethiolylamino)methyl]-2-oxo-1,3-oxazolidin-3-yl}-2-fluorophenyl)piperazin-1-yl]-4-oxobutyl}phenyl)-2-(dimethylamino)acetamide;

N$^1$-(3-{4-[4-(4-{(5S)-5-[(Acetylamino)methyl]-2-oxo-1,3-oxazolidin-3-yl}-2-fluorophenyl)piperazin-1-yl]-1-hydroxy-4-oxobutyl}phenyl)glycinamide;

N$^1$-[3-(4-{4-[4-((5S)-5-{[(2,2-Difluoroethanethiolyl)amino]methyl}-2-oxo-1,3-oxazolidin-3-yl)-2-fluorophenyl]piperazin-1-yl}-4-oxobutanoyl)phenyl]glycinamide;

N-{[(5S)-3-(3-Fluoro-4-{4-[4-(3-nitrophenyl)-4-oxobutanoyl]piperazin-1-yl}phenyl)-2-oxo-1,3-oxazolidin-5-yl]methyl}actamide;

N$^1$-(3-{4-[4-(4-{(5S)-5-[(Acetylamino)methyl]-2-oxo-1,3-oxazolidin-3-yl}-2-fluorophenyl)piperazin-1-yl]-4-oxobutanoyl}phenyl)glycinamide;

N-{[(5S)-3-(4-{4-[4-(2-Aminophenyl)-4-oxobutanoyl]piperazin-1-yl}-3-fluorophenyl)-2-oxo-1,3-oxazolidin-5-yl]methyl}acetamide;

N-{[(5S)-3-(4-{4-[(5-Amino-1,3-dioxo-1,3-dihydro-2H-isoindol-2-yl)acetyl]piperazin-1-yl}-3-fluorophenyl)-2-oxo-1,3-oxazolidin-5-yl]methyl}acetamide;

N$^1$-(2-{2-[4-(4-{(5S)-5-[(Acetylamino)methyl]-2-oxo-1,3-oxazolidin-3-yl}-2-fluorophenyl)piperazin-1-yl]-2-oxoethyl}-1,3-dioxo-2,3-dihydro-1H-isoindol-5-yl)glycinamide; or N$^1$-[2-(3-{4-[4-((5S)-5-{[(2,2-Difluoroethanethiolyl)amino]methyl}-2-oxo-1,3-oxazolidin-3-yl)-2-fluorophenyl]piperazin-1-yl}-3-oxopropyl)-1,3-dioxo-2,3-dihydro-1H-isoindol-5-yl)glycinamide.

36. A method for the treatment of microbial infections in mammals comprising administration of an effective amount of compound of claim 1 to said mammal.

37. The method of claim 36 wherein said compound of claim 1 is administered to the mammal orally, parenterally, transdermally, or topically in a pharmaceutical composition.

38. The method of claim 37 wherein said compound is administered in an amount of from about 0.1 to about 100 mg/kg of body weight/day.

39. The method of claim 37 wherein said compound is administered in an amount of from about 1 to about 50 mg/kg of body weight/day.

40. A pharmaceutical composition comprising a compound of claim 1 and a pharmaceutically acceptable carrier.

* * * * *